Figure 1:
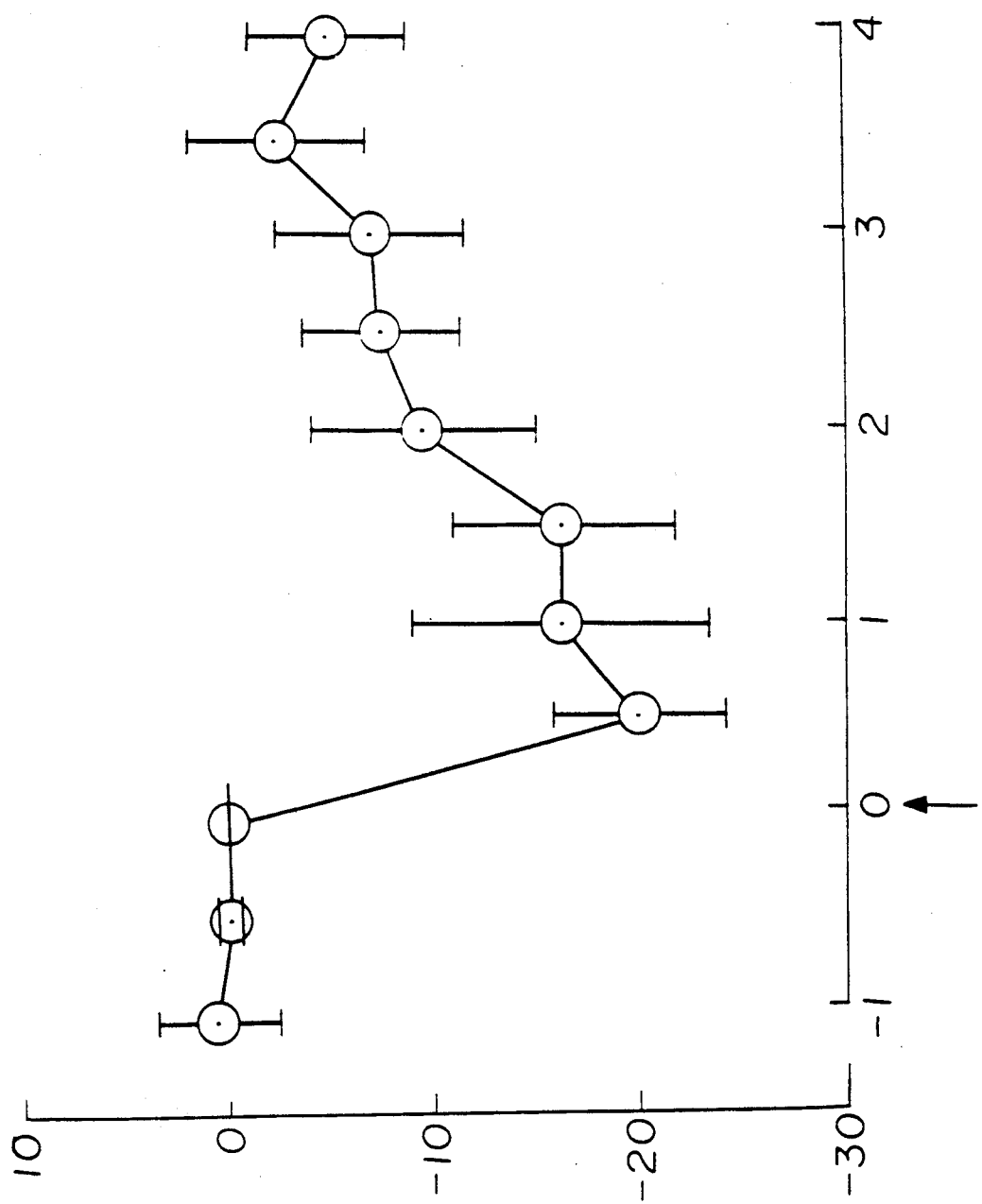

United States Patent [19]

Morishima et al.

[11] Patent Number: 5,240,924
[45] Date of Patent: Aug. 31, 1993

[54] N-ACYLAMINO ACID DERIVATIVES AND THEIR USE

[75] Inventors: Hajime Morishima, Tokyo; Yutaka Koike, Koshigaya; Masato Nakano, Ichikawa; Shugo Atsuumi; Seiichi Tanaka, both of Tokyo; Kenji Matsuyama, Kashiwa, all of Japan

[73] Assignee: Banyu Pharmaceutical Co., Ltd., Tokyo, Japan

[21] Appl. No.: 815,412

[22] Filed: Dec. 31, 1991

Related U.S. Application Data

[62] Division of Ser. No. 240,725, Sep. 6, 1988, Pat. No. 5,122,523.

[30] Foreign Application Priority Data

Sep. 29, 1987 [JP] Japan .................. 62-244934

[51] Int. Cl.$^5$ .................. A61K 31/535; C07D 413/12
[52] U.S. Cl. .................. 514/235.5; 514/235.8; 514/236.8; 514/269; 514/363; 514/381; 544/122; 544/141; 544/142; 544/152; 544/316; 548/136; 548/251
[58] Field of Search .............. 544/122, 142, 152, 316, 544/141; 514/235.5, 236.8, 236.8, 269, 363, 381; 548/251, 136

[56] References Cited

PUBLICATIONS

Bolis et al, J. Med. Chem. 1987, 30, 1729–1737.
Haber et al, J. Cardiovascular Pharm., 10 (Supp. 7):554–558, 1987.
Plattner et al. J. Med Chem. 1988:31, 2277–2288.
Denkewatter et al, Progress in Drug Research, 1966, 510–515.
Burger, Medicinal Chemistry 2nd ed, 1960, pp. 565–571, 579–581.
Patent Abstracts Japan, C Field vol. 11, No. 136, 1987, Kokai 61-275258.
Patent Abstracts Japan, C field, vol. 11 No. 349, 1987, Kokai 62-120370.

*Primary Examiner*—Mary C. Lee
*Assistant Examiner*—Jacqueline Haley
*Attorney, Agent, or Firm*—Oblon, Spivak, McClelland, Maier & Neustadt

[57] ABSTRACT

An N-acylamino acid derivative of the formula:

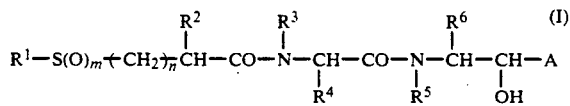

wherein the substituents are herein defined, or a salt thereof, which is useful as hypotensive drugs.

6 Claims, 1 Drawing Sheet

N-ACYLAMINO ACID DERIVATIVES AND THEIR USE

This is a division of application Ser. No. 07/240,725, filed on Sep. 6, 1988 now U.S. Pat. No. 5,122,523.

The present invention relates to N-acylamino acid derivatives or their salts useful in the pharmaceutical field. More particularly, the present invention relates to N-acylamino acid derivatives or their salts which have renin inhibiting activities and which are thus expected to be useful as hypotensive drugs.

A renin-angiotensin system is one of hypertensive systems in the living body, and it is an important system for regulating the blood pressure-body fluid electrolyte. Renin is secreted from renal juxtaglomerular cells and enters into the whole body circulation system via the renal vein. In the blood, there exists angiotensinogen which is a glycoprotein produced in the liver. Renin reacts on angiotensinogen to form angiotensin I. Most of angiotensin I will be converted to angiotensin II by angiotensin I-converting enzyme which is present in the pulmonary vascular endothelial cells in one cycle of pulmonary circulation. Angiotensin II thus formed directly induces contraction of smooth muscles of peripheral blood vessels and thus shows a strong hypertensive activity. It further acts on the adrenal cortex to induce secretion of aldosterone, which in turn acts on the renal to facilitate reabsorption of sodium, whereby the effective circulatory blood flow increases, the cardiac output increases and the peripheral vascular resistance increases so that the blood pressure increases.

It is known that hypertension will be brought about if this renin-angiotensin system was enhanced abnormally. Typical examples are renal vascular hypertension and malignant hypertension. Further, as a rare case, hypertension caused by a renin producing tumor is known.

For the treatment of the hypertension due to the enhancement of the renin-angiotensin system, inhibitors against the angiotensin I-converting enzyme have been studied, developed and subjected to clinical tests. However, such inhibitors are suspected to have side effects, since the substrate specificity of the angiotensin I-converting enzyme is broad to some extent and there exist some enzymes similar to the angiotensin I-converting enzyme in the living body. On the other hand, it is known that renin has a strict substrate specificity. Accordingly, an inhibitor against renin has a strong specificity and can be a superior hypotensive drug. For this reason, the research on renin inhibitors has been very active, and a number of renin inhibitors have been proposed.

However, most of these inhibitors are polypeptides, which are hardly absorbable by oral administration and which are susceptible to decomposition by a protease in vivo. Besides, they have high lipophilicity and are likely to be readily excreted to bile, whereby the retention of the hypotensive effects can not be expected.

On the other hand, Japanese Unexamined Patent Publication No. 275258/1986 discloses dipeptides represented by the formula:

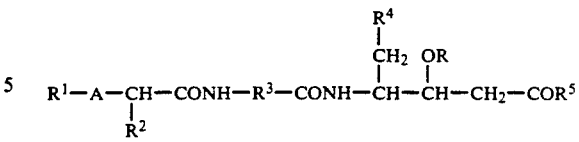

wherein each of $R^1$ and $R^2$ which may be the same or different is a $-B-R^6$ group wherein B is a single bond or a straight chain or branched chain lower alkylene group which may have a double bond in the chain, and $R^6$ is an aryl group or a heteroaryl group, a $C_1-C_{10}$ alkyl group or a $-E-R^7$ group wherein E is a lower alkylene group which may be interrupted by one oxygen atom, and $R^7$ is a lower alkoxy group, an aryloxy group, an arylthio group, an aralkyloxy group or a nitrogen-containing heterocyclyl group; $R^3$ is an ethylene, trimethylene or tetramethylene group which may be substituted by a lower alkyl, phenyl or hydroxyl group, a

group wherein $R^8$ is a nitrogen-containing heterocyclyl-substituted lower alkyl group, a $C_5-C_{18}$ alkyl group, a $C_2-C_5$ alkenyl or $C_2-C_5$ alkynyl group which may be substituted by halogen, or a

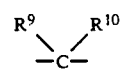

wherein each of $R^9$ and $R^{10}$ which may be the same or different is a lower alkyl group, or $R^9$ and $R^{10}$ form together with the adjacent carbon atom a $C_3-C_8$ cycloalkyl group; $R^4$ is an isopropyl group, a $C_3-C_8$ cycloalkyl group or a phenyl group; $R^5$ is a hydroxyl group, a $C_1-C_{10}$ alkoxy group, an aryloxy group, an amino group, a mono- or di-($C_1-C_{10}$ alkyl)amino group (wherein the alkyl group may have one or two substituents which may be the same or different and which are selected from the group consisting of a hydroxyl group, a lower alkoxy group, a halogen atom, an unsubstituted or substituted phenyl group, a pyridyl group, a $C_3-C_8$ cycloalkyl group, a di(lower alkyl)amino group, a di(-hydroxy lower alkyl)amino group or a nitrogen-containing heterocyclyl group), a mono or di($C_3-C_4$ alkenyl)amino group, a $C_3-C_8$ cycloalkylamino group, an arylamino group, a nitrogen-containing heterocyclylamino group wherein the amino and heterocyclyl are linked by N—C, a nitrogen-containing heterocyclyl group wherein the heterocyclyl group is linked to a carbonyl group by a nitrogen atom contained in the group, or a $-NHR^{11}$ group wherein $R^{11}$ is an amino group, a $C_1-C_{10}$ aliphatic acylamino group which may be substituted by a halogen atom, a lower alkoxy group, an aryloxy group, an arylacyl group, an aryl group or a $C_3-C_8$ cycloalkyl group, an arylacylamino group, a cinnamoylamino group, a heteroarylacylamino group, a lower alkylamino group which may be substituted by a hydroxyl group, a lower alkoxy group, a $C_1-C_5$ aliphatic acyloxy group, an arylacyloxy group or an aryl group, an arylamino group or a nitrogen-containing heterocyclyl group wherein the heterocyclyl group is linked to $-NH-$ by a nitrogen atom; R is a hydrogen atom, a $C_1-C_6$ aliphatic acyl group or an arylacyl group; and A is a single bond, an oxygen atom or a sulfur atom. Further, Japanese Unexamined Patent Publication No. 120370/1987 discloses dipeptide derivatives represented by the formula:

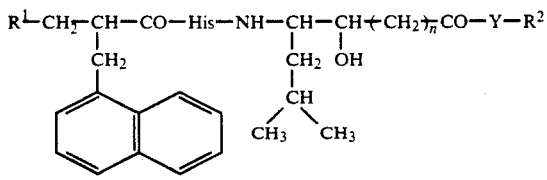

wherein $R^1$ is a carbamoyl group or a lower alkoxycarbonyl group, His is a L-histidine group, n is 0 or 1, Y is —O— or —NH—; and $R^2$ is a $C_1$-$C_7$ straight chain or branched alkyl group.

The compounds disclosed in the above publications have relatively short peptide chains and are therefore expected to have improved absorbability by oral administration. However, because of the short peptide chains, their renin-inhibiting activities are poor.

To reduce the molecular size is the most effective means to improve the absorbability by oral administration, to be stable against a protease in vivo and to avoid the rapid excretion to bile. However, such a means is likely to lead to a substantial decrease of the renin-inhibiting activities as shown by the above publications.

As a result of years of extensive researches on the peptide derivatives and on the renin-inhibitors, the present inventors have found that N-acylamino acid derivatives having a novel structure exhibits strong renin-inhibiting activities in spite of their short peptide chains, and yet they have excellent absorbability by oral administration. The present invention is based on this discovery.

The present invention provides an N-acylamino acid derivative of the formula:

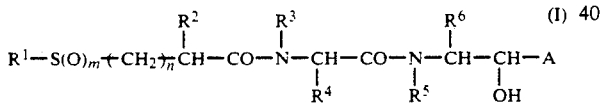

wherein each of $R^1$, $R^2$, $R^4$ and $R^6$ which may be the same or different is a hydrogen atom, a substituted or unsubstituted lower alkyl group, a substituted or unsubstituted cycloalkyl group, a substituted or unsubstituted cycloalkylalkyl group, a substituted or unsubstituted aryl group, a substituted or unsubstituted aralkyl group or a substituted or unsubstituted monocyclic or bicyclic heterocyclic group containing from 1 to 4 hetero atoms selected from the group consisting of nitrogen, sulfur and oxygen atoms;

each of $R^3$ and $R^5$ which may be the same or different is a hydrogen atom or a lower alkyl group;

A is a —CH(OH)—(CH$_2$)$_q$R$^7$ wherein $R^7$ is a hydrogen atom, a substituted or unsubstituted lower alkyl group, a substituted or unsubstituted cycloalkyl group, a substituted or unsubstituted cyloalkylalkyl group, a substituted or unsubstituted aryl group, a substituted or unsubstituted aralkyl group, a substituted or unsubstituted monocyclic or bicyclic heterocyclic group containing from 1 to 4 hetero atoms selected from the group consisting of nitrogen, sulfur and oxygen atoms or a —E—R$^{10}$ group wherein E is a —S(O)$_i$— group wherein i is 0, 1 or 2, an oxygen atom, a —NR$^{11}$— group wherein $R^{11}$ is a hydrogen atom, a substituted or unsubstituted lower alkyl group, a substituted or unsubstituted cycloalkyl group, a substituted or unsubstituted cycloalkylalkyl group, a substituted or unsubstituted aryl group or a substituted or unsubstituted aralkyl group, or a

group wherein each of $R^{12}$ and $R^{13}$ which may be the same or different is a hydrogen atom, a substituted or unsubstituted lower alkyl group, a substituted or unsubstituted cycloalkyl group, a substituted or unsubstituted cycloalkylalkyl group, a substituted or unsubstituted aryl group or a substituted or unsubstituted aralkyl group, and $R^{10}$ is a hydrogen atom, a substituted or unsubstituted lower alkyl group, a substituted or unsubstituted cycloalkyl group, a substituted or unsubstituted cycloalkylalkyl group, a substituted or unsubstituted aryl group, a substituted or unsubstituted aralkyl group or a monocyclic or bicyclic heterocyclic group containing from 1 to 4 hetero atoms selected from the group consisting of nitrogen, sulfur and oxygen atoms, provided that when $R^{10}$ is a hydrogen atom, i is 0, and q is an integer of from 0 to 5; or a '—CH$_2$—CHR$^8$—CO—R$^9$ group wherein $R^8$ is a hydrogen atom, a substituted or unsubstituted lower alkyl group, a substituted or unsubstituted cycloalkyl group, a substituted or unsubstituted cycloalkylalkyl group, a substituted or unsubstituted aryl group, a substituted or unsubstituted aralkyl group or a substituted or unsubstituted monocyclic or bicyclic heterocylic group containing from 1 to 4 hetero atoms selected from the group consisting of nitrogen, surfur and oxygen atoms, and $R^9$ is a hydroxyl group, a -OX group wherein X is a substituted or unsubstituted alkyl group, a substituted or unsubstituted aryl group, a lower alkoxycarbonyloxyalkyl group or a 1-phthalidyl group, or a —N(Y$^1$)(Y$^2$) group wherein each of Y$^1$ and Y$^2$ which may be the same or different is a hydrogen atom, a substituted or unsubstituted lower alkyl group, a substituted or unsubstituted aryl group, a substituted or unsubstituted aralkyl group or a substituted or unsubstituted cycloalkyl group, or Y$^1$ and Y$^2$ form together with the adjacent nitrogen atom a 5- or 6-membered heterocyclic group which may contain a further hetero atom selected from the group consisting of nitrogen, oxygen and sulfur atoms;

m is 0, 1 or 2; and n is an integer of from 1 to 5, provided that when $R^1$ is a hydrogen atom, m is 0; or a salt thereof.

The present invention also provides a hypotensive drug comprising an effective amount of an N-acylamino acid derivative of the formula I or its pharmaceutically acceptable salt and a pharmaceutically acceptable carrier.

The N-acylamino acid derivative of the formula I can be prepared by a process which comprises condensing an N-acylamino acid of the formula:

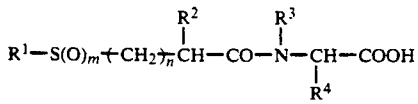

$$R^1-S(O)_m+CH_2)_n CH-CO-N-CH-COOH \quad (II)$$
with $R^2$, $R^3$ substituents and $R^4$ on N wherein $R^1$, $R^2$, $R^3$, $R^4$, m and n are as defined above, or a reactive derivative at the carboxyl group thereof with an amine of the formula:

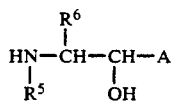

$$HN-CH-CH-A \quad (III)$$
with $R^6$, $R^5$, $OH$ wherein $R^5$, $R^6$ and A are as defined above, or condensing a carboxylic acid of the formula:

$$R^1-S(O)_m+CH_2)_n CH-COOH \quad (IV)$$
with $R^2$ wherein $R^1$, $R^2$, m and n are as defined above, or a reactive derivative at the carboxyl group thereof with an amino acid amide of the formula:

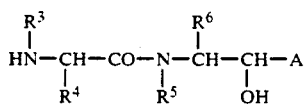

$$HN-CH-CO-N-CH-CH-A \quad (V)$$
with $R^3$, $R^4$, $R^6$, $R^5$, $OH$ wherein $R^3$, $R^4$, $R^5$, $R^6$ and A are as defined above.

Further, the present invention provides novel intermediates represented by the following formulas A and B which are useful for the production of the compound of the formula I:

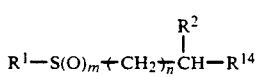

$$R^1-S(O)_m+CH_2)_n CH-R^{14} \quad (A)$$
with $R^2$ wherein each of $R^1$ and $R^2$ which may be the same or different is a hydrogen atom, a substituted or unsubstituted lower alkyl group, a substituted or unsubstituted cycloalkyl group, a substituted or unsubstituted cycloalkylalkyl group, a substituted or unsubstituted aryl group, a substituted or unsubstituted aralkyl group or a substituted or unsubstituted monocyclic or bicyclic heterocyclic group containing from 1 to 4 hetero atoms selected from the group consisting of nitrogen, sulfur and oxygen atoms; $R^{14}$ is a carboxyl group, a reactive derivative of a carboxyl group or a protected carboxyl group; m is 0, 1 or 2; and n is an integer of from 1 to 5; provided that when $R^1$ is a hydrogen atom, m is 0.

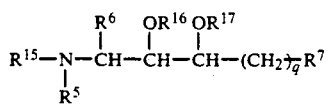

$$R^{15}-N-CH-CH-CH-(CH_2)_q R^7 \quad (B)$$
with $R^6$, $OR^{16}$, $OR^{17}$, $R^5$ wherein $R^5$ is a hydrogen atom or a lower alkyl group; $R^6$ is a hydrogen atom, a substituted or unsubstituted lower alkyl group, a substituted or unsubstituted cycloalkyl group, a substituted or unsubstituted cycloalkylalkyl group, a substituted or unsubstituted aryl group, a substituted or unsubstituted aralkyl group or a substituted or unsubstituted monocyclic or bicyclic heterocyclic group containing from 1 to 4 hetero atoms selected from the group consisting of nitrogen, sulfur and oxygen atoms; $R^7$ is a hydrogen atom, a substituted or unsubstituted lower alkyl group, a substituted or unsubstituted cycloalkyl group, a substituted or unsubstituted cycloalkylalkyl group, a substituted or unsubstituted aryl group, a substituted or unsubstituted aralkyl group, a substituted or unsubstituted monocyclic or bicyclic heterocyclic group containing from 1 to 4 hetero atoms selected from the group consisting of nitrogen, sulfur and oxygen atoms or a —E—$R^{10}$ group, wherein E is a —S(O)$_i$—group wherein i is 0, 1 or 2, an oxygen atom, a —NR$^{11}$—group wherein $R^{11}$ is a hydrogen atom, a substituted or unsubstituted lower alkyl group, a substituted or unsubstituted cycloalkyl group, a substituted or unsubstituted cycloalkylalkyl group, a substituted or unsubstituted aryl group or a substituted or unsubstituted aralkyl group, or

$$-\overset{R^{12}}{\underset{R^{13}}{N^{\oplus}}}-$$

wherein each of $R^{12}$ and $R^{13}$ which may be the same or different is a hydrogen atom, a substituted or unsubstituted lower alkyl group, a substituted or unsubstituted cycloalkyl group, a substituted or unsubstituted cycloalkylalkyl group, a substituted or unsubstituted aryl group or a substituted or unsubstituted aralkyl group, and $R^{10}$ is a hydrogen atom, a substituted or unsubstituted lower alkyl group, a substituted or unsubstituted cycloalkyl group, a substituted or unsubstituted cycloalkyalkyl group, a substituted or unsubstituted aryl group, a substituted or unsubstituted aralkyl group or a monocyclic or bicyclic heterocyclic group containing from 1 to 4 hetero atoms selected from the group consisting of nitrogen, sulfur and oxygen atoms, provided that when $R^{10}$ is a hydrogen atom, i is 0; $R^{15}$ is a hydrogen atom or a protecting group for an amino group, each of $R^{16}$ and $R^{17}$ which may be the same or different is a hydrogen atom or a protecting group for a hydroxyl group; and q is an integer of from 0 to 5.

Now, the present invention will be described in detail with reference to the preferred embodiments.

In the accompanying drawing, FIG. 1 is a graph showing the hypotensive activities of the compound of the present invention as administered to monkeys in Test Example 3 given hereinafter.

Firstly, the definitions of various terms referred to in this specification and some specific examples falling within such terms will be given.

The substituted or unsubstituted lower alkyl group may be a straight chain or branched lower alkyl group having from 1 to 6 carbon atoms such as a methyl group, an ethyl group, a propyl group, an isopropyl group, a butyl group, an isobutyl group, a sec-butyl group, a tert-butyl group, a pentyl group, a neopentyl group, an isopentyl group, a hexyl group or an isohexyl group, which is unsubstituted or substituted by a halogen atom such as a chlorine atom, a fluorine atom or a bromine atom; a hydroxyl group; a lower alkoxy group such as a methoxy group, an ethoxy group, a propoxy group, an isopropoxy group, a butoxy group, an isobutoxy group, a sec-butoxy group or a tert-butoxy group; an aryloxy group such as a phenoxy group, a 1-naphthyloxy group or a 2-naphthyloxy group; an aralkyloxy group such as a benzyloxy group, a phenetyloxy group, a 1-naphthylmethyloxy group or a 2-naphthylmethyloxy group; an amino group; a mono- or di-lower alkylamino group such as a methylamino group, an ethylamino group, a propylamino group, an isopropylamino group, a butylamino group, a sec-butylamino group, an isobutylamino group, a tert-butylamino group, a dimethylamino group or a diethylamino group; an arylamino group such as a phenylamino group, a 1-naphthylamino group or a 2-naphthylamino group; an aralkylamino group such as a benzylamino group, a phenetylamino group, a 1-naphthylmethylamino group or a 2-naphthylmethylamino group; a carboxyl group; a formyl group; a lower alkoxycarbonyl group such as a methoxycarbonyl group, an ethoxycarbonyl group, a propoxycarbonyl group, an isopropoxycarbonyl group, a butoxycarbonyl group, a sec-butoxycarbonyl group, an isobutoxycarbonyl group or a tert-butoxycarbonyl group; an aryloxy carbonyl group such as a phenoxycarbonyl group, a 1-naphthyloxycarbonyl group or a 2-naphthyloxycarbonyl group; an aralkyloxycarbonyl group such as a benzyloxycarbonyl group, a phenetyloxycarbonyl group, a 1-naphthylmethyloxycarbonyl group or a 2-naphthylmethyloxycarbonyl group; a mercapto group; a lower alkylthio group such as a methylthio group, an ethylthio group, a propylthio group, an isopropylthio group, a butylthio group, a sec-butylthio group, an isobutylthio group or a tert-butylthio group; an arylthio group such as a phenylthio group, a 1-naphthylthio group or a 2-naphthylthio group; an aralkylthio group such as a benzylthio group, a phenetylthio group, a 1-naphthylmethylthio group or a 2-naphthylmethylthio group; an arylsulfinyl group such as a phenylsulfinyl group, a 1-naphthylsulfinyl group or a 2-naphthylsulfinyl group; an aralkylsulfinyl group such as a benzylsulfinyl group, a phenetylsulfinyl group, a 1-naphthylmethylsulfinyl group or a 2-naphthylmethylsulfinyl group; a lower alkylsulfonyl group such as a mesyl group, an ethylsulfonyl group, a propylsulfonyl group, an isopropylsulfonyl group, a butylsulfonyl group, an isobutylsulfonyl group, a sec-butylsulfonyl group or a tert-butylsulfonyl group; an arylsulfonyl group such as a phenylsulfonyl group, a 1-naphthylsulfonyl group or a 2-naphthylsulfonyl group; an aralkylsulfonyl group such as a benzylsulfonyl group, a phenetylsulfonyl group, a 1-naphthylmethylsulfonyl group or a 2-naphthylmethylsulfonyl group; or a heterocyclic group such as a pyrrolyl group, a furyl group, a thienyl group, a pyridyl group, an imidazolyl group, a pyrazolyl group, a thiazolyl group, an isothiazolyl group, an isoxazolyl group, an oxazolyl group, a pyrazinyl group, a pyrimidinyl group, a pyridazinyl group, an indolyl group, a quinolyl group, an isoquinolyl group, a phthalazinyl group, a naphthidinyl group, a quinoxalinyl group, a quinazolinyl group, a 1,4-benzodioxanyl group, a 1,3-benzodioxanyl group, a 1,2,3-triazolyl group, a 1,3,4-triazolyl group, a 1,3,4-thiadiazolyl group, a 1,2,3-thiadiazolyl group, a tetrazolyl group, a tetrahydrofuranyl group, a tetrahydrothienyl group, a pyrrolidinyl group, an imidazolidinyl group, a 2-imidazolinyl group, a morpholinyl group, a morpholino group, a morpholine N-oxide group, a lower alkyl morpholino group such as an N-methylmorpholino group, an N-ethylmorpholino group or an N-propylmorpholino group, a piperazinyl group, a piperidino group, a piperidinyl group, a thiomorpholino group or a thiomorpholinyl group.

The substituted or unsubstituted cycloalkylalkyl group may be a cycloalkylalkyl group having from 4 to 10 carbon atoms such as a cyclopropylmethyl group, a cyclobutylmethyl group, a cyclopentylmethyl group, a cyclohexylmethyl group, 1-cyclopropylethyl group, a 2-cyclopropylethyl group, a 1-cyclobutylethyl group, a 2-cyclobutylethyl group, a 1-cyclopentylethyl group, a 2-cyclopentylethyl group, a 1-cyclohexylethyl group, a 3-cyclohexylpropyl group, a 3-cyclopentylpropyl group, a 4-cyclohexylbutyl group or a 4-cyclopentylbutyl group, which is unsubstituted or substituted by a halogen atom such as a chlorine atom, a fluorine atom or a bromine atom; a hydroxyl group; a lower alkyl group such as a methyl group, an ethyl group, a propyl group, an isopropyl group, a butyl group, an isobutyl group, a sec-butyl group or a tert-butyl group; a lower alkoxy group such as a methoxy group, an ethoxy group, a propoxy group, an isopropoxy group, a butoxy group, an isobutoxy group, a sec-butoxy group or a tert-butoxy group; an aryloxy group such as a phenoxy group, a 1-naphthyloxy group or a 2-naphthyloxy group; an aralkyloxy group such as a benzyloxy group, a phenetyloxy group, a 1-naphthylmethyloxy group or a 2-naphthylmethyloxy group; an amino group; a mono- or di-lower alkylamino group such as a methylamino group, an ethylamino group, a propylamino group, an isopropylamino group, a butylamino group, a sec-butylamino group, an isobutylamino group, a tert-butylamino group, a dimethylamino group or a diethylamino group; an arylamino group such as a phenylamino group, a 1-naphthylamino group or a 2-naphthylamino group; an aralkylamino group such as a benzylamino group, a phenetylamino group, a 1-naphthylmethylamino group or a 2-naphthylmethylamino group; a carboxyl group; a formyl group; a lower alkoxycarbonyl group such as a methoxycarbonyl group, an ethoxycarbonyl group, a propoxycarbonyl group, an isopropoxycarbonyl group, a butoxycarbonyl group, a sec-butoxycarbonyl group, an isobutoxycarbonyl group or a tert-butoxycarbonyl group; an aryloxy carbonyl group such as a phenoxycarbonyl group, a 1-naphthyloxycarbonyl group or a 2-naphthyloxycarbonyl group; an aralkyloxycarbonyl group such as a benzyloxycarbonyl group, a phenetyloxycarbonyl group, a 1-naphthylmethyloxycarbonyl group or a 2-naphthylmethyloxycarbonyl group; a mercapto group; a lower alkylthio group such as a methylthio group, an ethylthio group, a propylthio group, an isopropylthio group, a butylthio group, a sec-butylthio group, an isobutylthio group or a tert-butylthio group; an arylthio group such as a phenylthio group, a 1-naphthylthio group or a 2-naphthylthio group; an aralkylthio group such as a benzylthio group, a phenetylthio group, a 1-naphthylmethylthio group or a 2-naphthylmethylthio group; an arylsulfinyl group such as a phenylsulfinyl group, a 1-naphthylsulfinyl group or a 2-naphthylsulfinyl group; an aralkylsulfinyl group such as a benzylsulfinyl group, a phenetylsulfinyl group, a 1-naphthylmethylsulfinyl group or a 2-naphthylmethylsulfinyl group; a lower alkylsulfonyl group such as a mesyl group, an ethylsulfonyl group, a propylsulfonyl group, an isopropylsulfonyl group, a butylsulfonyl group, an isobutylsulfonyl group; a sec-butylsulfonyl group or a tert-butylsulfonyl group; an arylsulfonyl group such as phenylsulfonyl group, a 1-naphthylsulfonyl group or a 2-naphthylsulfonyl group; an aralkylsulfonyl group such as a benzylsulfonyl group, a phenetylsulfonyl group, a 1-naphthylmethylsulfonyl group or a 2-naphthylmethylsulfonyl group; or a heterocyclic group such as a pyrrolyl group, a furyl group, a thienyl group, a pyridyl group, an imidazolyl group, a pyrazolyl group, a thiazolyl group, an isothiazolyl group, an isoxazolyl group, an oxazolyl group, a pyrazinyl group, a pyrimidinyl group, a pyridazinyl group, an indolyl group, a quinolyl group, an isoquinolyl group, a phthalazinyl group, a naphthidinyl group, a quinoxalinyl group, a quinazolinyl group, a 1,4-benzodioxanyl group, a 1,3-benzodioxanyl group, a 1,2,3-triazolyl group, a 1,3,4-triazolyl group, a 1,3,4-thiadiazolyl group, a 1,2,3-thiadiazolyl group, a tetrazolyl group, a tetrahydrofuranyl group, a tetrahydrothienyl group, a pyrrolidinyl group, an imidazolidinyl group, a 2-imidazolinyl group, a morpholinyl group, a morpholino group, a morpholine N-oxide group, a lower alkyl morpholino group such as an N-methylmorpholino group, an N-ethylmorpholino group or an N-propylmorpholino group, a piperazinyl group, a piperidino group, a piperidinyl group, a thiomorpholino group or a thiomorpholinyl group.

The substituted or unsubstituted cycloalkyl group may be a cycloalkyl group having from 3 to 6 carbon atoms such as a cyclopropyl group, a cyclobutyl group, a cyclopentyl group or a cyclohexyl group, which is unsubstituted or substituted by a halogen atom such as a chlorine atom, a fluorine atom or a bromine atom; a hydroxyl group; a lower alkyl group such as a methyl group, an ethyl group, a propyl group, an isopropyl group, a butyl group, an isobutyl group, a sec-butyl group or a tert-butyl group; a lower alkoxy group such as a methoxy group, an ethoxy group, a propoxy group, an isopropoxy group, a butoxy group, an isobutoxy group, a sec-butoxy group or a tert-butoxy group; an aryloxy group such as a phenoxy group, a 1-naphthyloxy group or a 2-naphthyloxy group; an aralkyloxy group such as a benzyloxy group, a phenetyloxy group, a 1-naphthylmethyloxy group or a 2-naphthylmethyloxy group; an amino group; a mono- or di-lower alkylamino group such as a methylamino group, an ethylamino group, a propylamino group, an isopropylamino group, a butylamino group, a sec-butylamino group, an isobutylamino group, a tert-butylamino group, a dimethylamino group or a diethylamino group; an arylamino group such as a phenylamino group, a 1-naphthylamino group or a 2-naphthylamino group; an aralkylamino group such as a benzylamino group, a phenetylamino group, a 1-naphthylmethylamino group or a 2-naphthylmethylamino group; a carboxyl group; a formyl group; a lower alkoxycarbonyl group such as a methoxycarbonyl group, an ethoxycarbonyl group, a propoxycarbonyl group, an isopropoxycarbonyl group, a butoxycarbonyl group, a sec-butoxycarbonyl group, an isobutoxycarbonyl group or a tert-butoxycarbonyl group; an aryloxy carbonyl group such as a phenoxycarbonyl group, a 1-naptyloxycarbonyl group or a 2-naphthyloxycarbonyl group; an aralkyloxycarbonyl group such as a benzyloxcarbonyl group, a phenetyloxycarbonyl group, a 1-naphthylmethyloxycarbonyl group or a 2-naphthylmethyloxycarbonyl group; a mercapto group; a lower alkylthio group such as a methylthio group, an ethylthio group, a propylthio group, an isopropylthio group, a butylthio group, a sec-butylthio group, an isobutylthio group or a tert-butylthio group; an arylthio group such as a phenylthio group, a 1-naphthylthio group or a 2-naphthylthio group; an aralkylthio group such as a benzylthio group, a phenetylthio group, a 1-naphthylmethylthio group or a 2-naphthylmethylthio group; an arylsulfinyl group such as a phenylsulfinyl group, a 1-naphthylsulfinyl group or a 2-naphthylsulfinyl group; an aralkylsulfinyl group such as a benzylsulfinyl group, a phenetylsulfinyl group, a 1-naphthylmethylsulfinyl group or a 2-naphthylmethylsulfinyl group; a lower alkylsulfonyl group such as a mesyl group, an ethylsulfonyl group, a propylsulfonyl group, an isopropylsulfonyl group, a butylsulfonyl group, an isobutylsulfonyl group, a sec-butylsulfonyl group or a tert-butylsulfonyl group; an arylsulfonyl group such as a phenylsulfonyl group, a 1-naphthylsulfonyl group or a 2-naphthylsulfonyl group; an aralkylsulfonyl group such as a benzylsulfonyl group, a phenetylsulfonyl group, a 1-naphthylmethylsulfonyl group or a 2-naphthylmethylsulfonyl group; or a heterocyclic group such as a pyrrolyl group, a furyl group, a thienyl group, a pyridyl group, an imidazolyl group, a pyrazolyl group, a thiazolyl group, an isothiazolyl group, an isoxazolyl group, an oxazolyl group, a pyrazinyl group, a pyrimidinyl group, a pyridazinyl group, an indolyl group, a quinolyl group, an isoquinolyl group, a phthalazinyl group, a naphthidinyl group, a quinoxalinyl group, a quinazolinyl group, a 1,4-benzodioxanyl group, a 1,3-benzodioxanyl group, a 1,2,3-triazolyl group, a 1,3,4-triazolyl group, a 1,3,4-thiadiazolyl group, a 1,2,3-thiadiazolyl group, a tetrazolyl group, a tetrahydrofuranyl group, a tetrahydrothienyl group, a pyrrolidinyl group, an imidazolidinyl group, a 2-imidazolinyl group, a morpholinyl group, a morpholino group, a morpholine N-oxide group, a lower alkyl morpholino group such as an N-methylmorpholino group, an N-ethylmorpholino group or an N-propylmorpholino group, a piperazinyl group, a piperidino group, a piperidinyl group, a thiomorpholino group or a thiomorpholinyl group.

The substituted or unsubstituted aryl group may be an aryl group having from 6 to 15 carbon atoms such as a phenyl group, a biphenylyl group, a 1-naphthyl group or a 2-naphthyl group, which is unsubstituted or substituted by a halogen atom such as a chlorine atom, a fluorine atom or a bromine atom; a nitro group; a hydroxyl group; a lower alkyl group such as a methyl group, an ethyl group, a propyl group, an isopropyl group, a butyl group, an isobutyl group, a sec-butyl group or a tert-butyl group; a lower alkoxy group such as a methoxy group, an ethoxy group, a propoxy group, an isopropoxy group, a butoxy group, an isobutoxy group, a sec-butoxy group or a tert-butoxy group; an aryloxy group such as a phenoxy group, a 1-naphthyloxy group or a 2-naphthyloxy group; an aralkyloxy group such as a benzyloxy group, a phenetyloxy group, a 1-naphthylmethyloxy group or a 2-naphthylmethyloxy group; an amino group; a mono- or di-lower alkylamino group such as a methylamino group, an ethylamino group, a propylamino group, an isopropylamino group, a butylamino group, a sec-butylamino group, an isobutylamino group, a tert-butylamino group, a dimethylamino group or a diethylamino group; an arylamino group such as a phenylamino group, a 1-naphthylamino group or a 2-naphthylamino group; an aralkylamino group such as a benzylamino group, a phenetylamino group, a 1-naphthylmethylamino group or a 2-naphthylmethylamino group; a carboxyl group; a formyl group; a lower alkoxycarbonyl group such as a methoxycarbonyl group, an ethoxycarbonyl group, a propoxycarbonyl group, an isopropoxycarbonyl group, a butoxycarbonyl group, a sec-butoxycarbonyl group, an isobutoxycarbonyl group or a tert-butoxycarbonyl group; an aryloxy carbonyl group such as a phenoxycarbonyl group, a 1-naphthyloxycarbonyl group or a 2-naphthyloxycarbonyl group; an aralkyloxycarbonyl group such as a benzyloxycarbonyl group, a phenetyloxycarbonyl group, a 1-naphthylmethyloxycarbonyl group or a 2-naphthylmethyloxycarbonyl group; a mercapto group; a lower alkylthio group such as a methylthio group, an ethylthio group, a propylthio group, an isopropylthio group, a butylthio group, a sec-butylthio group, an isobutylthio group or a tert-butylthio group; an arylthio group such as a phenylthio group, a 1-naphthylthio group or a 2-naphthylthio group; an aralkylthio group such as a benzylthio group, a phenetylthio group, a 1-naphthylmethylthio group or a 2-naphthylmethylthio group; an arylsulfinyl group such as a phenylsulfinyl group, a 1-naphthylsulfinyl group or a 2-naphthylsulfinyl group; an aralkylsulfinyl group such as a benzylsulfinyl group, a phenetylsulfinyl group, a 1-naphthylmethylsulfinyl group or a 2-naphthylmethylsulfinyl group; a lower alkylsulfonyl group such as a mesyl group, an ethylsulfonyl group, a propylsulfonyl group, an isopropylsulfonyl group, a butylsulfonyl group, an isobutylsulfonyl group, a sec-butylsulfonyl group or a tert-butylsulfonyl group; an arylsulfonyl group such as a phenylsulfonyl group, a 1-naphthylsulfonyl group or a 2-naphthylsulfonyl group; an aralkylsulfonyl group such as a benzylsulfonyl group, a phenetylsulfonyl group, a 1-naphthylmethylsulfonyl group or a 2-naphthylmethylsulfonyl group; or a heterocyclic group such as a pyrrolyl group, a furyl group, a thienyl group, a pyridyl group, an imidazolyl group, a pyrazolyl group, a thiazolyl group, an isothiazolyl group, an isoxazolyl group, an oxazolyl group, a pyrazinyl group, a pyrimidinyl group, a pyridazinyl group, an indolyl group, a quinolyl group, an isoquinolyl group, a phthalazinyl group, a naphthidinyl group, a quinoxalinyl group, a quinazolinyl group, a 1,4-benzodioxanyl group, a 1,3-benzodioxanyl group, a 1,2,3-triazolyl group, a 1,3,4-triazolyl group, a 1,3,4-thiadiazolyl group, a 1,2,3-thiadiazolyl group, a tetrazolyl group, a tetrahydrofuranyl group, a tetrahydrothienyl group, a pyrrolidinyl group, an imidazolidinyl group, a 2-imidazolinyl group, a morpholinyl group, a morpholino group, a morpholine N-oxide group, a lower alkyl morpholino group such as an N-methylmorpholino group, an N-ethylmorpholino group or an N-propylmorpholino group, a piperazinyl group, a piperidino group, a piperidinyl group, a thiomorpholino group or a thiomorpholinyl group.

The substituted or unsubstituted aralkyl group may be an aralkyl group having from 7 to 15 carbon atoms such as a benzyl group, a 1-naphthylmethyl group, a 2-naphthylmethyl group, a 5,6,7,8-tetrahydro-1-naphthyl group, a 5,6,7,8-tetrahydro-2-naphthyl group, a phenetyl group, a 3-phenylpropyl group or a 4-phenylbutyl group, which is unsubstituted or substituted by a halogen atom such as a chlorine atom, a fluorine atom or a bromine atom; a nitro group; a hydroxyl group; a lower alkyl group such as a methyl group, an ethyl group, a propyl group, an isopropyl group, a butyl group, an isobutyl group, a sec-butyl group or a tert-butyl group; a lower alkoxy group such as a methoxy group, an ethoxy group, a propoxy group, an isopropoxy group, a butoxy group, an isobutoxy group, a sec-butoxy group or a tert-butoxy group; an aryloxy group such as a phenoxy group, a 1-naphthyloxy group or a 2-naphthyloxy group; an aralkyloxy group such as a benzyloxy group, a phenetyloxy group, a 1-naphthylmethyloxy group or a 2-naphthylmethyloxy group; an amino group; a mono- or di-lower alkylamino group such as a methylamino group, an ethylamino group, a propylamino group, an isopropylamino group, a butylamino group, a sec-butylamino group, an isobutylamino group, a tert-butylamino group, a dimethylamino group or a diethylamino group; an arylamino group such as a phenylamino group; a 1-naphthylamino group or a 2-naphthylamino group; an aralkylamino group such as a benzylamino group, a phenetylamino group, a 1-naphthylmethylamino group or a 2-naphthylmethylamino group; a carboxyl group; a formyl group; a lower alkoxycarbonyl group such as a methoxycarbonyl group, an ethoxycarbonyl group, a propoxycarbonyl group, an isopropoxycarbonyl group, a butoxycarbonyl group, a sec-butoxycarbonyl group, an isobutoxycarbonyl group or a tert-butoxycarbonyl group; an aryloxy carbonyl group such as a phenoxycarbonyl group, a 1-naphthyloxycarbonyl group or a 2-naphthyloxycarbonyl group; an aralkyloxycarbonyl group such as a benzyloxycarbonyl group, a phenetyloxycarbonyl group, a 1-naphthylmethyloxycarbonyl group or a 2-naphthylmethyloxycarbonyl group; a mercapto group; a lower alkylthio group such as a methylthio group, an ethylthio group, a propylthio group, an isopropylthio group, a butylthio group, a sec-butylthio group, an isobutylthio group or a tert-butylthio group; an arylthio group such as a phenylthio group, a 1-naphthylthio group or a 2-naphthylthio group; an aralkylthio group such as a benzylthio group, a phenetylthio group, a 1-naphthylmethylthio group or a 2-naphthylmethylthio group; an arylsulfinyl group such as a phenylsulfinyl group, a 1-naphthylsulfinyl group or a 2-naphthylsulfinyl group; an aralkylsulfinyl group such as a benzylsulfinyl group, a phenetylsulfinyl group, a 1-naphthylmethylsulfinyl group or a 2-naphthylmethylsulfinyl group; a lower alkylsulfonyl group such as a mesyl group, an ethylsulfonyl group, a propylsulfonyl group, an isopropylsulfonyl group, a butylsulfonyl group, an isobutylsulfonyl group, a sec-butylsulfonyl group or a tert-butylsulfonyl group; an arylsulfonyl group such as a phenylsulfonyl group, a 1-naphthylsulfonyl group or a 2-naphthylsulfonyl group; an aralkylsulfonyl group such as a benzylsulfonyl group, a phenetylsulfonyl group, a 1-naphthylmethylsulfonyl group or a 2-naphthylmethylsulfonyl group; or a heterocyclic group such as a pyrrolyl group, a furyl group, a thienyl group, a pyridyl group, an imidazolyl group, a pyrazolyl group, a thiazolyl group, an isothiazolyl group, an isoxazolyl group, an oxazolyl group, a pyrazinyl group, a pyrimidinyl group, a pyridazinyl group, an indolyl group, a quinolyl group, an isoquinolyl group, a phthalazinyl group, a naphthidinyl group, a quinoxalinyl group, a quinazolinyl group, a 1,4-benzodioxanyl group, a 1,3-benzodioxanyl group, a 1,2,3-triazolyl group, a 1,3,4-triazolyl group, a 1,3,4-thiadiazolyl group, a 1,2,3-thiadiazolyl group, a tetrazolyl group, a tetrahydrofuranyl group, a tetrahydrothienyl group, a pyrrolidinyl group, an imidazolidinyl group, a 2-imidazolinyl group, a morpholinyl group, a morpholino group, a morpholine N-oxide group, a lower alkyl morpholino group such as an N-methylmorpholino group, an N-ethylmorpholino group or an N-propylmorpholino group, a piperazinyl group, a piperidino group, a piperidinyl group, a thiomorpholino group or a thiomorpholinyl group.

The substituted or unsubstituted monocyclic or bicyclic heterocyclic group containing from 1 to 4 hetero atoms selected from the group consisting of nitrogen, sulfur and oxygen atoms, may be a heterocyclic group such as a pyrrolyl group, a furyl group, a thienyl group, a pyridyl group, an imidazolyl group, a pyrazolyl group, a thiazolyl group, an isothiazolyl group, an isoxazolyl group, an oxazolyl group, a pyrazinyl group, a pyrimidinyl group, a pyridazinyl group, an indolyl group, a quinolyl group, an isoquinolyl group, a phthalazinyl group, a naphthidinyl group, a quinoxalinyl group, a quinazolinyl group, a 1,4-benzodioxanyl group, a 1,3-benzodioxanyl group, a 1,2,3-triazolyl group, a 1,3,4-triazolyl group, a 1,3,4-thiadiazolyl group, a 1,2,3-thiadiazolyl group, a tetrazolyl group, a tetrahydrofuranyl group, a tetrahydrothienyl group, a pyrrolidinyl group, an imidazolidinyl group, a 2-imidazolinyl group, a morpholinyl group, a morpholino group, a piperizine N-oxide group, a piperazine N-oxide group, a morpholine N-oxide group, a lower alkyl morpholino group such as an N-methylmorpholino group, an N-ethylmorpholino group or an N-propylmorpholino group, a piperazinyl group, a piperidino group, a piperidinyl group, a thiomorpholino group or a thiomorpholinyl group, which is unsubstituted or substituted by a halogen atom such as a chlorine atom, a fluorine atom or a bromine atom; a nitro group; a hydroxyl group; a lower alkyl group such as a methyl group, an ethyl group, a propyl group, an isopropyl group, a butyl group, an isobutyl group, a sec-butyl group or a tert-butyl group; a triphenylmethyl group; a lower alkoxy group such as a methoxy group, an ethoxy group, a propoxy group, an isopropoxy group, a butoxy group, an isobutoxy group, a sec-butoxy group or a tert-butoxy group; an aryloxy group such as a phenoxy group, a 1-naphthyloxy group or a 2-naphthyloxy group; an aralkyloxy group such as a benzyloxy group, a phenetyloxy group, a 1-naphthylmethyloxy group or a 2-naphthylmethyloxy group; an amino group; a mono- or di-lower alkylamino group such as a methylamino group, an ethylamino group, a propylamino group, an isopropylamino group, a butylamino group, a sec-butylamino group, an isobutylamino group, a tert-butylamino group, a dimethylamino group or a diethylamino group; an arylamino group such as a phenylamino group, a 1-naphthylamino group or a 2-naphthylamino group; an aralkylamino group such as a benzylamino group, a phenetylamino group, a 1-naphthylmethylamino group or a 2-naphthylmethylamino group; a carboxyl group; a formyl group; a lower alkoxycarbonyl group such as a methcxycarbonyl group, an ethoxycarbonyl group, a propoxycarbonyl group, an isopropoxycarbonyl group, a butoxycarbonyl group, a sec-butoxycarbonyl group, an isobutoxycarbonyl group or a tert-butoxycarbonyl group; an aryloxy carbonyl group such as a phenoxycarbonyl group, a 1-naphthyloxycarbonyl group or a 2-naphthyloxycarbonyl group; an aralkyloxycarbonyl group such as a benzyloxycarbonyl group, a phenetyloxycarbonyl group, a 1-naphthylmethyloxycarbonyl group or a 2-naphthylmethyloxycarbonyl group; a mercapto group; a lower alkylthio group such as a methylthio group, an ethylthio group, a propylthio group, an isopropylthio group, a butylthio group, a sec-butylthio group, an isobutylthio group or a tert-butylthio group; an arylthio group such as a phenylthio group, a 1-naphthylthio group or a 2-naphthylthio group; an aralkylthio group such as a benzylthio group, a phenetylthio group, a 1-naphthylmethylthio group or a 2-naphthylmethylthio group; an arylsulfinyl group such as a phenylsulfinyl group, a 1-naphthylsulfinyl group or a 2-naphthylsulfinyl group; an aralkylsulfinyl group such as a benzylsulfinyl group, a phenetylsulfinyl group, a 1-naphthylmethylsulfinyl group or a 2-naphthylmethylsulfinyl group; a lower alkylsulfonyl group such as a mesyl group, an ethylsulfonyl group, a propylsulfonyl group, an isopropylsulfonyl group, a butylsulfonyl group, an isobutylsulfonyl group, a sec-butylsulfonyl group or a tert-butylsulfonyl group; an arylsulfonyl group such as a phenylsulfonyl group, a 1-naphthylsulfonyl group or a 2-naphthylsulfonyl group; or an aralkylsulfonyl group such as a benzylsulfonyl group, a phenetylsulfonyl group, a 1-naphthylmethylsulfonyl group or a 2-naphthylmethylsulfonyl group.

In the $-N(Y^1)(Y^2)$ group, when $Y^1$ and $Y^2$ form together with the adjacent nitrogen atom a 5- or 6-membered heterocyclic group which may contain a further hetero atom selected from the group consisting of nitrogen, oxygen and sulfur atoms, such a heterocyclic group may be, for example, a morpholino group, a thiomorpholino group, a piperidino group, a pyrrolidinyl group or a piperazinyl group.

The lower alkoxycarbonyloxyalkyl group may be a lower alkyloxycarbonylalkyl group having from 3 to 9 carbon atoms such as a methoxycarbonyloxymethyl group, an ethoxycarbonyloxymethyl group, a propoxycarbonyloxymethyl group, an isopropoxycarbonyloxymethyl group, a butoxycarbonyloxymethyl group, a tert-butoxycarbonyloxymethyl group, a 1-methoxycarbonyloxyethyl group, a 2-methoxycarbonyloxyethyl group, a 1-ethoxycarbonyloxyethyl group, a 2-ethoxycarbonyloxyethyl group, a 1-tert-butoxycarbonyloxyethyl group, a 2-tert-butoxycarbonyloxyethyl group, a 1-butoxycarbonyloxyethyl group, a 1-pentylcarbonyloxyethyl group or a 1-hexylcarbonyloxyethyl group.

In the compound of the formula I of the present invention, the asymmetric carbon atoms may have R-configuration, S-configuration or RS-configuration.

The salt of the compound of the present invention may be any pharmaceutically acceptable non-toxic salt. For example, it may be a salt with anion such as $Cl^\ominus$, $F^\ominus$, $Br^\ominus$ or $I^\ominus$ with an inorganic acid such as hydrochloric acid, sulfuric acid, hydrobromic acid, hydriodic acid or phosphoric acid, or a salt with an organic acid such as oxalic acid, maleic acid, acetic acid, formic acid or tartaric acid.

Representative compounds of the present invention are listed in Tables A and B, wherein Et means ethyl, $^i$Pr isopropyl, $^n$Bu n-butyl, $^i$Bu isobutyl, $^t$Bu tert-butyl, Tri triphenylmethyl, Z benzyloxycarbonyl and Nap-CH$_2$-1-naphthylmethyl, and each of A, B, C, D and E indicates the steric configuration (R, S or RS).

TABLE A $$R^{1'}-\underset{\underset{(O)_{m'}}{\|}}{S}-(CH_2)_{n'}-\overset{R^{2'}}{\underset{(A)}{*CH}}-CO-\overset{R^{3'}\;R^{4'}}{\underset{(B)}{N}}-\overset{R^{5'}\;R^{6'}}{\underset{(C)}{*CH}}-CO-\overset{OH}{\underset{(D)}{N}}-\overset{R^{8'}}{\underset{(E)}{*CH}}-CO-R^{9'}$$

| R¹' | R²' | R³' | R⁴' | R⁵' | R⁶' | R⁸' | R⁹' | m' | n' | A | B | C | D | E |
|---|---|---|---|---|---|---|---|---|---|---|---|---|---|---|
| Et | Nap-CH₂— | H | ⁿBu | H | ⁱBu | Et | —NHⁱBu | 2 | 1 | R or S | S | S | S | RS |
|  | Nap-CH₂— | H | ⁿBu | H | ⁱBu | Et | —NHⁱBu | 2 | 1 | R or S | S | S | S | RS |
| Et |  | H | —CH₂CH₂CH₂OH | H | ⁱBu | Et | —NHⁱBu | 2 | 1 | R or S | S | S | S | RS |
| 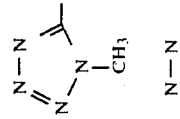 | Nap-CH₂— | H | ⁿBu | H | ⁱBu | Et | —NHⁱBu | 2 | 1 | R or S | S | S | S | S |
| 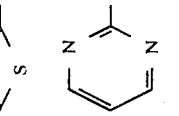 | Nap-CH₂— | H | ⁿBu | H | ⁱBu | Et | —NHⁱBu | 0 | 1 | S | S | S | S | RS |
| 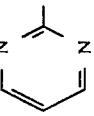 | Nap-CH₂— | H | ⁿBu | H | ⁱBu | Et | —NHⁱBu | 0 | 1 | S | S | S | S | RS |
|  | Nap-CH₂— | H | ⁿBu | H | ⁱBu | Et | —NHⁱBu | 1 | 1 | S | S | S | S | RS |

TABLE A-continued $$R^{1'}-\underset{\underset{(O)_{m'}}{\|}}{S}-(CH_2)_{n'}-\overset{R^{2'}}{\underset{(A)}{*CH-CO}}-\overset{R^{3'}\ R^{4'}}{\underset{(B)}{N-*CH-CO}}-\overset{R^{5'}\ R^{6'}}{\underset{(C)}{N-*CH-CH_2}}-\overset{OH}{\underset{(D)}{*CH-CH_2}}-\overset{R^{8'}}{\underset{(E)}{*CH-CO-R^{9'}}}$$

| R¹' | R²' | R³' | R⁴' | R⁵' | R⁶' | R⁸' | R⁹' | m' | n' | A | B | C | D | E |
|---|---|---|---|---|---|---|---|---|---|---|---|---|---|---|
| Et | Nap-CH₂— | H | ⁿBu | H | ⁱBu | Et | —NHCH₂CH₂—N(morpholine) | 2 | 1 | R or S | S | S | S | R or S |
| Et | 4-quinolinyl-CH₂— | H | ⁿBu | H | ⁱBu | Et | —NHⁱBu | 2 | 1 | S | S | S | S | RS |
| Et | 8-quinolinyl-CH₂— | H | ⁿBu | H | ⁱBu | Et | —NHⁱBu | 2 | 1 | S | S | S | S | RS |
| Et | 8-quinolinyl-CH₂— | H | imidazolyl-CH₂— | H | ⁱBu | Et | —NHⁱBu | 2 | 1 | S | S | S | S | RS |
| Et | Nap-CH₂— | H | ⁿBu | H | ⁱBu | Et | —NHⁱBu | 0 | 3 | R or S | S | S | S | RS |
| Et | Nap-CH₂— | H | ⁿBu | H | ⁱBu | Et | —NHⁱBu | 2 | 3 | R or S | S | S | S | RS |

TABLE A-continued $$R^{1'}-S-(CH_2)_{n'}-\underset{(A)}{\overset{R^{2'}}{*CH-CO}}-\underset{(B)}{\overset{R^{3'}\ R^{4'}}{N-*CH-CO}}-\underset{(C)}{\overset{R^{5'}\ R^{6'}}{N-*CH-CH_2}}-\underset{(D)}{\overset{OH}{*CH-CH_2}}-\underset{(E)}{\overset{R^{8'}}{*CH-CO-R^{9'}}}$$
$$\overset{\|}{(O)_{m'}}$$

| R¹' | R²' | R³' | R⁴' | R⁵' | R⁶' | R⁸' | R⁹' | m' | n' | A | B | C | D | E |
|---|---|---|---|---|---|---|---|---|---|---|---|---|---|---|
| Et | Nap-CH₂— | H | ![imidazole-Tri](CH₂— attached to N-imidazole with Tri) | H | ᵗBu | Et | —NHᵗBu | 2 | 1 | RS | S | S | S | RS |
| Et | Nap-CH₂— | H | ![imidazole-H](CH₂— attached to N-imidazole with H) | H | ᵗBu | Et | —NHᵗBu | 2 | 1 | S | S | S | S | RS |

TABLE B $$R^{1'}-S(CH_2)_{n'}-\overset{R^{2'}}{\underset{(A)}{*CH}}-CO-\overset{R^{3'}}{\underset{(B)}{N}}-\overset{R^{4'}}{\underset{}{*CH}}-CO-\overset{R^{5'}}{\underset{(C)}{N}}-\overset{R^{6'}}{\underset{}{*CH}}-\overset{OH}{\underset{(D)}{*CH}}-\overset{OH}{\underset{(E)}{*CH}}(CH_2)_{q'}-R^{7'}$$

$$\overset{\|}{(O)_{m'}}$$

| $R^{1'}$ | $m'$ | $n'$ | $R^{2'}$ | $R^{3'}$ | $R^{4'}$ | $R^{5'}$ | $R^{6'}$ | $q'$ | $R^{7'}$ | A | B | C | D | E |
|---|---|---|---|---|---|---|---|---|---|---|---|---|---|---|
| Et | 2 | 1 | Nap-CH$_2$— | H | $^n$Bu | H | Cyclohexyl-CH$_2$— | 1 | morpholino (N-linked, O) | | S | S | RS | RS |
| Et | 2 | 1 | Nap-CH$_2$— | H | $^n$Bu | H | Cyclohexyl-CH$_2$— | 1 | piperidino | S | S | S | R | S |
| Et | 2 | 1 | Nap-CH$_2$— | H | $^n$Bu | H | Cyclohexyl-CH$_2$— | 1 | 4-CH$_3$-piperidino | S | S | S | R | S |
| Et | 2 | 1 | Nap-CH$_2$— | H | $^n$Bu | H | $^i$Bu | 1 | morpholino | S | S | S | R | S |
| Et | 2 | 1 | Nap-CH$_2$— | H | $^n$Bu | H | Cyclohexyl-CH$_2$— | 1 | —NHCH$_2$CH$_2$OCH$_3$ | S | S | S | R | S |
| Et | 2 | 1 | Nap-CH$_2$— | H | $^n$Bu | H | Cyclohexyl-CH$_2$— | 1 | —SCH$_3$ | S | S | S | R or S | RS |
| Et | 2 | 1 | Nap-CH$_2$— | H | $^n$Bu | H | Cyclohexyl-CH$_2$— | 1 | —NHCH$_2$CH$_2$OH | S | S | S | R | S |

TABLE B-continued $$R^{1'}-\underset{\underset{(O)_{m'}}{\|}}{S}(CH_2)_{n'}-\overset{R^{2'}}{\underset{(A)}{*CH}}-CO-\overset{R^{3'}}{\underset{(B)}{N}}-\overset{R^{4'}}{*CH}-CO-\overset{R^{5'}}{N}-\overset{R^{6'}}{\underset{(C)}{*CH}}-\overset{OH}{\underset{(D)}{*CH}}-\overset{OH}{\underset{(E)}{*CH}}(CH_2)_{q'}-R^{7'}$$

| $R^{1'}$ | m' | n' | $R^{2'}$ | $R^{3'}$ | $R^{4'}$ | $R^{5'}$ | $R^{6'}$ | q' | $R^{7'}$ | A | B | C | D | E |
|---|---|---|---|---|---|---|---|---|---|---|---|---|---|---|
| Et | 2 | 1 | Nap-CH$_2$— | H | $^n$Bu | H | 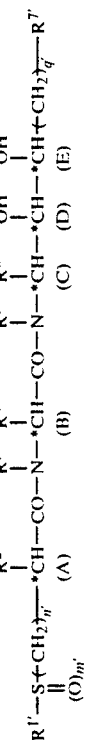 | 1 | —N(Et)(Et) | S | S | S | R | S |
| Et | 2 | 1 | Nap-CH$_2$— | H | $^n$Bu | H | 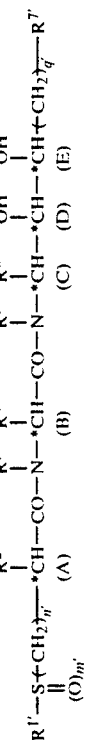 | 1 | —N(Et)(CH$_2$CH$_2$OH) | S | S | S | RS | RS |
| Et | 2 | 1 | Nap-CH$_2$— | H | $^n$Bu | H | $^i$Bu | 1 | —S—$^i$Pr | S | S | S | RS | RS |
| Et | 2 | 1 | Nap-CH$_2$— | H | $^n$Bu | H | $^i$Bu | 1 | thiomorpholino (N,S ring) | S | S | S | RS | RS |
| Et | 2 | 1 | $^i$Bu | H | $^n$Bu | H | 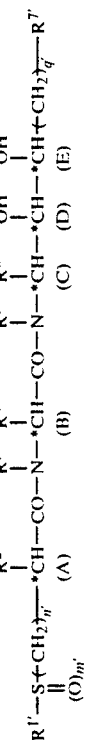 | 1 | morpholino | S | S | S | R | S |
| Et | 0 | 3 | Nap-CH$_2$— | H | $^n$Bu | H | 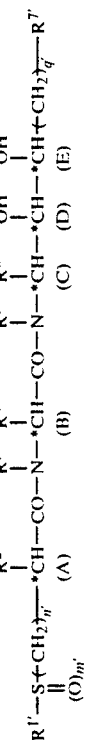 | 1 | morpholino | S or R | S | S | R | S |
| Et | 2 | 3 | Nap-CH$_2$— | H | $^n$Bu | H | 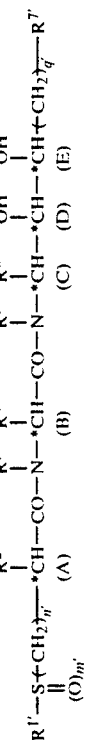 | 1 | morpholino | S or R | S | S | R | S |

TABLE B-continued $$R^{1'}-S(CH_2)_{n'}-*CH-CO-N-*CH-CO-N-*CH-CH(CH_2)_{q'}-R^{7'}$$
$$\quad\quad\|\quad\quad\quad|\quad\quad\quad\quad|\quad\quad|\quad\quad|\quad OH\quad OH$$
$$\quad\quad(O)_{m'}\quad\quad R^{2'}\quad R^{3'}\quad R^{4'}\quad R^{5'}\quad R^{6'}$$
$$\quad\quad\quad\quad\quad\quad(A)\quad\quad(B)\quad\quad(C)\quad(D)\quad(E)$$

| R¹' | m' | n' | R²' | R³' | R⁴' | R⁵' | R⁶' | q' | R⁷' | A | B | C | D | E |
|---|---|---|---|---|---|---|---|---|---|---|---|---|---|---|
| Et | 2 | 1 | 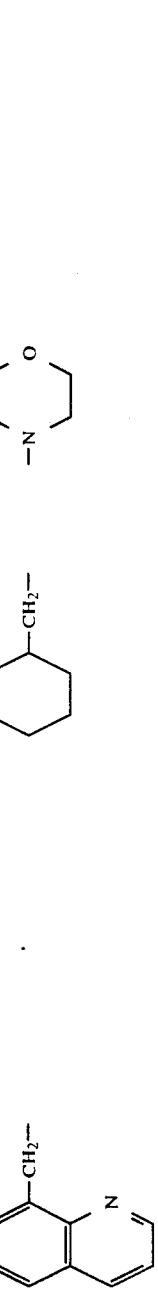 | H | ⁿBu | H | 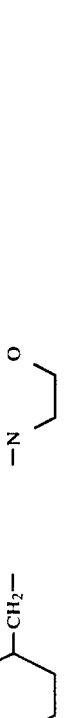 | 1 | 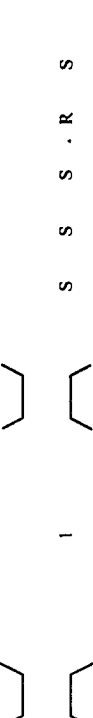 | S | S | S | R | S |
| Et | 2 | 1 | Nap-CH₂— | H | 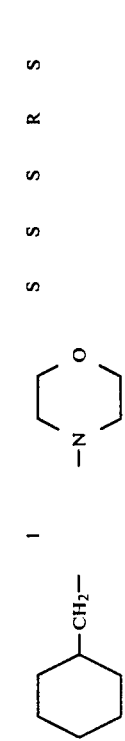 | H | 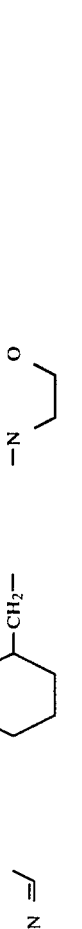 | 1 | 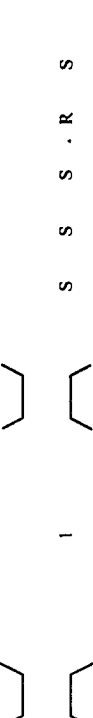 | S | S | S | R, | S |
| Et | 2 | 1 | Nap-CH₂— | H | —CH₂OH | H | 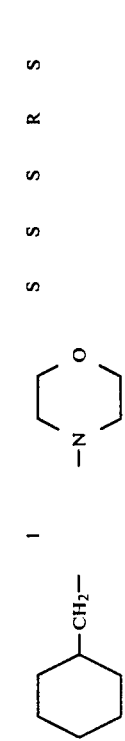 | 1 |  | S | S | S | R | S |
| Et | 2 | 1 | Nap-CH₂— | H | —CH₂CH₂SCH₃ | H | 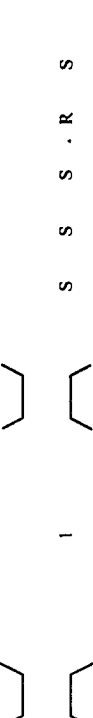 | 1 | 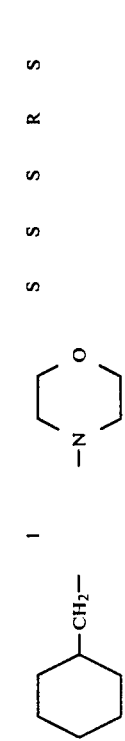 | S | S | S | R | S |
| ⁱPr | 2 | 1 |  | H | ⁱBu | H | 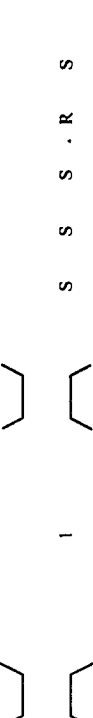 | 1 | 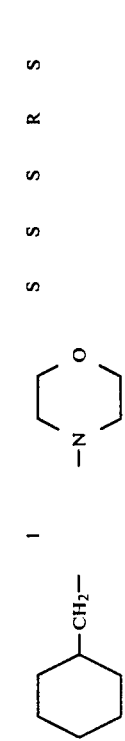 | S | S | S | R | S |
| ⁱPr | 1 | 1 | Nap-CH₂— | H |  | H | 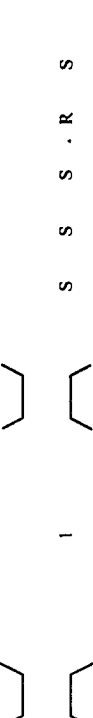 | 1 | 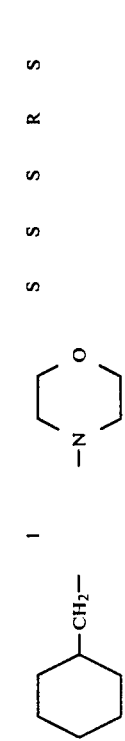 | S | S | S | R | S |

TABLE B-continued $$R^{1'}-S(CH_2)_{n'}-\overset{R^{2'}}{\underset{(A)}{*CH}}-CO-\overset{R^{3'} R^{4'}}{\underset{(B)}{N}}-\overset{R^{5'} R^{6'}}{\underset{(C)}{*CH}}-CO-\overset{}{\underset{}{N}}-\overset{OH}{\underset{(D)}{*CH}}-\overset{OH}{\underset{(E)}{*CH}}(CH_2)_{q'}-R^7$$
$$\underset{(O)_{m'}}{\parallel}$$

| R¹' | m' | n' | R²' | R³' | R⁴' | R⁵' | R⁶' | q' | R⁷ | A | B | C | D | E |
|---|---|---|---|---|---|---|---|---|---|---|---|---|---|---|
| HOCH₂CH₂ | 2 | 1 | Nap-CH₂— | H | ⁿBu | H | cyclohexyl-CH₂— | 1 | morpholinyl (N-linked) | S or R | S | S | R | S |
| Et | 2 | 1 | Ph-CH₂— | H | ⁿBu | H | cyclohexyl-CH₂— | 1 | morpholinyl (N-linked) | S | S | S | R | S |
| ᵗBu | 2 | 1 | Nap-CH₂— | H | ⁿBu | H | cyclohexyl-CH₂— | 1 | morpholinyl (N-linked) | S | S | S | R | S |
| pyrrolidinyl-CH₂— | 2 | 1 | Nap-CH₂— | H | ⁿBu | H | cyclohexyl-CH₂— | 1 | morpholinyl (N-linked) | S | S | S | R | S |
| pyrimidinyl | 0 | 1 | Nap-CH₂— | H | ⁿBu | H | cyclohexyl-CH₂— | 1 | morpholinyl (N-linked) | S | S | S | R | S |
| pyrimidinyl | 2 | 1 | Nap-CH₂— | H | ⁿBu | H | cyclohexyl-CH₂— | 1 | morpholinyl (N-linked) | S | S | S | R | S |
| pyrimidinyl | 1 | 1 | Nap-CH₂— | H | ⁿBu | H | cyclohexyl-CH₂— | 1 | morpholinyl (N-linked) | S | S | S | R | S |

TABLE B-continued $$R^{1\prime}-\underset{\underset{(O)_{m'}}{\|}}{S}+CH_2)_{n'}-\overset{R^2}{\underset{(A)}{*CH}}-CO-\overset{R^3}{\underset{(B)}{N}}-\overset{R^4}{\underset{(C)}{*CH}}-CO-\overset{R^5}{\underset{}{N}}-\overset{R^6}{\underset{(D)}{*CH}}-\overset{OH}{\underset{}{*CH}}+\overset{OH}{CH_2})_q-\overset{}{\underset{(E)}{R^7}}$$

| R$^{1\prime}$ | m' | n' | R$^{2\prime}$ | R$^{3\prime}$ | R$^{4\prime}$ | R$^{5\prime}$ | R$^{6\prime}$ | q' | R$^{7}$ | A | B | C | D | E |
|---|---|---|---|---|---|---|---|---|---|---|---|---|---|---|
| 2-pyrrolidinyl-CH$_2$— | 2 | 1 | Nap-CH$_2$— | H | $^n$Bu | H | cyclohexyl-CH$_2$— | 1 | morpholino | S | S | S | R | S |
| 2-pyrimidinyl | 2 | 1 | Ph-CH$_2$— | H | $^n$Bu | H | cyclohexyl-CH$_2$— | 1 | morpholino | S | S | S | R | S |
| Et | 2 | 1 | Nap-CH$_2$— | H | —CH$_2$CH$_2$OCOCH$_3$ | H | cyclohexyl-CH$_2$— | 1 | morpholino | S | S | S | R | S |
| Et | 2 | 1 | Nap-CH$_2$— | H | —CH$_2$CH$_2$OH | H | cyclohexyl-CH$_2$— | 1 | morpholino | S | S | S | R | S |
| 2-furyl-CH$_2$— | 2 | 1 | Nap-CH$_2$— | H | $^n$Bu | H | cyclohexyl-CH$_2$— | 1 | morpholino | S | S | S | R | S |
| HOCH$_2$CH$_2$— | 1 | 1 | Nap-CH$_2$— | H | $^n$Bu | H | cyclohexyl-CH$_2$— | 1 | morpholino | S or R | S | S | R | S |
| Et | 1 | 1 | Nap-CH$_2$— | H | $^n$Bu | H | cyclohexyl-CH$_2$— | 1 | morpholino | S | S | S | R | S |

TABLE B-continued $$R^{1'}-\underset{\underset{(O)_{m'}}{\|}}{S}(CH_2)_{n'}-\overset{R^{2'}}{\underset{(A)}{*CH}}-CO-\overset{R^{3'}}{\underset{(B)}{N}}-\overset{R^{4'}}{\underset{}{*CH}}-CO-\overset{R^{5'}}{\underset{(C)}{N}}-\overset{R^{6'}}{\underset{}{*CH}}-\overset{OH}{\underset{(D)}{*CH}}-\overset{OH}{\underset{(E)}{*CH}}(CH_2)_{q'}-R^{7'}$$

| R¹' | m' | n' | R²' | R³' | R⁴' | R⁵' | R⁶' | q' | R⁷' | A | B | C | D | E |
|---|---|---|---|---|---|---|---|---|---|---|---|---|---|---|
| Et | 2 | 1 | Nap-CH₂— | H | ⁿBu | H | cyclohexyl-CH₂— | 1 | morpholine N-oxide | S | S | S | R | S |
| cyclopentyl | 2 | 1 | Ph—CH₂— | H | ⁿBu | H | cyclohexyl-CH₂— | 1 | morpholine | S or R | S | S | R | S |
| 2,5-dihydrofuran-2-yl-CH₂— | 2 | 1 | Ph—CH₂— | H | ⁿBu | H | cyclohexyl-CH₂— | 1 | morpholine | S | S | S | R | S |
| cyclopentyl | 2 | 1 | Ph—CH₂— | H | ⁿBu | H | cyclohexyl-CH₂— | 1 | morpholine N-oxide | S | S | S | R | S |
| Et | 2 | 1 | tetrahydronaphthyl-CH₂— | H | ⁿBu | H | cyclohexyl-CH₂— | 1 | morpholine | S | S | S | R | S |
| Et | 2 | 1 | Nap-CH₂— | H | ⁿBu | H | cyclohexyl-CH₂— | 1 | piperidine N-oxide | S | S | S | R | S |

TABLE B-continued $$R^{1'}-\underset{(O)_{m'}}{\overset{\|}{S}}(CH_2)_{n'}-\overset{R^{2'}}{\underset{(A)}{\overset{|}{*CH}}}-CO-\overset{R^{3'}}{\underset{(B)}{\overset{|}{N}}}-\overset{R^{4'}}{\underset{}{\overset{|}{*CH}}}-CO-\overset{R^{5'}}{\underset{(C)}{\overset{|}{N}}}-\overset{R^{6'}}{\underset{(D)}{\overset{|}{*CH}}}-\overset{OH}{\underset{}{\overset{|}{*CH}}}(CH_2)_{q'}-R^{7'}$$

| $R^{1'}$ | m' | n' | $R^{2'}$ | $R^{3'}$ | $R^{4'}$ | $R^{5'}$ | $R^{6'}$ | q' | $R^{7'}$ | A | B | C | D | E |
|---|---|---|---|---|---|---|---|---|---|---|---|---|---|---|
| Et | 2 | 1 | Nap-CH$_2$— | H | $^n$Bu | H | cyclohexyl-CH$_2$— | 1 | —N$^+$(CH$_3$)-morpholine I$^-$ | S | S | S | R | S |
| Et | 2 | 1 | 3-CH$_3$-C$_6$H$_4$-CH$_2$— | H | $^n$Bu | H | cyclohexyl-CH$_2$— | 1 | —N-morpholine | S | S | S | R | S |
| Et | 2 | 1 | 2-CH$_3$-C$_6$H$_4$-CH$_2$— | H | $^n$Bu | H | cyclohexyl-CH$_2$— | 1 | —N-morpholine | S | S | S | R | S |

Now, the process for the preparation of the compound of the formula I of the present invention will be described.

In the following formulas, $R^1$, $R^2$, $R^3$, $R^4$, $R^5$, $R^6$, m, n and A are as defined above, and T is a leaving group.

Basically, the N-acylamino acid derivative of the formula I of the present invention can be prepared by condensing an N-acylamino acid of the formula:

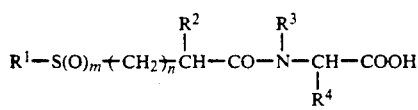
(II)

or a reactive derivative at the carboxyl group thereof with an amine of the formula:

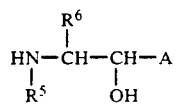
(III)

or condensing a carboxylic acid of the formula:

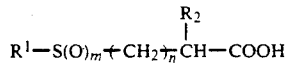
(IV)

or a reactive derivative at the carboxyl group thereof with an amino acid amide of the formula:

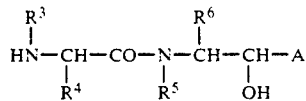
(V)

The condensation of the compounds of the formulas II and III or the condensation of the compounds of the formulas IV and V can be conducted by a usual method for the synthesis of a peptide, such as an azide method, an active ester method, a mixed acid anhydride method, a carbodiimide method, an imidazole method, a diphenylphosphoryl azide method, a Woodward method or condensation method in an oxidation and reduction system.

When a functional group which may adversely affect the condensation reaction, such as an amino group, or a carboxyl group, is present, such a functional group may be protected and then condensed, and the protecting group is then removed to obtain the compound of the present invention. Such a condensation method, protection of a functional group and removal of the functional group are disclosed in detail, for example, in "Basic for the Peptide Synthesis and Experiments" edited by Nobuo Izumiya et al, Maruzen (1985), "Protein Chemistry I" edited by Shiro Akabori et al, Kyoritsu Shuppan (1969), or "Chemistry of the Amino Acids" edited by J. P. Greenstein and M. Winitz, John Wiley & Sons, Inc. (1961).

The compound of the formula II can be prepared by the process shown by reaction scheme I.

Reaction scheme 1

1. Step of alkylation or arylation (1)

-continued
Reaction scheme 1

↓ $R^2-X$

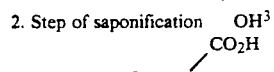
(2)

2. Step of saponification

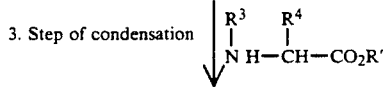
(3)

3. Step of condensation

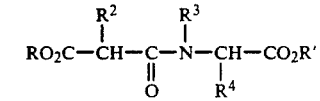

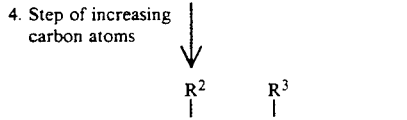
(4)

4. Step of increasing carbon atoms

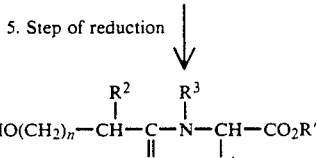
(5)

5. Step of reduction

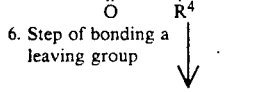
(6)

6. Step of bonding a leaving group

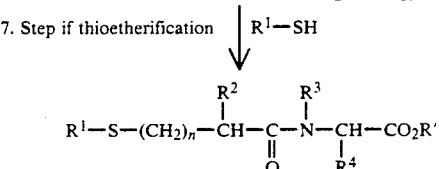
(7)

7. Step if thioetherification  ↓ $R^1-SH$

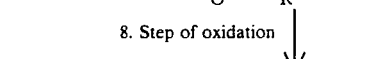
(8)

8. Step of oxidation

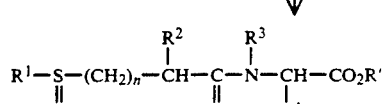
(9)

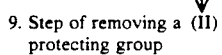

9. Step of removing a (II) protecting group

To a dialkyl malonate, a halide such as 1-(chloromethyl)naphthalene is reacted at room temperature in a solvent such as tetrahydrofuran in the presence of a base such as sodium hydride to, obtain a compound of the formula 2, which is then subjected to a saponification reaction at room temperature in ethanol by means of e.g. potassium hydroxide or sodium hydroxide to obtain a half ester of the formula 3. If this hydrolytic reaction is conducted by means of an enzyme such as esterase or lipase, or an insolubilized enzyme thereof, it is possible to obtain an optically active half ester of the formula 3.

The compound of the formula 3 is condensed with an amino acid having a protected carboxyl group by the above-mentioned usual method for the peptide synthesis, to obtain a compound of the formula 4. As a preferred embodiment, a tert-butyl ester of an amino acid and the compound of the formula 3 are condensed at room temperature in dimethylformamide by means of N,N'-dicyclohexylcarbodiimide in the presence of 1-hydroxybenzotriazole. Depending upon the purpose, the compound of the formula 4 is subjected to an extension of the carbon chain, for example, by the method shown by reaction scheme 2.

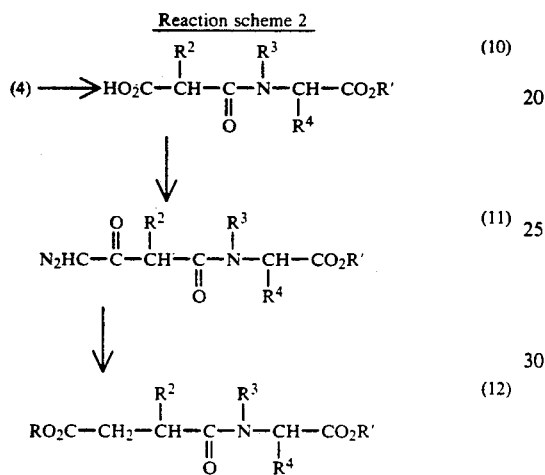

Reaction scheme 2

The compound of the formula 4 has two ester moieties. By differenciating the types of the ester moieties, it is possible to convert only one of the ester moieties to a carboxylic acid group. For example, by selecting an ethyl group for R and a tert-butyl group for R', it is possible to hydrolyze only the ethyl ester moiety by saponification with an alkali. The resulting carboxylic acid compound of the formula 10 may be converted to an acid anhydride or to an acid halide by a usual method and then reacted with a diazomethane to obtain a diazoketone compound of the formula 11, which is then reacted with a silver compound such as silver benzoate or silver oxide dissolved in triethylamine, in a lower alkanol such as methanol or ethanol to obtain a compound of the formula 12 having the carbon number increased by one. By repeating this reaction, it is possible to obtain a compound of the formula 5 having various carbon numbers. The compound of the formula 5 has two ester moieties. By differenciating the types of the ester moieties, it is possible to reduce only one of the ester moieties. For example, by using an ethyl group for R and a tert-butyl group for R', it is possible to obtain the desired compound of the formula 6 by the reduction with sodium borohydride in ethanol at room temperature. To facilitate the thioetherification, the hydroxyl group formed by the reduction of the ester of the compound of the formula 5 is converted to an excellent leaving group shown by T such as a tosyloxy group, a mesyloxy group or a halogen. This step can readily be conducted by reacting p-toluene sulfonyl chloride to the compound of the formula 6 at room temperature in the presence of a base such as pyridine. Then, the compound of the formula 7 and a thiol compound are reacted usually at room temperature in the presence of a base such as sodium hydride in a solvent such as dimethylformamide to obtain a compound of the formula 8. The oxidation of the compound of the formula 8 can be conducted by a usual method, for example, with a manganese compound, chromic acid, a lead compound, a halogen, hydrogen peroxide, an organic per acid, an inorganic nitrogen compound or an organic compound such as dimethylsulfoxide. By selecting the oxidizing agent or reaction conditions, a sulfoxide compound (compound wherein $m=1$) and a sulfone compound (compound wherein $m=2$) can be prepared, respectively. For example, when a compound of the formula 8 is oxidized at room temperature by means of an aqueous hydrogen peroxide solution in a solvent such as methanol by using sodium tungstate as a catalyst, a sulfonic compound (compound wherein $m=2$) can be obtained. By removing the protecting group from the compound of the formula 9 by a method suitable for the removal of the particular protecting group, compound of the formula II can be obtained.

Further, the steric chemistry on the carbon to which $R^2$ is bonded, can be freely controlled by utilizing the Sharpless oxidation reaction, for example, by a method represented by Reaction scheme 3.

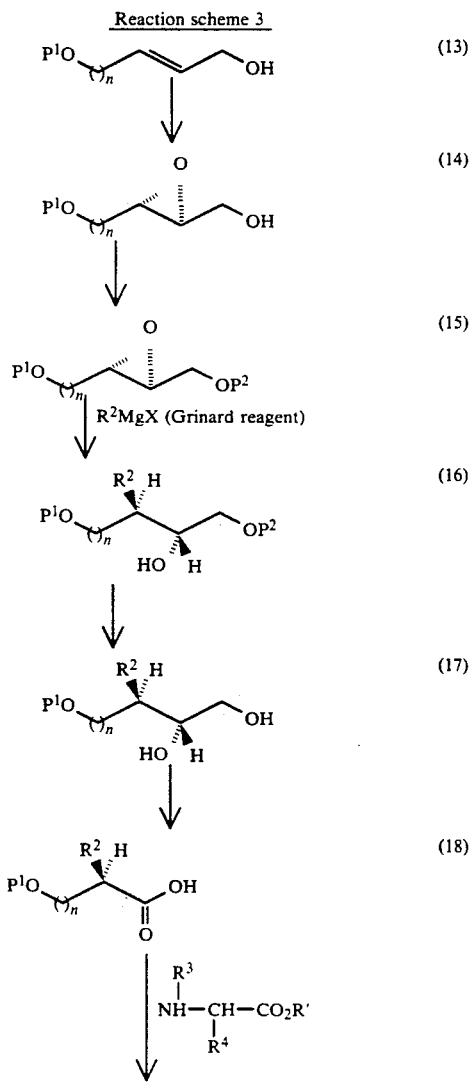

Reaction scheme 3

-continued
Reaction scheme 3

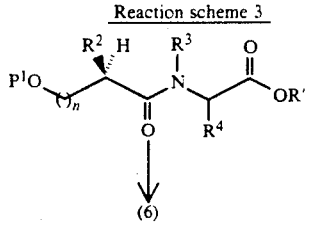
(19)

In the above formulas, $R^2$, $R^3$, $R^4$, R' and n are as defined above, and $P^1$ and $P^2$ represent hydroxyl-protecting groups.

An allylic alcohol of the formula 13 is subjected to asymmetric epoxidation in accordance with the method disclosed by A. Pfenninger in "Synthesis" p80-116 (1986). Then, the hydroxyl group is protected by a hydroxyl-protecting group $P^2$, and then the epoxy ring is selectively opened by a Grignard reagent. Then, $P^2$ is removed. Then, oxidation is conducted by e.g. sodium periodate to obtain a carboxylic acid, which is then condensed with an amino acid having a protected carboxylic acid by a usual method for peptide synthesis such as a dicyclohexylcarbodiimide method. Then, the hydroxy-protecting group $P^1$ is removed to obtain the compound of the formula 6 having the desired steric coodination. The hydroxyl-protecting group $P^1$ is preferably a benzyl group, and $P^2$ is preferably a tert-butyl-dimethylsilyl group.

Further, the synthesis can be conducted stereoselectively also by the following Reaction scheme 4.

Reaction scheme 4

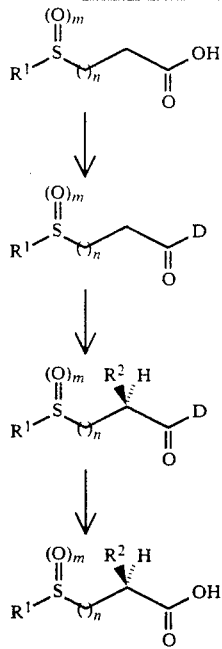

wherein $R^1$, $R^2$, m and n are as defined above, and D is an optically active amine.

A compound of the formula 20 obtained by reacting a fatty acid having a mercapto group at the terminal with $R^1$-X wherein X is a halogen such as bromine, is converted to a mixed acid anhydride by using e.g. pivaloyl chloride and then condensed with an optically active compound such as (4R,5S)-4-methyl-5-phenyl-2-oxazolidinone in the presence of e.g. n-butyl lithium.

Then, $R^2$-X wherein X is a halogen such as bromine is reacted thereto by using a base such as lithium diisopropylamide to stereospecifically introduce the $R^2$ group. Then, if necessary, after an addition of hydrogen peroxide, the product is hydrolyzed with an alkali to obtain a compound of the formula 23. If necessary, by using a suitable oxidizing agent such as hydrogen peroxide, a sulfoxide compound (a compound wherein m is 1) or sulfonic compound (compound wherein m is 2) can be obtained. The optically active compound of the formula D may be recovered and again used for the reaction.

Some of the compounds of the formula II can also be prepared by a process shown by Reaction scheme 5.

Reaction scheme 5

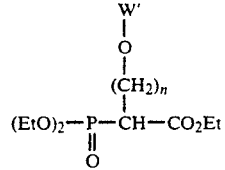 (1')

1. Step of Horner-Emmons reaction    $R^{2'}$—CHO

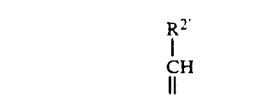 (2')

2. Step of reduction

 (3')

3. Step of removing a protecting group

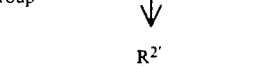 (4')

4. Step of bonding a leaving group

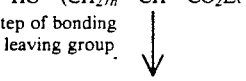 (5')

5. Step of thioetherification    $R^1$—SH

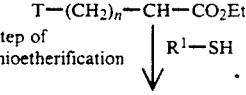 (6')

6. Step of oxidation

-continued
Reaction scheme 5

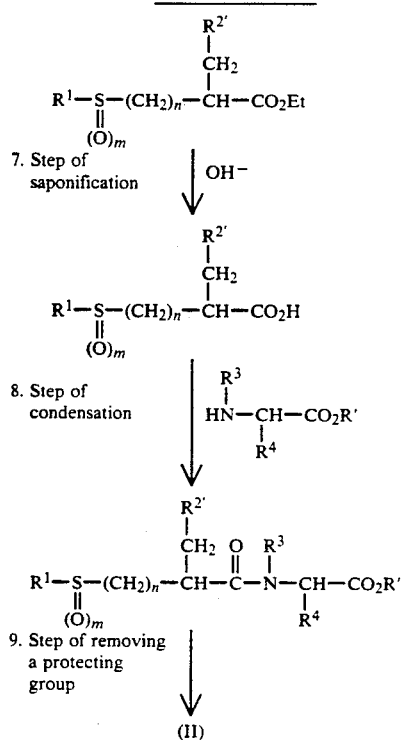

(II)

In the above formulas, $R^{2'}$ is a substituent of $R^2$ wherein the 1-position is methylene group, such as a naphthylmethyl group. A Horner-Emmon's reagent of the formula 1' and an aldehyde are reacted usually at room temperature preferably under an inert gas stream in a solvent which does not adversely affect the reaction, such as tetrahydrofuran or dimethylformamide, if necessary, by an addition of an alkali metal or alkaline earth metal halide such as lithium chloride, lithium bromide or magnesium bromide and by a further addition of a base e.g. a tertiary amine such as diazabicycloundecene, triethylamine or diisopropylethylamine or an alkali metal halide, hydroxide, alcoholate or alkyl compound such as sodium hydride, sodium hydroxide, sodium ethoxide or butyl lithium, to obtain a compound of the formula 2'. The hydroxyl-protecting group W' may be a commonly employed hydroxyl-protecting group such as a tetrahydropyranyl group, a trityl group or a benzyl group, but preferably is a tetrahydropyranyl group. As the Horner-Emmon's reagent, any reagent equivalent to the compound of the formula 1' may be employed. The compound of the formula 2' is catalytically reduced under atmospheric pressure or elevated pressure in the presence of a metal catalyst such as palladium black, palladium-carbon or platinum oxide to obtain a compound of the formula 3', followed by the removal of the protective group to obtain a compound of the formula 4'. Steps 4, 5 and 6 can be conducted in the same manner as Steps 6, 7 and 8, respectively, of Reaction scheme 1. The saponification of Step 7 can be conducted in a usual manner, for example, saponification with an alkali such as sodium hydroxide in a solvent mixture of water and a lower alkanol, to obtain a compound of the formula 8'. The condensation of Step 8 can be conducted in the same manner as Step 3 in Reaction scheme 1. Then, the removal of the protective group is conducted to obtain a compound of the formula II.

The compound of the formula II can be prepared by a process shown by Reaction scheme 6 in the case of a compound wherein A is

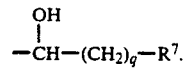

Reaction scheme 6

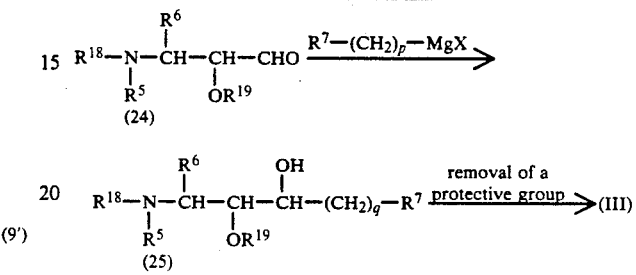

In the above formulas, $R^{18}$ is an amino-protecting group, and $R^{19}$ is a hydroxyl-protecting group. The compound of the formula 24 can be prepared by a method disclosed in J. Med. Chem., Vol. 30, p.976-982 (1987). The compound of the formula 24 is reacted with $R^7—(CH_2)_q—MgX$ wherein X is chlorine or bromine, and $R^7$ is as defined above in a solvent such as dry tetrahydrofuran at a temperature of from $-78°$ C. to room temperature, to obtain a compound of the formula 25. By removing the protective group, a compound of the formula III can be obtained.

Some of the compounds can also be prepared by a process shown by Reaction scheme 7.

Reaction scheme 7

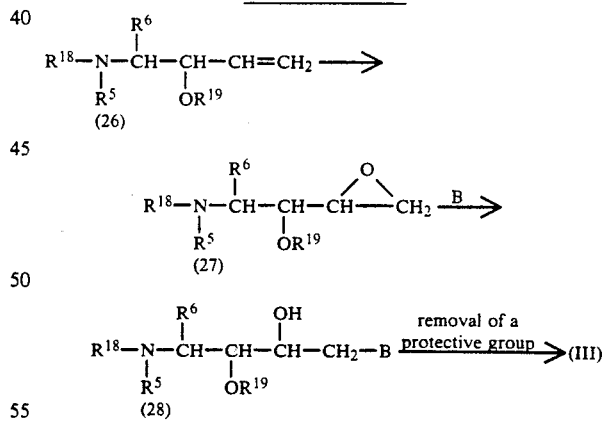

The compound of the formula 26 is a starting material for the preparation of the compound of the formula 24, and the method for the preparation thereof is also disclosed in J. Med. Chem., Vol 30, p.976-982 (1987). The compound of the formula 26 is reacted with an oxidizing agent such as m-chloro perbenzoic acid at room temperature in a solvent such as methylene chloride to obtain a compound of the formula 27, which is then reacted with a nucleophilic reagent B such as a thiol compound to obtain a compound of the formula 28. By the removal of a protecting group, a compound of the formula 3 can be obtained.

Some of the compounds of the formula III can be prepared stereospecifically by utilizing the asymmetric center of a saccharide by a process as shown by Reaction scheme 8.

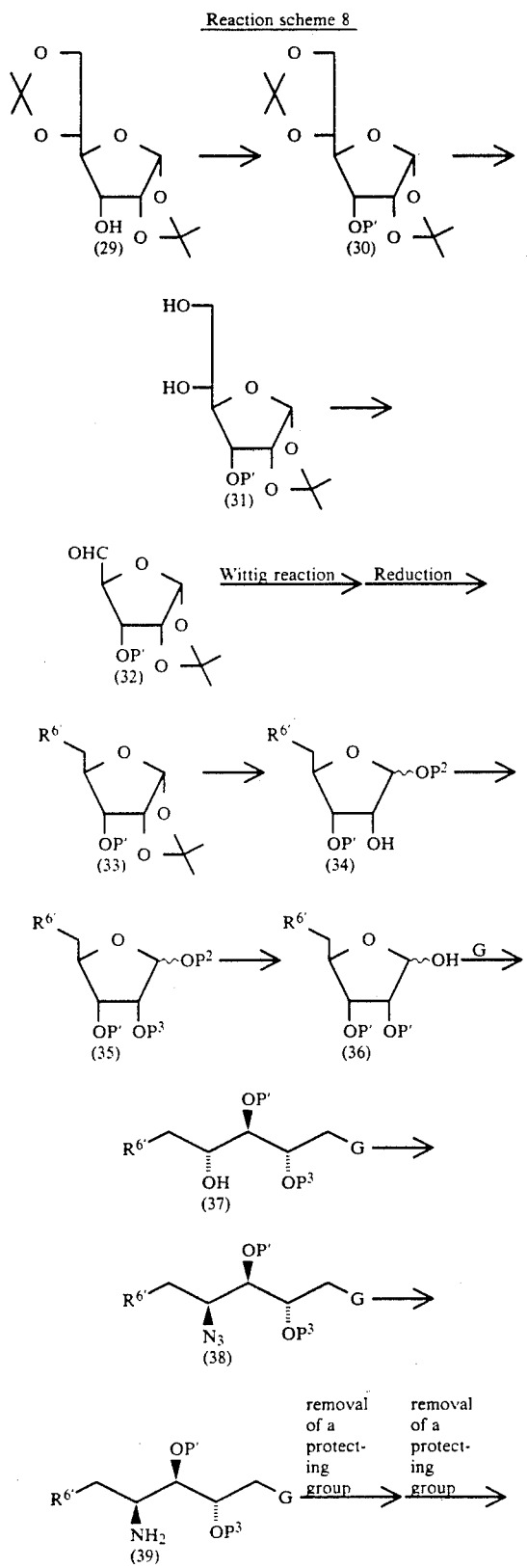

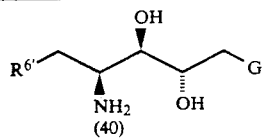

In the above formulas, $R^{6'}$ corresponds to $R^6$ except that it is shorter than $R^6$ by one methylene, and $P^1$, $P^2$ and $P^3$ are hydroxy-protecting groups, and G represents an amine compound.

The starting material 1,2:5,6-diisopropylidene-α-D-allofuranose can readily be prepared from a D-glucose by a method disclosed by J. D. Stevens in "Methods in Carbohydrate Chemistry", Vol. VI, p.123 (1972). After protecting the hydroxyl group at the 3-position by $P^1$, only the 5,6-isopropylidene was selectively removed by means of e.g. acetic acid. Then, by means of a suitable oxidizing agent such as sodium periodate, the product is converted to an aldehyde. Then, a desired side chain is introduced by Witting reaction. If necessary, the olefin is reduced by means of e.g. Raney nickel. The 1,2-isopropylidene is removed by treatment with an acid in a lower alcohol, and at the same time, the hydroxyl group at the 1-position is protected by $P^2$. Further, the hydroxyl group at the 2-position is protected by $P^3$, and then the hydroxyl-protecting group $P^2$ at the 1-position is removed. An amine compound G such as morpholine is added, and the amino alkylation reaction is conducted by means of a metal hydride complex compound such as sodium cyano borohydride. Then, the free hydroxyl group at the 4-position is stereoinversibly converted to an azide group by means of diphenylphospholyl azide in the presence of suitable azide-forming agents, preferably triphenylphosphine and diethyl azodicarboxylate. This azide group is reduced to an amino group in a usual manner. Then, the hydroxyl-protecting groups $P^1$ and $P^3$ are removed. Thus, some of the compounds of the formula III can be stereospecifically prepared. A benzyl group may be mentioned as a preferred example for the hydroxyl-protecting group $P^1$ or $P^3$, and a methyl group may be mentioned as a preferred example for the hydroxyl protecting group $P^2$.

Further, as shown by a typical example in Reaction scheme 9, such a stereospecific synthesis can be conducted by the above Sharpless asymmetric epoxidation reaction by using an optically inactive compound as the starting material.

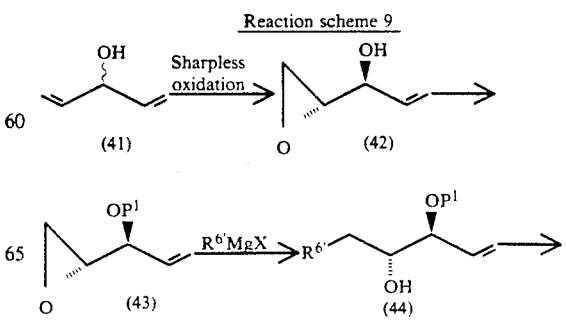

45

-continued
Reaction scheme 9

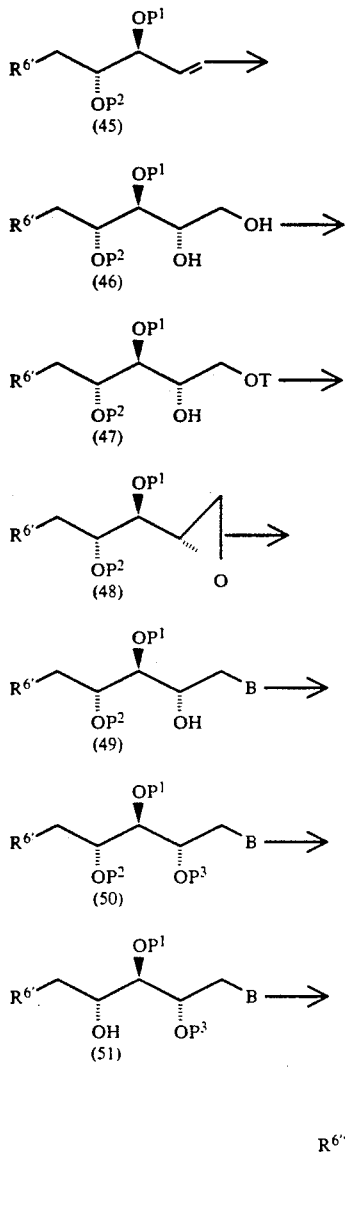

In the above formulas, $R^{6'}$, T, B, $P^1$, $P^2$ and $P^3$ are as defined above.

1,4-Pentadien-3-ol of the formula 41 prepared from vinyl magnesium bromide and methyl formate, is subjected to the above-mentioned Sharpless asymmetric epoxidation reaction to obtain an epoxy compound of the formula 42. After protecting the hydroxyl group by $P^1$, the epoxy ring is selectively opened by means of a Grignard reagent $R^{6'}MgX$, and the side chain is introduced. After protecting the formed hydroxyl group by $P^2$, a hydroxyl group is stereoselectively introduced by an oxidizing agent such as osmium tetraoxide to obtain a compound of the formula 46. A leaving group such as a tosyl group or a mesyl group is bonded to the primary hydroxyl group, followed by treatment with an alkali such as potassium carbonate, whereby an epoxy compound of the formula 48 can be stereospecifically obtained. This compound of the formula 48 can also be prepared by removing the hydroxyl-protecting group

46

$P^1$ of the compound of the formula 45, followed by the above sharpless asymmetric epoxidation reaction and against protecting the hydroxyl group by $P^1$. A nucleophilic reagent B such as a thiol compound or an amine compound is reacted to the compound of the formula 48, and the formed hydroxyl group is protected by $P^3$, and the hydroxyl-protecting group $P^2$ is removed to obtain a compound of the formula 51. A compound of the formula III can be stereospecifically prepared from the compound of the formula 51 in the same manner as shown by the process steps 37→38→39→40 as shown in Reaction Scheme 8.

Further, the compound of the formula III wherein A is

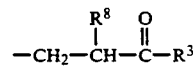

can be prepared by the process shown by Reaction scheme 10.

Reaction scheme 10

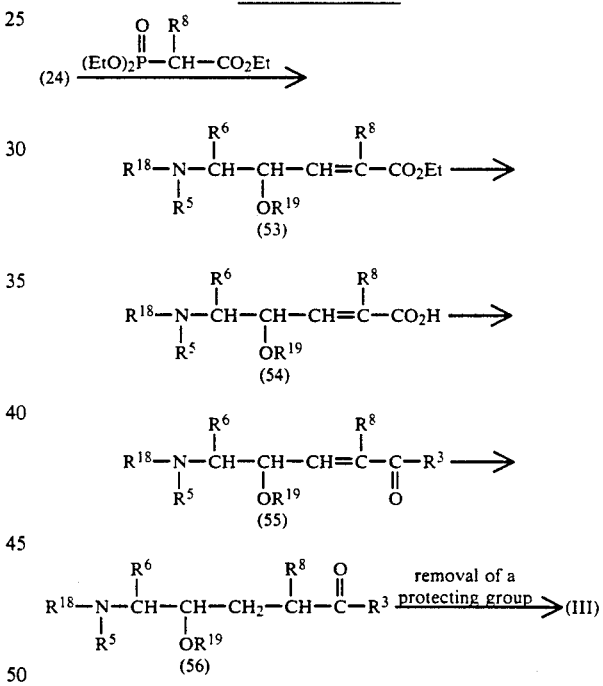

The compound of the formula 24 is reacted with the Horner-Emmon's reagent

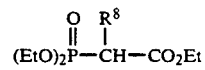

preferably in an inert gas stream such as argon or nitrogen in a solvent which does not adversely affect the reaction, such as tetrahydrofuran or dimethylformamide, if necessary by an addition of an alkali metal or alkaline earth metal halide such as lithium chloride, lithium bromide or magnesium bromide and further by an addition of a base, for example, a tertiary amine such as diazabicycloundecene, triethylamine or diisopropylethylamine or an alkali metal hydride, hydroxide, alcoholate or alkyl compound such as sodium hydride, sodium hydroxide, sodium ethoxide or butyl lithium, usually at room temperature, to obtain a compound of the formula 53. The Horner-Emmon's reagent may be any reagent so long as it is equivalent to

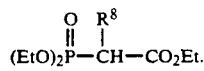

The ester of the compound of the formula 53 is hydrolyzed at room temperature with sodium hydroxide or potassium hydroxide in e.g. a solvent mixture of a lower alkanol and water to obtain a carboxylic acid of the formula 54. Then, this carboxylic acid is converted to a reactive derivative such as a halide, an acid anhydride, an active ester or an azide by a usual method and then reacted with an amine compound or an alcohol compound to obtain a compound of the formula 55. In this condensation step, any one of the above peptide syntheses can be employed. In a preferred embodiment, the compound of the formula 54 is dissolved in an anhydrous solvent such as dimethylformamide, and triethylamine, diphenylphospholyl azide and an alkylamine were added at a low temperature at a level of −20° C. to conduct a reaction at room temperature to obtain a compound of the formula 55. The compound of the formula 55 is catalytically reduced in the presence of e.g. palladium black, palladium-carbon or platinum oxide under atmospheric pressure or elevated pressure to obtain a compound of the formula 56. Then, the protecting group is removed to obtain a compound of the formula III. Depending upon the type of the protecting group, the step of this catalytic reduction and the step of removal of the protecting group can be conducted simultaneously.

The compound of the formula IV can be prepared in the same manner as in Reaction scheme 1 except that the condensation step 3 is omitted. Namely, the compound of the formula 3 is converted to

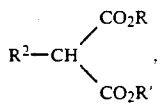

and the subsequent steps are the same as the steps 4→5→6→7→8→9 to obtain a compound of the formula IV.

The compound of the formula V can readily be obtained by condensing an amino-protecting amino acid and the compound of the formula III in accordance with a usual method for the peptide synthesis, followed by removal of the protecting group.

When the compound of the present invention is to be used as a medicine, it may be administered by itself, but it is usually administered as a mixture with a carrier suitably selected depending upon the route for administration and standard formulations. For example, for oral administration, the compound of the present invention may be administered in the form of tablets which may be prepared by adding to a powder of the active ingredient of the present invention an excipient such as starch, lactose, sucrose, glucose, crystalline cellulose, calcium carbonate or kaolin, a binder such as a starch solution, a gelatin solution, a hydroxypropyl cellulose, a glucose solution, a sucrose solution, water or ethanol, a disintegrator such as starch, agar, gelatin powder, carboxymethyl cellulose calcium (CMC-Ca), carboxymethyl cellulose sodium (CMC-Na), crystalline cellulose, calcium carbonate or sodium hydrogencarbonate, or a lubricant such as magnesium stearate, calcium stearate, talc, macrogoal 4,000, macrogoal 6,000 or stearic acid, subjecting the mixture to compression molding by a conventional tabletting method, and if necessary, applying a sugar coating by means of a concentrated sugar solution containing e.g. gum arabic, talc, polyvinyl pyrrolidone, polyethylene glycol and/or titanium oxide, applying a film coating by means of a film-forming agent composed of e.g. polyvinyl acetal, diethylaminoacetate, cellulose acetate, N,N-dibutylaminohydroxypropyl ether, hydroxypropylmethyl cellulose, hydroxypropyl cellulose, ethyl cellulose or polyvinyl pyrrolidone, or applying an enteric coating by means of a film-forming agent composed of e.g. ethyl cellulose phthalate cerac, cellulose acetate phthalate or hydroxypropylmethyl cellulose phthalate; granules or fine granules which may be prepared by adding to the active ingredient of the present invention a binder such as starch, gelatin, gum arabic, methyl cellulose, sodium carboxymethyl cellulose, heavy silicic anhydride or light silicic anhydride, followed by kneading and granulation by usual methods; a powder of the active ingredient of the present invention by itself; or capsules which may be prepared by adding to the active ingredient of the present invention an excipient such as lactose, starch or crystalline cellulose and/or a lubricant such as magnesium stearate, calcium stearate or talc, and filling the mixture into capsules. For non-oral administration, an injection formulation may be used wherein an emulsifying agent such as propylene glycol, polyethylene glycol or a vegetable oil such as olive oil, or a solubilization agent such as sodium benzoate, sodium salicylate, N-hydroxyethyllactamide, calcium α-saccharide, mannitol, nicotic acid amide or cyclodextrin, is suitably used.

Further, to such formulations, other medicinal substances may be incorporated. Such medicinal substances include, for example, acetazolamide, amiloride, chlorothiazide, furosemide, timolol, propranolol, cetamolol, clonidine, methyldopa, minoxydil, hydralazine, captopril, pivalopril, enalapril, lidinopril, verapamil, nifedipine, nicardipine, felodipine, nimodipine and diltiazem.

An advantageous formulation contains from about 0.1 mg to 500 mg of the compound of the present invention. A preferred range of a daily dose for oral administration is from about 0.1 mg/kg to 500 mg/kg, and such a daily dose may be administered at once or in three times a day. For non-oral administration, it is preferred to administer the compound of the present invention in an amount of from about 0.1 mg/kg to 10 mg/kg per day at once. The dose may be increased or reduced by a doctor's prescription depending upon e.g. the sex and diseased condition of the patient.

FIG. 1 represents a graph wherein a compound of the invention is administered over a period of time, plotted against the drop in blood pressure of the subject treated.

Now, the present invention will be described in further detail with reference to the Test Example for renin inhibiting activities of the compounds of the present invention and Working Examples.

TEST EXAMPLE 1

Renin inhibiting activities

To 156 μl of a 0.2M sodium phosphate buffer solution (pH7.4), 40 μl of a solution mixture of 34 mM 8-hydroxyquinoline and 100 mM disodium ethylenediamine tetraacetate, 4 μl of dimethyl sulfoxide or a dimethyl sulfoxide solution of an inhibitor and 200 μl of human plasma were added and reacted at 37° C. for one hour. Then, pepstatin was added thereto to terminate the reaction, and the amount of the resulting angiotension I was measured by radio immunoassay whereby the inhibiting activity was determined. The 50% inhibition concentrations (IC$_{50}$ values) of the compounds of the present invention are shown below.

TABLE 1

| Tested Compounds | IC$_{50}$ (M) |
|---|---|
| Compound of Example 1 | $5.0 \times 10^{-10}$ |
| Compound of Example 2 | $1.7 \times 10^{-10}$ |
| Compound of Example 4 | $9.6 \times 10^{-10}$ |
| Compound of Example 5 | $1.4 \times 10^{-9}$ |
| Compound of Example 6 | $1.6 \times 10^{-9}$ |
| Compound of Example 7 | $8.3 \times 10^{-10}$ |
| Compound of Example 8 | $1.5 \times 10^{-9}$ |
| Compound of Example 10 | $2.0 \times 10^{-9}$ |
| Compound of Example 11 | $3.1 \times 10^{-9}$ |
| Compound of Example 12 | $9.7 \times 10^{-9}$ |
| Compound of Example 13 | $1.9 \times 10^{-9}$ |
| Compound of Example 15 | $5.0 \times 10^{-10}$ |
| Compound of Example 16 | $3.4 \times 10^{-9}$ |
| Compound of Example 19 | $8.3 \times 10^{-9}$ |
| Compound of Example 21 | $8.9 \times 10^{-9}$ |
| Compound of Example 31 | $4.2 \times 10^{-9}$ |
| Compound of Example 35 | $5.9 \times 10^{-9}$ |
| Compound of Example 36 | $2.7 \times 10^{-9}$ |
| Compound of Example 38 | $5.9 \times 10^{-9}$ |
| Compound of Example 40 | $5.3 \times 10^{-9}$ |
| Compound of Example 41 | $1.7 \times 10^{-9}$ |
| Compound of Example 42 | $3.6 \times 10^{-9}$ |
| Compound of Example 44 | $3.8 \times 10^{-9}$ |
| Compound of Example 47 | $2.3 \times 10^{-9}$ |
| Compound of Example 49(A) | $6.1 \times 10^{-9}$ |
| Compound of Example 51(B) | $2.0 \times 10^{-9}$ |
| Compound of Example 52 | $3.0 \times 10^{-9}$ |
| Compound of Example 56 | $2.0 \times 10^{-9}$ |

From the above results, it is evident that the compounds of the present invention have remarkably strong inhibiting activities against human plasma renin.

TEST EXAMPLE 2

Absorption test by oral administration 10 mg/kg of the compound of Example 16 was orally administered to rats (n=4), whereupon the concentration of the compound in the plasma was measured. The concentration in the plasma was calculated by the inhibiting activities against human plasma renin. The results are shown in Table 2.

TABLE 2

| | Time (hrs.) | | | | | | | |
|---|---|---|---|---|---|---|---|---|
| | 1/12 | 1/6 | ¼ | ½ | 1 | 2 | 4 | 8 | 24 |
| Concentration of the compound of Example 16 (ng/ml) | 89 | 136 | 212 | 267 | 183 | 85 | 34 | 12 | 7 |

It is evident from Table 2 that the compound of the present invention is efficiently absorbed by oral administration and shows a continual concentration in blood.

TEST EXAMPLE 3

Hypotensive activities in monkeys

The hypotensive activities were measured in accordance with a method disclosed in J. Cardiovascular Pharmacology, Vol. 7, (Suppl. 4) S58–S61 (1985). Namely, 30 mg/kg of furosemido (diuretic) was intracutaneously injected to three marmosets i.e. small size monkeys to produce a high renin active state. To these marmosets, 30 mg/kg of the compound of Example 16 was orally administered, whereupon the hypotensive activities were measured. The results are shown in FIG. 1.

It is evident from FIG. 1 that the compound of the present invention exhibits hypotensive activities by the oral administration. Thus, the compound of the present invention has properties useful as a medicine.

Now, the present invention will be described in further detail with reference to Examples. However, it should be understood that the present invention is by no means restricted to such specific Examples.

EXAMPLE 1

(2RS,4S,5S)-5-{L-N-[(2R or S)-3-ethylsulfonyl-2-(1-naphthylmethyl)propionyl]norleucyl}amino-2-ethyl-4-hydroxy-7-methyloctanoic acid isobutylamide (1) Ethyl (1-naphthylmethyl)malonate (a) Into a reactor, 1 g of sodium hydride (60% in oil) was introduced and washed a few times with dry n-hexane. Then, it was dried in dry argon to dry powder, and then 10 ml of dry tetrahydrofuran (hereinafter referred to simply as THF) was promptly added thereto and the reactor was sealed under an argon stream. While cooling the reaction solution with ice, 4.2 ml of diethyl malonate was dropwise added. Generation of hydrogen started, but ended upon completion of the dropwise addition, whereby a uniform transparent reaction solution was obtained. The reaction solution was returned to room temperature, then stirred for 15 minutes and again cooled with ice. To this reaction solution, a solution of 4.86 g of 1-(chloromethyl)naphthalene in 5 ml of dry THF was dropwise added. The mixture was returned to room temperature and stirred overnight.

Then, the reaction solution was diluted with 200 ml of ethyl acetate and washed with 100 ml of water and then with 100 ml of a saturated sodium chloride aqueous solution. The organic layer was separated, dried over anhydrous magnesium sulfate and concentrated under reduced pressure. The syrup thereby obtained was purified by silica gel column chromatography (n-hexane/ethyl acetate=10/1) to obtain 5.61 g (yield: about 64%) of diethyl (1-naphthylmethyl)malonate as crude syrup.

Rf value (measured by silica gel plate Merck 5715, the same applies hereinafter): 0.3 (n-hexane/ethyl acetate=10/1).

Nuclear magnetic resonance spectrum (hereinafter referred to simply as NMR.) (300 MHz, CDCl$_3$) δppm: 1.2(6H,t,J=7 Hz), 3.7(2H,d,J=8 Hz), 3.84(1H,dd,J=6.5,8 Hz), 4.15(4H,m).

(b) 5.32 g of the syrup of diethyl (1-naphthylmethyl)-malonate was dissolved in 20 ml of absolute ethanol. To this solution, a solution of 1.17 g of potassium hydroxide (85%) in 45 ml of absolute ethanol was dropwise added over a period of 1.5 hours. Thereafter, the stirring was continued overnight. Then, the resulting suspension was weakly acidified with 3 ml of 6N hydrochloric acid under cooling with ice, and 20 ml of water was further added thereto. Then, the mixture was concentrated under reduced pressure at a temperature of not higher than 40° C. The concentrated suspension after sufficient evaporation of ethanol was dissolved in 300 ml of ethyl acetate. The solution was washed sequentially with 200 ml of water and with 200 ml of a saturated sodium chloride aqueous solution. The ethyl acetate layer was separated, dried over anhydrous magnesium sulfate and then concentrated under reduced pressure. The syrup thereby obtained was purified by silica gel column chromatography (benzene/ethanol/acetic acid=100/4/0.5). The purified fractions of the eluted solutions were collected (about 200 ml), and 100 ml of ethyl acetate was added thereto to bring the total volume to about 300 ml. The mixture was thoroughly washed with a saturated sodium chloride aqueous solution (200 ml×3 times). The organic layer was dried over anhydrous sodium sulfate. The inorganic salt was filtered off, and the filtrate was concentrated and dried to obtain 3.64 g of ethyl (1-naphthylmethyl)malonate.

Rf: 0.54 (benzene/ethanol/acetic acid=10/1/0.5).

NMR (300 MHz, CDCl$_3$) δppm: 1.16(3H,t,J=7 Hz), 3.73(2H), 3.90(1H,dd,J=6.5,8 Hz), 4.16(m,2H), (2) L-norleucine tert-butyl ester 2.0 g of L-norleucine was introduced into a pressure tube, and about 30 ml of dry dioxane was added thereto to obtain a suspension. Then, 2 ml of concentrated sulfuric acid was added thereto, and the reactor was cooled to −75° C. Then, isobutene gas was blown thereinto. When about 10 ml of isobutene gas was introduced, the tube was sealed. The temperature was gradually returned to room temperature under stirring, and then the stirring was continued overnight. Then, the reactor was opened, and isobutene was evaporated under atmospheric pressure. Then, the reaction solution was poured into 200 ml of a 2M sodium hydroxide aqueous solution under cooling with ice, and the mixture was vigorously stirred. Then, the mixture was extracted with diethyl ether (250 ml×2 times). The separated ether layer was washed with a saturated sodium chloride aqueous solution (100 ml×2 times) and then dried over anhydrous magnesium sulfate. The inorganic salt was filtered off, and the filtrate was concentrated to obtain a syrup. The syrup was thoroughly dried under reduced pressure and then stored at a temperature of not higher than 5° C., whereby 1.46 g (yield: 51%) of the above identified compound precipitated as white crystals.

Rf: 0.71 (chloroform/methanol/conc.aqueous ammonia=(10/0.5/0.2).

NMR (300 MHz, CDCl$_3$) δppm: 0.9(3H,m), 1.2–1.8(15H,m), 3.29(1H).

(3) L-N-{2-ethoxycarbonyl-3-(1-naphthyl)propionyl}norleucine tert-butyl ester 1.59 g of ethyl (1-naphthylmethyl)malonate was dissolved in 15 ml of anhydrous dimethylformamide (hereinafter referred to simply as DMF). Then, a solution of 1.20 g of L-norleucine tert-butyl ester in 5 ml of dry DMF was added thereto. The reaction solution was cooled to −15° C., and 1.28 g of 1-hydroxybenzotriazole and 1.68 g of N,N-dicyclohexylcarbodiimide (hereinafter referred to simply as DCC) were added thereto. The mixture was stirred for 1 hour at −15° C. and then stirred overnight at room temperature. Then, precipitated dicyclohexylurea was filtered off, the collected filtration product was washed with a small amount of a solvent mixture of n-hexane/ethyl acetate (4/1) and the washing solutions were put together. The filtrate was diluted with 200 ml of ethyl acetate and then washed sequentially with 150 ml of a 4% sodium hydrogencarbonate aqueous solution and with 150 ml of a saturated sodium chloride aqueous solution. The separated ethyl acetate layer was dried over anhydrous magnesium sulfate. The inorganic salt was filtered off, and the filtrate was concentrated under reduced pressure. The syrup thereby obtained was purified by silica gel column chromatography (n-hexane/ethyl acetate=4/1). The eluted fractions were collected, concentrated under reduced pressure and dried to obtain 2.45 g (yield: 95%) of the above identified compound as gelled solid.

Rf: 0.41, 0.35 (n-hexane/ethyl acetate=3/1).

NMR (300 MHz, CDCl$_3$) δppm: 0.89(3H,t,J=7 Hz), 1.07(3H,t,J=7 Hz), 1.14–1.58(13H), 1.65(1H,m), 1.82(1H,m), 3.59–3.82(3H,m), 4.06(2H,m), 4.45(1H,m), 6.92(1H,d,J=8 Hz), 7.34(2H,m), 7.46–7.61(2H,m), 7.73(1H,m), 7.85(1H,d,J=8 Hz), 8.06(1H,d,J=8 Hz).

(4) L-N-{(2R or S)-2-hydroxymethyl-3-(1-naphthyl)propionyl}norleucine tert-butyl ester 2.45 g of L-N-{2-ethoxycarbonyl-3-(1-naphthyl)propionyl}norleucine tert-butyl ester was dissolved in 60 ml of ethanol. Then, 1.48 g of sodium borohydride was gradually added thereto. The mixture was stirred for 5.5 hours and then concentrated under reduced pressure at a temperature of not higher than 40° C. to obtain a suspension syrup. The syrup was dissolved in 250 ml of ethyl acetate and then washed with 200 ml of water and then with 200 ml of a saturated sodium chloride aqueous solution. The organic layer was separated and dried over anhydrous magnesium sulfate. Then, the inorganic salt was filtered off, and the filtrate was concentrated under reduced pressure to obtain a solid. The product was purified by silica gel column chromatography (n-hexane/ethyl acetate=1/1-2/1). Among the purified fractions, the fraction having a Rf value of 0.58 (n-hexane/ethyl acetate=1/1) was collected and extracted. The extract solution was concentrated and dried to obtain 0.74 g (yield: 33%) of crystalline solid. Further, the fraction having a Rf value of 0.45 (under the same condition as in the case of the Rf value of 0.58) was collected and concentrated to obtain 0.97 g (yield: 44%) of crystalline solid.

Product having a Rf value of 0.58:

NMR (300 MHz, CDCl$_3$) δppm: 0.86(3H,t,J=7 Hz), 1.15–1.38(4H), 1.43(9H,s), 1.6(1H,m), 1.8(2H,m), 2.78(2H,m), 3.33(1H,dd,J=7.5,14 Hz), 3.49(1H,dd,J=7.5,14 Hz), 3.82(2H,m), 4.37(1H,m), 6.12(1H,br s,J=7 Hz), 7.38(2H,d,J=5 Hz), 7.45–7.57(2H,m), 7.74(1H,m), 7.86(1H,d,J=8 Hz), 8.05(1H,d,J=8 Hz).

Melting point: 94°–95° C.

Angle of rotation [α]$_D^{20}$ = +50.5° (C 1.00, CHCl$_3$).

Product having a Rf value of 0.45

NMR (300 MHz, CDCl$_3$) δppm: 0.82(3H,t,J=7 Hz), 0.85–1.0(2H,m), 1.12–1.22(2H,m), 1.36–1.56(11H,m), 2.79(1H,m), 3.27(2H,m), 3.48(1H,dd,J=9,14 Hz), 3.86(2H,t,J=6 Hz), 4.36(1H,m), 5.74(1H,br d,J=8 Hz), 7.37(2H,m), 7.51(2H,m), 7.73(1H,m), 7.86(1H,dd,J=1.5,8 Hz), 8.02(1H,d,J=8 Hz).

Melting point: 92°–94° C.

Angle of rotation [α]$_D^{20}$ = +72.6° (C 1.00, CHCl$_3$).

(5) L-N-{(2R or S)-2-(1-naphthylmethyl)-3-p-toluenesulfonyloxypropionyl}norleucine tert-butyl ester 202 mg of the solid of L-N-{(2R or S)-3-hydroxy-2-(1-naphthylmethyl)propionyl}norleucine tert-butyl ester (the product having a Rf value of 0.58 obtained in the Process (4)) was dissolved in 3 ml of dry pyridine. Then, 107 mg of p-toluene sulfonylchloride was added thereto, and the mixture was reacted at room temperature for 24 hours. 15 mg of the same reagent was additionally added thereto, and the mixture was reacted for further 24 hours. Then, the reaction solution was concentrated under reduced pressure. The residue was dissolved in 20 ml of ethyl acetate and then washed sequentially with 10 ml of a 4% potassium hydrogen sulfate aqueous solution, with 10 ml of a 4% sodium hydrogencarbonate aqueous solution and with 10 ml of a saturated sodium chloride aqueous solution. The organic layer was separated and dried over anhydrous magneisum sulfate. Then, the inorganic salt was removed by filtration, and the filtrate was concentrated under reduced pressure. The residue was purified by silica gel column chromatography (n-hexane/ethyl acetate=4/1), and the eluted solution was concentrated and dried under reduced pressure to obtain 264 mg of L-N-{(2R or S)-2-(1-naphthylmethyl)-3-p-toluenesulfonyloxypropionyl}norleucine tert-butyl ester as colorless transparent syrup.

Rf: 0.44 (n-hexane/ethyl acetate=3/1).

NMR (300 MHz, CDCl$_3$): δppm: 0.86(3H,t,J=7 Hz), 1.05-1.4(4H,m), 1.39(9H,s), 1.52(1H,m), 1.70(1H,m), 2.44(3H,s), 2.93(1H,m), 3.28(2H,m), 4.15(1H,dd,J=6,10 Hz), 4.28(2H,m), 5.78(1H,d,J=8 Hz), 7.19-7.38(5H,m), 7.51(2H,m), 7.72(2H,m), 7.85(1H,m), 7.93(1H,m).

(6) L-N-{(2R or S)-3-ethylthio-2-(1-naphthylmethyl)-propionyl}norleucine tert-butyl ester 30 mg of L-N-{(2R or S)-2-(1-naphthylmethyl)-3-p-toluenesulfonyloxy propionyl}norleucine tert-butyl ester was dissolved in 0.2 ml of dry DMF. Separately, a suspension of a thioalkoxide (in 1.8 ml of dry DMF) prepared from 64 mg of sodium hydride and 0.3 ml of ethyl mercaptan, was prepared, and 0.5 ml of the suspension was added to the above solution. The mixture was reacted at room temperature for 30 minutes, and then about 1 ml of water was added. Then, the reaction solution was diluted by an addition of 20 ml of benzene and washed sequentially with 10 ml of water and with 10 ml of a saturated sodium chloride aqueous solution. The organic layer was separated and dried over anhydrous magnesium sulfate, and then concentrated and dried under reduced pressure to obtain 23 mg of L-N-{(2R or S)-3-ethylthio-2-(1-naphthylmethyl)propionyl} norleucine tert-butyl ester as colorless transparent syrup.

Rf: 0.56 (n-hexane/ethyl acetate=3/1).

NMR (300 MHz, CDCl$_3$) δppm: 0.88(3H, t, J=7 Hz), 1.1-1.4(7H,m), 1.41(9H, s), 1.59(1H,m), 1.75(1H,m), 2.51(1H,m), 2.72(2H,m), 2.93(1H,m), 3.39(2H,d,J=6.5 Hz), 4.36(1H,m), 5.86(1H,d,J=7 Hz), 7.35(2H,m), 7.52(2H,m), 7.72(1H), 7.85(1H), 8.07(1H)

Infrared absorption spectrum (hereinafter referred to simply as IR) (KBr) νcm$^{-1}$: 1740, 1660, 1540, 1520, 1390, 1160.

(7) L-N-{(2R or S)-3-ethylsulfonyl-2-(1-naphthylmethyl)propionyl}norleucine tert-butyl ester 23 mg of L-N-{(2R or S)-3-ethylthio-2-(1-naphthylmethyl)propionyl}norleucine tert-butyl ester was dissolved in 1 ml of methanol. To this solution, 0.1 ml of a 30% hydrogen peroxide aqueous solution and sodium tungstate dihydrate were added, and the mixture was stirred at room temperature for 1 hour. Then, the reaction solution was diluted with 20 ml of ethyl acetate and washed sequentially with 10 ml of water and with 10 ml of a saturated sodium chloride aqueous solution. The organic layer was separated and dried over anhydrous magnesium sulfate, and then concentrated and dried under reduced pressure to obtain 22 mg of the above identified compound as colorless transparent syrup.

Rf: 0.12 (n-hexane/ethyl acetate=3/1).

NMR (300 MHz, CDCl$_3$) δ ppm: 0.85(3H,t,J=7 Hz), 1.1-1.35(7H,m), 1.38(9H,s), 1.59(1H,m), 1.72(1H,m), 2.82(2H,m), 3.01(1H,dd,J=3,14.5 Hz), 3.26(1H,m), 3.41(2H,m), 3.70(1H,dd,J=9,14.5 Hz), 5.97(1H,d,J=7 Hz), 7.30(1H,d,J=6 Hz), 7.38(1H,t,J=8 Hz), 7.54(2H,m), 7.75(1H,d,J=8 Hz), 7.86(1H,d,J=8 Hz), 8.02(1H,d,J=8.5 Hz).

IR (KBr, neat) νcm$^{-1}$: 1740, 1660, 1540, 1310, 1160, 1110.

Mass spectrum (FAB-MS) 420, 476 (M$^+$+1).

(8) (2RS,4S,5S)-5-amino-2-ethyl-4-hydroxy-7-methyloctanoic acid isobutylamide hydrochloride (a) 856 mg of a sodium hydride (60% in oil) was washed three times with n-hexane under a nitrogen atmosphere. After drying, the obtained powder was suspended in 7.2 ml of dry DMF under a nitrogen atmosphere, and 4.26 ml of ethyl diethylphosphono acetate was dropwise added thereto over a period of one hour under stirring at 0° C. After stirring at room temperature for about one hour, the mixture was cooled to 0° C., and 1.92 ml of bromoethane was added thereto under stirring. The mixture was then stirred overnight at 55° C. The reaction solution was poured into 40 ml of water and extracted three times with 20 ml of ethyl acetate. The organic layer was washed with water and then with a saturated sodium chloride aqueous solution and dried over anhydrous sodium sulfate. Then, the solvent was distilled off under reduced pressure. The residue was purified by silica gel column chromatography (n-hexane/acetone=4/1) to obtain 2.76 g of ethyl 2-diethylphosphonobutanoate as oily substance.

Rf: 0.63 (n-hexane/ethyl acetate=1/5).

Mass spectrum m/z 253 (M$^+$+1).

NMR (60 MHz, CDCl$_3$) δ ppm: 0.95(3H,t,J=8 Hz), 1.25(3H,t,J=8 Hz) 1.29(6H,t,J=7 Hz), 1.6-2.1(2H,m), 2.8(1H,ddd,J=22,7,7 Hz), 4.05(2H,q,J=8 Hz), 4.15(2H,q,J=7 Hz).

(b) 3-[(4S,5S)-3-benzyloxycarbonyl-2,2-dimethyl-4-isobutyloxazolidin-5-yl]-2-ethyl-2-propenoic acid isobutylamide 71.6 mg of lithium chloride was suspended in 5 ml of dry THF under an argon atmosphere, and 426 mg of ethyl 2-diethylphosphonobutanoate dissolved in 0.6 ml of dry THF was added thereto under stirring. The mixture was stirred at room temperature for 5 minutes, and then 323 mg of 1,8-diazabicyclo[5,4,0]-7-undecene (hereinafter referred to simply as DBU) was added thereto in the form of a 50% dry THF solution, and the mixture was stirred at room temperature for 10 minutes. Then, 450 mg of (4S,5R)-3-benzyloxycarbonyl-2,2-dimethyl-5-formyl-4-isobutyloxazolidine dissolved in 1.0 ml of dry THF was added thereto, and the mixture was stirred at room temperature overnight. The reaction solution was cooled to 0° C. and neutralized with 1N hydrochloric acid. Then, the solution was extracted three times with ethyl acetate. The organic layer was washed with water and with a saturated sodium chloride aqueous solution and dried over anhydrous sodium sulfate. The solvent was distilled off under reduced pressure, and the residue was purified by silica gel column chromatography (n-hexane/ethyl acetate=10/1) to obtain 518 mg of ethyl 3-[(4S,5S)-3-benzyloxycarbonyl-2,2-dimethyl-4-isobutyloxazolidin-5-yl]-2-ethyl-2-propenoate as colorless oily substance.

Rf: 0.53 (n-hexane/ethyl acetate=5/1). δNMR (60 MHz, CDCl$_3$). δppm: 0.7-1.8(21H,m),2.32(2H,m), 3.80(1H,m), 4.20(2H,q,J=7 Hz), 4.58(0.5H,dd,J=2,9

Hz), 5.10(0.5H,m), 5.11(2H,s), 5.85(0.5H,br d,J=9 Hz), 6.66(0.5H,d,J=9 Hz), 7.30(5H,s).

517 mg of ethyl 3-[(4S,5S)-3-benzyloxycarbonyl-2,2-dimethyl-4-isobutyloxazolidin-5-yl]-2-ethyl-2-propenoate was dissolved in 3.10 ml of an ethanol/water (9/1) solution of 2N potassium hydroxide, and the solution was stirred at room temperature for 3 hours. Then, the reaction solution was adjusted to pH2 with 1N hydrochloric acid under cooling with ice and after an addition of 24 ml of water, extracted three times with 20 ml of ethyl acetate. The organic layer was washed with water and with a saturated sodium chloride aqueous solution and dried over anhydrous sodium sulfate. The solvent was distilled off under reduced pressure to obtain 3-[(4S,5S)-3-benzyloxycarbonyl-2,2-dimethyl-4-isobutyloxazolidin-5-yl]-2-ethyl-2-propenoic acid as colorless oily substance.

This product was dissolved without purification in 1.0 ml of dry DMF. While stirring the solution at −10° C., 145 μl of isobutylamine, 320 μl of diphenylphosphorylazide (hereinafter referred to simply as DPPA) and 207 μl of triethylamine were added thereto. The mixture was stirred at −10° C. for one hour and further at room temperature overnight. Then, 60 ml of ethyl acetate was added to the reaction solution. The organic layer was washed sequentially with a 10% citric acid aqueous solution, with water, with a 4% sodium hydrogencarbonate aqueous solution, with water and with a saturated sodium chloride aqueous solution and then dried over anhydrous sodium sulfate. The solvent was distilled off under reduced pressure, and the residue was purified by silica gel column chromatography (n-hexane/ethyl acetate=5/1) to obtain 204 mg of 3-[(4S,5S)-3-benzyloxycarbonyl-2,2-dimethyl-4-isobutyloxazolidin-5-yl]-2-ethyl-2(Z)-propenoic acid isobutylamide, 151 mg of 3-[(4S, 5S)-3-benzyloxycarbonyl-2,2-dimethyl-4-isobutyloxazolidin-5-yl]-2-ethyl-2(E)-propenoic acid isobutylamide and 55 mg of a mixture of both as colorless oily substances.

Rf:
2(Z) isomer: 0.37 (n-hexane/ethyl acetate=5/2).
2(E) isomer: 0.28 (n-hexane/ethyl acetate=5/2).
NMR (60 MHz, CDCl$_3$)
2(Z) isomer: δppm: 0.7–1.3(15H,m), 1.4–2.1(10H,m) 2.30(2H,m), 3.20(2H,dd,J=6,6 Hz) 3.8(1H,m), 4.52(1H,dd,J=2,9 Hz) 5.12(2H,s), 5.60(1H,br d,J=9 Hz) 6.50(1H,m), 7.30(5H,s).
2(E) isomer: δppm: 0.7–1.3(15H,m), 1.3–2.0(10H,m) 2.30(2H,m), 3.10(2H,dd,J=6,6 Hz) 3.75(1H,m), 4.52(1H,dd,J=2,9 Hz) 5.04(2H,s), 5.75(1H,m), 6.00(1H,d, J=9 Hz), 7.25(5H,s).

(c) 578 mg of 3-[(4S,5S)-3-benzyloxycarbonyl-2,2-dimethyl-4-isobutyloxazolidin-5-yl]2-ethyl-2(Z,E)-propenoic acid isobutylamide was dissolved in 10 ml of methanol. A palladium black catalyst was added thereto, and hydrogen was continuously blown into it over a period of 4 hours. During the period, 0.2 ml of 1N hydrochloric acid was added seven times at intervals of about 30 minutes to maintain the reaction solution to be weakly acidic. The catalyst was removed by filtration, and the filtrate was concentrated under reduced pressure. The residue thereby obtained was dissolved in a solvent mixture of dichloromethane/benzene and azeotropically concentrated under reduced pressure for drying. Then, similar drying was conducted under a solvent mixture of dichloromethane/hexane to obtain 455 mg of (2RS,4S,5S)-5-amino-2-ethyl-4-hydroxy-7-methyloctanoic acid isobutylamide hydrochloride as white solid.

Rf: 0.52, 0.45 (chloroform/methanol/conc. aqueous ammonia=10/1/0.5).

(9) (2RS,4S,5S)-5-{L-N-[(2R or S)-3-ethylsulfonyl-2-(1-naphthylmethyl)propionyl]norleucyl}amino-2-ethyl-4-hydroxy-7-methyloctanoic acid isobutylamide 20 mg of L-N-{(2R or S)-3-ethylsulfonyl-2-(1-naphthylmethyl)propionyl}norleucine tert-butyl ester was dissolved in 0.5 ml of dichloromethane. Then, 0.5 ml of trifluoroacetic acid (hereinafter referred to simply as TFA) was added thereto, and the mixture was reacted at room temperature for one hour. Then, the reaction solution was concentrated under reduced pressure, and the resulting syrup was dissolved in benzene. This solution was concentrated under reduced pressure, and excess TFA was azeotropically evaporated and removed to finally obtain white solid. Obtained L-N-{(2R or S)-3-ethylsulfonyl-2-(1-naphthylmethyl)propionyl} norleucine was throughly dried under reduced pressure and dissolved in 0.3 ml of dry DMF. At a temperature of −20° C., 12 μl of triethylamine and 12 μl of DPPA were successively added, and the mixture was stirred. Five minutes later, 23 mg of (2RS,4S,5S)-5-amino-2-ethyl-4-hydroxy-7-methyloctanoic acid isobutylamide hydrochloride and 10 μl of triethylamine dissolved in 0.4 ml of dry DMF were added to the previous reaction solution.

The mixture was stirred at −20° C. for one hour and at 5° C. overnight and then at room temperature for 3 hours. Then, the reaction solution was diluted with 20 ml of ethyl acetate and washed sequentially with 10 ml of a 5% potassium hydrogen sulfate aqueous solution, with 10 ml of a 4% sodium hydrogen carbonate aqueous solution and with 10 ml of a saturated sodium chloride aqueous solution. The separated ethyl acetate layer was dried over anhydrous magnesium sulfate. The inorganic salt was removed by filtration, and the filtrate was concentrated under reduced pressure. The residue thereby obtained was purified by silica gel column chromatography (chloroform/methanol=40/1). The eluted fractions of the desired product were collected and concentrated, and the resulting syrup was azeotropically concentrated under an ethyl ether solution to dryness to obtain 23 mg of the above identified compound as white solid.

Rf: 0.65 (chloroform/methanol=10/1).

EXAMPLE 2

(2RS,4S,5S)-5-{L-N-[(2R or S)-3-(pyrimidin-2-yl)sulfonyl-2-(1-naphthylmethyl)propionyl]norleucyl}amino-2-ethyl-4-hydroxy-7-methyloctanoic acid isobutylamide (1) L-N-{(2R or S)-3-(pyrimidin-2-yl)thio-2-(1-naphthylmethyl)propionyl}norleucine tert-butyl ester 52 mg of L-N-{(2R or S)-2-(1-naphthylmethyl)3-p-toluenesulfonyloxypropionyl}norleucine tert-butyl ester obtained in Example 1 was dissolved in 0.5 ml of dry DMF. Separately, a suspension of a thioalkoxide (in 5 ml of dry DMF, prepared from about 80 mg of sodium hydride and 600 mg of 2-mercaptopyrimidine, and 0.5 ml of the suspension was added to the above reaction solution. The mixture was reacted at room temperature for 4 hours. Then, 1 ml of water was added, and the reaction solution was further diluted with 20 ml of ethyl acetate. The reaction solution was washed with water (10 ml×2 times) and then washed with a saturated sodium chloride aqueous solution. The organic layer was separated, dried over anhydrous magnesium sulfate and then concentrated under reduced pressure. The syrup thereby obtained was purified by silica gel column chromatography (n-hexane/ethyl acetate=3/1). The eluted fractions containing the desired product were collected, concentrated and dried to obtain 41 mg of L-N-{(2R or S)-3-(pyrimidin-2-yl)thio-2-(1-naphthylmethyl)propionyl}norleucine tert-butyl ester as syrup.

Rf: 0.22 (n-hexane/ethyl acetate=3/1).

NMR (300 MHz, CDCl$_3$).

δppm: 0.85(3H,t,J=7 Hz), 1.00–1.35(4H,m), 1.37(9H,s) 1.56(1H,m), 1.75(1H,m), 3.04(1H,m), 3.38(1H,dd,J=6,14 Hz), 3.48(2H,m), 4.36(1H,m), 6.13(1H,d,J=7.5 Hz), 6.96(1H,t,J=5 Hz), 7.3–7.5(4H,m), 7.70(dd,J=1.5,7.5 Hz), 7.83(1H,m), 8.12(1H,m), 8.45(1H,d,J=4.5 Hz).

(2) L-N-{(2R or S)-3-(pyrimidin-2-yl)sulfonyl-2-(1-naphthylmethyl)propionyl}norleucine tert-butyl ester 38 mg of L-N-{(2R or S)-3-(pyrimidin-2-yl)thio-2-(1-naphthylmethyl)propionyl}norleucine tert-butyl ester was dissolved in 1 ml of methanol. To the solution, 0.25 ml of a 30% hydrogen peroxide aqueous solution and 18 mg of sodium tungstate dihydrate were added, and the mixture was reacted at room temperature overnight. The reaction solution was diluted with 20 ml of ethyl acetate and washed sequentially with 10 ml of water and a saturated sodium chloride aqueous solution (10 ml×2 times). The organic layer was separated, dried over anhydrous magnesium sulfate, and concentrated and dried under reduced pressure to obtain 29 mg of the above identified compound as white powder.

Rf: 0.26 (n-hexane/ethyl acetate=1/1).

NMR (300 MHz, CDCl$_3$): δppm: 0.86(3H,t,J=7 Hz), 1.20–1.38(4H,m), 1.39(9H,s), 1.61(1H,m), 1.74(1H,m), 3.26(1H,m), 3.2–3.3(3H,m), 3.50(1H,dd,J=8,14 Hz), 3.72(1H,dd,J=3,15 Hz), 4.14(1H,dd,J=8,15 Hz), 4.30(1H,q,J=6 Hz), 6.08(1H,d,J=8 Hz), 7.3–7.4(3H,m), 7.5(2H,m), 7.71(1H,d,J=8 Hz), 7.82(1H,m), 7.97(1H,d,J=8 Hz), 8.63(1H,d,J=4.5 Hz).

IR (KBr, neat) νcm$^{-1}$: 3380, 2960, 2940, 1730, 1670, 1570, 1390, 1320, 1160, 1120.

(3) (2RS,4S,5S)-5-{L-N-[(2R or S)-3-(pyrimidin-2-yl)sulfonyl-2-(1-naphthylmethyl)propionyl]norleucyl-}amino-2-ethyl-4-hydroxy-7-methyloctanoic acid isobutylamide 27 mg of L-N-{(2R or S)-3-(pyrimidin-2-yl)sulfonyl-2-(1-naphthylmethyl)propionyl}norleucine tert-butyl ester was dissolved in 0.5 ml of dichloromethane. Then, 0.5 ml of TFA was added thereto, and the mixture was reacted at room temperature for 3 hours. Then, the reaction solution was concentrated under reduced pressure and the syrup thereby obtained was dissolved in benzene. The solution was concentrated under reduced pressure and excess TFA was azeotropically removed. The solution was finally evaporated to dryness to obtain white solid. L-N-{-(2R or S)-3-(pyrimidin-2-yl)sulfonyl-2-(1-naphthylmethyl)propionyl}norleucine thus obtained was throughly dried under reduced pressure and then dissolved in 0.4 ml of dry DMF. Then, 21 μl of triethylamine and 14 μl of DPPA were added sequentially at −20° C., and the mixture was stirred. Five minutes later, a solution prepared by adding 27 mg of (2RS,4S,5S)-5-amino-2-ethyl-4-hydroxy-7-methyloctanoic acid isobutylamide hydrochloride and 15 μl of triethylamine to 0.5 μl of dry DMF, was added to the previous reaction solution and the mixture was stirred at −20° C. for one hour, at 5° C. overnight and then at room temperature for 3 hours. The reaction solution was diluted with 20 ml of ethyl acetate and washed sequentially with 10 ml of a 5% potassium hydrogensulfate aqueous solution, 10 ml of a 4% sodium hydrogencarbonate aqueous solution and with 10 ml of a saturated sodium chloride aqueous solution. The ethyl acetate layer was separated and dried over anhydrous magnesium sulfate. The inorganic salt was removed by filtration, and the filtrate was concentrated under reduced pressure. The residue thereby obtained was purified by silica gel column chromatography (chloroform/methanol=40/1). The eluted fractions containing the desired product were collected and concentrated. The syrup thereby obtained was azeotropically concentrated with dichloromethane/hexane and evaporated to dryness to obtain 31 mg of the above identified compound as white solid.

Rf: 0.54 (chloroform/methanol=10/1).

NMR (300 MHz, CDCl$_3$) δppm: 2.20(0.5H,m), 2.30(0.5H,m), 3.0(1H,m), 3.12(1H,m), 3.28(2H,m), 3.5(1H,br), 3.6(1H,br), 3.7(1H,dd,J=2,14 Hz), 3.8–3.9(1H,br), 4.0–4.1(1H,m), 4.22(1H,m), 5.85(1H,br), 6.2(1H,br), 6.42(1H,br), 7.27–7.40(3H,m), 7.50(2H,m), 7.72(1H,d,J=8 Hz), 7.83(1H,m), 7.91(1H,m), 8.55(1H,t,J=4.5 Hz).

IR (KBr, neat) νcm$^{-1}$: 3300, 2960, 2870, 1650, 1560, 1470, 1390, 1320, 1220, 1130.

EXAMPLE 3

(2RS,4S,5S)-5-{L-N-[(2R or S)-3-ethylsulfonyl-2-(2,3-ethylenedioxybenzyl)propionyl]-δ-hydroxynorvalyl}amino-2-ethyl-4-hydroxy-7-methyloctanoic acid isobutylamide (1) 2,3-ethylenedioxybenzaldehyde 12.04 g of 2,3-dihydroxybenzaldehyde was dissolved in 120 ml of dry DMF. To this solution, 9.0 ml of 1.2-dibromoethane, 12.1 g of anhydrous potassium carbonate and 1.1 g of cupric oxide were added. The reaction solution was refluxed under heating for three hours on a hot water bath at 135° C. The reaction solution was diluted with 700 ml of benzene and then washed with 500 ml of water. The aqueous layer was separated and extracted with benzene (500 ml×2 times). The extracted organic layers were combined to the previously separated organic layer, the combined organic layer was dried over anhydrous magnesium sulfate. The inorganic salt was removed by filtration, and the reaction solution was concentrated under reduced pressure to obtain a brown syrup. This syrup was purified by silica gel column chromatography (n-hexane/acetone=5/1). The eluted solution was concentrated under reduced pressure, and the residue was recrystallized from n-hexane/acetone to obtain 7.0 g of the above identified compound as white crystals (melting point: 63°–64° C.) (yield: 49%). The mother solution was concentrated and dried to obtain 3.2 g of the above identified compound as crude syrup (yield: 22%).

NMR (300 MHz, CDCl$_3$): δppm: 4.31(2H,m), 4.37(2H,m), 6.89(1H,t,J=8 Hz), 7.08(1H,dd,J=1,8 Hz), 7.39(1H,dd,J=1,8 Hz), 10.35(1H,s).

(2) 2,3-ethylenedioxybenzyl alcohol 3.15 g of 2,3-ethylenedioxybenzaldehyde was dissolved in 50 ml of ethanol. Then, 1.17 g of sodium borohydride was added thereto, and the mixture was stirred at room temperature for one hour. The reaction solution was concentrated under reduced pressure and then suspended with an addition of 100 ml of ethyl acetate.

The suspension was washed with 100 ml of water and then with 100 ml of saturated sodium chloride aqueous solution. The separated ethyl acetate layer was dried over anhydrous magnesium sulfate. The inorganic salt was removed by filtration, and the filtrate was concentrated under reduced pressure and then purified by silica gel column chromatography (n-hexane/ethyl acetate=2/1) to obtain 1.78 g of the above identified compound as white solid.

Rf: 0.2 (n-hexane/ethyl acetate=2/1).

(3) 2,3-ethylenedioxybenzyl chloride 4.3 g of 2,3-ethylenedioxybenzyl alcohol was dissolved in 50 ml of dry dichloromethane. Then, 2.1 ml of dry pyridine was dropwise added thereto, and 3.8 ml of thionyl chloride was gradually added under cooling. The reaction solution was returned to room temperature and then the reaction solution was refluxed for 3 hours on a hot water bath at 60° C. The reaction solution was concentrated under reduced pressure to obtain a syrup, which was then dissolved in 300 ml of ethyl acetate. The solution was washed with 200 ml of 0.1N hydrochloric acid and then twice with 200 ml of a saturated sodium chloride aqueous solution. Then, the solution was dried over anhydrous magnesium sulfate. The inorganic salt was removed by filtration, and the filtrate was concentrated under reduced pressure and purified by silica gel column chromatography (n-hexane/ethyl acetate=60/1) to obtain 4.0 g of the above identified compound as syrup.

Rf: 0.64 (n-hexane/ethyl acetate=2/1).

(4) Diethyl (2,3-ethylenedioxybenzyl)malonate

Diethyl (2,3-ethylenedioxybenzyl)malonate was obtained from 2,3-ethylenedioxybenzyl chloride and diethyl malonate in the same manner as the preparation of diethyl (1-naphthylmethyl)malonate.

NMR (300 MHz, CDCl$_3$) $\delta$ppm: 1.21(3H,t,J=7 Hz), 3.17(2H,d,J=8 Hz) 3.82(2H,d,J=8 Hz), 4.15(4H,m), 4.26(4H,m), 6.72(3H,m).

IR (KBr) $\nu$cm$^{-1}$: 2990, 2940, 2880, 1740, 1610, 1480, 1370.

(5) Ethyl (2,3-ethylenedioxybenzyl)malonate

Ethyl (2,3-ethylenedioxybenzyl)malonate was prepared from the product of (4) in the same manner as in the preparation of ethyl (1-naphthylmethyl)malonate.

NMR (300 MHz, CDCl$_3$) $\delta$ppm: 1.20(3H,t,J=7 Hz), 3.20(2H,m), 3.85(1H,t,J=7.5 Hz), 4.15(2H,m), 4.24(4H,m), 6.72(3H,m).

IR (KBr) $\nu$cm$^{-1}$: 2990, 2940, 2880, 1740, 1610, 1480.

(6) Tert-butyl (2,3-ethylenedioxybenzyl)malonate 846 ml of ethyl (2,3-ethylenedioxybenzyl)malonate was dissolved in 20 ml of dry dichloromethane. After an addition of 0.2 ml of conc. sulfuric acid, isobutene gas was blown into the reaction solution under cooling at −78° C. and collected. After about 20 ml of isobutene was collected, the reactor was sealed. The reactor was returned to room temperature and stirred overnight. Then, the reactor was opened, and isobutene was removed by evaporation at room temperature under atmospheric pressure. The reaction solution was added to a solution mixture comprising 100 ml of a 0.5M sodium carbonate aqueous solution and 150 ml of dichloromethane. and the mixture was vigorously stirred. The organic layer was separated, washed with 100 ml of a saturated sodium chloride aqueous solution and then dried over anhydrous magnesium sulfate. The inorganic salt was removed by filtration, and the filtrate was concentrated under reduced pressure and purified by silica gel column chromatography (n-hexane/ethyl acetate=4/1) to obtain 765 mg (yield: 75%) of the above identified compound as colorless transparent syrup.

NMR (300 MHz, CDCl$_3$) $\delta$ppm: 1.23(3H,t,J=7 Hz), 1.39(9H,s), 3.13(2H,d,J=8 Hz), 3.74(1H,t,J=8 Hz), 4.15(2H,m), 4.25(4H,m), 6.72(3H,m).

IR (KBr) $\nu$cm$^{-1}$: 2990, 1730, 1480, 1370, 1310, 1280.

(7) Tert-butyl 2-(2,3-ethylenedioxybenzyl)-3-hydroxypropionate 761 mg of tert-butyl (2,3-ethylenedioxybenzyl)malonate was dissolved in 20 ml of ethanol. Then, 0.57 g of sodium borohydride was added thereto, and the mixture was stirred at room temperature overnight. The reaction solution was diluted with 150 ml of ethyl acetate and washed with 100 ml of water and then with 100 ml of a saturated sodium chloride aqueous solution. The organic layer was dried over anhydrous magnesium sulfate, then concentrated under reduced pressure and purified by silica gel column chromatography (n-hexane/ethyl acetate=3/1) to obtain 241 mg (yield: 36%) of the desired product as syrup.

NMR (300 MHz, CDCl$_3$) $\delta$ppm: 1.41(9H,s), 2.39(1H,t,J=6.5 Hz), 2.88(3H,m), 3.70(2H,m), 4.25(4H,m), 6.73(3H,m), IR (KBr) $\nu$cm$^{-1}$: 3480, 2980, 2930, 2880, 1730, 1610, 1480, 1370.

(8) Tert-butyl 2-(2,3-ethylenedioxybenzyl)-3-p-toluenesulfonyloxypropionate 238 mg of tert-butyl 2-(2,3-ethylenedioxybenzyl)-3-hydroxypropionate was dissolved in 4 ml of dry pyridine, and 170 mg of p-toluenesulfonyl chloride was added thereto. The mixture was reacted at room temperature overnight and then concentrated under reduced pressure. The residue was dissolved in 50 ml of ethyl acetate and washed sequentially with 50 ml of a 5% potassium hydrogensulfate aqueous solution, with 50 ml of a 4% sodium hydrogencarbonate aqueous solution and with 50 ml of a saturated sodium chloride aqueous solution. The organic layer was dried over anhydrous magnesium sulfate, then concentrated under reduced pressure and purified by silica gel column chromatography (n-hexane/ethyl acetate=3/1) to obtain 257 mg of tert-butyl 2-(2,3-ethylenedioxybenzyl)-3-p-toluenesulfonyloxypropionate as colorless transparent syrup.

NMR (300 MHz, CDCl$_3$) $\delta$ppm: 1.32(9H,s), 2.45(3H,s), 2.78(2H,m), 3.02(1H,m), 4.11(2H,m), 4.22(4H,m), 6.55(1H,dd,J=8,1 Hz), 6.68(1H,t,J=8 Hz), 6.74(1H,dd,J=8,1 Hz), 7.32(2H,d,J=8 Hz), 7.75(2H,d,J=8 Hz).

(9) Tert-butyl 3-ethylsulfonyl-2-(2,3-ethylenedioxybenzyl)propionate 87 mg of the tosyl compound obtained in the above step (8) was dissolved in 0.5 ml of dry DMF, and a suspension comprising 27 mg of sodium hydride, 65 $\mu$l of ethylmercaptan and 0.5 ml of dry DMF was added thereto. The mixture was stirred at room temperature for one hour, and then 1 ml of water was added to the reaction solution. After an addition of 20 ml of benzene, the reaction solution was washed sequentially with water (10 ml×2 times) and with 10 ml of a saturated sodium chloride aqueous solution. The organic layer was dried over anhydrous magnesium sulfate and concentrated under reduced pressure to obtain 58 mg of a syrup. Then, the syrup was dissolved in 2.5 ml of methanol, and 0.25 ml of a 30% hydrogen peroxide aqueous solution and 14 mg of sodium tungstate dihydrate were added thereto. The mixture was stirred vigorously at room temperature for one hour. The reaction solution was diluted with 20 ml of benzene and washed with 10 ml of water and then 10 ml of a saturated sodium chloride aqueous solution. The organic layer was dried over anhydrous magnesium sulfate and then concentrated under reduced pressure to obtain 57 mg (yield: 79%) of the syrup of the above identified compound.

NMR (300 MHz, CDCl₃): δppm: 1.33(3H,t,J=8 Hz), 1.37(9H,s), 2.8–3.0(5H,m), 3.39(1H,m), 3.55(1H,dd,J=14,10 Hz), 4.28(4H,m), 6.65(dd,J=8,1 Hz), 6.76(1H,t,J=8 Hz) 6.79(1H,dd,J=8,1 Hz).

(10) L-O-acetyl-N-[3-ethylsulfonyl-2-(2,3-ethylenedioxybenzyl)propionyl]-δ-hydroxynorvaline tert-butyl ester Tert-butyl 3-ethylsulfonyl-2-(2,3-ethylenedioxybenzyl)propionate was dissolved in 1.2 ml of a dichloromethane/TFA (1/1) solution. The solution was stirred at room temperature for 3 hours and then concentrated under reduced pressure. The residue was dissolved in benzene, and the benzene solution was concentrated under reduced pressure and azeotropically dried. The syrup thereby obtained was subjected to condensation reaction with L-O-acetyl-δ-hydroxynorvaline tert-butyl ester by using a DPPA method (18 μl of triethylamine, 12 μl of DPPA and 2 ml of dry DMF), and the reaction mixture was purified by silica gel column chromatography to obtain 26 mg (yield: 34%) of a diastereomer of a polar component and 36 mg (yield: 47%) of a diastereomer of a less-polar component, respectively, as syrups.

Polar component

NMR δppm: 1.32(3H,t,J=8 Hz), 1.45(9H,s), 2.05(3H,s), 2.78(1H,dd,J=14,9 Hz), 2.85–3.0(4H,m), 3.26(1H,m), 3.67(1H,dd,J=14,10 Hz), 4.05(2H,t,J=7 Hz), 4.2–4.4(5H,m), 6.29(1H,d,J=8 Hz), 6.6(1H,dd,J=8,1 Hz), 6.72(1H,t,J=8 Hz), 6.77(1H,dd,J=8,1 Hz).

IR (KBr) νcm⁻¹: 3370, 2980, 2940, 1740, 1680, 1540, 1480, 1460, 1400, 1370.

Less-polar component

NMR δppm: 1.32(3H,t,J=8 Hz), 1.45(9H,s), 2.05(3H,s), 2.8–3.0(5H,m), 3.30(1H,m), 3.67(1H,dd,J=14,10 Hz), 3.93(2H,t,J=6.5 Hz), 4.25–4.4(5H,m), 6.26(1H,d,J=8 Hz), 6.62(1H,dd,J=8,1 Hz), 6.73(1H,t,J=8 Hz), 6.78(1H,dd,J=8,1 Hz).

IR (KBr) νcm⁻¹: 3360, 2980, 2940, 1740, 1680, 1540, 1480, 1460, 1400, 1370.

(11) (2RS,4S,5S)-5-{L-N-[(2R or S)-3-ethylsulfonyl-2-(2,3-ethylenedioxybenzyl)propionyl]δ-hydroxynorvalyl}amino-2-ethyl-4-hydroxy-7-methyloctanoic acid isobutylamide 34 mg of the less-polar component obtained in the above step (10) was subjected to ester-removal in a solution mixture of dichloromethane/TFA in a usual method and then condensed with 24 mg of (2RS,4S,5S)-5-amino-2-ethyl-4-hydroxy-7-methyloctanoic acid isobutylamide by a DPPA method. The product was purified by column chromatography to obtain 50 mg of a condensed product, which was dissolved in 1.5 ml of ethanol/water (10/1), and 0.8 ml of a 2N potassium hydroxide solution (ethanol/water=10/1) was added for deacetylation. One hour later, the reaction solution was neutralized and extracted with ethyl acetate. The extract was washed with a saturated sodium chloride aqueous solution and purified by silica gel column chromatography and dried to obtain 23 mg of the above identified compound as white solid.

Rf: 0.33 (chloroform/methanol=10/1).

(12) (2RS,4S,5S)-5-{L-N-[(2S or R)-3-ethylsulfonyl-2-(2,3-ethylenedioxybenzyl)propionyl]-ε-hydroxynorvalyl}-amino-2-ethyl-4-hydroxy-7-methyloctanoic acid isobutylamide 24 mg of the polar component obtained in the above step (10) was treated in the same manner as in step (11) to obtain 10 mg of the above identified compound as a stereoisomer of the compound obtained in step (11).

Rf: 0.33 (chloroform/methanol=10/1).

EXAMPLE 4

(2S,4S,5S)-5-{L-N-[(2R or S)-3-(1-methyltetrazol-5-yl)sulfonyl-2-(1-naphthylmethyl)propionyl]norleucyl}amino-2-ethyl-4-hydroxy-7-methyloctanoic acid isobutylamide (a) 40 mg of L-N-[(2R or S)-2-(1-naphthylmethyl)-3-p-toluenesulfonyloxypropionyl]norleucine tert-butyl ester obtained in Example 1-(5) was dissolved in 0.5 ml of dry DMF. Then, 20 mg of 1-methyl-5-mercaptotetrazol sodium was added thereto, and the mixture was reacted at room temperature overnight. The reaction solution was diluted with 15 ml of ethyl acetate and washed with water (10 ml) and a saturated sodium chloride aqueous solution (10 ml×2 times). The organic layer was separated, dried over anhydrous sodium sulfate and then concentrated under reduced pressure to 36 mg of L-N-[(2R or S)-3-(1-methyltetrazol-5-yl)thio-2-(1-naphthylmethyl)propionyl]-norleucine tert-butyl ester as syrup.

Rf: 0.79 (n-hexane/ethyl acetate=1/1).

(b) 36 mg of L-N-[(2R or S)-3-(1-methyltetrazol-5-yl)thio-2-(1-naphthylmethyl)propionyl]norleucine tert-butyl ester was dissolved in 1.2 ml of methanol. Then, 0.3 ml of a 30% hydrogen peroxide aqueous solution and 20 mg of sodium tungstate dihydrate were added thereto. The reaction solution was stirred at room temperature for two hours. Then, the reaction solution was diluted with 15 ml of ethyl acetate and then washed sequentially with 10 ml of water and with 10 ml of a saturated sodium chloride aqueous solution. The organic layer was separated and dried over anhydrous magnesium sulfate. The inorganic salt was removed by filtration, and the filtrate was concentrated under reduced pressure to obtain 34 mg of L-N-[(2R or S)-3-(1-methyltetrazol-5-yl)sulfonyl-2-(1-naphthylmethyl)propionyl]norleucine tert-butyl ester as syrup.

Rf: 0.70 (n-hexane/ethyl acetate=1/1).

NMR (300 MHz, CDCl₃) δppm: 0.85(3H,t,J=7 Hz), 1.02–1.40(13H,m), 1.55(1H,m), 1.70(1H,m), 3.35(1H,m), 3.45(2H,m), 3.74(1H,dd,J=3,15 Hz), 4.17(1H,m), 4.24(3H,s), 4.33(1H,dd,J=8,15 Hz), 5.81(1H,d,J=8 Hz), 7.30(1H,d,J=8 Hz), 7.38(1H,t,J=8 Hz), 7.55(2H,m), 7.76(1H,d,J=8 Hz), 7.87(1H,d,J=8 Hz), 8.01(1H,d,J=8 Hz).

IR (KBr, neat) νcm⁻¹: 3350, 2970, 2940, 2870, 1740, 1670, 1530, 1460, 1400, 1370, 1350, 1250, 1220, 1140.

(c) 32 mg of L-N-[(2R or S)-3-(1-methyltetrazol-5-yl)sulfonyl-2-(1-naphthylmethyl)propionyl]norleucine tert-butyl ester was dissolved in 0.7 ml of dichloromethane. Then, 0.5 ml of TFA was added thereto, and the mixture was reacted at room temperature for one hour. Then, the reaction solution was concentrated under reduced pressure. The syrup thereby obtained was sequentially dissolved in benzene and benzene/n-hexane and then subjected to azeotropic concentration under reduced pressure to obtain a slightly yellow powder. L-N-[(2R or S)-3-(1-methyltetrazol-5-yl)sulfonyl-2-(1- naphthylmethyl)propionyl]norleucine thus obtained was throughly dried under reduced pressure and then dissolved in 0.5 ml of dry DMF. Then, 21 μl of triethylamine and 17 μl of DPPA were sequentially added thereto at −20° C., and the mixture was stirred. Five minutes later, a solution mixture comprising 22 mg of (2RS,4S,5S)-5-amino-2-ethyl-4-hydroxy-7-methyloctanoic acid isobutylamide hydrochloride, 22 μl of triethylamine and 8.5 ml of dry DMF, was added to the reaction solution, and the mixture was stirred at −20° C. for one hour and at 5° C. overnight. The reaction solution thereby obtained was diluted with 20 ml of ethyl acetate and washed sequentially with 10 ml of a 2% sodium hydrogencarbonate aqueous solution and with 10 ml of a saturated sodium chloride aqueous solution. The ethyl acetate layer was separated and dried over anhydrous sodium sulfate. Then, the inorganic salt was removed by filtration, and the filtrate was concentrated under reduced pressure. The residue thereby obtained was purified by silica gel column chromatography (chloroform/methanol=10/1). The eluted fractions containing the desired product were collected and concentrated. The residue was reprecipitated in an ethyl ether/pentane solution to obtain 33 mg of (2S,4S,5S)-5-{L-N-[(2R or S)-3-(1-methyltetrazol-5-yl)sulfonyl-2-(1-naphthylmethyl)propionyl]norleucil}-amino-2-ethyl-4-hydroxy-7-methyloctanoic acid isobutylamide as white solid.

Rf: 0.64, 0.59 (chloroform/methanol=10/1).

NMR (300 MHz, CDCl$_3$) δppm: 2.18(0.5H,m), 2.29(0.5H,m), 3.03(1H,m), 4.20 (3H,s), 4.28(1H,m), 5.79(0.5H,br t), 5.83(0.5H,br t), 5,98(0.5H,d,J=8 Hz), 6.02(0.5H,d,J=8 Hz), 6.15(0.5H,d,J=8 Hz), 6.22(0.5H,d,J=8 Hz), 7.31(1H,d,J=8 Hz), 7.38(1H,t,J=8 Hz), 7.55(2H,m), 7.78(1H,d,J=8 Hz), 7.87(1H,d,J=8 Hz), 7.99(1H,d,J=8 Hz).

IR (KBr) νcm$^{-1}$: 3320, 2960, 1650, 1550, 1470, 1340, 1140.

EXAMPLE 5

(2RS,4S,5S)-5-{L-N-[2S)-3-(1,3,4-thiadiazol-2-yl)thio-2-(1-naphthylmethyl)propionyl]norleucyl}amino-2-ethyl-4-hydroxyl-7-methyloctanoic acid isobutylamide (1) L-N-{(2S)-3-(1,3,4-thiadiazol-2-yl)thio-2-(1-naphthylmethyl)propionyl}norleucine tert-butyl ester 37 mg of L-N-{(2R)-(1-naphthylmethyl)-3-p-toluenesulfonyloxypropionyl}norleucine tert-butyl ester was dissloved in 0.5 ml of dry DMF. Then, a solution comprising 21 mg of sodium hydride, 85 mg of 2-mercapto-1,3,4-thiadiazol and 0.8 ml of dry DMF was prepared and added to the above solution. The mixture was reacted at room temperature overnight. Then, the reaction solution was diluted with 20 ml of ethyl acetate and washed sequentially with 20 ml of water and with 10 ml of a saturated sodium chloride aqueous solution. The organic layer was separated, dried over anhydrous sodium sulfate and then concentrated under reduced pressure. The residue was purified by silica gel column chromatography (n-hexane/ethyl acetate=2/1) to obtain 42 mg of the above identified compound as syrup.

NMR (300 MHz, CDCl$_3$) δ ppm: 0.84(3H,t,J=8.5 Hz), 1.1–1.4 (4H,m) 1.4–1.8(2H,m), 3.24(1H,m), 3.4–3.5(2H,m), 3.69(2H,m), 7.34(2H,d,J=7 Hz), 7.46(2H,dt,J=7,1 Hz), 7.53(2H,dt,J=7,1 Hz), 7.70(1H,m), 7.82(1H,dd,J=8,1 Hz), 8.07(1H,dd,J=8,1 Hz), 9.01(1H,s).

(2) (2RS,4S,5S)-5-{L-N-[(2S)-3-(1,3,4-thiadiazol-2-yl)thio-2-(1-naphthylmethyl)propionyl]norleucyl}amino-2-ethyl-4-hydroxy-7-methyloctanoic acid isobutylamide 40 mg of L-N-{(2S)-3-(1,3,4-thiadiazol-2-yl)thio(1-naphthylmethyl)propionyl}norleucine tert-butyl ester obtained in step (1) was deprotected in a solution mixture comprising 0.5 ml of dichloromethane and 0.5 ml of TFA. The reaction mixture was concentrated under reduced pressure, and the product was adsorbed on a resin of DEAE TOYO Pearl 650 mesh (OH$^-$) by a methanol/water (10/1) solution and then eluted with a 0.2N acetic acid solution (methanol/water=10/1). The eluted fractions containing the desired product were collected and concentrated under reduced pressure. The residual syrup was dissolved in 10 ml of ethyl acetate and then washed with a saturated sodium chloride aqueous solution (8 ml×2 times). The organic layer was separated, dried over anhydrous sodium sulfate and concentrated under reduced pressure to obtain 22 mg of solid L-N-[(2S)-3-(1,3,4-thiadiazol-2-yl)thio-2-(1-naphthylmethyl)propionyl]norleucine. This is condensed with (2RS,4S,5S)-5-amino-2-ethyl-4-hydroxy-7-methyloctanoic acid isobutylamide by a usual DPPA method. The product was purified by silica gel column chromatography (chloroform/methanol×40/1) to obtain 21 mg of the above identified compound.

Rf: 0.15 (chloroform/methanol×30/1).

EXAMPLE 6

(2RS,4S,5S)-5-{L-N-[(2S)-3-(pyrimidin-2-yl)thio-2-(1-naphthylmethyl)propionyl]norleucyl}amino-2-ethyl-4-hydroxy-7-methyloctanoic acid isobutylamide 22 mg of L-N-{(2S)-3-(pyrimidin-2-yl)thio-2-(1-naphthylmethyl)propionyl}norleucine tert-butyl ester was dissolved in 1 ml of a dichloromethane/TFA (1/1) solution. Three hours later, the solution was concentrated under reduced pressure and then azeotropically concentrated with a benzene solution and evaporated to dryness. The product is condensed by a DPPA method (triethylamine 18 μl, DPPA 12 μl, (2RS,4S,5S)-5-amino-2-ethyl-4-hydroxy-7-methyloctanoic acid isobutylamide 18 mg, dry DMF 2 ml). The product was subjected to work up by a usual method and purified by silica gel column chromatography (chloroform/methanol=40/1) to obtain 24 mg of the above identified compound as slightly yellow solid.

Rf: 0.33 (chloroform/methanol=30/1).

EXAMPLE 7

(2RS,4S,5S)-5-{L-N-[(2S)-3-(pyrimidin-2-yl)sulfinyl-2-(1-naphthylmethyl)propionyl]norleucyl}amino-2-ethyl-4-hydroxy-7-methyloctanoic acid isobutylamide (1) L-N-{(2S)-3-(pyrimidin-2-yl)sulfinyl-2-(1-naphthylmethyl)propionyl}norleucine tert-butyl ester 29 mg of L-N-{(2S)-3-(pyrimidin-2-yl)thio-2-(1-naphthylmethyl)propionyl}norleucine tert-butyl ester was dissolved in a solution mixture comprising 1 ml of methanol and 0.1 ml of a 30% hydrogen peroxide aqueous solution. Then, 2 mg of sodium tungstate dihydrate was added thereto, and the mixture was stirred at room temperature for 3 hours. The reaction solution was diluted with 20 ml of ethyl acetate and washed with 10 ml of water and then with 10 ml of a saturated sodium chloride aqueous solution. The ethyl acetate layer was separated, dried over anhydrous sodium sulfate and then concentrated under reduced pressure. The residue was purified by silica gel column chromatography (n- hexane/ethyl acetate=1/1-½) to obtain 8 mg of the above identified compound i.e. a sulfinyl compound in addition to 12 mg of sulfone compound.

Rf: 0.14 (n-hexane/ethyl acetate=1/1).

NMR spectrum (300 MHz, CDCl₃) δ ppm: 0.83(1H,t,J=7.5 Hz), 0.89(2H,t,J=7.5 Hz).

(2) (2RS,4S,5S)-5-{L-N-[(2S)-3-(pyrimidin-2-yl)sulfinyl-2-(1-naphthylmethyl)propionyl]norleucyl}amino-2-ethyl-4-hydroxy-7-methyloctanoic acid isobutylamide 8 mg of the compound obtained in step (1) was dissolved in 0.2 ml of dichloromethane, and 0.35 ml of TFA was added thereto. After 1.5 hours at room temperature, the mixture was concentrated under reduced pressure. The residue was dissolved in benzene/pentane solution and concentrated under reduced pressure to dryness. The residue was dissolved in 0.5 ml of dry DMF and cooled to −15° C., and then 5 μl of triethylamine, 6 μl of DPPA and a solution in dry DMF (0.3 ml) of 7 mg of (2RS,4S,5S)-5-amino-2-ethyl-4-hydroxy-7-methyloctanoic acid isobutylamide and 4 μl of triethylamine, were sequentially added. The mixture was stirred at −15° C. for one hour and then at 5° C. overnight. Then, the mixture was diluted with 20 ml of ethyl acetate and washed sequentially with 10 ml of a 4% sodium hydrogen carbonate aqueous solution with 10 ml of a saturated sodium chloride aqueous solution. The organic layer was separated, dried over anhydrous sodium sulfate and then concentrated under reduced pressure. The residue was purified by silica gel column chromatography (chloroform/methanol=30/1) to obtain 7.1 mg of the above identified compound.

Rf: 0.13, 0.17 (chloroform/methanol=30/1).

NMR (300 MHz, CDCl₃) δppm: 0.8-1.0(18H,m), 1.0-2.0(14H,m), 2.25(1H,m), 3.8-4.3(11H).

EXAMPLE 8

(2R or S,4S,5S)-5-{L-N-[(2R or S)-3-ethylsulfonyl-2-(1-naphthylmethyl)propionyl]norleucyl}amino-2-ethyl-4-hydroxy-7-methyloctanoic acid 2-morpholinoethylamide 41.1 mg of L-N-(3-ethylsulfonyl-2-naphthylmethylpropionyl)norleucine was dissolved in 0.25 ml of dry DMF. Then, 52 μl of triethylamine, 26 μl of DPPA and 0.5 ml of a solution in dry DMF of 49 mg of (2RS,4S,5S)-5-amino-2-ethyl-4-hydroxyoctanoic acid 2-morpholinoethylamide dihydrochloride were added thereto under stirring at −15° C. The mixture was stirred at room temperature overnight. Then, 20 ml of ethyl acetate was added to the reaction solution, and the mixture was washed with water and a saturated sodium chloride aqueous solution. The organic layer was separated and dried over anhydrous magnesium sulfate. Then, the solvent was distilled off under reduced pressure, and the residue was purified by silica gel column chromatography (chloroform/methanol=30/1) to obtain 20.2 mg of the above identified compound as white powder.

Rf: 0.10 (chloroform/methanol=30/1).

Mass spectrum m/z 731(M⁺+1).

NMR (300 MHz, CDCl₃) δppm: 0.83-1.02(12H,m), 1.19-1.94(14H,m), 2.18-2.59(7H,m), 2.72-2.90(2H,m), 3.00(1H,d,J=14 Hz), 3.25-3.92(12H,m), 4.21(1H,ddd,J=4.7,13 Hz), 6.05-6.20(2H,m) 6.28-6.35(1H,m), 7.32-7.46(2H,m), 7.49-7.64(2H,m), 7.78(1H,d,J=8 Hz), 7.88(1H,d,J=8 Hz), 8.03(1H,d,J=8 Hz).

EXAMPLE 9

(2RS,4S,5S)-5-{L-N-[(2S)-3-ethylsulfonyl-2-(4-quinolylmethyl)propionyl]norleucyl}amino-2-ethyl-4-hydroxy-7-methyloctanoic acid isobutylamide (1) Ethyl 2-diethylphosphono-3-(4-quinolyl)propionate 1.2 g of sodium hydride was suspended in 30 ml of dry DMF, and 5.9 ml of ethyl diethylphosphonoacetate was dropwise added thereto under cooling with ice. The mixture was stirred at room temperature for one hour, and 12 ml of a solution in dry DMF of 5.31 g of (4-chloromethyl)quinoline was added under cooling with ice. Ten minutes later, the reaction solution was returned to room temperature and stirred overnight. Then, the reaction solution was acidified by an addition of 200 ml of 0.5N hydrochloric acid and washed with 200 ml of ethyl acetate. The aqueous layer was separated and made basic by an addition of about 20 g of sodium hydrogen carbonate. The product was extracted with 300 ml of ethyl acetate. The ethyl acetate layer was washed with 200 ml of a saturated sodium chloride aqueous solution, dried over anhydrous sodium sulfate and concentrated under reduced pressure. The residue was purified by silica gel column chromatography (ethyl acetate) and dried under reduced pressure to obtain 6.41 g (yield: 59%) of the above identified compound as yellow syrup.

NMR (300 MHz, CDCl₃) δppm: 1.13(3H,t,J=7.0 Hz), 1.38(3H,t,J=7.1 Hz), 1.40(3H,t,J=7.2 Hz), 3.40(ddd,J=23.0,10.9,3.6 Hz), 3.65(1H,m), 3.76(1H,m), 4.10(2H,m), 4.24(4H,m), 7.27(1H,d,J=4.9 Hz), 7.61(ddd,J=8.5,7.0,1.6 Hz), 7.73(ddd,J=8.3,6.9,1.5), 8.07(1H,dd,J=8.6,1.0), 8.12(1H,dd,J=8.6,1.0 Hz), 8.80(1H,d,J=4.4 Hz).

(2) Ethyl 2-(4-quinolylmethyl)acrylate 140 mg of anhydrous lithium chloride was dissolved in 7 ml of dry THF, and 3 ml of a THF solution of 1.04 g of ethyl 2-diethylphosphono-3-(4-quinolyl)propionate was added thereto. Then, 1.7 ml of DBU/THF (12/25) was added, and then a 3 ml of a THF solution of 0.14 g of paraformaldehyde was added thereto. The mixture was stirred at room temperature for one hour, and then the insoluble materials were removed by filtration. The product collected by filtration was washed with a small amount of benzene, and the washed solution was combined with the filtrate. The combined filtrate was diluted with 60 ml of ethyl acetate and washed with 40 ml of water and then with 40 ml of a saturated sodium chloride aqueous solution. The organic layer was separated, dried over anhydrous sodium sulfate, concentrated and then purified by silica gel column chromatography (n-hexane/ethyl acetate=3/1) to obtain 601 mg of the above identified compound as syrup.

NMR (300 MHz, CDCl₃) δ ppm: 1.29(3H,t,J=7.2 Hz), 4.11(2H,s), 4.24(2H,q,J=7.1 Hz), 5.32(1H,s), 6.32(1H,s), 7.24(1H,d,J=4.3 Hz), 7.55(1H,ddd,J=8.3,6.8,1.5 Hz), 7.71(1H,ddd,J=8.3,6.8,1.5 Hz) 7.97(1H,dd,J=8.7,1.6 Hz), 8.13(1H,dd,J=7.9,0.7 Hz), 8.84(1H,d,J=4.3 Hz).

(3) 3-Ethylthio-2-(4-quinolylmethyl)propionic acid 597 mg of ethyl 2-(4-quinolylmethyl)acrylate was dissolved in 3 ml of ethylmercaptan. Then, 50 mg of potassium tert-butoxide was added thereto, and the mixture was stirred at room temperature for two hours. Then, the reaction solution was diluted with 60 ml of ethyl acetate and washed with 40 ml of water and then with 40 ml of a saturated sodium chloride aqueous solution. The organic layer was separated, dried over anhydrous magnesium sulfate and then concentrated under reduced pressure. The residual syrup was purified by silica gel column chromatography (n-hexane/ethyl acetate=5/2) and dried to obtain 640 mg (yield: 85%) of the desired product as syrup.

Rf: 0.47 (n-hexane/ethyl acetate=1/1).

NMR (300 MHz, CDCl$_3$) δppm: 1.10(3H,t,J=7.3 Hz), 1.25(3H,t,J=7.3 Hz), 2.56(2H,q,J=7.5 Hz), 2.74(1H,dd,J=13.0,7.0 Hz), 2.91(1H,dd,J=13.2,7.2 Hz), 3.04(1H,m), 3.39(1H,dd,J=13.9,8.5 Hz), 3.51(1H,dd,J=13.9,5.9 Hz), 4.05(2H,m), 7.26(1H,d,J=4.4 Hz), 7.59(1.5H,ddd,J=8.4,6.9 Hz), 7.72(ddd,J=8.3,6.9,1.4 Hz), 8.09(1H,dd,J=8.7,1.4 Hz), 8.12(1H,dd,J=9.7,0.9 Hz), 8.80(1H,d,J=4.4 Hz).

Then, this product was saponified by using 12 ml of a 1N potassium hydroxide in ethanol/water (10/1). The reaction mixture was left at room temperature for 3 hours and then concentrated at room temperature to a volume of from 2 to 3 ml. The mixture was diluted with 35 ml of water and washed with 40 ml of ethyl ether. The aqueous layer was separated and neutralized by an addition of about 10 ml of 1N hydrochloric acid, and then 5 g of sodium chloride was added thereto. The aqueous layer was extracted four times with 40 ml of ethyl acetate/ethanol (10/1), and the extract was dried over anhydrous magnesium sulfate. The inorganic salt was removed by filtration, and the filtrate was concentrated under reduced pressure to obtain 502 mg (yield: 54%) of the above identified compound as white crystals.

Melting point: 168°–170° C.

(4) L-N-[(2R or S)-3-ethylthio-2-(4-quinolylmethyl)-propionyl]norleucine tert-butyl ester 255 mg of 3-ethylthio-2-(4-quinolylmethyl)-propionic acid was subjected to a condensation reaction with 0.19 ml (1.5 eq) of triethylamine, 0.26 ml (1.3 eq) of DPPA and 248 mg of L-norleucine tert-butyl ester in 4 ml of dry DMF. The product was subjected to a usual after treatment and the purified by silica gel column chromatography (n-hexane/ethyl acetate=2/1) to obtain 189 mg (yield: 46%) of a diastereomer (polar component) and 188 mg (yield: 46%) of a diastereomer (less-polar component), respectively, as syrups.

NMR (300 MHz, CDCl$_3$).

Polar component: δppm: 2.54(2H,m), 2.72(2H,m), 2.93(1H,dd,J=14.2, 9.5 Hz), 3.41(2H,m), 4.34(1H,m), 5.89(1H,d,J=7.5 Hz).

Less-polar component: δppm: 2.59(2H,q,J=7.0 Hz), 2.71(1H,m), 2.79(1H,dd,J=13.1,7.2), 2.97(1H,dd,J=12.8,6.9 Hz), 3.33(1H,dd,J=13.2,9.8 Hz), 3.55(1H,dd,J=13.6,4.3 Hz), 4.34(1H,m), 5.74(1H,d,J=7.5 Hz).

(5) (2RS,4S,5S)-5-{L-N-[(2S)-3-ethylsulfonyl-2-(4-quinolylmethyl)propionyl]norleucyl}amino-2-ethyl-4-hydroxy-7-methyloctanoic acid isobutylamide 86 mg of L-N-[(2S)-3-ethylthio-2-(4-quinolylmethyl)-propionyl]norleucine obtained as the polar component in step (4) was oxidized with a hydrogen peroxide aqueous solution/sodium tungstate in a usual manner to obtain 88 mg of L-N-[(2S)-3-ethylsulphonyl-2-(4-quinolylmethyl)propionyl]norleucine tert-butyl ester. This was deprotected with a dichloromethane/TFA solution in a usual manner and condensed with (2SR,4S,5S)-5-amino-2-ethyl-4-hydroxy-7-methyloctanoic acid isobutylamide by a usual DPPA method to obtain 39 mg of the above identified compound.

Rf: 0.48 (chloroform/methanol=10/1).

EXAMPLE 10

(2RS,4S,5S)-5-{L-N-[(2S)-3-ethylsulfonyl-2-(8-quinolylmethyl)propionyl]norleucy}amino-2-ethyl-4-hydroxy-7-methyloctanoic acid isobutylamide (1) 3-ethylthio-2-(8-quinolylmethyl)propionic acid In the same manner as in Example 9 (1) to (3), the above identified compound was obtained from ethyl 2-diethylphosphono-3-(8-quinolyl)propionate by the Horner-Emmons reaction with formalin, followed by the Michael addition reaction with ethylmercaptane and the saponification by means of potassium hydroxide.

Melting point: 143°–145° C.

NMR (300 MHz, CDCl$_3$) δppm: 1.16(3H,t,J=7.5 Hz), 2.41(2H,m), 2.83(1H,dd,J=9.1 Hz), 2.96(1H,m), 3.15(1H,dd,J=5.4,12.4 Hz), 3.22(1H,dd,J=4.7,14.9 Hz), 3.87(1H,dd,J=4.2,14.6 Hz), 7.59(2H,m), 7.83(2H,m), 8.38(1H,dd,J=1.1,8.5 Hz), 8.92(1H,dd,J=1.7,4.7 Hz).

(2) N-[3-ethylsulfonyl-2-(8-quinolylmethyl)propionylnorleucine tert-butyl ester 114 mg of 3-ethylthio-2-(8-quinolylmethyl)propionic acid obtained in step (1) was condensed with norleucine tert-butyl ester by a usual DPPA method. The product was purified by silica gel column chromatography to obtain 149 mg of a condensed product (yield: 81%). Then, it was subjected to oxidation with a hydrogen peroxide aqueous solution/sodium tungstate in a usual manner, and the product was separated and purified by silica gel column chromatography (n-hexane/ethyl acetate=1/1) to obtain 79 mg (yield: 50%) of a polar diastereoisomer and 68 mg (yield: 43%) of a less-polar diastereoisomer, respectively, as syrups.

NMR

Less-polar component: δppm: 2.83–3.03(3H,m), 3.22(1H,dd,J=7.3,13.0 Hz), 3.60(1H,m), 3.71(1H,m), 3.87(1H,dd,J=9.7,14.5 Hz), 4.32(1H,m)

Polar component: δppm: 2.8–3.0(3H,m), 3.08(1H,dd,J=8.7,13.2 Hz), 3.53(1H,br), 3.88(dd,J=10.2,14.7 Hz), 3.91(1H,m), 4.42(1H,m)

(3) (2RS,4S,5S)-5-{L-N-[(2S)-3-ethylsulfonyl-2-(8-quinolylmethyl)propionyl]norleucyl}amino-2-ethyl-4-hydroxy-7-methyloctanoic acid isobutylamide 19 mg of the polar diastereoisomer obtained in step (2) was dissolved in 0.5 ml of dichloromethane and 0.7 ml of TFA, and the solution was reacted at room temperature for 5 hours. Then, the reaction mixture was concentrated under reduced pressure. The residue thereby obtained was dissolved in dichloromethane, benzene and n-pentane and concentrated under reduced pressure and azeotropically dried to obtain 21 mg of a solid. This product was condensed with (2RS,4S,5S)-5-amino-2-ethyl-4-hydroxy-7-methyloctanoic acid isobutylamide by a usual DPPA method. The product was purified by silica gel column chromatography (chloroform/methanol=30/1) to obtain 10 mg of the above identified compound as solid.

Rf: 0.54 (chloroform/methanol=10/1).

(4) (2RS, 4S, 5S)-5-{L-N-[(2R)-3-ethylsulfonyl-2-(8-quinolylmethyl)propionyl]norleucyl}amino-2-ethyl-4-hydroxy-7-methyloctanoic acid isobutylamide 21 mg of the less-polar diastereoisomer obtained in step (2) was treated in the same manner as in step (3), and after the tert-butyl group was deprotected, subjected to the condensation reaction by a DPPA method.

The product was purified by silica gel column chromatography to obtain 15 mg of the above identified compound as white solid, which is the stero isomer of the compound obtained in step (3).

Rf: 0.49 (chloroform/methanol=10/1).

EXAMPLE 11

(2SR, 4S, 5S)-5-{L-N$^\alpha$-[2(S)-3-ethylsulfonyl-2-(8-quinolylmethyl)propionyl]histidyl}amino-2-ethyl-4-hydroxy-7-methyloctanoic acid isobutylamide (1) L-N$^\alpha$-tert-butoxycarbonyl-N$^{im}$-triphenylmethylhistidine methyl ester 1.43 g of L-N$^\alpha$-tert-butoxycarbonylhistidine methyl ester was dissolved in 15 ml of dry dichloromethane. Then, 1.8 g of triphenylmethyl chloride was added thereto, and 0.18 ml of triethylamine was further added thereto. The mixture was stirred at room temperature for 30 minutes, and the reaction solution was diluted with 150 ml of chloroform. The reaction solution was washed with 100 ml of water and then dried over anhydrous sodium sulfate. The inorganic salt was removed by filtration, and the filtrate was concentrated under reduced pressure and purified by silica gel column chromatography (chloroform/methanol=30/1) to obtain 2.6 g (yield: 89%) of the above identified compound as white solid.

Rf: 0.31 (chloroform/methanol=30/1)

(2) L-N$^{im}$-triphenylmethylhistidine methyl ester 1.2 g of L-N$^\alpha$-tert-butoxycarbonyl-N$^{im}$-triphenylmethylhistidine methyl ester was dissolved in 4 ml of dichloromethane. Then, 4 ml of TFA was added thereto, and the mixture was left to stand at room temperature for 15 minutes and then immediately diluted by an addition of 50 ml of benzene. The mixture was quickly concentrated under reduced pressure. The residue was concentrated under reduced pressure in the benzene/hexane solution and was azeotropically removed excess TFA. The residue was dissolved in 100 ml of ethyl acetate and washed sequentially with 100 ml of a 4% sodium hydrogen carbonate aqueous solution and with 100 ml of a saturated sodium chloride aqueous solution. The organic layer was dried over anhydrous sodium sulfate. The reaction solution was concentrated under reduced pressure, and the residue was purified by silica gel column chromatography (chloroform/methanol/conc. aqueous ammonia=400/15/0.4). The eluted fractions containing the desired product were collected and dried over anhydrous magnesium sulfate. The inorganic salt was removed by filtration, and the filtrate was concentrated under reduced pressure to obtain 474 mg (yield: 49%) of the desired product as white solid.

Rf: 0.59 (chloroform/methanol/conc. aqueous ammonia=10/0.5/0.2).

NMR (300 MHz, CDCl$_3$) δppm: 2.87(1H,dd,J=14,7 Hz), 2.99(1H,dd,J=14,6 Hz), 6.59(1H,s), 7.12(6H,m), 7.33(9H,m), 7.37(1H,s).

(3) L-N$^\alpha$-[3-ethylthio-2-(8-quinolylmethyl)propionyl]N$^{im}$-triphenylmethylhistidine methyl ester 69 mg of 3-ethylthio-2-(8-quinolylmethyl)propionic acid obtained in Example 10 (1) and 113 mg of L-N$^{im}$-tirphenylmethylhistidine methyl ester obtained in step (2) of this Example were condensed by a DPPA method (52 μl of triethylamine, 65 μl of DPPA and 2.6 ml of dry DMF). The product was purified by silica gel column chromatography (benzene/methanol=25/1) to obtain 64 mg of hygroscopic solid as a mixture of diastereomers.

NMR (300 MHz, CDCl$_3$): δppm: 1.08(3H,tx2,J=7.5 Hz), 3.58,3.66(3H,sx2).

(4) L-N$^\alpha$-[2(R or S)-3-ethylsulfonyl-2-(8-quinolylmethyl)propionyl]-N$^{im}$-triphenylmethylhistidine 61 mg of L-N$^\alpha$-[3-ethylthio-2-(8-quinolylmethyl)propionyl]-N$^{im}$-triphenylmethylhistidine methyl ester obtained in the preceeding step was dissolved in 1 ml of methanol. Then, 1 ml of a 2N potassium hydroxide solution (methanol/water=10/1) was added thereto, and the mixture was stirred at room temperature for 1.5 hours. Then, the reaction solution was neutralized with 1N hydrochloric acid under cooling with ice. The reaction solution was diluted with 10 ml of a saturated sodium chloride aqueous solution and extracted with ethyl acetate (20 ml×2 times), and the extract was concentrated under reduced pressure. The residue was dissolved in 2.2 ml of methanol/30% hydrogen peroxide aqueous solution (10/1). Then, 4 mg of sodium tungstate dihydrate was added thereto, and the mixture was stirred for two hours. The reaction solution was diluted with 20 ml of ethyl acetate and washed with 10 ml of a saturated sodium chloride aqueous solution. The organic layer was dried over anhydrous magnesium sulfate and evaporated under reduced pressure to dryness to obtain 53 mg of the above identified compound as yellow solid.

Rf: 0.28, 0.36 (chloroform/methanol/33% acetic acid=10/1/0.5).

(5) (2SR,4S,5S)-5-{L-N$^{60}$-[2(R or S)-3-ethylsulfonyl-2-(8-quinolylmethyl)propionyl]histidyl}amino-2-ethyl-4-hydroxy-7-methyloctanoic acid isobutylamide 53 mg of L-N$^\alpha$-[2(R or S)-3-ethylsulfonyl-2-(8-quinolylmethyl)propionyl]-N$^{im}$-triphenylmethylhistidine obtained by the preceeding step was condensed with 30 mg of (2SR,4S,5S)-5-amino-2-ethyl-4-hydroxy-7-methyloctanoic acid isobutylamide by a DPPA method (20 μm of triethylamine and 0.8 ml of DPPA). The product was subjected to work up in a usual manner and purified by silica gel column chromatography to obtain 63 mg of yellow solid. This product was dissolved in 1.0 ml of dichloromethane, and 0.5 ml of TFA was added to remove the protective group for the trityl group. The product was concentrated and dried under reduced pressure, and then steroisomers of the above identified compound were separated by means of preparative TLC (Merck Art. 5715) to obtain 14.3 mg of a polar component (identified as the titled compound) and 9.4 mg of a less-polar component.

Rf: (benzene/methanol=10/1).
Polar component: 0.16.
Less-polar component: 0.20.

EXAMPLE 12

(2RS,4S,5S)-5-{L-N-[(2R or S)-5-ethylthio-2-(1-naphthylmethyl)pentanoyl]norleucyl}amino-2-ethyl-4-hydroxy-7-methyloctanoic acid isobutylamide (1) Ethyl 2-diethylphosphono-5-(2-tetrahydropyranyloxy)pentanoate 0.58 ml of 3-bromo-1-propanol was dissolved in 6 ml of dry dichloromethane, and 1.22 ml of dihydropyrane and 10 mg of dry p-toluenesulfonic acid were added thereto. The mixture was stirred at room temperature overnight. The reaction solution was separated with 30 ml of chloroform and 15 ml of a 4% sodium hydrogencarbonate aqueous solution. The organic layer was washed with water and dried over anhydrous magnesium sulfate, and the solvent was distilled off under reduced pressure. The residue was separated by silica gel column chromatography (chloroform). Then, the fraction containing the product was purified by silica gel column chromatography (n-hexane/ethyl acetate=20/1). The combined fraction containing the product was subjected to the removal of the solvent under reduced pressure to obtain 1.44 g of 3-bromo-1-(2-tetrahydropyranyloxy)propane as colorless oily substance.

Rf: 0.33 (n-hexane/ethyl acetate=10/1).

215 mg of sodium hydride (50% in oil) was washed three times with n-hexane under argon atmosphere to separate the oil. The powder obtained after drying was suspended in 1.5 ml of dry DMF under an argon stream, and the suspension was cooled to 0° C. Then, to this mixture, 0.9 ml of ethyl diethylphosphonoacetate was dropwise added over a period of one hour. The mixture was stirred at room temperature for 30 minutes and cooled to 0° C. Then, 1.23 g of 3-bromo-1-(2-tetrahydropyranyloxy)propane was added thereto. The mixture was stirred at room temperature overnight and at 65° C. for 8 hours. The mixture was poured into 15 ml of water and extracted three times with 20 ml of chloroform. The organic solvent layer was washed with water and dried over anhydrous magnesium sulfate. The solvent was distilled off under reduced pressure. The residue was separated by silica gel column chromatography (n-hexane/ehtyl acetate=2/1). The fraction containing the product was again purified by silica gel column chromatography to obtain 583 mg of ethyl 2-diethylphosphono-5-(2-tetrahydropyranyloxy)pentanoate as colorless oily substance.

Mass spectrum m/z 367 (M$^+$+1). Rf: 0.33 (n-hexane/ethyl acetate =1/5).

(2) Ethyl (2RS)-(1-naphthylmethyl)-5-(2-tetrahydropyranyloxy)-2-pentanoate (a) 579 mg of lithium chloride was suspended in 20 ml of dry THF under an argon stream, and 5.0 g of ethyl 2-diethylphosphono-5-(2-tetrahydropyranyloxy)pentanoate was added under stirring. After stirring the mixture for 5 minutes at room temperature, 2.6 g of DBU was added, and the mixture was stirred at room temperature for 10 minutes. Then, 1.7 g of α-naphthoaldehyde was added, and the mixture was stirred at room temperature overnight. Then, the reaction solution was neutralized with 1N hydrochloric acid under cooling with ice and extracted with ethyl acetate. The ethyl acetate layer thereby obtained was washed with water and with a saturated sodium chloride aqueous solution and dried over anhydrous sodium sulfate. The solvent was distilled off under reduced pressure, and the residue was purified by silica gel column chromatography (n-hexane/ethyl acetate=10/1) to obtain 3.37 g of ethyl 3-(1-naphthyl)-2-[3-(2-tetrahydropyranyloxy)propyl]-2-propenoate as slightly yellow oily substance.

Rf: 0.15 (n-hexane/ethyl acetate=10/1).

NMR (300 MHz, CDCl$_3$) δppm: 1.20–1.52(8H), 1.65(1H,m), 1.78(2H,m), 2.51(2H,m), 3.25(1H,m), 3.33(1H,m), 3.57–3.74(2H,m), 4.27(1H,m), 4.35(2H,q,J=7 Hz), 7.36–7.56(4H), 7.78–7.95(3H), 8.18(1H,s).

(b) 3.37 g of ethyl 3-(1-naphthyl)-2-[3-(2-tetrahydropyranyloxy)propyl]-2-propenoate was dissolved in 5 ml of ethanol and hydrogenated under atmospheric pressure by means of 10% palladium carbon. The reaction mixture was subjected to filtration, the solvent of the filtrate was distilled off under reduced pressure to obtain 3.36 g of ethyl (2RS)-2-(1-naphthylmethyl)-5-(2-tetrahydropyranyloxy)pentanoate as oily substance.

Rf: 0.18 (n-hexane/ethyl acetate=10/1)

NMR (300 MHz, CDCl$_3$) δppm: 1.10(3H,t,J=7.5 Hz), 1.42–1.91(10H), 2.89(1H,m), 3.22(1H,m), 3.29–3.50(3H), 3.64–3.84(2H,m), 4.04(2H,q,J=7.5 Hz), 4.52(1H,m), 7.35(2H,m), 7.50(2H,m), 7.73(1H,d,J=8 Hz), 7.85(1H,d,J=8 Hz), 8.03(1H,d,J=8 Hz).

(3) (2RS)-5-ethylthio-2-(1-naphthylmethyl)pentanoic acid (a) 3.36 g of ethyl (2RS)-2-(1-naphthylmethyl)-5-(2-tetrahydropyranyloxy)pentanoate was dissolved in 19 ml of methanol. Then, 3 ml of 1N hydrochloric acid was added, and the mixture was stirred at room temperature for two hours. The reaction solution was neutralized with a saturated sodium hydrogencarbonate aqueous solution under cooling with ice, and the solvent was distilled off under reduced pressure. To the residue, 15 ml of water was added, and the mixture was extracted with ethyl acetate. The ethyl acetate layer was washed with water and with a saturated sodium chloride aqueous solution and then dried over anhydrous sodium sulfate. On the other hand, the separated aqueous layer was adjusted to pH2 with 1N hydrochloric acid under cooling with ice and then extracted with ethyl acetate. This ethyl acetate layer was also washed with water and with a saturated sodium chloride aqueous solution and dried over anhydrous sodium sulfate. The organic layers were put together, and the solvent was distilled off under reduced pressure to obtain 2.31 g of a mixture of the ethyl ester and methyl ester of (2RS)-5-hydroxy-2-(1-naphthylmethyl)pentanoic acid was obtained as colorless oily substance.

Rf: 0.40, 0.44 (n-hexane/ethyl acetate=1/1).

NMR (300 MHz, CDCl$_3$) δppm: 1.10(3Hx0.5,t,J=7.1 Hz), 1.48–1.90(8H), 2.89(1H;m), 3.20(1H,m), 3.42(1H,m), 3.58(3Hx0.5,s), 3.61(2H,t,J=7.9 Hz), 4.03(2Hx0.5,q,J=7.1 Hz), 7.27–7.40(2H,m), 7.44–7.58(2H), 7.73(1H,d,J=7.9 Hz), 7.86(1H,d,J=7.9 Hz), 8.01(1H,d,J=7.9 Hz).

(b) 2.31 g of the mixture of the ethyl ester and methyl ester of (2RS)-5-hydroxy-2-(1-naphthylmethyl)pentanoic acid was dissolved in 35 ml of dry pyridine, and 1.69 g of p-toluenesulfonyl chloride was added thereto. The mixture was stirred at room temperature overnight. The reaction solution was concentrated under reduced pressure, and 200 ml of ethyl acetate was added to the residue. The ethyl acetate layer was washed with a 5% potassium hydrogensulfate aqueous solution, with a 5% sodium hydrogencarbonate aqueous solution and with a saturated sodium chloride aqueous solution and dried over anhydrous sodium sulfate. The solvent was distilled off under reduced pressure and the residue was purified by silica gel column chromatography (n-hexane/ethyl acetate=5/1) to obtain 643 mg of ethyl (2RS)-2-(1-naphthylmethyl)-5-p-toluenesulfonyloxypentanoate, 184 mg of methyl (2RS)-2-(1-naphthylmethyl)-5-p-toluenesulfonyloxypentanoate and 650 mg of a mixture of the two compounds.

Ethyl ester

Rf: 0.37 (n-hexane/ethyl acetate=3/1).

NMR (300 MHz, CDCl$_3$) δppm: 1.07(3H,t,J=7.1 Hz), 1.52–1.80(4H) 2.41(3H,s), 2.78(1H,m), 3.12(1H,m), 3.38(1H,m), 3.98(2H,m), 4.01(2H,q,J=7.1 Hz), 7.20–7.40(4H), 7.44–7.57(2H), 7.74(3H), 7.85(1H,d,J=7.9 Hz), 7.95(1H,d,J=7.9 Hz).

Methyl ester

Rf: 0.30 (n-hexane/ethyl acetate=3/1).

NMR (300 MHz, CDCl$_3$) δppm: 1.50-1.82(4H), 2.42(3H,s), 2.80(1H,m), 3.12(1H,m), 3.40(1H,m), 3.54(3H,s), 3.95(2H,m), 7.20-7.31(4H), 7.35-7.60(2H), 7.74(3H), 7.85(1H,d,J=7.9 Hz), 7.96(1H,d,J=7.9 Hz).

(c) 454 mg of sodium hydride (60% in oil) was washed three times with n-pentane under an argon stream to remove the oil. The powder obtained after drying was suspended in 10 ml of dry DMF under an argon stream, and 882 mg of ethylmercaptan was added thereto under stirring at 0° C. The mixture was stirred at room temperature for one hour. The suspension thus prepared was added to a solution in dry DMF (10 ml) of 1.47 g of the mixture of the ethyl ester and methyl ester of (2RS)-2-(1-naphthylmethyl)-5-p-toluenesulfonyloxypentanoic acid under stirring with ice. The mixture was stirred at room temperature for one hour. Then, 25 ml of water was added and then 200 ml of benzene was added to the reaction solution. The organic layer was separated, washed with water and with a saturated sodium chloride aqueous solution and dried over anhydrous sodium sulfate. Then, the solvent was distilled off under reduced pressure to obtain 1.2 g of a mixture of the ethyl ester and methyl ester of (2RS)-5-ethylthio-2-(1-naphthylmethyl)pentanoic acid.

Rf: 0.68, 0.63 (n-hexane/ethyl acetate=3/1).

NMR (300 MHz, CDCl$_3$) δppm: 1.19(3H,t,J=7.1 Hz), 1.29(3Hx0.5,t,J=7.1 Hz), 1.45-1.68(3H), 1.80(1H,m), 2.45(3H,m), 2.66(1H,m), 2.82(1H,m), 3.16(1H,m), 3.38(1H,m), 3.54(3Hx0.5,s), 3.98(2Hx0.5,q,J=7.1 Hz), 7.22-7.36(2H), 7.40-7.53(2H), 7.68(1H,d,J=7.9 Hz), 7.81(1H,d,J=7.9 Hz), 7.97(1H,d,J=7.9 Hz).

(d) 1.2 g of the mixture of the ethyl ester and methyl ester of (2RS)-5-ethylthio-2-(1-naphthylmethyl)pentanoic acid was dissolved in 12 ml of ethanol/water (10/1). Then, 9.3 ml of a solution of 2N potassium hydroxide in ethanol/water (10/1) was dropwise added thereto under stirring. The mixture was stirred at room temperature overnight. Then, the reaction solution was concentrated under reduced pressure to about 3 ml, and then 40 ml of water was added thereto. The aqueous solution was adjusted to pH2 by an addition of 1N hydrochloric acid under cooling with ice and then extracted with ethyl acetate. The ethyl acetate layer was washed with water and with a saturated sodium chloride aqueous solution and then dried over anhydrous sodium sulfate. Then, the solvent was distilled off under reduced pressure to obtain 953 mg of (2RS)-5-ethylthio-2-(1-naphthylmethyl)pentanoic acid.

Rf: 0.42 (chloroform/methanol/acetic acid=10/0.5/0.1).

NMR (300 MHz. CDCl$_3$) δppm: 1.22(3H,t,J=7.1 Hz), 1.49-1.91(4H) 2.42-2.55(4H), 2.90(1H,m), 3.20(1H,m), 3.50(1H,m), 7.30-7.42(2H) 7.45-7.58(2H), 7.75(1H,d,J=7.9 Hz) 7.88(1H,d,J=7.9 Hz), 8.02(1H,d,J=7.9 Hz).

(4) L-N-[(2R or S)-5-ethylthio-2-(1-naphthylmethyl)pentanoyl]norleucine (a) 953 mg of (2RS)-5-ethylthio-2-(1-naphthylmethyl)pentanoic acid was dissolved in 9 ml of dry DMF, and 649 mg of L-norleucine tert-butyl ester, 782 mg of 1-hydroxybenzotriazol and 904 mg of DCC were added under cooling with ice. The mixture was stirred at room temperature overnight. The precipitated dicyclohexyl urea was removed by filtration, and the precipitates were washed with a small amount of a solvent mixture of n-hexane/ethyl acetate (4/1). The washing solution was combined to the filtrate. Then, 100 ml of ethyl acetate was added to the filtrate, and the ethyl acetate layer was washed with a 10% citric acid aqueous solution, with water, with a 4% sodium hydrogencarbonate aqueous solution, with water and with a saturated sodium chloride aqueous solution and dried over anhydrous sodium sulfate. The solvent was distilled off under reduced pressure. To the residue, a small amount of chloroform was added, and insolubles were removed by filtration. Then, the solvent in the filtrate was distilled off. The residue was purified by silica gel column chromatography (n-hexane/ethyl acetate=7/1) to obtain 1.23 g of L-N-[(2RS)-5-ethylthio-2-(1-naphthylmethyl)pentanoyl]norleucine tert-butyl ester. 610 mg thereof is further purified by silica gel column chromatography (toluene/ethyl acetate=25/1) to obtain 280 mg of L-N-[(2R or S)-5-ethylthio-2-(1-naphthylmethyl)pentanoyl]norleucine tert-butyl ester having a high Rf value and 210 mg of L-N-[(2R or S)-5-ethylthio-2-(1-naphthylmethyl)pentanoyl]norleucine tert-butyl ester having a low Rf value.

(2R or S) isomer having a high Rf value

Rf: 0.53 (n-hexane/ethyl acetate=3/1).

NMR (300 MHz, CDCl$_3$) δppm: 0.85(3H,t,J=7.5 Hz), 1.06-1.32(7H) 1.40(9H,s), 1.45-1.80(5H), 1.90(1H,m), 2.40-2.60(5H), 3.20(1H,m), 3.36(1H,m), 4.33(1H,m), 5.72(1H,d,J=7.9 Hz), 7.21-7.40(2H), 7.45-7.58(2H), 7.70(1H,d,J=7.9 Hz), 7.84(1H,d,J=7.9 Hz), 8.01(1H,d,J=7.9 Hz).

(2S or R) isomer having a low Rf value

Rf: 0.49 (n-hexane/ethyl acetate=3/1).

NMR (300 MHz, CDCl$_3$) δppm: 0.60(2H,m), 0.76(3H,t,J=7.5 Hz), 1.06(2H,m), 1.17-1.35(5H), 1.40(9H,s) 1.56-1.81(5H), 1.92(1H,m), 2.45-2.60(5H), 3.29(2H), 4.32(1H,m), 5.46(1H,d,J=7.9 Hz), 7.26-7.40(2H), 7.45-7.59(2H), 7.70(1H,d,J=7.9 Hz), 7.84(1H,d,J=7.9 Hz), 8.00(1H,d,J=7.9 Hz).

(b) 23.5 mg of L-N-[(2R or S)-5-ethylthio-2-(1-naphthylmethyl)pentanoyl]norleucine tert-butyl ester was dissolved in 0.2 ml of dichloromethane, and 0.1 ml of trifluoro acetic acid was added thereto. The mixture was stirred at room temperature for four hours. Then, the reaction solution was concentrated under reduced pressure to obtain 20.7 mg of L-N-[(2R or S)-5-ethylthio-2-(1-naphthylmethyl)pentanoyl]norleucine as colorless solid.

Rf: 0.39 (chloroform/methanol/acetic acid=10/0.5/0.1).

(5) (2RS,4S,5S)-5-{L-N-[(2R or S)-5-ethylthio-2-(1-naphthylmethyl)pentanoyl]norleucyl}amino-2-ethyl-4-hydroxy-7-methyloctanoic acid isobutylamide 20.7 mg of L-N-[(2R or S)-5-ethylthio-2-(1-naphthylmethyl)pentanoyl]norleucine was dissolved in 0.5 ml of dry DMF. Then, 17.4 μl of triethylamine, 12.9 μl of DPPA and 20 mg of (2RS,4S,5S)-5-amino-2-ethyl-4-hydroxy-7-methyloctanoic acid isobutylamide monohydrochloride was added thereto under stirring at −15° C. The mixture was stirred at the same temperature for one hour and then at 5° C. overnight. The reaction solution was diluted with 20 ml of ethyl acetate, washed with water and with a saturated sodium chloride aqueous solution and dried over anhydrous sodium sulfate. Then, the solvent was distilled off under reduced pressure. The residue was purified by silica gel column chromatography (chloroform/methanol=50/1) to obtain 16.9 mg of (2RS,4S,5S)-5-{L-N-[(2R or S)-5-ethylthio-2-(1-naphthylmethyl)pentanoyl]norleucyl- }amino-2-ethyl-4-hydroxy-7-methyloctanoic acid isobutylamide as colorless solid.

Rf: 0.30, 0.34 (chloroform/methanol=20/1).

Mass spectrum m/z 670 (M$^+$ +1).

NMR (300 MHz, CDCl$_3$) δppm: 0.80–0.98(18H), 1.14–1.90(22H), 2.18(0.5H,m), 2.31(0.5H,m), 2.39–2.64(4H), 2.93–3.42(4H), 3.60(1H,m) 3.83 (1H,m), 4.31(1H,m), 5.80(0.5H,m), 5.92–6.18(2H), 6.28(0.5H,m), 7.22–7.40(2H), 7.45–7.58(2H,m), 7.72(1H,d,J=7.9 Hz), 7.85(1H,d,J=7.9 Hz), 7.98(1H,m).

EXAMPLE 13

(2RS,4S,5S)-5-{L-N-[(2R or S)-5-ethylsulfonyl-2-(1-naphthylmehtyl)pentanoyl]norleucyl}amino-2-ethyl-4-hydroxy-7-methyloctanoic acid isobutylamide (1) L-N-[(2R or S)-5-ethylsulfonyl-2-(1-naphthylmethyl)pentanoyl]norleucine tert-butyl ester 600 mg of L-N-[(2RS)-5-ethylthio-2-(1-naphthylmethyl)pentanoyl]norleucine tert-butyl ester was dissolved in 10 ml of methanol, and 2.3 ml of a hydrogen peroxide aqueous solution (30%) and 65 mg of sodium tungstate dihydrate were added thereto. The mixture was stirred at room temperature for 30 minutes. The reaction solution was diluted with 100 ml of ethyl acetate and washed with water and with a saturated sodium chloride aqueous solution and then dried over anhydrous sodium sulfate. The solvent was distilled off, and the residue was purified by silica gel column chromatography to obtain 315 mg of an isomer having a high Rf value of L-N-[(2R or S)-5-ethylsulfonyl-2-(1-naphthylmethyl)pentanoyl]norleucine tert-butyl ester and 318 mg of an isomer having a low Rf value.

Isomer having a high Rf value

Rf: 0.29 (benzene/ethyl acetate=3/1),

NMR (300 MHz, CDCl$_3$) δ ppm: 0.87(3H,t,J=7.1 Hz), 1.04–1.45(16H), 1.50–2.05(6H), 2.58(1H,m), 2.90(4H,m), 3.20(2H,m), 3.38(2H,m), 4.30(1H,m), 5.80(1H,d,J=7.9 Hz), 7.24–7.40(2H), 7.52(2H,m), 7.72(1H,d,J=7.9 Hz), 7.85(1H,d,J=7.9 Hz) 8.00(1H,d,J=7.9 Hz).

Isomer having a low Rf value

Rf: 0.27 (benzene/ethyl acetate=3/1);

(2) L-N-[(2R or S)-5-ethylsulfonyl-2-(1-naphthylmethyl)-pentanoyl]norleucine 25.8 mg of the isomer having a high Rf value of L-N-[(2R or S)-5-ethylsulfonyl-2-(1-naphthylmethyl)-pentanoyl]norleucine tert-butyl ester was dissolved in 0.2 ml of dichloromethane. Then, 0.1 ml of TFA was added thereto, and the mixture was stirred at room temperature for 4 hours. Then, the reaction solution was concentrated under reduced pressure. The residue thereby obtained was diluted with diethyl ether and concentrated under reduced pressure. This operation was repeated to obtain 22.9 mg of L-N-[(2R or S)-5-ethylsulfonyl-2-(1-naphthylmethyl)-pentanoyl]norleucine.

Rf: 0.35 (chloroform/methanol/acetic acid=10/0.5/0.1), (3) (2RS,4S,5S)-5-{L-N-[(2R or S)-5-ethylsulfonyl-2-(1-naphthylmethyl)pentanoyl]norleucyl}amino-2-ethyl-4-hydroxy-7-methyloctanoic acid isobutylamide 22.9 mg of L-N-[(2R or S)-5-ethylsulfonyl-2-(1-naphthylmethyl)pentanoyl]norleucine was dissolved in 0.2 ml of dry DMF, and 6.23 mg of triethylamine and 16.9 mg of DPPA were added under stirring at −15° C. Then, 26.8 mg of (2RS,4S,5S)-5-amino-2-ethyl-4-hydroxy-7-methyloctanoic acid isobutylamide monohydrochloride was dissolved in 0.1 ml of dry DMF and neutralized with 8.79 mg of triethylamine. This dry DMF solution was added to the previous reaction solution, and the mixture was stirred at −10° C. for one hour and at 5° C. overnight. The reaction solution was diluted with 20 ml of ethyl acetate, and the ethyl acetate layer was washed with water and with a saturated sodium chloride aqueous solution and dried over anhydrous sodium sulfate. Then, the solvent was distilled off, and the residue thereby obtained was purified by silica gel column chromatography (chloroform/methanol=75/1) to obtain 18.2 mg of (2RS,4S,5S)-5-{L-N-[(2R or S)-5-ethylsulfonyl-2-(1-naphthylmethyl)pentanoyl]norleucyl}amino-2-ethyl-4-hydroxy-7-methyloctanoic acid isobutylamide as colorless solid.

Rf: 0.27, 0.31 (chloroform/methanol=20/1).

Mass spectrum m/z 702(M$^+$ +1).

NMR (300 MHz, CDCl$_3$) δppm: 0.80–1.00(18H), 1.17–1.40(8H), 1.40–1.70(7H), 1.70–2.00(6H), 2.20(0.5H,m), 2.30(0.5H,m), 2.62(1H,m), 2.78–3.08(4H), 3.18(2H,m) 3.35(2H,m), 3.62(1H,m), 3.82(1H,m), 4.26(1H,m), 5.78(0.5H,m), 5.86(0.5H,m), 6.05(2H,m), 7.22–7.42(2H), 7.52(2H,m), 7.74(1H,d,J=7.9 Hz), 7.86(1H,d,J=7.9 Hz), 7.96(1H,d,J=7.9 Hz).

EXAMPLE 14

(2RS,4S,5S)-5-{L-N$^α$-[(2RS)-3-ethylsulfonyl-2-(1-naphthylmethyl)propionyl]-N$^{im}$-triphenylmethylhistidyl}-amino-2-ethyl-4-hydroxy-7-methyloctanoic acid isobutylamide (a) 53 mg of L-N$^α$-[(2RS)-3-ethylsulfonyl-2-(1-naphthylmethyl)propionyl]-N$^{im}$-triphenylmethylhistidine methyl ester was dissolved in 0.8 ml of methanol/water (10/1), and 0.387 ml of a solution of 1N potassium hydroxide in methanol/water (10/1) was added thereto. The mixture was stirred at room temperature for 50 minutes. The mixture was neutralized with 1N hydrochloric acid under cooling with ice, and 20 ml of ethyl acetate was added thereto. The ethyl acetate layer was washed with water and with a saturated sodium chloride aqueous solution and dried over anhydrous sodium sulfate. The solvent was distilled off, and the residue thereby obtained was purified by silica gel column chromatography (chloroform/methanol/acetic acid=15/1/0.15). The fractions containing the desired product were collected, and the organic layer was washed with a 4% sodium hydrogencarbonate aqueous solution and with a saturated sodium chloride aqueous solution and dried over anhydrous sodium sulfate. Then, the solvent was distilled off to obtain 49 mg of L-N$^α$-[(2RS)-3-ethylsulfonyl--2-(1-naphthylmethyl)propionyl]-N$^{im}$-triphenylmethylhistidine as colorless solid.

Rf: 0.56, 0.44 (chloroform/methanol/acetic acid=10/1.5/0.1).

(b) 33.5 mg of L-N$^α$-[3-ethylsulfonyl-2-(1-naphthylmethyl)propionyl]-N$^{im}$-triphenylmethylhistidine was dissolved in 0.4 ml of dry DMF, and 5.92 mg of triethylamine and 16.1 mg of DPPA were added thereto under stirring at −15° C. Further, 6.9 mg of triethylamine and a dry DMF solution (0.4 ml) of 21.1 mg of (2RS,4S,5S)-5-amino-2-ethyl-4-hydroxy-7-methyloctanoic acid isobutylamide monohydrochloride were added thereto, and the mixture was stirred at the same temperature for two hours and at room temperature overnight. The reaction solution was diluted with 20 ml of ethyl acetate, and the ethyl acetate layer was washed with water and with a saturated sodium chloride aqueous solution and dried over anhydrous sodium sulfate. Then, the solvent was distilled off, and the residue was purified by silica gel column chromatography (chloroform/methanol=40/1) to obtain 37.5 mg of (2RS,4S,5S)-5-{L-N$^\alpha$-[(2RS)-3-ethylsulfonyl-2-(1-naphthylmethyl)propionyl]-N$^{im}$-triphenylmethylhistidyl}-amino-2-ethyl-4-hydroxy-7-methyloctanoic acid isobutylamide as colorless solid.

Rf: 0.27 (chloroform/methanol=20/1).
Mass spectrum m/z 940(M$^+$+1).

EXAMPLE 15

(2RS,4S,5S)-5-{L-N$^\alpha$-[(2S)-3-ethylsulfonyl-2-(1-naphthylmethyl)propionyl]histidyl}amino-2-ethyl-4-hydroxy-7-methyloctanoic acid isobutylamide 28 mg of (2RS,4S,5S)-5-{L-N$^\alpha$-[(2RS)-3-ethylsulfonyl-2-(1-naphthylmethyl)propionyl]-N$^{im}$-triphenylmethylhistidyl}amino-2-ethyl-4-hydroxy-7-methyloctanoic acid isobutylamide obtained in the above step (b) was dissolved in 0.4 ml of dichloromethane, and 0.1 ml of TFA was added thereto. The mixture was stirred at room temperature for 3 hours. The solvent was distilled off, and benzene was added to the residue, and the solvent was distilled off. This operation was repeated twice. The residue was dissolved in 15 ml of ethyl acetate, and the ethyl acetate layer was washed with a 4% sodium hydrogencarbonate aqueous solution with water and with a saturated sodium chloride aqueous solution and dried over anhydrous sodium sulfate. The solvent was distilled off, the residue was purified by silica gel column chromatography (chloroform/methanol=20/1) to obtain 6.2 mg of (2RS,4S,5S)-5-{L-N$^\alpha$-[(2S)-3-ethylsulfonyl-2-(1-naphthylmethyl)propionyl]histidyl}-amino-2-ethyl-4-hydroxy-7-methyloctanoic acid isobutylamide.

Rf: 0.11 (chloroform/methanol=10/1).
Mass spectrum m/z 698(M$^+$+1).
NMR (300 MHz, CDCl$_3$) δ ppm: 0.56–1.00(14H), 1.10–1.81(12H), 2.24(0.5H), 2.34(0.5H), 2.70–3.28(9H), 3.40–3.88(5H), 4.72(1H,br), 6.44(1H,br), 6.56(1H,br), 6.94(1H), 7.22–7.40(2H), 7.40–7.55(3H) 7.72(1H,d,J=7.9 Hz), 7.82(1H,m), 8.02(1H,m).

EXAMPLE 16

(2RS,3RS,4S)-4-{L-N-[3-ethylsulfonyl-2-(1-naphthylmethyl)-propionyl]norleucyl}amino-5-cyclohexyl-1-morpholino-2,3-pentandiol (1) L-N-benzyloxycarbonylcyclohexylalanine 3,5-dimethylpyrazolide (a) 2 g of L-phenylalanine was dissolved in 30 ml of 50% acetic acid, and high pressure hydrogenation was conducted (hydrogen pressure: 50 kg/cm$^2$, 40°–70° C., two hours) by an addition of 200 mg of platinum oxide. The catalyst was removed by filtration, and the solvent was distilled off under reduced pressure to obtain 2.2 g of L-cyclohexylalanine as colorless needles.

(b) 2.2 g of L-cyclohexylalanine was suspended in 8 ml of water and dissolved by an addition of 2.7 ml of triethylamine. Then, 8 ml of a dioxane solution of 4.2 g of S-(benzyloxycarbonyl)-4,6-dimethyl-2-mercaptopyrimidine was added thereto, and the mixture was stirred at room temperature for two hours. After an addition of 100 ml of water, the reaction mixture was extracted with ethyl acetate. Then, the aqueous layer was adjusted to pH2 with 6N hydrochloric acid at 0° C. The aqueous layer was extracted with ethyl acetate, and the ethyl acetate layer was washed with 1N hydrochloric acid and a saturated sodium chloride aqueous solution and then dried over anhydrous magnesium sulfate. The solvent was distilled off under reduced pressure to obtain 4.1 g of L-N-benzyloxycarbonylcyclohexylalanine as colorless oily substance.

Rf: 0.48 (benzene/methanol/acetic acid=10/1/0.5).

(c) 2 g of L-N-benzyloxycarbonylcyclohexylalanine was dissolved in 20 ml of dichloromethane, and 0.84 g of 3,5-dimethylpyrazole was added thereto. Further, 1.8 g of DCC was added thereto, and the mixture was stirred at from 0° to 8° C. overnight. The precipitates were removed by filtration, and the solvent was distilled off under reduced pressure. The residue was dissolved in ethyl acetate, and the solution was washed with a 10% citric acid aqueous solution, water, a 4% sodium hydrogencarbonate aqueous solution, water and a saturated sodium chloride aqueous solution and dried over anhydrous magnesium sulfate. Then, the solvent was distilled off under reduced pressure, and the residue was crystallized from diethyl ether/n-hexane to obtain 2.1 g of L-N-benzyloxycarbonylcyclohexylalanine 3,5-dimethylpyrazolide as colorless needles.

mp: 93°–94° C.
Rf: 0.45 (n-hexane/ethyl acetate=3/1).

(2) (3RS,4S)-4-(benzyloxycarbonyl)amino-5-cyclohexyl-3-hydroxypentene (a) 792 mg of lithium aluminum hydride was suspended in 50 ml of dry THF. Then, 50 ml of a dry THF solution of 4 g of L-N-benzyloxycarbonylcyclohexylalanine 3,5-dimethylpyrazolide was dropwise added thereto over a period of about 40 minutes at −40° to −45° C. under argon. The mixture was further stirred at the same temperature for 20 minutes, and then 5 ml of 5N hydrochloric acid was added thereto. The insolubles were removed by filtration, and the solvent was distilled off under reduced pressure. The residue was dissolved in ethyl acetate. The ethyl acetate layer was washed with 1N hydrochloric acid and with a saturated sodium chloride aqueous solution and then dried over anhydrous magnesium sulfate. Then, the solvent was distilled off under reduced pressure to obtain 3.4 g of L-N-benzyloxycarbonylcyclohexylalaninal as colorless oily substance.

Rf: 0.30 (n-hexane/ethyl acetate=4/1).

(b) 3.4 g of L-N-benzyloxycarbonylcyclohexylaninal was dissolved in 25 ml of dry THF. Then, 36 ml of a THF solution of 0.88M vinyl magnesium bromide was dropwise added thereto over a period of 40 minutes at −78° C. under an argon gas atmosphere. After completion of the dropwise addition, the reaction mixture was returned to room temperature and stirred at room temperature for 30 minutes. The reaction solution was poured into 250 ml of a saturated ammonium chloride aqueous solution and extracted with ethyl acetate. The ethyl acetate layer was washed with a saturated sodium chloride aqueous solution and dried over anhydrous magnesium sulfate. Then, the solvent was distilled off under reduced pressure. The residue was purified by silica gel column chromatography (toluene/ethyl acetate=7/1) to obtain 1.9 g of the above identified compound as colorless oily substance.

Rf: 0.18 (n-hexane/ethyl acetate=4/1).

(3) (4S,5RS)-3-benzyloxycarbonyl-4-cyclohexylmethyl-5-ethenyl-2,2-dimethyloxazolidine 983 mg of (3RS,4S)-4-(benzyloxycarbonyl)amino-5-cyclohexylpentene-3-ol was dissolved in 5 ml of dichloromethane, and 4 ml of 2,2-dimethoxypropane and 30 mg of dry p-toluenesulfonic acid were added thereto.

The mixture was stirred at room temperature overnight. Then, 100 ml of ethyl acetate was added to the reaction mixture. The mixture was washed with a saturated sodium hydrogencarbonate aqueous solution and with a saturated sodium chloride aqueous solution. Then, the organic layer was dried over anhydrous magnesium sulfate. The solvent was distilled off under reduced pressure, and the residue was purified by silica gel column chromatography (n-hexane/ethyl acetate=20/1) to obtain 967 mg of (4S,5RS)-3-benzyloxycarbonyl-4-cyclohexylmethyl-5-ethenyl-2,2-dimethyloxazolidine as colorless oily substance.

Rf: 0.74 (n-hexane/ethyl acetate=3/1).

(4) (4S,5RS)-3-benzyloxycarbonyl-4-cyclohexylmethyl-2,2-dimethyl-5-[(1RS)-1-hydroxy-2-morpholinoethyl]oxazolidine (a) 440 mg of (4S,5RS)-3-benzyloxycarbonyl-4-cyclohexylmethyl-5-ethenyl-2,2-dimethyloxazolidine was dissolved in 12 ml of dichloromethane, and 850 mg of m-chloroperbenzoic acid (hereinafter referred to simply as MCPBA) was added thereto. The mixture was stirred at room temperature overnight, and then refluxed under heating for three hours. Then, 60 ml of ethyl acetate was added to the reaction mixture, and the mixture was washed with a 10% sodium hydrogensulfite aqueous solution, a saturated sodium hydrogencarbonate aqueous solution and a saturated sodium chloride aqueous solution. The ethyl acetate layer was dried over anhydrous magnesium sulfate, and then the solvent was distilled off under reduced pressure. The residue was purified by silica gel column chromatography (n-hexane/ethyl acetate=10/1) to obtain 318 mg of (1RS)-1-[(4S, 5RS)-3-benzyloxycarbonyl-4-cyclohexylmethyl-2,2-dimethyloxazolidin-5-yl]oxirane as colorless oily substance.

Rf: 0.19 (n-hexane/ethyl acetate=10/1).

(b) 80 mg of (1RS)-1-[(4S,5RS)-3-benzyloxycarbonyl-4-cyclohexylmethyl-2,2-dimethyloxazolidin-5-yl]oxirane was dissolved in 3.5 ml of methanol, and 22 μl of morpholine was added thereto. The mixture was refluxed under heating for five hours. The reaction mixture was subjected to distillation under reduced pressure to remove the solvent. The residue was purified by silica gel column chromatography (n-hexane/ethyl acetate=1/1) to obtain 78 mg of (4S,5RS)-3-benzyloxycarbonyl-4-cyclohexylmethyl-2,2-dimethyl-5-[(1RS)-1-hydroxy-2-morpholinoethyl]oxazolidine as colorless oily substance.

Rf: 0.23, 0.32 (n-hexane/ethyl acetate=1/1).

(5) (2RS,3RS,4S)-4-{L-N-[3-ethylsulfonyl-2-(1-naphthylmethyl)propionyl]norleucyl}amino-5-cyclohexyl-1-morpholino-2,3-pentanediol (a) 61 mg of (4S,5RS)-3-benzyloxycarbonyl-4-cyclohexylmethyl-2,2-dimethyl-5-[(1RS-1-hydroxymorpholinoethyl]oxazolidine was dissolved in 1.5 ml of ethanol, and palladium black was added thereto. Then, hydrogenation was conducted at room temperature under atmospheric pressure. The catalyst was removed by filtration, and the solvent was distilled off under reduced pressure to obtain 38 mg of (2RS,3RS,4S)-4-amino-5-cyclohexyl-1-morpholino-2,3-pentanediol as colorless oily substance.

Rf: 0.32, 0.42 (chloroform/methanol/aqueous ammonia=10/2/0.2).

(b) 18 mg of L-N-[3-ethylsulfonyl-2-(1-naphthylmethyl)propionyl]norleucine was dissolved in 0.2 ml of dry DMF. Then, 8 μl of triethylamine, 11 μl of DPPA and a solution of 18.4 mg of (2RS,3RS,4S)-4-amino-5-cyclohexyl-1-morpholino-2,3-pentanediol in 0.4 ml of dry DMF, were added thereto under stirring at −15° C. The mixture was stirred at room temperature ovenight. Then, 20 ml of ethyl acetate was added to the reaction mixture, and the mixture was washed with water and a saturated sodium chloride aqueous solution. The ethyl acetate layer was dried over anhydrous magnesium sulfate, and then the solvent was distilled off under reduced pressure. The residue was purified by silica gel column chromatography (chloroform/methanol=100/1) to obtain 10.9 mg of the above identified compound as colorless powder.

Rf: 0.20 (chloroform/methanol=20/1).

Mass spectrum m/z 688(M$^+$+1).

NMR (300 MHz, CDCl$_3$) δppm: 0.82–0.97(3H,m), 1.20(3H,t,J=7.6 Hz), 1.12–1.85(19H,m), 2.42–2.58(2H,m), 2.58–2.91(6H,m), 3.03(1H,dd,J=13.7,3.4 Hz), 3.25–3.78(11H,m), 4.19–4.33(2H,m), 6.01(1H,d,J=7.9 Hz), 6.09(1H,d,J=6.3 Hz), 7.33–7.69(4H,m), 7.82(1H,d,J=7.9 Hz), 7.92(1H,d,J=7.9 Hz), 8.03(1H,d,J=7.9 Hz).

EXAMPLE 17

(2S,3R,4S)-4-{L-N-[(2S)-3-ethylsulfonyl-2-(1-naphthylmethyl)propionyl]norleucyl}amino-5-cyclohexyl-1-piperidino-2,3-pentanediol (a) 62 mg of (1RS)-1-[(4S,5RS)-3-benzyloxycarbonyl-4-cyclohexylmethyl-2,2-dimethyloxazolidin-5-yl]oxirane obtained in step (4)-(a) of Example 16 was dissolved in 2.6 ml of methanol, and 18 μl of piperidine was added thereto. The mixture was refluxed under heating for 5 hours. The reaction solution was subjected to distillation under reduced pressure to remove the solvent. The residue was purified by silica gel column chromatography (n-hexane/ethyl acetate=1/1) to obtain 73 mg of (4S,5RS)-3-benzyloxycarbonyl-4-cyclohexylmethyl-2,2-dimethyl-5-[(1RS)-1-hydroxy-2-piperidinoethyl]oxazolidine as colorless oily substance.

Rf: 0.5 (n-hexane/ethyl acetate=1/1)

(b) 71 mg of (4S,5RS)-3-benzyloxycarbonyl-4-cyclohexylmethyl-2,2-dimethyl-5-[(1RS)-1-hydroxy-2-piperidinoethyl]oxazolidine was dissolved in 1.5 ml of ethanol, and palladium black was added thereto. Then, hydrogenation was conducted at room temperature under atmospheric pressure. The catalyst was removed by filtration, and then the solvent was distilled off under reduced pressure to obtain 41 mg of (2RS,3RS,4S)-4-amino-5-cyclohexyl-1-piperidino-2,3-pentanediol as colorless oily substance.

Rf: 0.41 (chloroform/methanol/aqueous ammonia=10/2/0.2)

(c) 45 mg of L-N-[3-ethylsulfonyl-2-(1-naphthylmethyl)propionyl]norleucine was dissolved in 0.5 ml of dry DMF. Then, 18 μl of triethylamine, 28 μl of DPPA and 0.5 ml of a dry DMF solution of 41 mg of (2RS,3RS,4S)-4-amino-5-cyclohexyl-1-piperidino-2,3-pentanediol, were added thereto under stirring at −15° C. The mixture was stirred at room temperature overnight, and then treated in the same manner as in step (5)-(b) of Example 16. The product was purified by silica gel column chromatography (chloroform/methanol=20/1) to obtain 30.2 mg of the above identified compound as white powder.

Rf: 0.30 (chloroform/methanol=10/1).

Mass spectrum (FAB) m/z 686(M$^+$+1).

NMR (300 MHz, CDCl$_3$) δppm: 0.80-0.92(3H,m), 1.20(3H,t,J=7.6 Hz) 0.92-1.84(25H,m), 2.25-2.50(2H,m) 2.50-2.90(6H,m), 3.02(1H,dd,J=13.7,3.4 Hz), 3.25-3.52(5H,m), 3.56-3.69(1H,m), 4.18-4.30(2H,m), 5.89-6.18(2H,m), 7.35-7.49(2H,m), 7.49-7.65(2H,m), 7.79(1H,d,J=7.9 Hz), 7.90(1H,d,J=7.9 Hz), 8.03(1H,d,J=7.9 Hz).

EXAMPLE 18

(2S,3R,4S)-4-{L-N-[(2S)-3-ethylsulfonyl-2-(1-naphthylmethyl)propionyl]norleucyl}amino-5-cyclohexyl-1-(4-methylpiperidino)-2,3-pentanediol (a) 62 mg of (1RS)-1-[(4S,5RS)-3-benzyloxycarbonyl-4-cyclohexylmethyl-2,2-dimethyloxazolidin-5-yl]oxirane obtained in Example 16 (4)-(a) was dissolved in 2.6 ml of methanol, and 21 μl of 4-methylpiperidine was added thereto. The mixture was treated in the same manner as in Example 17. The product was purified by silica gel column chromatography (n-hexane/ethyl acetate=½) to obtain 72 mg of (4S,5RS)-3-benzyloxycarbonyl-4-cyclohexylmethyl-2,2-dimethyl-5-[(1RS)-1-hydroxy-2-(4-methylpiperidino)ethyl]oxazolidine as colorless oily substance.

Rf: 0.13-41 (n-hexane/ethyl acetate=½).

(b) 70 mg of (4S,5RS)-3-benzylozycarbonyl-4-cyclohexylmethyl-2,2-dimehtyl-5-[(1RS)-1-hydroxy-2-(4-methylpiperidino)ethyl]oxazolidine was dissolved in 1.5 ml of ethanol, and palladium black was added thereto. The mixture was treated in the same manner as in Example 17 to obtain 45 mg of (2RS,3RS,4S)-4-amino-5-cyclohexyl-1-(4-methylpiperidino)-2,3-pentanediol as colorless oily substance.

Rf: 0.47 (chloroform/methanol/aqueous ammonia=10/2/0.2).

(c) 43 mg of L-N-[2(S)-3-ethylsulfonyl-2-(1-naphthylmethyl)propionyl]norleucine was dissolved in 0.4 ml of dry DMF. Then, 17 μl of triethylamine, 27 μl of DPPA and 0.6 ml of a dry DMF solution of 45 mg of (2RS,3RS,4S)-4-amino-5-cyclohexyl-1-(4-methylpiperidino)-2,3-pentanediol, were added thereto under stirring at −15° C. The mixture was treated in the same manner as in Example 16 (5)-(b). The product was purified by silica gel column chromatography (chloroform/methanol=20/1) to obtain 36.5 mg of the above identified compound as white powder.

Rf: 0.29 (chloroform/methanol=10/1),

Mass spectrum (FAB) m/z 700(M$^+$ +1),

NMR (300 MHz, CDCl$_3$) δppm: 0.78-0.92(6H,m), 0.92-1.82(27H,m), 1.90-2.04(1H,m), 2.17-2.31(1H,m), 2.51-2.91(5H,m), 3.00(1H,dd,J=13.7,3.4 Hz), 3.05-3.18(1H,m), 3.24-3.49(5H,m), 3.61(1H,dd,J=15.0,7.9 Hz), 4.15-4.29(2H,m), 5.88-6.01(1H,6s), 6.01-6.18(1H,6s), 7.32-7.46(2H,m), 7.46-7.63(2H,m), 7.78(1H,d,J=7.9 Hz) 7.88(1H,d,J=7.9 Hz), 8.01(1H,d,J=7.9 Hz).

EXAMPLE 19

(2S,3R,4S)-4-{L-N-[(2S)-3-ethylsulfonyl-2-(1-naphthylmethyl)propionyl]norleucyl}amino-6-methyl-1-morpholino-2,3-heptanediol (1) (3RS,4S)-4-(benzyloxycarbonyl)amino-6-methylhepten-3-ol (a) 120 mg of lithium aluminum hydride was suspended in 3 ml of dry THF, and 12 ml of a dry THF solution of 1 g of L-N-benzyloxycarbonylleucine pirazolide was dropwise added over a period of 35 minutes at −35° to −40° C. under an argon gas atmosphere. The mixture was left at the same temperature for one hour, and then 0.64 ml of 5N hydrochloric acid was added thereto. The insolubles were removed by filtration, and the solvent was distilled off under reduced pressure from the filtrate. The residue was dissolved in ethyl acetate. The ethyl acetate layer was washed with 1N hydrochloric acid and with a saturated sodium chloride aqueous solution and dried over anhydrous magnesium sulfate. The solvent was distilled off under reduced pressure to obtain 634 mg of L-N-benzyloxycarbonylleucinal as colorless oily substance.

Rf: 0.34 (n-hexane/ethyl acetate=3/1), (b) 634 mg of L-N-benzyloxycarbonylleucinal was dissolved in 7 ml of dry THF, and 10 ml of a THF solution of 0.87M vinyl magnesium bromide was dropwise added over a period of 25 minutes at −78° C. under an argon gas atmosphere. After completion of the dropwise addition, the reaction mixture was returned to room temperature and further stirred for 15 hours. The reaction solution was poured into 20 ml of a saturated ammonium chloride aqueous solution and extracted with diethyl ether. The ether layer was washed with a saturated sodium chloride aqueous solution and dried over anhydrous magnesium sulfate. The solvent was distilled off under reduced pressure. The residue was purified by silica gel column chromatography (n-hexane/ethyl acetate=5/1) to obtain 384 mg of (3RS,4S)-4-(benzyloxycarbonyl)amino-6-methylhepten-3-ol as colorless oily substance.

Rf: 0.29 (n-hexane/ethyl acetate=3/1).

(2) (4S,5RS)-3-benzyloxycarbonyl-2,2-dimethyl-5-ethenyl-4-isobutyloxazolidine 124 mg of (3RS,4S)-4-(benzyloxycarbonyl)amino-6-methylhepten-3-ol was dissolved in 0.33 ml of 2,2-dimethoxypropane, and 4 mg of dry p-toluenesulfonic acid was added thereto. The mixture was stirred at room temperature overnight. Then, 20 ml of ethyl acetate was added to the reaction solution, and the mixture was washed with a saturated sodium hydrogencarbonate aqueous solution and a saturated sodium chloride aqueous solution. The organic layer was dried over anhydrous magnesium sulfate. The solvent was distilled off under reduced pressure, and the residue was purified by silica gel column chromatography (n-hexane/ethyl acetate=10/1) to obtain 101 mg of (4S,5RS)-3-benzyloxycarbonyl-2,2-dimethyl-5-ethenyl-4-isobutyloxazolidine as colorless oily substance.

Rf: 0.73 (n-hexane/ethyl acetate=3/1).

(3) (4S,5RS)-3-benzyloxycarbonyl-2,2-dimethyl-5-[(1RS)-1-hydroxy-2-morpholinoethyl]-4-isobutyloxazolidine (a) 98.4 mg of (4S,5RS)-3-benzyloxycarbonyl-2,2-dimethyl-5-ethenyl-4-isobutyloxazolidine was dissolved in 6 ml of dichloromethane, and 212 mg of MCPBA was added thereto. The mixture was stirred at room temeprature for one hour and futher refluxed for 4.5 hours. Then, 20 ml of ethyl acetate was added to the reaction solution, and the mixture was washed with a cold 5% sodium hydrogensulfite aqueous solution, with a saturated sodium hydrogencarbonate aqueous solution and with a saturated sodium chloride aqueous solution. The ethyl acetate layer was dried over anhydrous magnesium sulfate. The solvent was distilled off under reduced pressure, and the residue was purified by silica gel column chromatography (n-hexane/ethyl acetate=10/1) to obtain 50 mg of (1RS)-1-[(4S,5RS)-3-benzyloxycarbonyl-2,2-dimethyl-4-isobutyloxazolidin-5-yl]oxirane as colorless oily substance.

Rf: 0.25 (n-hexane/ethyl acetate=5/1).

(b) 48 mg of (1RS)-1-[(4S,5RS)-3-benzyloxycarbonyl-2,2-dimethyl-4-isobutyloxazolidin-5-yl]oxirane was dissolved in 2 ml of methanol, and 14 µl of morpholine was added thereto. The mixture was refluxed overnight. The reaction solution was subjected to distillation under reduced pressure for the removal of the solvent, and the residue was purified by silica gel column chromatography (n-hexane/ethyl acetate=1/1) to obtain 55 mg of (4S,5RS)-3-benzyloxycarbonyl-2,2-dimethyl-5-[(1RS)-1-hydroxy-2-morpholinoethyl]-4-isobutyloxazolidine as colorless oily substance.

Rf: 0.32 (n-hexane/ethyl acetate=1/1).

(4) (2S,3R,4S)-4-{L-N-[(2S)-3-ethylsulfonyl-2-(1-naphthylmethyl)propionyl]norleucyl}amino-6-methyl-1-morpholino-2,3-heptanediol (a) 53.7 mg of (4S,5RS)-3-benzyloxycarbonyl-2,2-dimethyl-5-[(1RS)-1-hydroxy-2-morpholinoethyl]-4-isobutyloxazolidine was dissolved in 0.8 ml of ethanol, and palladium black was added thereto. Then, hydrogenation was conducted at room temperature at atmospheric pressure. The catalyst was removed by filtration, and the solvent was distilled off to obtain 23 mg of (2RS,3RS,4S)-4-amino-6-methyl-1-morpholino-2,3-heptanediol as colorless oily substance.

Rf: 0.32, 0.43 (chloroform/methanol/aqueous ammonia=10/1/0.2).

(b) 38.8 mg of L-N-[3-ethylsulfonyl-2-(1-naphthylmethyl)propionyl]norleucine was dissolved in 0.3 ml of dry DMF. Then, 16 µl of triethylamine, 22 µl of DPPA and 0.6 ml of a dry DMF solution of 23 mg of (2RS,3RS,4S)-4-amino-6-methyl-1-morpholino-2,3-heptanediol, were added thereto under stirring at −15° C. The mixture was stirred at room temperature overnight. Then, 20 ml of ethyl acetate was added to the reaction mixture, and the mixture was washed with a 10% citric acid solution, with a 4% sodium hydrogencarbonate aqueous solution and with a saturated sodium chloride aqueous solution. The ethyl acetate layer was dried over anhydrous magnesium sulfate, and the solvent was distilled off under reduced pressure. The residue was purified by silica gel column chromatography (chloroform/methanol=50/1) to obtain 19.6 mg of the above identified compound as colorless powder.

Rf: 0.23 (chloroform/methanol=30/1).

Mass spectrum m/z 648(M+ +1).

NMR (300 MHz, CDCl$_3$) δppm: 0.84(3H,t,J=7.5 Hz), 0.92(3H,d,J=7.5 Hz), 0.97(3H,d,J=7.5 Hz), 1.20(3H,t,J=7.5 Hz), 1.20–1.35(4H,m), 1.34–1.47(1H,m), 1.47–1.85(5H,m), 2.41–2.55(2H,m), 2.55–2.86(6H,m), 3.01(1H,dd,J=2.4,14.4 Hz), 3.22–3.74(10H,m), 4.16–4.26(2H,m), 4.58(1H,s), 5.96(1H,d,J=9.4 Hz), 6.08(1H,d,J=7.1 Hz), 7.20–7.62(4H,m), 7.78(1H,d,J=7.9 Hz), 7.88(1H,d,J=7.9 Hz), 7.98(1H,d,J=7.9 Hz).

EXAMPLE 20

(2S,3R,4S)-4-{L-N-[(2S)-3-ethylsulfonyl-2-(1-naphthylmethyl)propionyl]norleucyl}amino-5-cyclohexyl-1-(2-methoxyethylamino)-2,3-pentanediol (a) 64 mg of (1RS)-1-[(4S,5RS)-3-benzyloxycarbonyl-4-cyclohexylmethyl-2,2-dimethyloxazolidin-5-yl]oxirane obtained in Example 16(4)-(a) was dissolved in 2.6 ml of methanol, and 16 µl of 2-methoxyethylamine was added thereto. The mixture was treated in the same manner as in Example 17. The product was purified by silica gel column chromatography (chloroform/methanol=10/1) to obtain 44 mg of (4S,5RS)-3-benzyloxycarbonyl-4-cyclohexylmethyl-2,2-dimethyl-5-[(1RS)-1-hydroxy-2-(2-methoxyethylamino)ethyl]oxazolidine as colorless oily substance.

Rf: 0.35 (chlorofrom/methanol=10/1).

(b) 44 mg of (4S,5RS)-3-benzyloxycarbonyl-4-cyclohexylmethyl-2,2-dimethyl-5-[(1RS)-1-hydroxy-2-(2-methoxyethylamino)ethyl]oxazolidine was dissolved in 1.5 ml of ethanol, and palladium black was added thereto. The mixture was treated in the same manner as in Example 17 to obtain 27 mg of (2RS,3RS,4S)-4-amino-5-cyclohexyl-1-(2-methoxyethylamino)-2,3-pentanediol as colorless oily substance.

Rf: 0.17, 0.29 (chloroform/methanol/ammonia=10/2/0.2).

(c) 29 mg of L-N-[(2S)-3-ethylsulfonyl-2-(1-naphthylmethyl)propionyl]norleucine was dissolved in 0.4 ml of dry DMF. Then, 11.4 µl of triethylamine, 18 µl of DPPA and 0.6 ml of a dry DMF solution of 27 mg of (2RS,3RS,4S)-4-amino-5-cyclohexyl-1-(2-methoxyethylamino)-2,3-pentanediol, were added thereto under stirring at −15° C. The mixture was treated in the same manner as in Example 16 (5)-(b). The product was purified by silica gel column chromatography (chloroform/methanol=20/1) to obtain 12.8 mg of the above identified compound as white powder.

Rf: 0.21 (chloroform/methanol=10/1).

Mass spectrum m/z 677(M+ +1).

NMR (300 MHz,CDCl$_3$) δppm: 0.87(3H,t,J=7.1 Hz), 1.16(3H,t,J=7.9 Hz), 0.92–1.86(19H,m), 2.20–2.97(6H,m), 3.02(1H,dd,J=13.7,3.4 Hz), 3.18(1H,dd,J=12.0,4.7 Hz), 3.24–3.61(6H,m), 3,47(3H,t,J=7.1 Hz), 3.70(1H,dd,J=14.2,7.9 Hz), 4.14–4.26(2H,m), 6.40(1H,bs), 6.57(1H,bs), 7.34–7.48(2H,m), 7.48–7.64(2H,m), 7.79(1H,d,J=7.9 Hz), 7.88(1H,d,J=7.9 Hz), 8.03(1H,d,J=7.9 Hz).

EXAMPLE 21

(2RS,3R or S,4S)-4-{L-N-[(2S)-3-ethylsulfonyl-2-(1-naphthylmethyl)propionyl]norleucyl}amino-5-cyclohexyl-1-methylthio-2,3-pentanediol (1) L-N-tert-butoxycarbonylcyclohexylalanine 3,5-dimethylpyrazolide (a) 1.0 g of L-cyclohexylalanine obtained in the process of Example 16 (1)-(a) was suspended in 5 ml of water, and 1.2 ml of triethylamine was added thereto. 5 ml of a dioxane solution of 1.7 g of S-(tert-butoxycarbonyl)-4,6-dimethyl-2-mercaptopyrimidine was added thereto, and the mixture was stirred at room temperature for 18 hours. Then, 50 ml of water was added to the reaction mixture, and the mixture was extracted with ethyl acetate. The aqueous layer was adjusted pH4 with 5N hydrochloric acid under cooling with ice and extracted with ethyl acetate. The ethyl acetate layer was washed with 1N hydrochloric acid and with a saturated sodium chloride aqueous solution and dried over anhydrous magnesium sulfate. The solvent was distilled off under reduced pressure to obtain 1.1 g of L-N-tert-butoxycarbonylcyclohexylalanine as slightly yellow oily substance.

Rf: 0.35 (chloroform/methanol/acetic acid=20/1/0.5).

(b) 1.4 g of L-N-tert-butoxycarbonylcyclohexylalanine was dissolved in 20 ml of dichloromethane, and 0.54 g of 3,5-dimethylpyrazole was added thereto. Further, 1.15 g of DCC was added under cooling with ice, and the mixture was stirred at room temperature overnight. The precipitates were removed by filtration, and the solvent was distilled off under reduced pressure. The residue was purified by silica gel column chromatography (n-hexane/ethyl acetate=5/1) to obtain 1.75 g of L-N-tert-butoxycarbonylcyclohexylalanine 3,5-dimethylpyrazolide as colorless oily substance.

Rf: 0.70 (n-hexane/ethyl acetate=3/1).

(2) (3RS,4S)-4-(tert-butoxycarbonyl)amino-5-cyclohexylpenten-3-ol.

(a) 192 mg of lithium aluminum hydride was suspended in 5 ml of dry THF. Then, 20 ml of a dry THF solution of 1.58 g of L-N-tert-butoxycarbonylcyclohexylalanine 3,5-dimethylpyrazolide was dropwise added over a period of about 40 minutes at about −40° C. under an argon gas atmosphere. Then, the mixture was left at the same temperature for one hour and 20 minutes, and then 1 ml of 5N hydrochloric acid was added thereto. The insolubles were removed by filtration, and the solvent was distilled off under reduced pressure. The residue was dissolved in ethyl acetate. The ethyl acetate layer was washed with 1N hydrochloric acid and with a saturated sodium chloride aqueous solution and dried over anhydrous magnesium sulfate. The solvent was distilled off under reduced pressure to obtain 0.91 g of L-N-tert-butoxycarbonyl cyclohexylalaninal as colorless oily substance.

Rf: 0.58 (n-hexane/ethyl acetate=3/1).

(b) 0.91 g of L-N-tert-butoxycarbonyl cyclohexylalaninal was dissolved in 12 ml of dry THF, and 16 ml of a THF solution of 0.87M vinyl magnesium bromide was dropwise added over a period of 45 minutes at −78° C. under an argon gas atmosphere. After completion of the dropwise addition, the reaction mixture was returned to room temperature and further stirred overnight. The reaction solution was poured into 30 ml of a saturated ammonium chloride aqueous solution and extracted with ethyl acetate. The ethyl acetate layer was washed with a saturated sodium chloride aqueous solution and dried over anhydrous magnesium sulfate. Then, the solvent was distilled off under reduced pressure. The residue was purified by silica gel column chromatography (n-hexane/ethyl acetate=5/1) to obtain 0.3 g of the above identified compound as colorless oily substance.

Rf: 0.41 (n-hexane/ethyl acetate=3/1).

(3) (4S,5RS)-3-tert-butoxycarbonyl-4-cyclohexylmethyl-2,2-dimethyl-5-ethenyloxazolidine 293 mg of (3RS,4S)-4-(tert-butoxycarbonyl)amino-5-cyclohexyl penten-3-ol was dissolved in 0.78 ml of 2,2-dimethoxypropane, and 9 mg of dry p-toluenesulfonic acid was added thereto. The mixture was stirred at room temperature overnight. Then, 20 ml of ethyl acetate was added to the reaction mixture, and the mixture was washed with a saturated sodium hydrogencarbonate aqueous solution and with a saturated sodium chloride aqueous solution. Then, the organic layer was dried over anhydrous magnesium sulfate. The solvent was distilled off under reduced pressure, and the residue was purified by silica gel column chromatography (n-hexane/ethyl acetate=10/1) to obtain 259 mg of the above identified compound as colorless oily substance.

Rf: 0.80 (n-hexane/ethyl acetate=3/1)

(4) (4S,5R or S)-3-tert-butoxycarbonyl-4-cyclohexylmethyl-2,2-dimethyl-5-[(1RS)-1-hydroxy-2-methylthioethyl]oxazolidine (a) 145 mg of (4S,5RS)-3-tert-butoxycarbonyl-4-cyclohexylmethyl-2,2-dimethyl-5-ethenyloxazolidine was dissolved in 4.5 ml of dichloromethane, and 309 mg of MCPBA was added thereto. The mixture was refluxed under heating for 5 hours. Then, 50 ml of ethyl acetate was added to the reaction mixture, and the mixture was washed with a 1N sodium hydroxide aqueous solution and with a saturated sodium chloride aqueous solution. The organic layer was dried over anhydrous magnesium sulfate. Then, the solvent was distilled off under reduced pressure, and the residue was purified by silica gel column chromatography (n-hexane/ethyl acetate=10/1) to obtain 75.1 mg of (1RS)-1-[(4S,5RS)-3-tert-butoxycarbonyl-4-cyclohexylmethyl-2,2-dimethyloxazolidin-5-yl]oxirane as colorless oily substance.

Rf: 0.69 (n-hexane/ethyl acetate=3/1), (b) 70 mg of (1RS)-1-[(4S,5RS)-3-tert-butoxycarbonyl-4-cyclohexylmethyl-2,2-dimethyloxazolidin-5-yl]oxirane was dissolved in 3 ml of methanol, and 106 μl of sodium methylmercaptan aqueous solution (15%) was added thereto. The mixture was refluxed under heating for five hours. Then, ethyl acetate was added to the reaction solution, and the mixture was washed with water and with a saturated sodium chloride aqueous solution. The organic layer was dried over anhydrous magnesium sulfate. Then, the solvent was distilled off under reduced pressure, and the residue was purified by silica gel column chromatography (n-hexane/ethyl acetate =10/1) to obtain 29.8 mg of (4S,5R or S)-3-tert-butoxycarbonyl-4-cyclohexylmethyl-2,2-dimethyl-5-[(1RS)-1-hydroxy-2-methylthioethyl]-oxazolidine as white solid.

Rf: 0.68 (n-hexane/ethyl acetate=3/1).

(5) (2RS,3R or S,4S)-4-{L-N-[3-ethylsulfonyl-2-(1-naphthylmethyl)propionyl]norleucyl}amino-5-cyclohexyl-1-methylthio-2,3-pentanediol (a) 29.4 mg of (4S,5R or S)-3-tert-butoxycarbonyl-4-cyclohexylmethyl-2,2-dimethyl-5-[(1RS)-1-hydroxy-2-methylthioethyl]oxazolidine was dissolved in 0.3 ml of dioxane, and 0.42 ml of a dioxane solution of 3.6M hydrogen chloride was added thereto. From the reaction solution, the solvent was distilled off under reduced pressure to obtain 22.5 mg of (2RS,3R or S,4S)-4-amino-5-cyclohexyl-1-methylthio-2,3-pentanediol hydrochloride as colorless oily substance.

Rf: 0.66 (chloroform/methanol/aqueous ammonia=10/1/0.5)

(b) 18 mg of L-N-[(2S)-3-ethylsulfonyl-2-(1-naphthylmethyl)propionyl]norleucine was dissolved in 0.1 ml of dry DMF. Then, 20 μl of triethylamine, 14 μl of DPPA and 0.5 ml of a dry DMF solution of 22.5 mg of (2RS,3R or S,4S)-4-amino-5-cyclohexyl-1-methylthio-2,3-pentanediol hydrochloride, were added under stirring at −15° C. The mixture was stirred at room temperature overnight. Then, 20 ml of ethyl acetate was added to the reaction solution, and the mixture was washed with water and with a saturated sodium chloride aqueous solution. The ethyl acetate layer was dried over anhydrous magnesium sulfate. Then, the solvent was distilled off under reduced pressure. The residue was purified by silica gel column chromatography (chloroform/methanol=100/1) to obtain 18.5 mg of the above identified compound as colorless solid.

Rf: 0.27 (chloroform/methanol=30/1).

Mass spectrum m/z 649(M+ +1).

NMR (300 MHz, CDCl$_3$) δppm: 0.85(3H,t,J=7.6 Hz), 0.80–1.10(2H,m), 1.10–1.50(9H,m), 1.25(3H,t,J=7.6 Hz), 1.50–1.92(6H,m), 2.18(3H,s), 2.64–2.98(5H,m), 3.08(1H,dd,J=2,14 Hz), 3.28–3.66(7H,m), 4.03(1H,m), 4.24(1H,m), 4.45(1H,d,J=3 Hz), 6.08(1H,d,J=6 Hz), 6.46(1H,d,J=9 Hz), 7.20–7.63(4H,m), 7.80(1H,d,J=8 Hz), 7.90(1H,d,J=8 Hz) 8.00(1H,d,J=8 Hz).

EXAMPLE 22

(2S,3R,4S)-4-{L-N-[(2S)-3-ethylsulfonyl-2-(1-naphthylmethyl)propionyl]norleucyl}amino-5-cyclohexyl-1-(2-hydroxyethylamino)-2,3-pentanediol (a) 67 mg of (1RS)-1-[(4S,5RS)-3-benzyloxycarbonyl-4-cyclohexylmethyl-2,2-dimethyloxazolidin-5-yl]oxirane obtained in Example 16 (4)-(a) was dissolved in 2.6 ml of methanol. Then, 12 µl of 2-ethanolamine was added thereto. The mixture was treated in the same manner as in Example 17. The product was purified by silica gel column chromatography (chloroform/methanol = 10/1, 5/1) to obtain 39.7 mg of (4S,5RS)-3-benzyloxycarbonyl-4-cyclohexylmethyl-2,2-dimethyl-5-[(1RS)-1-hydroxy-2-(2-hydroxyethylamino)ethyl]oxazolidine as colorless oily substance.

Rf: 0.15–0.35 (chloroform/methanol = 5/1).

(b) 38.5 mg of (4S,5RS)-3-benzyloxycarbonyl-4-cyclohexylmethyl-2,2-dimethyl-5-[(1RS)-1-hydroxy-2-(2-hydroxyethylamino)ethyl]oxazolidine was dissolved in 1.5 ml of ethanol, and palladium black was added thereto. The mixture was treated in the same manner as in Example 17 to obtain 25.8 mg of (2RS,3RS,4S)-4-amino-5-cyclohexyl-1-(2-hydroxyethylamino)-2,3-pentanediol as colorless oily substance.

Rf: 0.05, 0.08 (chloroform/methanol/aqueous ammonia = 10/2/0.2).

(c) 23 mg of L-N-[(2S)-3-ethylsulfonyl-2-(1-naphthylmethyl)propionyl]norleucine was dissolved in 0.3 ml of dry DMF. Then, 10.4 µl of triethylamine, 16 µl of DPPA and 0.6 ml of a dry DMF solution of 25.8 mg of (2RS,3RS,4S)-4-amino-5-cyclohexyl-1-(2-hydroxyethylamino)-2,3-pentanediol were added thereto under stirring at −15° C. The mixture was treated in the same manner as in Example 16 (5)-(b), and the product was purified by silica gel column chromatography (chloroform/methanol = 5/1) to obtain 13.1 mg of the above identified compound as white powder.

Rf: 0.30–0.41 (chloroform/methanol = 5/1).

Mass spectrum (FAB) m/z 662(M+ + 1).

NMR (300 MHz, CDCl$_3$) δppm: 0.70–2.20(25H,m), 2.61–2.99(7H,m) 3.08–3.92(11H,m), 3.99–4.19(2H,m) 6.90–7.01(2H,m), 7.28–7.41(2H,m), 7.41–7.59(2H,m), 7.75(1H,d,J=7.9 Hz), 7.85(1H,d,J=7.9 Hz), 8.08(1H,d,J=7.9 Hz).

EXAMPLE 23

(2S,3R,4S)-4-{L-N-[(2S)-3-ethylsulfonyl-2-(1-naphthylmethyl)propionyl]norleucyl}amino-5-cyclohexyl-1-diethylamino-2,3-pentanediol (a) 62 mg of (1RS)-1-[(4S,5RS)-3-benzyloxycarbonyl-4-cyclohexylmethyl-2,2-dimethyloxazolidin-5-yl]oxirane obtained in Example 16 (4)-(a) was dissolved in 2.6 ml of methanol, and 19 µl of diethylamine was added thereto. The mixture was treated in the same manner as in Example 17. The product was purified by silica gel column chromatography (chloroform/methanol = 10/1) to obtain 45.5 mg of (4S,5RS)-3-benzyloxycarbonyl-4-cyclohexylmethyl-2,2-dimethyl-5-[(1RS)-1-hydroxy-2-(diethylamino)ethyl]oxazolidine as colorless oily substance.

Rf: 0.38 (chloroform/methanol = 10/1).

(b) 44 mg of (4S,5RS)-3-benzyloxycarbonyl-4-cyclohexylmethyl-2,2-dimethyl-5-[(1RS)-1-hydroxy-2-(diethylamino)ethyl]oxazolidine was dissolved in 1.5 ml of ethanol, and palladium black was added thereto. The mixture was treated in the same manner as in Example 17 to obtain 29.5 mg of (2RS,3RS,4S)-4-amino-5-cyclohexyl-1-diethylamino-2,3-pentanediol as colorless oily substance.

Rf: 0.31, 0.41 (chloroform/methanol/aqueous ammonia = 10/2/0.2).

(c) 28 mg of L-N-[(2S)-3-ethylsulfonyl-2-(1-naphthylmethyl)propionyl]norleucine was dissolved in 0.3 ml of dry DMF, and 12 µl of triethylamine, 18 µl of DPPA and 0.6 ml of a dry DMF solution of 29.5 mg of (2RS,3RS,4S)-4-amino-5-cyclohexyl-1-diethylamino-2,3-pentanediol were added thereto under stirring at −15° C. The mixture was treated in the same manner as in Example 16 (5)-(b). The product was purified by silica gel column chromatography (chloroform/methanol = 20/1) to obtain 12.9 mg of the above identified compound as white powder.

Rf: 0.22 (chloroform/methanol = 10/1).

Mass spectrum (FAB) m/z 674(M+ + 1).

NMR (300 MHz, CDCl$_3$) δppm: 0.85(3H,t,J=7.1 Hz), 1.20(3H,t,J=7.9 Hz), 0.92–1.93(25H,m), 2.37–2.91(8H,m), 3.01(1H,dd,J=13.7,3.4 Hz), 3.21–3.53(5H,m), 3.53–3.72(1H,m), 4.15–4.31(2H,m), 5.90–6.39(2H,m), 7.31–7.48(2H,m), 7.48–7.66(2H,m), 7.79(1H,d,J=7.9 Hz), 7.89(1H,d,J=7.9 Hz), 8.02(1H,d,J=7.9 Hz).

EXAMPLE 24

(2RS,3RS,4S)-4-{L-N-[(2S)-3-ethylsulfonyl-2-(1-naphthylmethyl)propionyl]norleucyl}amino-5-cyclohexyl-1-[ethyl(2-hydroxyethyl)amino]-2,3-pentanediol (1) (4S,5RS)-3-benzyloxycarbonyl-4-cyclohexylmethyl-2,2-dimethyl-5-{(1RS)-2-[ethyl(2-hydroxyethyl)amino]-1-hydroxyethyl}oxazolidine 71 mg of (1RS)-1-[(4S,5RS)-3-benzyloxycarbonyl-4-cyclohexylmethyl-2,2-dimethyloxazolidin-5-yl]oxirane obtained by the process of Example 16 (4)-(a) was dissolved in 2 ml of methanol, and 30 µl of 2-ethylaminoethanol was added thereto. The mixture was refluxed under heating for 7 hours. The solvent was distilled off under reduced pressure from the reaction solution. The residue was purified by silica gel column chromatography (chloroform/methanol = 30/1) to obtain 84 mg of the above identified compound as colorless oily substance.

Rf: 0.48 (chloroform/methanol = 10/1).

(2) (2RS,3RS,4S)-4-{L-N-[(2S)-3-ethylsulfonyl-2-(1-naphthylmethyl)propionyl]norleucyl}amino-5-cyclohexyl-1-[ethyl(2-hydroxyethyl)amino]-2,3-pentanediol (a) 83 mg of the compound obtained in step (1) was dissolved in 0.8 ml of ethanol, and palladium black was added thereto. The hydrogenation was conducted at room temperature under atmospheric pressure. The catalyst was removed by filtration, and the solvent was distilled off under reduced pressure to obtain 49 mg of (2RS,3RS,4S)-4-amino-5-cyclohexyl-1-[ethyl(2-hydroxyethyl)amino]-2,3-pentanediol as colorless oily substance.

(b) 52 mg of L-N-{(2S)-3-ethylsulfonyl-2-(1-naphthylmethyl)propionyl}norleucine was dissolved in 0.3 ml of dry DMF. Then, 21 µl of triethylamine and 32 µl of DPPA were sequentially added thereto at −15° C., and then 0.5 ml of a dry DMF solution of 49 mg of (2RS,3RS,4S)-4-amino-5-cyclohexyl-1-[ethyl(2-hydroxyethyl)amino]-2,3-pentanediol was added thereto. The mixture was stirred at room temperature overnight, and the reaction solution was diluted by an addition of 20 ml of ethyl acetate. The organic layer was washed with a 10% citric acid aqueous solution, with a 4% sodium hydrogencarbonate aqueous solution and with a saturated sodium chloride aqueous solution and dried over anhydrous magnesium sulfate. The solvent was distilled off under reduced pressure, and the residue was purified by silica gel column chromatography (chloroform/methanol=10/1) to obtain 17.6 mg of the above identified compound as colorless crystals.

Rf: 0.38 (chloroform/methanol=10/1).

Mass spectrum m/z 690(M++1).

NMR (300 MHz, CDCl$_3$) δppm: 0.82(3H,t,J=7.6 Hz), 0.80-1.83(22H,m), 2.46-2.95(8H,m), 3.12(1H,dd,J=3,14 Hz), 3.28-3.72(8H,m), 4.08-4.15(2H,m), 6.00-6.32(2H,m), 7.35-7.60(4H,m), 7.70-7.80(1H,m), 7.88(1H,d,J=8 Hz), 7.99(1H,d,J=8 Hz).

EXAMPLE 25

(2RS,3RS,4S)-4-{L-N-[(2S)-3-ethylsulfonyl-2-(1-naphthylmethyl)propionyl]norleucyl}amino-1-isopropylthio-6-methyl-2,3-heptanediol (1) (3RS,4S)-4-(tert-butoxycarbonyl)amino-6-methylhepten-3-ol (a) 5 g of L-N-tert-butoxycarbonylleucine monohydrate was dissolved in 50 ml of dichloromethane, and 2.1 g of 3,5-dimethylpyrazole was added thereto. Further, 4.6 g of DCC was added thereto under cooling with ice, and the mixture was stirred at 0° C. for two hours and at room temperature overnight. The precipitates were removed by filtration, and the solvent was distilled off under reduced pressure. The residue was recrystallized from methanol/water and washed with water to obtain 6.2 g of L-N-tert-butoxycarbonylleucine 3,5-dimethylpyrazolide as colorless crystals.

Rf: 0.59 (n-hexane/ethyl acetate=3/1).

(b) 847 mg of lithium aluminum hydride was suspended in 18 ml of dry THF, and 72 ml of a dry THF solution of 6.2 g of L-N-tert-butoxycarbonylleucine 3,5-dimethylpyrazolide was dropwise added over a period of 30 minutes at −30° C. under an argon gas atmosphere. Further, the mixture was left at the same temperature for one hour, and then 4.5 ml of 5N hydrochloric acid was added. The insolubles were removed by filtration, the solvent was distilled off under reduced pressure. The residue was dissolved in diethyl ether. The organic layer was washed with 1N hydrochloric acid and with a saturated sodium chloride aqueous solution and dried over anhydrous magnesium sulfate. The solvent was distilled off under reduced pressure to obtain 3.2 g of L-N-tert-butoxycarbonylleucinal as slightly yellow oily substance.

Rf: 0.51 (n-hexane/ethyl acetate=3/1).

(c) 3.2 g of L-N-tert-butoxycarbonylleucinal was dissolved in 30 ml of dry THF, and 50 ml of a THF solution of 0.98M vinyl magnesium bromide was dropwise added thereto over a period of 30 minutes at −78° C. under an argon gas atmosphere. The reaction solution was returned to room temperature and further stirred overnight. The reaction solution was poured into 20 ml of a saturated ammonium chloride aqueous solution and extracted with diethyl ether. The ether layer was washed with a saturated sodium chloride aqueous solution and dried over anhydrous magnesium sulfate. The solvent was distilled off under reduced pressure. The residue was purified by silica gel column chromatography (n-hexane/ethyl acetate=5/1) to obtain 1.1 g of (3RS,4S)-4-(tert-butoxycarbonyl)amino-6-methylhepten-3-ol as colorless oily substance.

Rf: 0.40 (n-hexane/ethyl acetate=3/1), (2) (1RS)-1-[(1RS,2S)-2-(tert-butoxycarbonyl)amino-1-hydroxy-4-methylheptyl]oxirane (a) 1 g of (3RS,4S)-4-(tert-butoxycarbonyl)amino-6-methylhepten-3-ol was dissolved in 2 ml of dry DMF, and 743 mg of tert-butyldimethylchlorosilane and 700 mg of imidazole were added thereto. The mixture was stirred at room temperature overnight. Then, 160 ml of ethyl acetate was added to the reaction solution. The mixture was washed with cooled 1N hydrochloric acid, with a saturated sodium hydrogencarbonate aqueous solution and a saturated sodium chloride aqueous solution and dried over anhydrous sodium sulfate. The solvent was distilled off under reduced pressure. The residue was purified by silica gel column chromatography (n-hexane/ethyl acetate=30/1) to obtain 1.21 g of (3RS,4S)-4-(tert-butoxycarbonyl)amino-3-(tert-butyldimethylsilyl)oxy-6-methylheptene as colorless oily substance.

Rf: 0.49 (n-hexane/ethyl acetate=20/1).

(b) 1.2 g of (3RS,4S)-4-(tert-butoxycarbonyl)amino-3-(tert-butyldimethylsilyl)oxy-6-methylheptene was dissolved in 30 ml of dichloromethane, and 2.2 g of MCPBA was gradually added thereto at 0° C. The temperature was returned to room temperature, and the mixture was stirred for 14 hours and then refluxed under heating for further 4 hours.

To the reaction solution, 210 ml of ethyl acetate was added, mixture was washed with a cooled 10% sodium sulfite aqueous solution, with a saturated sodium hydrogencarbonate aqueous solution and with a saturated sodium chloride aqueous solution. The ethy acetate layer was dried over anhydrous magnesium sulfate, and the solvent was distilled off under reduced pressure. The residue was purified by silica gel column chromatography (n-hexane/ethyl acetate=10/1) to obtain 943 mg of (1RS)-1-[(1RS,2S)-2-(tert-butoxycarbonyl)amino-1-(tertbutyldimethylsilyl)oxy-4-methylpentyl]oxirane as colorless oily substance.

Rf: 0.29 (n-hexane/ethyl acetate=10/1).

(c) 873 mg of (1RS)-1-[(1RS,2S)-2-(tertbutoxycarbonyl)amino-1-(tert-butyldimethylsilyl)oxy-4-methylpentyl]oxirane was dissolved in 4.5 ml of a THF solution of 1M tetrabutylammonium fluoride, and the solution was stirred at 0° C. for 30 minutes and at room temperature for 5.5 hours. To the reaction solution, 100 ml of ethyl acetate was added, and the mixture was washed with water and with a saturated sodium chloride aqueous solution. The organic layer was dried over anhydrous magnesium sulfate, and then the solvent was distilled off under reduced pressure. The residue was purified by silica gel column chormatography (n-hexane/ethyl acetate=5/1) to obtain 520 mg of (1RS)-1-[(1RS,2) -2-(tertbutoxycarbonyl)amino-1-hydroxy-4-methylpentyl]oxirane as colorless oily substance.

Rf: 0.13 (n-hexane/ethyl acetate=3/1).

(3) (2RS,3RS,4S)-4-(tert-butoxycarbonyl)amino-1-isopropylthio-6-methyl-2,3-heptanediol 46.7 mg of (1RS)-1-[(1RS,2S)-2-(tertbutoxycarbonyl)amino-1-hydroxy-4-methylpentyl]oxirane was dissolved in 1.8 ml of methanol, and 50 μl of triethylamine and 33 μl of isopropylmercaptan were added thereto. The mixture was refluxed under heating for 6 hours. The solvent was distilled off under reduced pressure from the reaction solution. The residue was purified by silica gel column chromatography (n-hexane/ethyl acetate=5/1) to obtain 23.7 mg of (2RS,3RS,4S)-4-(tert-butoxycarbonyl)amino-1-isopropylthio-6-methyl-2,3-heptanediol as colorless powder.

Rf: 0.42, 0.49 (n-hexane/ethyl acetate=3/1).

(4) (2RS,3RS,4S)-4-{L-N-[(2S)-3-ethylsulfonyl-2-(1-naphthylmethyl)propionyl]norleucyl}amino-1-isopropylthio-6-methyl-2,3-heptanediol (a) 21 mg of (2RS,3RS,4S)-4-(tert-butoxycarbonyl)amino-1-isopropylthio-6-methyl-2,3-heptanediol was dissolved in 0.3 ml of dioxane, and 0.32 ml of a 3.6M hydrogen chloride/dioxane solution was added thereto. The mixture was stirred at room temperature for 4 hours. The solvent was distilled off under reduced pressure from the reaction solution to obtain 16.9 mg of (2RS,3RS,4S)-4-amino-1-isopropylthio-6-methyl-2,3-heptanediol hydrochloride as colorless oily substance.

Rf: 0.22 (chloroform/methanol/aqueous ammonia=10/1/0.2).

(b) 17.3 mg of L-N-[(2S)-3-ethylsulfonyl-2-(1-naphthylmethyl)propionyl]norleucine in 0.2 ml of dry DMF. Then, 15 μl of triethylamine, 11 μl of DPPA and 0.5 ml of a dry DMF solution of 16.9 mg of (2RS,3RS,4S)-4-amino-1-isopropylthio-6-methyl-2,3-heptanediol hydrochloride, were added thereto under stirring at $-15°$ C. The mixture was stirred at room temperature overnight. Then, 15 ml of ethyl acetate was added to the reaction solution, and the mixture was washed with water and with a saturated sodium chloride aqueous solution. The organic layer was dried over anhydrous magnesium sulfate. The solvent was distilled off under reduced pressure. The residue was purified by silica gel column chromatography (chloroform/methanol=100/1) to obtain 19.0 mg of the above identified compound as colorless powder.

Rf: 0.22 (chloroform/methanol=50/1).

Mass spectrum m/z 637($M^{30}$+1).

NMR (300 MHz, CDCl$_3$) δppm: 0.85(3H,t,J=7.8 Hz), 0.90(3H,d,J=7.5 Hz), 0.96(3H,d,J=7.5 Hz), 1.13–1.40(12H,m), 1.53–1.90(6H,m), 2.22–3.11(6H,m), 4.09(1H,dd,J=7,14 Hz), 4.14–4.25(1H,m), 4.40(1H,br s), 6.16(1H,d,J=7 Hz), 6.44(1H,d,J=9 Hz), 7.31–7.46(2H,m), 7.49–7.53(2H,m), 7.79(1H,d,J=8 Hz), 7.89(1H,d,J=8 Hz), 7.99(1H,d,J=8 Hz).

EXAMPLE 26

(2RS,3RS,4S)-4-[L-N-{(2S)-3-ethylsulfonyl-2-(1-naphthylmethyl)propionyl}norleucyl]amino-6-methyl-1-thiomorpholino-2,3-heptanediol (a) 58.4 mg of (1RS)-1-[(1RS,2S)-2-(tertbutoxycarbonyl)amino-1-hydroxy-4-methylpentyl]oxirane obtained in step (2) was dissolved in 2.2 ml of methanol, and 24 μl of thiomorpholine was added thereto. The mixture was refluxed under heating for 3 hours. The solvent was distilled off under reduced pressure from the reaction solution, and the residue was purified by silica gel column chromatography (n-hexane/ethyl acetate=1/1) to obtain 72.7 mg of (2RS,3RS,4S)-4-(tert-butoxycarbonyl)amino-6-methyl-1-thiomorpholino-2,3-heptanediol as colorless powder.

Rf: 0.15, 0.33 (n-hexane/ethyl acetate=1/1).

(b) 68 mg of (2RS,3RS,4S)-4-(tert-butoxycarbonyl)amino-6-methyl-1-thiomorpholino-2,3-heptanediol was dissolved in 0.5 ml of dioxane, and 1 ml of a 3.6M hydrogen chloride/dioxane solution was added thereto. The mixture was stirred at room temperature for two hours. The solvent was distilled off under reduced pressure from the reaction solution to obtain 63 mg of (2RS,3RS,4S)-4-amino-6-methyl-1-thiomorpholino-2,3-heptanediol dihydrochloride as colorless oily substance.

Rf: 0.38, 0.43 (chloroform/methanol/aqueous ammonia=10/1/0.2).

(c) 51.2 mg of L-N-{(2S)-3-ethylsulfonyl-2-(1-naphthylmethyl)propionyl}norleucine was dissolved in 0.3 ml of dry DMF. Then, 69 μl of triethylamine, 32 μl of DPPA and a dry DMF solution of 63 mg of (2RS,3RS,4S)-4-amino-6-methyl-1-thiomorpholino-2,3-heptanediol dihydrochloride, were added thereto under stirring at $-15°$ C. The mixture was stirred at room temperature overnight. Then, 30 ml of ethyl acetate was added to the reaction solution, and the mixture was washed with water and with a saturated sodium chloride aqueous solution. The ethyl acetate layer was dried over anhydrous magnesium sulfate. Then, the solvent was distilled off, and the residue was purified by silica gel column chromatography (chloroform/methanol=10/1) to obtain 6.7 mg of the above identified compound as colorless powder.

Rf: 0.38 (chloroform/methanol=10/1).

Mass spectrum m/z 664($M^+$+1),

NMR (300 MHz, CDCl$_3$) δppm: 0.81(3H,t,J=7.6 Hz), 0.80–1.90(18H,m), 2.45–2.96(12H,m), 3.02–3.76(9H,m), 4.55–4.71(2H,m), 7.28–7.63(4H,m), 7.74–7.91(2H,m), 8.02(1H,d,J=8 Hz).

EXAMPLE 27

(2S,3R,4S)-4-[L-N-[(2S or R)-2-ethylsulfonylmethyl-4-methylpentanol]norleucyl]amino-5-cyclohexyl-1-morpholino-2,3-pentanediol (1) Ethyl 2-isobutyl-2-propenoate (a) 1.6 g of a sodium hydride dispersion (60% in oil) was washed three times with n-pentane and dried by an argon stream. The obtained powder was suspended in 14 ml of dry DMF under an argon stream and 8.97 g of ethyl diethylphosphonoacetate was dropwise added thereto under stirring at 0° C. The mixture was stirred at room temperature for one hour and then cooled to 0° C. Then, 6.58 g of 1-bromo-2-methylpropane was dropwise added under stirring. Then, the mixture was stirred at 55° C. overnight. Then, 80 ml of water was added thereto, and the mixture was extracted with ethyl acetate. The ethyl acetate layer was washed with water and with a saturated sodium chloride aqueous solution and dried over anhydrous sodium sulfate. Then, the solvent was distilled off. The residue was purified by silica gel column chromatography (n-hexane/acetone=4/1) to obtain 7.59 g of ethyl 2-diethylphosphono-4-methylpentanoate as colorless oily substance.

Rf: 0.23 (n-hexane/acetone=2/1).

NMR (300 MHz, CDCl$_3$) δppm: 0.84–0.95(6H), 1.22–1.36(9H), 1.58(1H,m), 1.86(1H,m), 1.98(1H,m), 3.02(1H,m), 4.06–4.25(6H).

(b) 333 mg of lithium chloride was suspended in 14 ml of dry THF. Then, 2.0 g of ethyl 2-diethylphosphono-4-methylpentanoate was added thereto under stirring. Then, 1.41 g of DBU was added thereto in the form of a dry THF solution. Then, a suspension of 348 mg of paraformaldehyde in dry THF was added thereto. The mixture was stirred at room temperature overnight. The reaction solution was subjected to filtration, and the collected substance was washed with a small amount of benzene. The filtrate and the washing solution were put together and concentrated under reduced pressure. The syrup thereby obtained was dissolved in 60 ml of ethyl acetate. The ethyl acetate layer was washed with water and with a saturated sodium chloride aqueous solution and dried over anhydrous sodium sulfate. Then, solvent was distilled off to obtain 700 mg of ethyl 2-isobutyl-2-propenoate as colorless oily substance.

Rf: 0.53 (n-hexane/ethyl acetate=20/1).

NMR (300 MHz, CDCl$_3$) δppm: 0.89(6H), 1.30(3H), 1.78(1H,m), 2.17(2H,m), 4.18(2H,m), 5.47(1H,s), 6.13(1H,s).

(2) L-N-[(2RS)-2-ethylthiomethyl-4-methylpentanoyl]norleucine tert-butyl ester (a) 650 mg of ethyl 2-isobutyl-2-propenoate was dissolved in 3 ml of methylmercaptan, and 50 mg of potassium tert-butoxide was added thereto. The mixture was stirred at room temperature for two hours. The reaction solution was diluted with 60 ml of ethyl acetate, washed with water and then with a saturated sodium chloride aqueous solution and dried over anhydrous sodium sulfate. The solvent was distilled off under reduced pressure to obtain 660 mg of ethyl 2-ethylthiomethyl-4-methylpentanoate as colorless oily substance.

Rf: 0.40 (n-hexane/ethyl acetate=20/1).

NMR (300 MHz, CDCl$_3$): δppm: 0.90(6H), 1.20–1.34(6H), 1.48–1.68(2H), 1.75(0.5H), 2.00(0.5H), 2.52(2H), 2.59–2.79(3H), 4.15(2H).

(b) 650 mg of ethyl 2-ethylthiomethyl-4-methylpentanoate was dissolved in 6 ml of an ethanol/water (10/1) solution, 8.9 ml of an ethanol/water (10/1) solution of 2N potassium hydroxide was added thereto. The solution was stirred at room temperature for 2.5 hours, and then, the reaction solution was distilled off under reduced pressure to obtain a suspension. To this suspension, 40 ml of water was added, and the reaction solution was adjusted to pH2 with 2N hydrochloric acid under cooling with ice, and extracted with ethyl acetate. The ethyl acetate layer was washed with water and then with a saturated sodium chloride aqueous solution and dried over anhydrous sodium sulfate. Then, the solvent was distilled off to obtain 577 mg of 2-ethylthiomethyl-4-methylpentanoic acid as colorless oily substance.

Rf: 0.41 (chloroform/methanol/acetic acid=10/0.5/0.1).

(c) 570 mg of 2-ethylthiomethyl-4-methylpentanoic acid was dissolved in 7 ml of dry DMF, and 618 mg of L-norleucine tert-butyl ester, 657 mg of 1-hydroxybenzotriazole and 860 mg of DCC were added thereto at 0° C. under stirring. The mixture was stirred at room temperature overnight. Then, the precipitated dicyclohexyl urea was removed by filtration. The filtrate was diluted with 100 ml of ethyl acetate. The ethyl acetate layer was washed sequentially with 10% citric acid aqueous solution, with water, with a 4% sodium hydrogencarbonate aqueous solution, with water, with a saturated sodium chloride aqueous solution and dried over anhydrous sodium sulfate. The solvent was distilled off. A small amount of chloroform was added to the residue, the insolubles were removed twice by filtration. The filtrate thereby obtained was distilled off under reduced pressure. The residue was purified by silica gel column chromatography (n-hexane/ethyl acetate=20/1) to obtain 679 mg of L-N-[(2RS)-2-ethylthiomethyl-4-methylpentanoy]norleucine tert-butyl ester.

Rf: 0.35 (n-hexane/ethyl acetae=5/1),

NMR (300 MHz, CDCl$_3$) δppm: 0.8(9H), 1.19–1.43(7H), 1.46(9H) 1.52–1.73(4H), 1.82(1H), 2.37(1H) 2.45–2.63(3H), 2.78(1H), 4.50(1H) 6.08(0.5H), 6.16(0.5H).

(3) (2S,3R,4S)-4)[L-N-[(2S or R)-2-ethylsulfonylmethyl-4-methylpentanoyl]norleucyl]amino-5-cyclohexyl-1-morpholino-2,3-pentanediol (a) 679 mg of L-N-[(2RS)-2-ethylthiomethyl-4-methylpentanoyl]norleucine tert-butyl ester was dissolved in 10 ml of methanol, and 3.21 ml of a 30% hydrogen peroxide aqueous solution and 62.4 mg of sodium tungstate dihydrate were added thereto. The mixture was stirred at room temperature for 2 hours. Then, 42 mg of sodium tungstate dihydrate was further added thereto, and the mixture was stirred at room temperature for 4 hours. 100 ml of ethyl acetate was added to the reaction solution, and the ethyl acetate layer was washed with water and with a sodium chloride aqueous solution and dried over anhydrous sodium sulfate. The solvent was distilled off, and the residue thereby obtained was purified by silica gel column chromatography (n-hexane/ethyl acetate=3/1) to obtain 358 mg of the isomer having a high Rf value of L-N-(2-ethylsulfonylmethyl-4-methylpentanoyl)norleucine tert-butyl ester and 315 mg of the isomer having a low Rf value.

Isomer having a high Rf value:

Rf: 0.66 (n-hexane/ethyl acetate=1/1).

NMR (300 MHz, CDCl$_3$). δppm: 0.85–1.00(9H), 1.20–1.40(7H), 1.46(9H,s), 1.53–1.73(4H), 1.80(1H,m), 2.79–3.06(4H), 3.57(1H,dd,J=8,15 Hz), 4.40(1H,dt,J=7,8 Hz), 6.27(1H,d,J=8 Hz).

Isomer having a low Rf value:

Rf: 0.56 (n-hexane/ethyl acetate=1/1)

NMR (300 MHz, CDCl$_3$) δppm: 0.85–1.00(9H), 1.22–1.42(7H), 1.47(9H,s), 1.52–1.88(5H), 2.80–3.02(4H), 3.60(1H,m), 4.46(1H,m), 6.16(1H,d,J=8 Hz).

(b) 358 mg of the isomer having a high Rf value of L-N-[(2S or R)-2-ethylsulfonylmethyl-4-methylpentanoyl]norleucine tert-butyl ester was dissolved in dry dichloromethane, and 1.5 ml of TFA was added thereto. The reaction solution was stirred at room temperature for 1.5 hours, and then concentrated under reduced pressure to obtain a syrup. The syrup was dissolved in benzene, and the solution was concentrated under reduced pressure. This operation was repeated. The syrup was crystallized from diethyl ether/n-hexane, and evaporated under reduced pressure to dryness to obtain 312 mg of L-N-[(2S or R)-2-ethylsulfonylmethyl-4-methylpentanoyl]norleucine as colorless solid.

Rf: 0.24 (chloroform/methanol/acetic acid=10/0.5/0.1).

NMR (300 MHz, CDCl$_3$) δppm: 0.85–1.00(9H), 1.20–1.45(8H), 1.51–1.83(3H), 1.93(1H,m), 2.82–3.17(4H), 3.62(1H,dd,J=8,15 Hz), 4.56(1H,dt,J=7,8 Hz), 6.91(1H,br).

(c) 25.6 mg of L-N-[(2S or R)-2-ethylsulfonylmethyl-4-methylpentanoyl]norleucine was dissolved in 0.5 ml of dry DMF, and a dry DMF solution of 30.8 mg of triethylamine, 25.2 mg of DPPA and 38.5 mg of (2RS,3R,4S)-4-amino-5-cyclohexyl-1-morpholino-2,3-pentanediol dihydrochloride was added thereto at −15° C. under stirring. The mixture was stirred at the same temperature for one hour and at room temperature overnight. The reaction solution was diluted with 10 ml of ethyl acetate. The ethyl acetate layer was washed with water and with a saturated sodium chloride aqueous solution and dried over anhydrous sodium sulfate. The solvent was distilled off under reduced pressure, and the residue thereby obtained was purified by silica gel column chromatography (chloroform/methanol=50/1) to obtain 21.7 mg of (2S,3R,4S)-4-{L-N-[(2S or R)-2-ethylsulfonylmethyl-4-methylpentanoyl]norleucyl}amino-5-cyclohexyl-1-morpholino-2,3-pentanediol as colorless solid.

Rf: 0.51 (chloroform/methanol=10/1).

Mass spectrum m/z 604(M++1).

NMR (300 MHz, CDCl$_3$) δppm: 0.85–1.02(9H), 1.08–1.98(25H), 2.46(2H,br), 2.62(1H,t,J=11 Hz), 2.72–3.06(5H), 3.24(2H,m), 3.38–3.52(2H,m), 3.52–3.77(5H), 4.24(2H,m), 4.90(1H,br), 6.18(1H,d,J=7.1 Hz) 7.12(1H,d,J=8.7 Hz).

EXAMPLE 28

(2S,3R,4S)-4-{L-N-[(2S or R)-5-ethylthio-2-(1-naphthylmethyl)pentanoyl]norleucyl}amino-5-cyclohexyl-1-morpholino-2,3-pentanediol 50.5 mg of L-N-[(2S or R)-5-ethylthio-2-(1-naphthylmethyl)pentanoyl]norleucine was dissolved in 0.5 ml of dry DMF, and a dry DMF solution of 58.2 mg of triethylamine, 47.4 mg of DPPA and 72.3 mg of (2RS,3R,4S)-4-amino-5-cyclohexyl-1-morpholino-2,3-pentanediol dihydrochloride was added thereto at −15° C. under stirring. The mixture was stirred at the same temperature for two hours and at room temperature overnight. The reaction solution was diluted with 30 ml of ethyl acetate, and the ethyl acetate layer was washed with water and wtih a saturated sodium chloride aqueous solution and dried over anhydrous sodium sulfate. The solvent was distilled off, and the residue thereby obtained was purified by silica gel column chromatography (chloroform/methanol=100/1) to obtain 25.5 mg of the above identified compound as colorless solid.

Rf: 0.50 (chloroform/methanol=20/1).

NMR (300 MHz, CDCl$_3$) δppm: 0.75–1.04(5H), 1.04–1.35(11H), 1.35–1.80(12H), 1.85(1H,m), 2.38–2.68(8H), 2.78(2H), 3.25(2H,d,J=7.9 Hz), 3.48(2H,m), 3.68(4H), 4.22(2H,m), 4.58(1H,br), 5.55(1H,d,J=7.1 Hz), 5.90(1H,d,J=8.7 Hz), 7.38(2H,m), 7.54(2H,m), 7.75(1H,d,J=7.9 Hz), 7.88(1H,d,J=7.9 Hz), 7.96(1H,d,J=7.9 Hz).

EXAMPLE 29

(2S,3R,4S)-4-{L-N-[(2S or R)-5-ethylsulfonyl-2-(1-naphthylmethyl)pentanoyl]norleucyl}amino-5-cyclohexyl-1-morpholino-2,3-pentanediol 90 mg of L-N-[(2S or R)-5-ethylsulfonyl-2-(1-naphthylmethyl)pentanoyl]norleucine was dissolved in 0.4 ml of dry DMF, and 81.4 mg of triethylamine, 66.3 mg of DPPA and 0.4 ml of a dry DMF solution of 101 mg of (2RS,3R,4S)-4-amino-5-cyclohexyl-1-morpholino-2,3-pentanediol dihydrochloride was added thereto at −15° C. under stirring. The mixture was stirred at the same temperature for 2 hours and at room temperature overnight. The reaction solution was diluted with 50 ml of ethyl acetate, and the ethyl acetate layer was washed with water and with a saturated sodium chloride aqueous solution and dried over anhydrous sodium sulfate. The solvent was distilled off, and the residue was purified by silica gel column chromatography (chloroform/methanol=50/1) to obtain 46.2 mg of the above identified compound as colorless solid.

Rf: 0.51 (chloroform/methanol=10/1).

NMR (300 MHz, CDCl$_3$) δppm: 0.76–1.05(5H), 1.05–2.02(24H), 2.48(2H,m), 2.62(2H,m), 2.70–3.00(6H), 3.22(1H,m), 3.32(1H,m), 3.48(2H,m), 3.65(4H), 4.22(2H,m), 4.60(1H,br), 5.84(1H,d,J=7.1 Hz), 5.96(1H,d,J=8.7 Hz), 7.38(2H,m), 7.54(2H,m), 7.76(1H,d,J=7.9 Hz), 7.88(1H,d,J=7.9 Hz), 7.98(1H,d,J=7.9 Hz).

EXAMPLE 30

(2S,3R,4S)-4-{L-N-[(2S)-3-ethylsulfonyl-2-(8-quinolylmethyl)propionyl]norluecyl}amino-5-cyclohexyl-1-morpholino-2,3-pentanediol The condensation reaction was conducted by using 33 mg of L-N-[(2S)-3-ethylsulfonyl-2-(8-quinolylmethyl)propionyl]norleucine which was one of diastereomers, as an acid component, and 1 mg of (2S,3R,4S)-4-amino-5-cyclohexyl-1-morpholino-2,3-pentanediol dihydrochloride, 51 μl of triethylamine and 21 μl of DPPA as amine components. The product was purified by silica gel column chromatography (chloroform/methanol/conc. ammonia=150/3/0.1) to obtain 27 mg of the above identified compound.

Rf: 0.48 (chloroform/methanol=10/1).

EXAMPLE 31

(2S,3R,4S)-4-{L-N$^\alpha$-[(2S)-3-ethylsulfonyl-2-(1-naphthylmethyl)propionyl]histidyl}amino-5-cyclohexyl-1-morpholino-2,3-pentanediol (a) 56.5 mg of L-N$^\alpha$-[(2RS)-3-ethylsulfonyl-2-(1-naphthylmethyl)propionyl]-N$^{im}$-triphenylmethylhistidine was dissolved in 0.4 ml of dry DMF, 10.4 mg of triethylamine and 28.3 mg of DPPA were added thereto at −15° C. under stirring. Further, 24.3 mg of triethylamine and 43.1 mg of (2RS,3R,4S)-4-amino-5-cyclohexyl-1-morpholino-2,3-pentanediol.dihydrochloride were added thereto, and the mixture was stirred at the same temperature for 1 hour and at room temperature overnight. The reaction solution was diluted with 30 ml of ethyl acetate, and the ethyl acetate layer was washed with water and with a saturated sodium chloride aqueous solution and dried over anhydrous sodium sulfate. Then, the solvent was distilled off. The residue was purified by silica gel column chromatography (chloroform/methanol=40/1) to obtain 32.3 mg of (2S,3R,4S)-4-{L-N$^\alpha$-[(2RS)-3-ethylsulfonyl-2-(1-naphthylmethyl)propionyl]-N$^{im}$-triphenylmethylhistidyl}amino-5-cyclohexyl-1-morpholino-2,3-pentanediol as colorless solid.

Rf: 0.45, 0.53 (chloroform/methanol=10/1).

Mass spectrum m/z 954(M++1).

(b) 32.3 mg of (2S,3R,4S)-4-{L-N$^\alpha$-[(2RS)-3-ethylsulfonyl-2-(1-naphthylmethyl)propionyl]-N$^{im}$-triphenylmethylhistidyl}amino-5-cyclohexyl-1-morpholino-2,3-pentanediol was dissolved in 0.4 ml of dichloromethane, and 0.1 ml of TFA was added thereto. The mixture was stirred at room temperature for one hour, and then the solvent was distilled off. The residue was dissolved in 15 ml of ethyl acetate, and the organic layer was washed sequentially with a 4% sodium hydrogencarbonate aqueous solution, with water and with a saturated sodium chloride aqueous solution and dried over anhydrous sodium sulfate. The solvent was distilled off, and the residue thereby obtained was purified by silica gel column chromatography (toluene/methanol=10/1) to obtain 19.1 mg of (2S,3R,4S)-4-{L-N$^\alpha$-[(2RS)-3-ethylsulfonyl]-2-(1-naphthylmethyl)pentanoyl]histidyl}amino-5-cyclohexyl-1-morpholino-2,3-pentanediol as colorless solid.

Rf: 0.07, 0.17 (chloroform/methanol=10/1).

Mass spectrum m/z 712(M$^{30}$+1).

NMR (300 MHz, CDCl₃) δppm: 0.62-1.87(16H), 2.48(2H), 2.55-2.95(5H), 3.05(4H,m), 3.23-3.58(5H), 3.58-3.80(5H), 4.10(0.7H,m), 4.19(0.3H,m), 4.43(0.7H,m), 4.53(0.3H,m), 6.88(0.3H,s), 6.91(0.7H,s), 7.30-7.65(5H), 7.76(1H), 7.87(1H), 8.04(1H).

(c) 16 mg of (2S,3R,4S)-4-{L-N$^\alpha$-[(2RS)-3-ethylsulfonyl-2-(1-naphthylmethyl)propionyl]histidyl}amino-5-cyclohexyl-1-morpholino-2,3-pentanediol was purified by high performance liquid chromatography (Inertsil, ODS, 7.6×250 mm) by using a solvent mixture of 0.01M phospholic acid-triethylamine bufer (pH7)-methanol (30-70) to obtain 2.45 mg of (2S, 3R, 4S)-4-{L-N$^\alpha$-[(2S)-3-ethylsulfonyl-2-(1-naphthylmethyl)propionyl]histidyl}amino-5-cyclohexyl-1-morpholino-2,3pentanediol as colorless solid.

Retention time: 29.30 minutes
Column: Inertsil ODS 7.6×250 mm
Moving phase: 0.01M phospholic acid-triethylamine (pH7)/methanol=30/70
Verosity: 2.5 ml/min.
Detector: UV (245 nm).

EXAMPLE 32

(2S,3R,4S)-4-{L-N-[(2S)-3-ethylsulfonyl-2-(1-naphthylmethyl)propionyl]seryl{amino-5-cyclohexyl-1-morpholino-2,3-pentanediol (1) L-N-[(2S)-3-ethylsulfonyl-2-(1-naphthylmethyl)-propionyl]serine (a) 72.5 mg of (2RS)-3-ethylthio-2-(1-naphthylmethyl)propionic acid was dissolved in 0.2 ml of dry DMF, and 99 μl of triethylamine, 77 μof DPPA and 0.6 ml of a dry DMF solution of 60.4 mg of L-serine ethyl ester hydrochloride was added thereto at −15° C. under stirring. The mixture was stirred at room temperature overnight. Then, 50 ml of ethyl acetate was added to the reaction solution, and the mixture was washed with water and with a saturated sodium chloride aqueous solution. The ethyl acetate layer was dried over anhydrous magnesium sulfate, and then the solvent was distilled off under reduced pressure. The residue was purified by silica gel column chromatography (n-hexane/ethyl acetate=2/1) to obtain 28.8 mg of L-N-{(2S)-3-ethylthio-2-(1-naphthylmethyl)propionyl}serine ethyl ester as colorless powder.

Rf: 0.32 (n-hexane/ethyl acetate=1/1).

(b) 28.8 mg of L-N-{(2S)-3-ethylthio-2-(1-naphthylmethyl)propionyl}serine ethyl ester was dissolved in 0.4 ml of ethanol, and 0.34 ml of an ethanol/water (10/1) solution of 1N potassium hydroxide was added thereto. The mixture was stirred at room temperature for 1.5 hours. Under cooling with ice, 1N hydrochloric acid was added to the reaction solution to adjust the solution to pH2, and the solution was extracted with ethyl acetate. The ethyl acetate layer was washed with water and with a saturated sodium chloride aqueous solution and dried over anhydrous magnesium sulfate. Then, the solvent was distilled off under reduced pressure to obtain 26.1 mg of L-N-{(2S)-3-ethylthio-2-(1-naphthylmethyl)propionyl}-serine as colorless oily substance.

Rf: 0.23 (chloroform/methanol/acetic acid=10/1/0.2).

(c) 26.1 mg of L-N-{(2S)-3-ethylthio-2-(1-naphthylmethyl)propionyl}serine was dissolved in 0.8 ml of methanol, and 0.14 ml of a 30% hydrogen peroxide aqueous solution and 2.6 mg of sodium tungstate dihydrate were added thereto. The mixture was stirred at room temperature for 5.5 hours. 30 ml of ethyl acetate was added to the reaction solution, and the mixture was washed sequentially with 1N hydrochloric acid, with water and with a saturated sodium chloride aqueous solution. The ethyl acetate layer was dried over anhydrous magnesium sulfate, and the solvent was distilled off under reduced pressure to obtain 28.3 mg of L-N-{(2S)-3-ethylsulfonyl-2-(1-naphthylmethyl)propionyl}serine as colorless oily substance.

Rf: 0.08 (chloroform/methanol/acetic acid=10/1/0.2).

(2) (2S,3R,4S)-4-{L-N-[(2S)-3-ethylsulfonyl-2-(1-naphthylmethyl)propionyl]seryl}amino-5-cyclohexyl-1-morpholino-2,3-pentanediol 28.3 mg of L-N-[(2S)-3-ethylsulfonyl-2-(1-naphthylmethyl)propionyl]serine was dissolved in 0.1 ml of dry DMF, and 44 μl of triethylamine, 22 μl of DPPA and 0.3 ml of a dry DMF solution of 38.1 mg of (2S,3R,4S)-4-amino-5-cyclohexyl-1-morpholino-2,3-pentanediol dihydrochloride was added thereto at −15° C. under stirring. The mixture was stirred at room temperature overnight. Then, 35 ml of ethyl acetate was added to the reaction solution, and the mixture was washed with water and with a saturated sodium chloride aqueous solution. The ethyl acetate layer was dried over anhydrous magnesium sulfate, and the solvent was distilled off under reduced pressure. The residue was purified by silica gel column chromatogrrphy (chloroform/methanol=30/1) to obtain 11.5 mg of the above identified compound as colorless powder.

Rf: 0.24 (chloroform/methanol=10/1).
Mass spectrum m/z 662(M⁺+1).
NMR (300 MHz, CDCl₃) δppm: 0.70-0.98(3H,m), 1.23(3H,t,J=7.6 Hz), 1.04-1.80(13H,m), 2.43-2.67(2H,m), 2.68-2.90(4H,m), 2.93-3.21(4H,m), 3.30-3.52(5H,m), 3.58-3.81(6H,m), 4.10-4.27(2H,m), 4.77(1H,br s), 6.08(1H,d,J=8 Hz), 6.96(1H,d,J=9 Hz), 7.28-7.63(4H,m), 7.79(1H,d,J=8 Hz), 7.89(1H,d,J=8 Hz), 7.99(1H,d,J=8 Hz).

EXAMPLE 33

(2S,3R,4S)-4-{L-N-[(2S)-3-ethylsulfonyl-2-(1-naphthylmethyl)propionyl]methionyl}amino-5-cyclohexyl-1-morpholino-2,3-pentanediol (1) L-N-[(2RS)-3-ethylsulfonyl-2-(1-naphthylmethyl)propionyl]methionine (a) 1.0 g of (2RS)-3-ethylthio-2-(1-naphthylmethyl)-propionic acid was dissolved in 36 ml of methanol, and 6.1 ml of a 30% hydrogen peroxide aqueous solution and 140 mg of sodium tungstate dihydrate were added thereto. The mixture was stirred at room temperature overnight. 350 ml of ethyl acetate was added to the reaction solution, and the mixture was washed sequentially with 1N hydrochloric acid, with water and with a saturated sodium chloride aqueous solution and dried over anhydrous magnesium sulfate. The solvent was distilled off under reduced pressure to obtain 1.08 g of (2RS)-3-ethylsulfonyl-2-(1-naphthylmethyl)propionic acid as colorless crystals.

Rf: 0.47 (chloroform/methanol/acetic acid=10/1/0.5).

(b) 99.2 mg of L-methionine ethyl ester monohydrochloride was dissolved in 1.5 ml of dichloromethane, and 65 μl of triethylamine was added thereto. Under cooling with ice, 129.9 mg of (2RS)-3-ethylsulfonyl-2-(1-naphthylmethyl)propionic acid, 71.5 mg of 1-hydroxybenzotriazole and 99.5 mg of DCC were added thereto. The mixture was stirred at room temperature overnight, and then, the insolubles substances were removed by filtration. The filtrate was diluted with ethyl acetate, washed sequentially with a 10% citric acid aqueous solution, with a saturated sodium carbonate aqueous solution and with a saturated sodium chloride aqueous solution and dried over anhydrous magnesium sulfate. The solvent was distilled off under reduced pressure, and the residue was purified by silica gel column chromatography (chloroform/ethyl acetate=3/1) to obtain 51.3 mg of L-N-{(2RS)-3-ethylsulfonyl-2-(1-naphthylmethyl)propionyl}methionine ethyl ester as colorless powder.

Rf: 0.38, 0.45 (chloroform/ethyl acetate=5/1).

(c) 80 mg of L-N-{(2RS)-3-ethylsulfonyl-2-(1-naphthylmethyl)propionyl}methionine was dissolved in 3.6 ml of ethanol, and 0.86 ml of an ethanol/water (10/1) solution of 1N potassium hydroxide was added thereto. The mixture was washed with water and with a saturated sodium chloride aqueous solution. The ethyl acetate layer was dried over anhydrous magnesium sulfate, and the solvent was distilled off under reduced pressure to obtain 75.3 mg of L-N-{(2RS)-3-ethylsulfonyl-2-(1-naphthylmethyl)propionyl}methionine as colorless crystals.

Rf: 0.31, 0.43 (chloroform/methanol/acetic acid=10/1/0.5).

(2) (2S,3R,4S)-4-{L-N-[(2S)-3-ethylsulfonyl-2-(1-naphthylmethyl)propionyl]methionyl}amino-5-cyclohexyl-1-morpholino-2,3-pentanediol 75.3 mg of the compound obtained in step (1) was dissolved in 0.5 ml of dry DMF, and 106 μl of triethylamine, 56 μl of DPPA and 90.4 mg of (2S,3R,4S)-4-amino-5-cyclohexyl-1-morpholino-2,3-pentanediol.-dihydrochloride were added thereto at −15° C. under stirring. The mixture was stirred at room temperature overnight. Ethyl acetate was added to the reaction solution, and the mixture was washed with water and with a saturated sodium chloride aqueous solution and dried over anhydrous magnesium sulfate. The residue was purified by silica gel column chromatography (chloroform/methanol=20/1), and separated and purificated by thin layer chromatography (silica gel plate, developer: chloroform/methanol=10/1) to obtain 12.6 mg of the above identified compound as colorless powder.

Rf: 0.41 (chloroform/methanol=10/1)

Mass spectrum m/z 706(M+ +1)

NMR (300 MHz, CDCl3) δppm: 0.80–1.06(2H,m), 1.06–2.10(16H,m), 2.03(3H,s), 2.40–2.90(10H,m), 3.02(1H,dd,J=3,14 Hz), 3.24–3.78(12H,m), 4.15–4.32(1H,m), 3.39–4.55(1H,m), 6.23(1H,d,J=9 Hz), 6.50(1H,d,J=6 Hz), 7.29–7.63(4H,m), 7.79(1H,d,J=8 Hz), 7.89(1H,d,J=8 Hz), 8.00(1H,d,J=8 Hz)

EXAMPLE 34

(2S,3R,4S)-4-{L-N-[(2S)-3-isopropylsulfonyl-2-(8-quinolylmethyl)propionyl]leucyl}amino-5-cyclohexyl-1-morpholino-2,3-pentanediol (a) The ethyl ester of the above identified compound was obtained in the same manner as in Example 10 by Michael addition reaction of ethyl 2-(8-quinolylmethyl)acrylate with isopropylmercaptan. The ester was subjected to saponification by an ethanol/water (10/1) solution of 1N potassium hydroxide, and then 3-isopropylthio-2-(8-quinolylmethyl)propionic acid as yellow solid (yield: 81%).

NMR (300 MHz, CDCl3) δppm: 1.16(3H,d,J=7 Hz), 1.23(3H,d,J=7 Hz), 2.75(1H,m), 2.8–2.9(2H,m), 3.18(2H,m), 3.87(1H,dd,J=2.4,15 Hz).

(b) (2RS)-3-isopropylthio-2-(8-quinolylmethyl)propionic acid with leucine tert-butyl ester were condensed by a usual DPPA method, followed by oxidation into the sulfonyl compound in methanol/30% hydrogen peroxide aqueous solution (10/1) in the presence of a sidium tungstate catalyst. The product was purified by silica gel column chromatography (n-hexane/ethyl acetate=1/1) to obtain L-N-[(2RS)-3-isopropylsulfonyl-2-(8-quinolylmethyl)propionyl]leucine tert-butyl ester as colorless transparent syrup.

Rf: 0.27, 0.30 (n-hexane/ethyl acetate=1/1).

(c) 54 mg of L-N-[(2RS)-3-isopropylsulfonyl-2-(8-quinolylmethyl)propionyl]leucine tert-butyl ester was dissolved in 0.8 ml of dichloromethane/TFA (1/1). The solution was concentrated under reduced pressure and dried to obtain 45 mg of L-N-[(2RS)-3-isopropylsulfonyl-2-(8-quinolylmethyl)propionyl]leucine as solid. This compound was subjected to condensation reaction with (2S,3R,4S)-4-amino-5-cyclohexyl-1-morpholino-2,3-pentanediol by a usual DPPA method. The product was purified by silica gel column chromatography (chloroform/methanol=50/1) and separated a stereoisomer to obtain 17 mg of the above-identified compound.

Rf: 0.46 (chloroform/methanol=50/1).

EXAMPLE 35

(2S,3R,4S)-4-{L-N$^a$-[(2S)-3-isopropylsulfinyl-2-(1-naphthylmethyl)propionyl]histidyl}amino-5-cyclohexyl-1-morpholino-2,3-pentanediol (a) 7 g of sodium hydroxide was dissolved in 30 ml of water. 45 ml of methanol was added thereto and throughly mixed therewith, and 6.86 ml of β-mercaptopropionic acid was dropwise added thereto. Then, 17.43 g of isopropyl bromide was added thereto, and the mixture was stirred at room temperature overnight. The isopropyl bromide was gradually dissolved and reacted. The reaction solution was diluted with 120 ml of water and washed with 120 ml of diethyl ether. The separated aqueous layer was adjusted to pH1 with conc. hydrochloric acid under cooling with ice, and extracted with ethyl acetate (200 ml×2, 100×1). Then, the organic layer was washed with a saturated sodium chloride aqueous solution (100 ml×2), dried over anhydrous magnesium sulfate, and then concentrated under reduced pressure to obtain 9.27 g of syrup of 3-isopropylthiopropionic acid.

Rf: 0.43 (chloroform/methanol/33% acetic acid=10/1/0.5).

(b) 226 mg of 3-isopropylthiopropionic acid was dissolved in 1.5 ml of dry dichloromethane. 0.22 ml (1.0 eq) of triethylamine was added thereto, and then the mixture was cooled with ice. 0.19 ml of pivaloyl chloride was added thereto under stirring to obtain a gelled reaction solution. The reaction solution was stirred at 10° C. for 10 minutes and then cooled with ice. A dichloromethane solution of lithium amide prepared from 270 mg of (4R,5S)-4-methyl-5-phenyl-2-oxazolidinone and 0.96 ml of 1.5M n-butyl lithium was prepared, and the solution was added to the previous reaction solution under cooling with ice. The mixture was stirred at room temperature overnight, and then the reaction solution was diluted with 20 ml of chloroform. After washing with 15 ml of a 4% sodium hydrogencarbonate aqueous solution, the chloroform solution was dried over anhydrous magnesium sulfate. The chloroform solution was concentrated under reduced pressure, and then purified by silica gel column chromatography (n-hexane/ethyl acetate=6/1) to obtain 240 mg of (4R,5S)-3-(3-isopropylthiopropionyl)-4-methyl-5-phenyl-2-oxazolidinone as colorless transparent syrup (yield: 51%).

(c) 4.47 g of (4R,5S)-3-(3-isopropylthiopropionyl)-4-methyl-5-phenyl-2-oxazolidinone was dissolved in 30 ml of dry THF. 24 ml of tetrahydrofuran solution of lithium diisopropylamide prepared from 2.36 g of diisopropylamine, 20 ml of THF and 14.7 ml of a n-hexane solution of 15% n-butyl lithium, was added thereto at −78° C. The mixture was stirred at −78° C. for 30 minutes. 15 ml of a THF solution of 3.57 g of 1-(bromomethyl)naphthalene was dropwise added thereto. Then, temperature of the reaction solution was raised to −35° C., and the stirring was continued overnight. 40 ml of a saturated ammonium chloride aqueous solution was added to the reaction solution to decompose excess anions in the reaction solution. Further, the reaction solution was diluted with 40 ml of water and extracted with 200 ml of ethyl acetate. The ethyl acetate layer was washed sequentially with 100 ml of a 5% potassium hydrogen sulfate aqueous solution, with 100 ml of a 4% sodium hydrogencarbonate aqueous solution and with 100 ml of a saturated sodium chloride aqueous solution. The ethyl acetate layer was dried over anydrous sodium sulfate, and then concentrated under reduced pressure. The resulting syrup was purified by silica gel column chromatography (n-hexane/ethyl acetate=7/1) to obtain 1.78 g of (4R,5S)-3-{(2S)-3-isopropylthio-2-(1-naphthylmethyl)propionyl}-4-methyl-5-phenyl-2-oxazolidinone as slightly yellow transparent syrup (yield: 27%).

NMR (300 MHz, CDCl$_3$), δppm: 0.65(3H,d,J=7.1 Hz), 1.14(3H,d,J=6.5 Hz), 1.20(3H,d,J=6.5 Hz), 2.63(1H,dd,J=5.7,12.6 Hz), 2.92(1H,m), 2.95(1H,dd,J=8.9,12.6 Hz), 3.41(1H,dd,J=9.9,13.8 Hz), 3.54(1H,dd,J=4.7,13.8 Hz), 4.70(1H,m), 4.77(1H,m), 5.62(1H,d,J=7.0 Hz).

Optical purity: 99% (HPLC analysis).

(d) 45 mg of (4R,5S)-3-{(2S)-3-isopropylthio-2-(1-naphthylmethyl)propionyl}-4-methyl-5-phenyl-2-oxazolidinone was dissolved in 0.6 ml of THF. 0.3 ml of a solution of 50 mg/ml lithium hydroxide monohydrate was added thereto under cooling with ice. The mixture was stirred at 0° C. for 1 hour and at room temperature for 3 hours. Only the THF was concentrated under reduced pressure, and water was added thereto. Then, the precipitated norephedrineamide was removed by filtration. The filtrate was adjusted to pH1 with 1N hydrochloric acid, and extracted with ethyl acetate (15 ml×2 times). The ethyl acetate layer was dried over anhydrous magnesium sulfate, and then concentrated under reduced pressure to obtain 24 mg (yield: 24%) of a syrup of (2S)-3-isopropylthio-2-(1-naphthylmethyl)propionic acid. This compound was condensed with L-N$^{im}$-triphenylmethylhistidine methyl ester by a usual DPPA method. The product was purified to obtain 40 mg of L-N$^{α}$-[(2S)-3-isopropylthio-2-(1-naphthylmethyl)propionyl]-N$^{im}$-triphenylmethylhistidine methyl ester as white solid.

Rf: 0.36 (benzene/methanol=20/1).

(e) 40 mg of L-N$^{α}$-[(2S)-3-isopropylthio-2-(1-naphthylmethyl)propionyl]-N$^{im}$-triphenylmethylhistidine methyl ester was dissolved in 0.6 ml of dioxane. 0.3 ml of a 37 mg/ml sodium bromide trihydrate aqueous solution was added thereto at room temperature. The reaction solution was stirred at room temperature for 15 minutes, and then diluted with 20 ml of ethyl acetate. The reaction solution was washed with 8 ml of water and then with 8 ml of a saturated sodium chloride aqueous solution and dried over anhydrous sodium sulfate. The reaction solution was concentrated under reduced pressure to obtain yellow solid. This product was saponified with a solution of 0.4N potassium hydroxide in methanol/water (10/1) to obtain 40 mg of L-N$^{α}$-[(2S)-3-isopropylsulfinyl-2-(1-naphthylmethyl)propionyl]-N$^{im}$-triphenylmethylhistidine (Rf: 0.48, chloroform/methanol/33% acetic acid=10/1/0.2). This compound was condensed in the same manner as in Example 11 with (2S,3R,4S)-4-amino-5-cyclohexyl-1-morpholino-2,3-pentanediol by a usual DPPA method, further subjected to removal of a triphenylmethyl group by dichloromethane/TFA (3/4). The product was purified by silica gel column chromatography (chloroform/methanol/conc. aqueous ammonia=30/3/0.02) to obtain 20 mg of (2S,3R,4S)-4-{L-N$^{α}$-[(2S)-3-isopropylsulfinyl-2-(1-naphthylmethyl)propionyl]-histidyl}amino-5-cyclohexyl-1-morpholino-2,3-pentanediol as white solid.

Rf: 0.28, 0.27 (chloroform/methanol/conc. aqueous ammonia=10/1/0.5).

EXAMPLE 36

(2S,3R,4S)-4-{L-N-[(2S or R)-3-(2-hydroxyethyl)sulfonyl-2-(1-naphthylmethyl)-propionyl]norleucyl}amino-5-cyclohexyl-1-morpholino-2,3-pentanediol (1) (2RS)-3-(2-hydroxyethyl)thio-2-(1-naphthylmethyl)propionic acid (a) 3.2 g of a sodium hydride dispersion (60% in oil) was washed three times with n-pentane and dried in an argon stream. The resulting powder was suspended in 30 ml of dry DMF under an argon stream, and 17.9 g of ethyl diethylphosphono acetate was dropwise added thereto over a period of 1 hour at 0° C. under stirring. The mixture was stirred at room temperature for 1 hour and cooled to 0° C. 17.0 g of 1-chloromethylnaphthalene was dropwise added thereto over a period of 50 minutes under stirring. The mixture was stirred at 55° C. overnight. Then, 160 ml of water was added to the reaction solution, and the mixture was extracted with ethyl acetate (80 ml×3 times). The ethyl acetate layer was washed with a saturated sodium chloride aqueous solution and dried over anhydrous sodium sulfate. The solvent was distilled off, and the syrup thereby obtained was purified by silica gel column chromatography (n-hexane/ethyl acetate=⅔) to obtain 28.7 g of ethyl 2-diethylphosphono-3-(1-naphthyl)propionate as colorless oily substance.

Rf: 0.37 (n-hexane/ethyl acetate=½).

(b) 1.92 g of lithium chloride was suspended in 50 ml of dry THF, and 15 g of ethyl 2-diethylphosphono-3-(1-naphthyl)propionate was dropwise added thereto. Then, 16 ml of a 50% dry THF solution of DBU was dropwise added thereto, and 2.01 g of paraformaldehyde suspended in dry THF was added thereto. The mixture was stirred at room temperature for 3 hours, and the insolubles were removed by filtration and washed with a small amount of diethyl ether. The washing solution and and the filtrate were put together, and the solvent was distilled off. The resulting syrup was dissolved in 180 ml of diethyl ether. The diethyl ether layer was washed sequentially with a 10% citric acid aqueous solution, with water and with a saturated sodium chloride aqueous solution and dried over anhydride sodium sulfate. The solvent was distilled off, and the syrup thereby obtained was purified by silica gel column chromatography (n-hexane/diethyl ether=20/1) to obtain 6.48 g of ethyl 2-(1-naphthyl)-methyl-2-propenoate as colorless oily substance.

Rf: 0.45 (n-hexane/ethyl acetate=10/1).

NMR (300 MHz, CDCl$_3$) δppm: 1.33(3H,t,J=6,9 Hz), 4.10(2H,s), 4.27(2H,q,J=6.9 Hz), 5.16(1H,d,J=1.5 Hz), 6.24(1H,d,J=1.5 Hz), 7.35(1H,d,J=8 Hz), 7.40–7.52(3H), 7.78(2H,d,J=8 Hz), 7.82–7.95(2H).

(c) 2.04 g of ethyl 2-(1-naphthyl)methyl-2-propenoate was dissolved in 714 μl of 2-mercaptoethanol, and 102 mg of potassium tert-butoxide was added thereto at room temperature under stirring. The mixture was stirred at room temperature for 15 minutes. 500 μl of 2-mercaptoethanol was added thereto and the mixture was stirred for 15 minutes. Then, the reaction solution was diluted with 150 ml of diethyl ether. The diethyl ether layer was washed with water and with a saturated sodium chloride aqueous solution and dried over anhydrous sodium sulfate. The solvent was distilled off to obtain 2.81 g of ethyl (2RS)-3-(2-hydroxyethyl)thio-2-(1-naphthylmethyl)propionate as colorless oily substance.

Rf: 0.43 (n-hexane/ethyl acetate=1/1).

NMR (300 MHz, CDCl$_3$) δppm: 1.08(3H,t,J=7.5 Hz), 2.40(1H,br), 2.63(2H,t,J=5.9 Hz), 2.69(1H,m), 2.84(1H,m), 3.04(1H,m), 3.35(2H,m), 3.61(2H,t,J=5.9 Hz), 4.04(2H,q,J=7.5 Hz), 7.30(2H,m), 7.48(2H,m), 7.70(1H,d,J=7.9 Hz), 7.82(1H,d,J=7.9 Hz), 8.00(1H,d,J=7.9 Hz).

(d) 151 mg of ethyl (2RS)-3-(2-hydroxyethyl)thio-2-(1-naphthylmethyl)propionate was dissolved in 0.9 ml of a solution of ethanol/water (10/1), and 1.18 ml of a solution of 2N potassium hydroxide in ethanol/water (10/1) was added thereto. The mixture was stirred at room temperature for 2 hours, and then the reaction solution was concentrated under reduced pressure. To the concentrated solution, water was added and the reaction solution was adujusted to pH2 with 2N hydrochloric acid at 0° C. under stirring, and extracted with ethyl acetate. The ethyl acetate layer was washed with water and with a saturated sodium chloride aqueous solution and dried over anhydrous sodium sulfate. Then, the solvent was distilled off, and the residue thereby obtained was purified by silica gel column chromatography (chloroform/ethyl acetate/acetic acid=6/3/0.1) to obtain 82 mg of (2RS)-3-(2-hydroxyethyl)thio-2-(1-naphthylmethyl)propionate as colorless solid.

Rf: 0.28 (chloroform/methanol/acetic acid=10/0.5/0.1).

NMR (300 MHz, CDCl$_3$) δppm: 2.68(2H,t,J=5.7 Hz), 2.74(1H,m), 2.86(1H,m), 3.14(1H,m), 3.33(1H,dd,J=6.3,13.8 Hz), 3.57(1H,dd,J=6.3,13.8 Hz), 3.64(2H,t,J=5.7 Hz), 7.38(2H,m), 7.52(2H,m), 7.77(1H,d,J=7.2 Hz), 7.88(1H,dd,J=1.8,7.8 Hz), 8.60(1H,d,J=8.4 Hz).

(2) (2S,3R,4S)-4-{L-N-[(2S or R)-3-(2-hydroxyethyl)-sulfonyl-2-(1-naphthylmethyl)propionyl]norleucyl-}amino-5-cyclohexyl-1-morpholino-2,3-pentanediol (a) 80 mg of (2RS)-3-(2-hydroxyethyl)thio-2-(1-naphthylmethyl)propionic acid was dissolved in 0.7 ml of dry DMF. 56.9 mg of L-norleucine tert-butyl ester, 68.6 mg of 1-hydroxybenzotriazole and 79.2 mg of DCC were added thereto at 0° C. under stirring. The mixture was stirred at room temperature overnight. The precipitated dicyclohexyl urea was removed by filtration, and the filtrate was diluted with 20 ml of ethyl acetate. The ethyl acetate layer was washed sequentially with a 10% citric acid aqueous solution, with water and with a saturated sodium chloride aqueous solution and dried over anhydrous sodium sulfate. Then, the solvent was distilled off, and the residue was purified by silica gel column chromatography (chloroform/ethyl acetate=7/1) to obtain 35.7 mg of the isomer having a high Rf value of L-N-[(2RS)-3-(2-hydroxyethyl)thio-2-(1-naphthylmethyl)propionyl]norleucine tert-butyl ester, and 15.9 mg of the isomer having a low Rf value and 32.3 mg of the mixture thereof.

Isomer having a high Rf value:

Rf: 0.60 (chloroform/ethyl acetate=1/1).

NMR (300 MHz, CDCl$_3$) δppm: 0.85(3H,t,J=7.1 Hz), 1.00–2.00(15H), 2.64(2H,t,J=5.1 Hz), 2.68–2.84(3H), 2.96(1H,m), 3.32(2H,m), 3.66(2H,d,J=5.1 Hz), 4.35(1H,m), 6.10(1H,d,J=7.9 Hz), 7.26–7.40(2H) 7.44–7.60(2H), 7.72(1H,d,J=7.9 Hz), 7.84(1H,d,J=7.9 Hz), 8.04(1H,d,J=7.9 Hz).

Isomer having a low Rf value:

Rf: 0.52 (chloroform/ethyl acetate=1/1).

(b) 359 mg of the isomer having a high Rf value of L-N-[3-(2-hydroxyethyl)thio-2-(1-naphthylmethyl)propionyl]norleucine tert-butyl ester was dissolved in 5 ml of methanol, and 1.33 ml of a 30% hydrogen peroxide aqueous solution and 25.7 mg of sodium tungstate dihydrate were added thereto. The mixture was stirred at room temperature for 2 hours. The reaction solution was diluted with 50 ml of ethyl acetate, and the mixture was washed with water and with a saturated sodium chloride aqueous solution and dried over anhydrous sodium sulfate. The solvent was distilled off to obtain 332 mg of L-N-[(2S or R)-3-(2-hydroxyethyl)sulfonyl-2-(1-naphthylmethyl)propionyl]norleucine tert-butyl ester.

Rf: 0.34 (chloroform/ethyl acetate=1/1).

NMR (300 MHz, CDCl$_3$) δppm: 0.86(3H,t,J=7.1 Hz), 1.05–1.35(4H), 1.40(9H,s), 1.54–1.82(3H), 3.02–3.24(3H), 3.24–3.50(3H), 3.92–4.06(3H), 4.26(1H,m), 6.05(1H,d,J=7.9 Hz), 7.28–7.42(2H), 7.48–7.63(2H), 7.76(1H,d,J=7.9 Hz), 7.88(1H,d,J=7.9 Hz), 8.01(1H,d,J=7.9 Hz).

(c) 315 mg of L-N-[(2S or R)-3-(2-hydroxyethyl)sulfonyl-2-(1-naphthylmethyl)propionyl]norleucine tert-butyl ester was dissolved in 2 ml of dry dichloromethane, and 1 ml of TFA was added thereto. The mixture was stirred at room temperature for three hours. The solvent was distilled off. The residue was recrystallized from ethyl acetate to obtain 267 mg of L-N-[(2S or R)-3-(2-hydroxyethyl)sulfonyl-2-(1-naphthylmethyl)-propionyl]norleucine as colorless solid.

Rf: 0.23 (chloroform/methanol/acetic acid=10/0.5/0.1).

(d) 50 mg of L-N-[(2S or R)-3-(2-hydroxyethyl)sulfonyl-2-(1-naphthylmethyl)propionyl]norleucine was dissolved in 0.2 ml of dry DMF, and 28.2 mg of 1-hydroxybenzotriazole and 33.2 mg of DCC were added thereto at 0° C. under stirring. Then, 55.2 mg of (2RS,3R,4S)-4-amino-5-cyclohexyl-1-morpholino-2,3-pentanediol dihydrochloride was dissolved in 0.2 ml of dry DMF, and 31.1 mg of triethylamine was added thereto for neutralization. This mixture was added to the previous reaction solution, and the mixture was stirred at 0° C. for two hours and at room temperature overnight. The precipitated dicyclohexyl urea was removed by filtration, and the filtrate was diluted with 10 ml of ethyl acetate. The ethyl acetate layer was washed sequentially with a 4% sodium hydrogencarbonate aqueous solution, with water and with a saturated sodium chloride aqueous solution and dried over anhydrous sodium sulfate. Then, the solvent was distilled off. The residue was purified by silica gel column chromatography (chloroform/methanol=20/1) to obtain 20.1 mg of (2S,3R,4S)-4-{L-N-[(2S or R)-3-(2-hydroxyethyl)sulfonyl-2-(1-naphthylmethyl)propionyl]norleucy}amino-5-cyclohexyl-1-morpholino-2,3-pentanediol as colorless solid.

Rf: 0.31 (chloroform/methanol=10/1).

Mass spectrum m/z 704(M++1).

NMR (300 MHz, CDCl$_3$) δ ppm: 0.74–1.10(4H), 1.10–1.40(4H), 1.40–1.82(14H), 2.50(2H), 2.58–2.83(4H), 3.09(2H,m), 3.24(1H,dd,J=2.7,14.0 Hz), 3.31–3.53(6H), 3.69(4H), 3.81(1H,dd,J=8.3,14.0 Hz), 3.98(2H,t,J=10.3 Hz), 4.17(1H,m), 4.62(1H,br), 5.98(1H,s), 4.26(1H,m), 6.10(2H,d,J=7.9 Hz), 7.31–7.50(2H), 7.50–7.65(2H), 7.81(1H,d,J=7.9 Hz), 7.91(1H,d,J=7.9 Hz), 8.02(1H,d,J=7.9 Hz).

EXAMPLE 37

(2S,3R,4S)-4-{L-N-[(2S)-2-benzyl-3-ethylsulfonylpropionyl]norleucyl}amino-5-cyclohexyl-1-morpholino-2,3-pentanediol (1) Ethyl (2RS)-2-benzyl-3-ethylthiopropionate (a) 2.1 g of sodium hydride (60% in oil) was suspended in DMF, and 10 g of ethyl diethylphosphonoacetate was dropwise added thereto at −20° C. under argon atmosphere. The mixture was stirred at room temperature for 30 minutes, and then 9.2 g of benzyl bromide was added thereto at 0° C. The mixture was stirred at 50° C. overnight. The reaction solution was poured into a saturated ammonium chloride aqueous solution, and extracted with ethyl acetate. The ethyl acetate layer was washed with a saturated sodium chloride aqueous solution, and then dried over anhydrous magnesium sulfate. The solvent was distilled off under reduced pressure. The residue was purified by silica gel column chromatography (n-hexane/acetone=6/1) to obtain 5.7 g of ethyl 2-diethylphosphono-3-phenylpropionate as colorless oily substance.

Rf: 0.32 (n-hexane/acetone=3/1).

(b) 1.0 g of lithium chloride was suspended in 20 ml of THF, and 5 g of ethyl 2-diethylphosphono-3-phenylpropionate was dropwise added thereto. The mixture was stirred at room temperature for seven minutes. Then, 3.6 ml of DBU was added thereto and further 11 minutes later, a suspension of 0.72 g of paraformaldehyde in THF (20 ml) was added thereto at 0° C. The mixture was stirred at room temperature overnight. Then, the mixture was neutralized with 1N hydrochloric acid, and water and ethyl acetate were added thereto. The organic layer was separted, and washed with a saturated sodium chloride aqueous solution and dried over anhydrous magnesium sulfate. The solvent was distilled off under reduced pressure, and the residue was purified by silica gel column chromatography (n-hexane/ethyl acetate=20/1) to obtain 2.4 g of ethyl 2-benzylacrylate as colorless oily substance.

Rf: 0.54 (n-hexane/ethyl acetate=15/1).

(c) To 1.95 g of ethyl 2-benzylacrylate, 1 ml of ethylmercaptan, and 20 mg of potassium tert-butoxide was added thereto under cooling with ice. The mixture was stirred at room temperature for one hour. Then, ethyl acetate was added to the reaction solution, and the mixture was washed sequentially with 1N hydrochloric acid, with water and with a saturated sodium chloride aqueous solution and dried over anhydrous magnesium sulfate. Then, the solvent was distilled off under reduced pressure to obtain 2.5 g of the above identified compound as slightly yellow oily substance.

Rf: 0.32 (n-hexane/ethyl acetate=15/1).

(2) L-N-[(2RS)-2-benzyl-3-ethylsulfonylpropionyl]-norleucine benzyl ester (a) 1 g of ethyl (2RS)-2-benzyl-3-ethylthiopropionate was dissolved in 4 ml of ethanol/water (9/1), and 8 ml of 2N potassium hydroxide in ethanol/water (9/1) was added thereto. The mixture was stirred at room temperature for 4 hours. The reaction solution was neutralized with 2N hydrochloric acid. Then, ethanol was distilled off under reduced pressure, and the residual solution was adjusted to pH2 with 2N hydrochloric acid and extracted with ethyl acetate. The extract was washed with water and with a saturated sodium chloride aqueous solution and then, dried over anhydrous magnesium sulfate. The solvent was distilled off under reduced pressure to obtain 0.9 g of a carboxylic acid as slightly yellow oily substance.

Rf: 0.40 (benzene/methanol/acetic acid=20/1/0.5).

(b) 520 mg of the carboxylic acid obtained in step (a) and 1.0 g of L-norleucine benzyl ester p-toluenesulfonate were dissolved in 10 ml of DMF, and 600 μl of DPPA and 744 μl of triethylamine were added thereto at −15° C. The mixture was stirred at 0° C. for three hours and further at room temperature overnight. Then, ethyl acetate was added to the reaction solution, and the mixture was washed sequentially with a 4% sodium hydrogencarbonate aqueous solution, with water, with 1N hydrochloric acid, with water and with a saturated sodium chloride aqueous solution and dried over anhydrous magnesium sulfate. Then, the solvent was distilled off under reduced pressure, and the residue thereby obtained was purified by silica gel column chromatography (n-hexane/ethyl acetate=6/1) to obtain 891 mg of L-N-[(2RS)-2-benzyl-3-ethylthiopropionyl]-norleucine benzyl ester as colorless powder.

Rf: 0.31 (n-hexane/ethyl acetate=4/1).

(c) 300 mg of the L-N-acylnorleucine benzyl ester obtained in step (b) was dissolved in 10 ml of methanol, and 1 ml of a 30% hydrogen peroxide aqueous solution and 20 mg of sodium tungstate were added thereto. The mixture was stirred at room temperature overnight. The reaction solution was diluted with ethyl acetate, washed with water and with a saturated sodium chloride aqueous solution and dried over anhydrous magnesium sulfate. Then, the solvent was distilled off under reduced pressure to obtain 325 mg of the above identified compound as colorless powder.

Rf: 0.23 (n-hexane/ethyl acetate=2/1)

(3) (2S,3R,4S)-4-{L-N-[(2S)-2-benzyl-3-ethylsulfonylpropionyl]norleucyl}amino-5cyclohexyl-1-morpholino-2,3-pentanediol (a) 320 mg of the sulfone compound obtained in step (2) was dissolved in 5 ml of ethanol, and subjected to hydrogenation at room temperature under an atmospheric pressure for 2 hours by an addition of palladium black. The catalyst was removed by filtration. Then, the filtrate was concentrated under reduced pressure to dryness to obtain 265 mg of a carboxylic acid as colorless powder.

Rf: 0.05, 0.14 (n-hexane/ethyl acetate/acetic acid=6/6/0.1).

(b) 100 mg of the carboxylic acid obtained in step (a), 97.3 mg of (2S,3R,4S)-4-amino-5-cyclohexyl-1-morpholino-2,3-pentanediol dihydrochloride and 120 mg of benzotriazolyl-N-hydroxytris(dimethylamino)phosphonium hexafluorophosphate (hereinafter referred to simply as BOP reagent) were dissolved in 2 ml of DMF, and 114 μl of triethylamine was dropwise added thereto at −10° C. The mixture was stirred at 8° C. overnight. Then, ethyl acetate was added to the reaction solution, and the mixture was washed sequentially with a 4% sodium hydrogencarbonate aqueous solution, with water and with a sodium chloride aqueous solution and dried over anhydrous magnesium sulfate. The solvent was distilled off under reduced pressure, and the residue was purified by silica gel column chromatography (chloroform/methanol=60/1) to obtain 31 mg of the above identified compound as colorless powder from the first fraction. Further, 75 mg of an optical isomer thereof was obtained as colorless powder from the second fraction.

Rf: 0.39 (chloroform/methanol=20/1).

Mass spectrum m/z 638(M+ +1).

EXAMPLE 38

(2S,3R,4S)-4-{L-N-[(2S)-3-tert-butylsulfonyl-2-(1-naphthylmethyl)propionyl]norleucyl}amino-5-cyclohexyl-1-morpholino-2,3-pentanediol (1) L-N-[2-(1-naphthylmethyl)acryloyl]norleucine tert-butyl ester (a) 469 mg of L-N-[(2R)-3-hydroxy-2-(1-naphthylmethyl)propionyl]norleucine tert-butyl ester was dissolved in 5 ml of dichloromethane, and 175 mg of methanesulfonyl chloride and 262 μl of triethylamine were dropwise added thereto. The mixture was stirred at 8° C. overnight. Then, ethyl acetate was added thereto, and the mixture was washed sequentially with water and with a saturated sodium chloride aqueous solution. The organic layer was dried over anhydrous magnesium sulfate, and then the solvent was distilled off under reduced pressure to obtain 566 mg of L-N-[(2S)-3-mesyloxy-2-(1-naphthylmethyl)propionyl]norleucine tert-butyl ester as slightly yellow oily substance.

Rf: 0.55 (n-hexane/ethyl acetate=1/1).

(b) 22 mg of the O-mesyl compound obtained in step (a) was dissolved in 0.3 ml of chloroform, and 28 μl of DBU was added thereto. The mixture was heated at 45° C. overnight. 8.3 μl of acetic acid and ethyl acetate were added to the reaction solution, and the mixture was washed with water and with a saturated sodium chloride aqueous solution and dried over anhydrous magnesium sulfate. Then, the solvent was distilled off under reduced pressure to obtain 17.4 mg of the above identified compound as slightly yellow oily substance.

Rf: 0.68 (n-hexane/ethyl acetate=2/1).

NMR (300 MHz, CDCl₃) δppm: 1.50(9H,s), 4.08(1H,d,J=17.7 Hz), 4.16(1H,d,J=16.2 Hz), 4.53–4.60(1H,m), 5.01(1H,s), 5.72(1H,s).

(2) L-N-[(2S)-3-tert-butylsulfonyl-2-(1-naphthylmethyl)propionyl]norleucine tert-butyl ester (a) To 365 mg of the exo-methylene compound obtained in step (1), 1.0 ml of tert-butylmercaptan and 15 mg of potassium tert-butoxide were added, and the mixture was heated at 40° C. for 30 minutes. Ethyl acetate was added to the reaction solution, and the mixture was adjusted to pH6 with acetic acid. The mixture was washed with water and with a saturated sodium chloride aqueous solution and dried over anhydrous magnesium sulfate. The solvent was distilled off under reduced pressure to obtain 400 mg of L-N-[(2RS)-3-tert-butylthio-2-(1-naphthylmethyl)propionyl]norleucine tert-butyl ester as slightly yellow oily substance.

Rf: 0.35 (n-hexane/ethyl acetate=4/1).

(b) 400 mg of the sulfide compound obtained in step (a) was dissolved in 10 ml of methanol, and 1 ml of a 30% hydrogen peroxide aqueous solution and 20 mg of sodium tungstate dihydrate were added thereto. Methanol was distilled off under redcued pressure for concentration. To the residual solution, water and ethyl acetate were added, and the organic layer was separated. The organic layer was washed with water and with a saturated sodium chloride aqueous solution and dried over anhydrous magnesium sulfate. The solvent was distilled off under reduced pressure to obtain 373 mg of a mixture of optical isomers of a sulfone compound as colorless solid.

The optical isomers were separated and purified by silica gel column chromatography (n-hexane/ethyl acetate=6/1) to obtain 126 mg of the above identified compound from the first fraction as colorless powder.

Rf: 0.37 (n-hexane/ethyl acetate=2/1).

(3) (2S,3R,4S)-4-{L-N-[(2S)-3-tert-butylsulfonyl-2-(1-naphthylmethyl)propionyl]norleucyl}amino-5-cyclohexyl-1-morpholino-2,3-pentanediol (a) 123 mg of the sulfone compound obtained in step (2) was dissolved in 2 ml of formic acid, and the solution was stirred at room temperature for 30 minutes. The reaction solution was concentrated under reduced pressure to dryness to obtain 116 mg of a carboxylic acid as colorless solid.

Rf: 0.47 (benzene/methanol/acetic acid=20/1/0.25).

(b) 30 mg of the above carboxylic acid of the above step (a), 24 mg of (2S,3R,4S)-4-amino-5-cyclohexyl-1-morpholino-2,3-pentanediol dihydrochloride and 30 mg of BOP reagent were dissolved in 1 ml of DMF. 29 μl of triethylamine was added thereto under cooling with ice, and the mixture was stirred at room temperature for 5 hours and further at 8° C. overnight. The reaction solution was diluted with ethyl acetate, washed sequentially with a 4% sodium hydrogencarbonate aqueous solution, with water and with a saturated sodium chloride aqueous solution and dried over anhydrous magnesium sulfate. Then, the solvent was distilled off under reduced pressure, and the residue thereby obtained was purified by silica gel column chromatography (chloroform/methanol=50/1) to obtain 44 mg of the above identified compound as colorless powder.

Rf: 0.30 (chloroform/methanol=20/1).

Mass spectrum m/z 716(M+ +1).

EXAMPLE 39

(2S,3R,4S)-4-[L-N-(2S)-3-[[(2S)-N-benzyloxycarbonyl-2-pyrrolidinyl]methyl]sulfonyl-2-(1-naphthylmethyl)-propionyl]norleucyl]amino-5-cyclohexyl-1-morpholino-2,3-pentanediol (1) L-N-benzyloxycarbonylprolinol 5 g of L-N-benzyloxycarbonylproline was dissolved in 100 ml of DMF, 8.1 ml of ethyl iodide and 3.4 g of sodium hydrogencarbonate were added thereto. The mixture was stirred at room temperature for 24 hours. Then, water was added to the reaction solution, and extracted with ethyl acetate. The ethyl acetate layer was washed with a saturated sodium chloride aqueous solution and dried over anhydrous magnesium sulfate. Then, the solvent was distilled off under reduced pressure. The residue thereby obtained was dissolved in a solvent mixture of 72 ml of ethanol and 48 ml of THF, and reacted at room temperature for two hours by an addition of 2.28 g of sodium borohydride and 2.25 g of lithium chloride. 3.45 ml of acetic acid was added to the reaction solution, and the mixture was concentrated under reduced pressure to dryness. Water and ethyl acetate were added to the residue, and the organic layer was speparated, washed with water and with a saturated sodium chloride aqueous solution and dried over anhydrous magnesium sulfate. The solvent was distilled off under reduced pressure to obtain 3.57 g of the above identified compound as colorless oily substance.

Rf: 0.23 (n-hexane/ethyl acetate=1/1).

(2) (2S)-2-(acetylthiomethyl)-N-benzyloxycarbonylpyrrolidine (a) 2 g of the N-protected prolinol compound obtained in step (1) was dissolved in 40 ml of dichloromethane, and 870 μl of methane sulfonyl chloride and 1.9 ml of triethylamine were added thereto at 0° C. The mixture was stirred at room temperature for 1 hour. Then, the reaction solution was poured into water, and the organic layer was separated. The organic layer was washed with water and with a saturated soium chloride aqueous solution and dried over anhydrous magnesium sulfate. Then, the solvent was distilled off under reduced pressure to obtain 2.8 g of L-N-benzyloxycarbonyl-O-mesylprolinol as slightly yellow oily substance.

Rf: 0.36 (n-hexane/ethyl acetate=1/1).

(b) 555 mg of sodium hydride (60% in oil) was suspended in 15 ml of DMF, and 1.2 ml of thioacetic acid was dropwise added thereto at −15° C. under an argon atmosphere. The mixture was stirred at the same temperature for ten minutes, and then a solution of 2.8 g of the mesyl compound obtained in step (a) in DMF (10 ml) was dropwise added thereto at −15° C. The mixture was stirred at room temperature overnight. Then, the reaction solution was poured into a saturated ammonium chloride aqueous solution and extracted with ethyl acetate. The ethyl acetate layer was washed with water and with a saturated sodium chloride aqueous solution and dried over anhydrous magnesium sulfate. The solvent was distilled off under reduced pressure, and the residue thereby obtained was purified by silica gel column chromatography (n-hexane/ethyl acetate=4/1) to obtain 1.06 g of the above identified compound as slightly yellow oily substance. Further, 1.53 g of the O-mesyl compound was recovered.

Rf: 0.49 (n-hexane/ethyl acetate=2/1).

(3) L-N-[(2RS)-3-[[(2S)-N-benzyloxycarbonyl-2-pyrrolidinyl]methyl]thio-2-(1-naphthylmethyl)propionyl]-norleucine tert-butyl ester 211 mg of the thio ester obtbined in step (2) was dissolved in 2 ml of methanol, and a solution of 41 mg of sodium methoxide in methanol (1 ml) was dropwise added thereto at 0° C. under an argon atmosphere. The mixture was stirred at room temperature for 15 minutes. Then, 42 μl of acetic acid was added to the reaction solution, and the mixture was concentrated under reduced pressure to dryness. To the residue, water and ethyl acetate were added, and the organic layer was separated. The organic layer was washed with water and with a saturated sodium chloride aqueous solution and dried over anhydrous magnesium sulfate. The solvent was distilled off under reduced pressure. The residue was dissolved in 2 ml of DMF, and a solution of 250 mg of L-N-[2-(1-naphthymethyl)acryloyl]norleucine tert-butyl ester in DMF (1 ml) and 20 mg of potassium tert-butoxide were added thereto. The mixture was stirred at room temperature for one hour and at 40° C. for one hour. Then, the reaction solution was washed with water and with a saturated sodium chloride aqueous solution and dried over anhydrous magnesium sulfate. The solvent was distilled off under reduced pressure, and the residue was purified by silica gel column chromatography (n-hexane/ethyl acetate=5/1, and then 2/1) to obtain 218 mg of the above identified compound from the second fraction. Further, 106 mg of the exo-methylene compound was recovered from the first fraction.

Rf: 0.53 (n-hexane/ethyl acetate=1/1).

(4) (2S,3R,4S)-4-[L-N-(2S)-3-[[(2S)-N-benzyloxycarbonyl-2-pyrrolidinyl]methyl]sulfonyl-2-(1-naphthylmethyl)propionyl]norleucyl]amino-5-cyclohexyl-1-morpholino-2,3-pentanediol (a) 200 mg of the sulfide compound obtained in step (3) was dissolved in 10 ml of methanol, and 1 ml of a 30% hydrogen peroxide aqueous solution and 20 mg of sodium tungstate dihydrate were added thereto. The mixture was stirred at room temperature overnight. The reaction solution was concentrated under reduced pressure to dryness to obtain 209 mg of a sulfone compound as colorless oily substance.

Rf: 0.26 (n-hexane/ethyl acetate=2/1).

(b) 209 mg of the sulfone compound obtained in step (a) was dissolved in 2 ml of formic acid, and reacted at room temperature for one hour. The reaction solution was concentrated under reduced pressure to dryness to obtain 191 mg of a carboxylic acid as colorless powder.

Rf: 0.26, 0.29 (benzene/methanol/acetic acid=10/1/0.25).

(c) 140 mg of the carboxylic acid obtained in step (b), 86 mg of (2S,3R,4S)-4-amino-5-cyclohexyl-1-morpholino-2,3-pentanediol dihyrochloride and 106 mg of BOP reagent were dissolved in 2 ml of DMF, and 100 μl of triethylamine was dropwise added thereto at −10° C. The mixture was stirred at room temperature for 5 hours and at 8° C. overnight. Then, ethyl acetate was added to the reaction solution, and the mixture was washed sequentially with a 4% sodium hydrogencarbonate aqueous solution, with water and with a saturated sodium chloride aqueous solution and dried over anhydrous magnesium sulfate. The solvent was distilled off under reduced pressure, and the residue was purified by silica gel column chromatography (chloroform/methanol=60/1) to obtain 28 mg of the above identified compound from the first fraction as colorless powder. Further, 75 mg of the optical isomer was obtained from the second fraction as colorless powder.

Rf: 0.33 (chloroform methanol=20/1).

Mass spectrum m/z 877(M+ +1).

EXAMPLE 40

(2S,3R,4S)-4-{L-N-[(2S)-2-(1-naphthylmethyl)-3-(pyrimidin-2-yl)thiopropionyl]norleucyl}amino-5-cyclohexyl-1-morpholino-2,3-pentanediol (1) L-N-[(2S)-2-(1-naphthylmethyl)-3-(pyrimidin-2-yl)thiopropionyl]norleucine tert-butyl ester 86.4 mg (2.2 eq) of 2-mercoptopyrimidine was dissolved in 1 ml of dry DMF, and 16.8 mg (2 eq) of sodium hydride (60% in oil) was added thereto. The mixture was stirred at room temperature for 30 minutes, and 193 mg of L-N-[(2R)-2-(1-naphthylmethyl)-3-(p- toluenesulfonyloxy)propionyl]norleucine tert-butyl ester dissolved in 1 ml of dry DMF was added thereto. The mixture was stirred at room temperature for five hours. About 50 ml of water was added to the reaction solution and the mixture was extracted with ethyl acetate. The organic layer was washed with a saturated sodium chloride aqueous solution and dried over anhydrous magnesium sulfate. The organic layer was subjected to filtration, concentration and purification by silica gel column chromatography (n-hexane/ethyl acete=3/1) to obtain 138.3 mg (yield: 80%) of the above identified compound.

Rf: 0.29 (n-hexane/ethyl acetate=3/1).

NMR (300 MHz, CDOD) δppm: 0.88(3H,t), 1.28(4H,m), 1.39(9H,s), 1.62(2H,m), 3.32(5H,m), 4.20(1H,dd), 7.03(1H,t), 7.38(2H,d), 7.48(2H,m), 7.74(1H,t), 7.87(1H,d), 8.19(1H,d), 8.35(2H,d).

(2) L-N-[(2S)-2-(1-naphthylmethyl)-3-pyrimidin-2-yl)thiopropionyl]norleucine 70 mg of the L-N-[(2S)-2-(1-naphthylmethyl)-3-(pyrimidin-2-yl)thiopropionyl]norleucine tert-butyl ester obtained in step (1) was dissolved in 2 ml of dry dichloromethane, and 0.5 ml of TFA was added thereto. The mixture was stirred at room temperature for 4 hours. Further, 1 ml of TFA was added thereto, and the mixture was stirred at room temperature for 2 hours. Benzene was added to the reaction solution, and the solvent was distilled off. The same operation was repeated three times. The residue was dried under reduced pressure to obtain 61.5 mg (yield: 100%) of the above identified compound.

Rf: 0.18 (benzene/methanol/acetic acid=20/1/0.5).

NMR (300 MHz, CD₃OD) δppm: 0.93(3H,t), 1.39(4H,m), 1.95(2H,m), 3.20(2H,m), 3.55(1H,dd), 3.65(1H,dd), 3.97(1H,dd), 4.32(1H,dd), 7.40(5H,m), 7.78(1H,d), 7.88(1H,m), 8.10(1H,m), 8.58(2H,d)

(3) (2S,3R,4S)-4-{L-N-[(2S)-2-(1-naphthylmethyl)-3-(pyrimidin-2-yl)thiopropionyl]norleucyl)}amino-5-cyclohexyl-1-morpholino-2,3-pentanediol 59.2 mg of L-N-[(2S)-2-(1-naphthylmethyl)-3-(pyrimidin-2-yl)thiopropionyl]norleucine was dissolved in 1 ml of dry DMF, and cooled with an ice bath. Then, 58.2 mg (1.2 eq) of (2S,3R,4S)-4-amino-5-cyclohexyl-1-morpholino-2,3-pentanediol dihydrochloride dissolved in 1 ml of dry DMF was added thereto, and 35 μl (1.2 eq) of DPPA and 65 μl (3.4 eq) of triethylamine were added thereto. The mixture was stirred at temperatures of 0° to 4° C. for 2.5 days. Excess ethyl acetate was added to the reaction solution. The organic layer was washed with a sodium chloride aqueous solution and dried over anhydrous magnesium sulfate. Then, the organic layer was purified by silica gel column chromatography (chloroform/methanol=50/1, and then 20/1) twice to obtain 20.8 mg (yield: 22%) of the above identified compound.

Rf: 0.26 (chloroform/methanol=20/1).

Mass spectrum m/z 706(M⁺ +1).

IR (KBr) νcm⁻¹: 1390, 1460, 1560, 1645, 2850, 2930, 3300, 3450.

NMR (300 MHz, CDCl₃) δppm: 0.83(3H,t), 1.20(10H,m), 1.60(9H,m), 2.49(2H,m), 2.62(1H,m), 2.78(3H,m), 3.08(1H,m), 3.44(7H,m), 2.70(4H,m), 4.22(2H,m), 4.59(1H,br s), 5.91(2H,m), 6.98(1H,t), 7.47(4H,m), 7.75(1H,m), 7.87(1H,m), 8.15(1H,m), 8.46(2H,d).

EXAMPLE 41

(2S,3R,4S)-4-{L-N-[(2S)-2-(1-naphthylmethyl)-3-(pyrimidin-2-yl)sulfonylpropionyl]norleucyl}amino-5-cyclohexyl-1-morpholino-2,3-pentanediol (1) L-N-[(2S)-2-(1-naphthylmethyl)-3-(pyrimidin-2-yl)sulfonylpropionyl]norleucine tert-butyl ester 100 mg of L-N-[(2S)-2-(1-naphthylmethyl)-3-(pyrimidin-2-yl)thiopropionyl]norleucine tert-butyl ester obtained in step (1) of Example 40, was dissolved in 1 ml of acetic acid, and 600 μl of a 30% hydrogen peroxide aqueous solution. The mixture was stirred at room temperature overnight. About 20 ml of benzene was added to the reaction solution, and the solvent was distilled off under redcued pressure. The azeotropic operation with benzene was repeated four times. The product was purified by silica gel column chromatography (n-hexane/ethyl acetate=166 , 1/5 and 0/100) to obtain 52.2 mg (yield: 50%) of the above identified compound.

Rf: 0.33 (n-hexane/ethyl acetate=⅓).

NMR (300 MHz, CDCl₃) δppm: 0.88(3H,t), 1.28(4H,m), 1.40(9H,s), 1.69(2H,m), 3.30(3H,m), 3.49(1H,dd), 4.12(1H,dd), 4.29(1H,dd), 6.10(1H,d), 7.32(3H,m), 7.49(2H,m), 7.70(1H,d), 7.82(1H,d), 7.85(1H,d), 8.62(2H,d).

(2) L-N-[(2S)-2-(1-naphthylmethyl)-3-(pyrimidin-2-yl)sulfonylpropionyl]norleucine 130 mg of L-N-[(2S)-2-(1-naphthylmethyl)-3(pyrimidin-2-yl)sulfonylpropionyl]norleucine tert-butyl ester was dissolved in 2 ml of dry dichloromethane, and 1 ml of TFA was added thereto. The mixture was stirred at room temperature for 1.5 hours. Benzene was added to the reaction solution, and the solvent was distilled off under reduced pressure. This operation was repeated four times. The product was dried under reduced pressure to obtain 113 mg (yield: 97%) of the above identified compound.

Rf: 0.09 (benzene/methanol/acetic acid=20/1/0.5).

NMR (300 MHz, CD₃OD) δppm: 0.93(3H,t), 1.39(4H,m), 1.75(2H,m), 3.20(1H,dd), 3.65(1H,dd), 3.97(1H,dd), 4.32(1H,dd), 7.40(5H,m), 7.78(1H,d), 7.88(1H,m), 8.10(1H,m), 8.58(2H,d).

(3) (2S,3R,4S)-4-{L-N-[(2S)-(1-naphthylmethyl)-3-(pyrimidin-2-yl)sulfonylpropionyl]norleucyl}amino-5-cyclohexyl-1-morpholino-2,3-pentanediol 110 mg of L-N-[(2S)-2-(1-naphthylmethyl)-3-(pyrimidin-2-yl)sulfonylpropionyl]norleucine was dissolved in 2 ml of dry DMF. The mixture was cooled with an ice bath. Then, 101 mg (1.2 eq) of (2S,3R,4S)-4-amino-5-cyclohexyl-1-morpholino-2,3-pentanediol dihydrochloride dissolved in 2 ml of dry DMF was added thereto, and 61 μl (1.2 eq) of DPPA and 112 μl (3.4 eq) of triethylamine were added thereto. The mixture was stirred at temperatures of 0° to 4° C. for 2.5 days. The aftertreatment was conducted in the same manner as in step (2) of Example 40, and the product was purified by silica gel column chromatography (chloroform/methanol=20/1) to obtain 64.3 mg (yield: 37%) of the above identified compound.

Rf: 0.2 (chloroform/methanol=20/1).

Mass spectrum m/z 738(M⁺ +1).

IR (KBr) νcm⁻¹: 1120(SO₂), 1320(SO₂), 1390, 1460, 1540, 1560, 1655, 2850, 2930, 3400.

NMR (300 MHz, CDCl₃) δ ppm: 0.87(3H,t), 1.25(10H,m), 1.60(9H,m), 2.48(2H,m), 2.62(1H,m), 2.75(3H,m), 3.29(2H,m), 3.46(3H,m), 3.65(5H,m), 3.99(1H,m), 4.25(2H,m), 4.60(1H.br s), 6.02(1H,d), 6.27(1H,d), 7.29(2H,m). 7.39(1H,t), 7.52(2H,m), 7.74(1H,d), 7.88(2H,m), 8.55(2H,d).

EXAMPLE 42

(2S,3R,4S)-4-{L-N-[(2S)-2-(1-naphthylmethyl)-3-(pyrimidin-2-yl)sulfinylpropionyl]norleucyl}amino-5-cyclohexyl-1-morpholino-2,3-pentanediol (1) L-N-[(2S)-2-(1-naphthylmethyl)-3-(pyrimidin-2-yl)sulfinylpropionyl]norleucine tert-butyl ester 60 mg of the L-N-[(2S)-2-(1-naphthylmethyl)-3-(pyrimidin-2-yl)thiopropionyl]norleucine tert-butyl ester obtained in step (1) of Example 40 was dissolved in 0.4 ml of acetic acid, and 27 μl (2 eq) of a 30% hydrogen peroxide aqueous solution was added thereto. The mixture was stirred at room temperature overnight. To the reaction solution, about 20 ml of benzene was added, and the solvent was distilled off. The azeotropic operation with benzene was repeated 4 times. Then, the product was purified by silica gel column chromatography (n-hexane/ethyl acetate=⅓, and 0/100) to obtain 38.7 mg (yield: 63.3%) of the above identified compound.

Rf: 0.07 (n-hexane/ethyl acetate=⅓).

(2) L-N-[(2S)-2-(1-naphthylmethyl)-3-(pyrimidin-2-yl)-sulfinylpropionyl]norleucine 58 mg of L-N-[(2S)-2-(1-naphthylmethyl)-3-(pyrimidin-2-yl)sulfinylpropionyl]norleucine tert-butyl ester was dissolved in 1 ml of dichloromethane, and 0.5 ml of TFA was added thereto. The mixture was stirred at room temperature for 1.5 hours. The aftertreatment was conducted in the same manner as in step (3) of Example 41 to obtain 52 mg (yield: 100%) of the above identified compound.

Rf: 0.06 (benzene/methanol/acetic acid=20/1/0.5).

(3) (2S,3R,4S)-4-{L-N-[(2S)-2-(1-naphthylmethyl)-3-(pyrimidin-2-yl)sulfinylpropionyl]norleucyl}amino-5-cyclohexyl-1-morpholino-2,3-pentanediol 51.7 mg of L-N-[(2S)-2-(1-naphthylmethyl)-3-(pyrimidin-2-yl)sulfinylpropionyl]norleucine was dissolved in 1 ml of dry DMF, and the solution was cooled with an ice bath. Then, 49 mg (1.2 eq) of (2S,3R,4S)-4-amino-5-cyclohexyl-1-morpholino-2,3-pentanediol dihydrochloride dissolved in 1 ml of dry DMF was added to the solution and 29 μl (1.2 eq) of DPPA and 55 μl (3.4 eq) of triethylamine were further added thereto. The mixture was stirred at 4° C. for 2.5 days. The aftertreatment was conducted in the same manner as in step (2) of Example 40, and the product was purified by silica gel column chromatography (chloroform/methanol=40/1) to obtain 31.5 mg of Isomer A and 16.2 mg of Isomer B of the above identified compound, respectively.

Isomer A

Rf: 0.28 (chloroform/methanol=20/1).

Mass spectrum m/z 722(M++1).

IR (KBr) νcm$^{-1}$: 1060(SO), 1390, 1460, 1560, 1650, 2860, 2930, 3300, 3420.

NMR (300 MHz, CDCl$_3$) δppm: 0.91(1H,t), 1.0–2.0(19H,m), 2.41(2H,m), 2.58(1H,t), 2.82(4H,m), 3.27(3H,m), 3.45(5H,m), 3.64(3H,m), 4.22(1H,m), 4.35(1H,m), 4.71(1H,br s), 6.37(1H,t), 6.60(1H,t), 7.09(1H,d), 7.32(1H,t), 7.45(2H,m), 7.61(2H,m), 7.72(1H,m), 7.97(1H,m), 8.01(2H,d).

Isomer B

Rf: 0.23 (chloroform/methanol=20/1),

Mass spectrum m/z 722(M++1),

IR (KBr) νcm$^{-1}$: 1060(SO), 1380, 1460, 1540, 1560, 1650, 2850, 2920, 3300, 3420.

NMR (300 MHz, CDCl$_3$) δppm: 0.83(3H,t), 1.20(2H,m), 1.65(8H,m), 2.47(2H,m), 2.62(1H,m); 2.76(3H,m), 3.45(6H,m), 3.64(6H,m), 3.89(1H,m), 4.32(1H,m), 4.68(1H,s), 6.07(1H,d), 6.14(1H,d), 7.39(3H,m), 7.57(2H,m), 7.77(1H,d), 7.88(1H,d), 8.03(1H,d), 8.80(2H,d).

EXAMPLE 43

(2S,3R,4S)-4-{L-N-[(2S)-2-(1-naphthylmethyl)-3-{[(2S)-2-pyrrolidinyl]methyl]sulfonylpropionyl]norleucyl}amino-5-cyclohexyl-1-morpholino-2,3-pentanediol dihydrochloride 21.6 mg of the N-benzyloxycarbonyl compound obtained in step (4) of Example 39 was dissolved in 2 ml of ethanol. The hydrogenation was conducted at room temperature under an atmospheric pressure for 2 hours by an addition of palladium black. The catalyst was removed by filtration. 55 μl of 1N hydrochloric acid was added to the filtrate, and the mixture was concentrated under reduced pressure to dryness. The residue was crystallized by an addition of diethyl ether to obtain 20.4 mg of the above identified compound as colorless powder.

Rf: 0.63 (chloroform/methanol=5/1).

Mass spectrum m/z 743(M++1).

EXAMPLE 44

(2S,3R,4S)-4-{L-N-[(2S)-2-benzyl-3-(pyrimidin-2-yl)sulfonylpropionyl]norleucyl}amino-5-cyclohexyl-1-morpholino-2,3-pentanediol (1) L-N-[(2RS)-2-ethoxycarbonyl-3-phenylpropionyl]norleucine tert-butyl ester 5 g of diethyl benzylmalonate was dissolved in 15 ml of ethanol, and an ethanol solution (12 ml) of 1.15 g of potassium hydroxide was dropwise added thereto. The mixture was stirred at room temperature overnight. Then, the reaction solution was concentrated under reduced pressure to dryness. The residue was dissolved in water and extracted with diethyl ether. The aqueous layer was adjusted to pH2 with 1N hydrochloric acid and extracted with diethyl ether. The diethyl ether layer was washed with a saturated sodium chloride aqueous solution and then dried over anhydrous magnesium sulfate. The solvent was distilled off under reduced pressure to obtain 3.7 g of a half ester as colorless oily substance.

1 g of the half ester was dissolved in 10 ml of DMF, and a DMF solution (15 ml) of 1.45 g of DPPA was added thereto. A DMF solution (15 ml) of 927 mg of L-norleucine tert-butyl ester containing 659 μl of triethylamine was dropwise added thereto at −5° C. The mixture was stirred at −5° C. for 2 hours and further at room temperature overnight. Then, ethyl acetate was added to the reaction solution, and the mixture was washed sequentially with 0.5N hydrochloric acid, with a 4% sodium hydrogencarbonate aqueous solution, with water and with a saturated sodium chloride aqueous solution and dried over anhydrous magnesium sulfate. Then, the solvent was distilled off under reduced pressure to obtain 1.99 g of the above identified compound as colorless powder.

Rf: 0.47 (n-hexane/ethyl acetate=3/1 ).

(2) L-N-[(2RS)-2-benzyl-3-hydroxypropionyl]norleucine tert-butyl ester 1.8 g of the L-N-acylnorleucine obtained in step (1) was dissolved in a solvent mixture of 20 ml of ethanol and 15 ml of THF, and 210 mg of sodium borohydride and 240 mg of lithium chloride were added thereto. The mixture was stirred at room temperature for 2 hours. Then, 53 mg of sodium borohydride and 60 mg of lithium chloride were further added thereto. The mixture was stirred at room temperature for 2 hours. Then, 396 μl of acetic acid was added thereto, and the mixture was concentrated under reduced pressure. To the residue, water and ethyl acetate was added, and the ethyl acetate layer was separated. The ethyl acetate layer was washed with a saturated sodium chloride aqueous solution and dried over anhydrous magnesium sulfate. Then, the solvent was distilled off under reduced pressure to obtain 1.7 g of the above identified compound as colorless powder.

Rf: 0.24, 0.31 (n-hexane/ethyl acetate=4/3).

(3) L-N-[(2S)-2-benzyl-3-(pyrimidin-2-yl)sulfonylpropionyl]norleucine tert-butyl ester (a) 400 mg of the alcohol compound obtained in step (2) was dissolved in 6 ml of dichloromethane, and 116 μl of methanesulfonyl chloride and 224 μl of triethylamine were dropwise added thereto at −5° C. The mixture was stirred at room temperature for one hour. Then, the reaction solution was diluted with ethyl acetate. The mixture was washed with water and with a saturated sodium chloride aqueous solution and dried over anhydrous magnesium sulfate. Then, the solvent was distilled off under reduced pressure to obtain 538 mg of L-N-[(2RS)-2-benzyl-3-mesyloxypropiony]norleucine tert-butyl ester as colorless solid.

Rf: 0.37 (n-hexane/ethyl acetate=2/1).

(b) 55 mg of sodium hydride (60% in oil) was suspended in 3 ml of DMF, and a DMF suspension (3 ml) of 154 mg of 2-mercaptopyrimidine was added thereto at −5° C. under an argon atmosphere. The mixture was stirred at room temperature for 20 minutes. Then, a DMF solution (4 ml) of 500 mg of O-mesyl compound obtained in step (a) was dropwise added thereto at −5° C. The mixture was stirred at room temperature for three hours, and then the reaction solution was poured into a saturated ammonium chloride aqueous solution and extracted with ethyl acetate. The ethyl acetate layer was washed with a saturated sodium chloride aqueous solution and dried over anhydrous magnesium sulfate. The solvent was distilled off under reduced pressure, and the residue was purified by silica gel column chromatography (n-hexane/ethyl acetate=5/1) to obtain 100 mg of L-N-[(2S)-2-benzyl-3-(pyrimidin-2-yl)thiopropionyl]norleucine tert-butyl ester as colorless powder from the first fraction.

Rf: 0.50 (n-hexane/ethyl acetate=4/3).

(c) 95 mg of the sulfide compound obtained in step (b) was dissolved in 4 ml of methanol, and 0.4 ml of a 30% hydrogen peroxide aqueous solution and 10 mg of sodium tungstate dihydrate were added thereto. The mixture was stirred at room temperature overnight. To the reaction solution, water was added, and methanol was distilled off under reduced pressure. To the residue, water and ethyl acetate were added, and the organic layer was separated. The organic layer was washed with a saturated sodium chloride aqueous solution and dried over anhydrous magnesium sulfate. Then, the solvent was distilled off under reduced pressure, and the residue was purified by silica gel column chromatography (n-hexane/ethyl acetate=4/3) to obtain 69 mg of the above identified compound as colorless powder.

Rf: 0.19 (n-hexane/ethyl acetate=1/1).

(4) (2S,3R,4S)-4-{L-N-[(2S)-2-benzyl-3-(pyrimidin-2-yl)sulfonylpropionyl]norleucyl}amino-5-cyclohexyl-1-morpholino-2,3-pentanediol (a) 63.6 mg of the sulfone compound obtained in step (3) was dissolved in 1 ml of dichloromethane, and 0.5 ml of TFA was added thereto. The mixture was stirred at room temperature for 30 minutes. Further, 0.5 ml of TFA was added thereto, and the mixture was stirred at room temperature for 30 minutes. Then, the reaction solution was concentrated under reduced pressure to dryness. Azeotropic evaporation with benzene was repeated twice to obtain 54.9 mg of a carboxylic acid as slightly yellow solid.

Rf: 0.10 (benzene/methanol/acetic acid =20/1/0.5).

(b) 54.9 mg of the carboxylic acid obtained in step (a), 48 mg of (2S,3R,4S)-4-amino-5-cyclohexyl-1-morpholino-2,3-pentanediol dihydrochloride and 60 mg of BOP reagent were dissolved in 2 ml of DMF, and 56 μl of triethylamine was added thereto at −5° C. The mixture was stirred at −5° C. for 30 minutes and further at 8 ° C. overnight. Then, to the reaction solution, ethyl acetate was added. The mixture was washed with a 4% sodium hydrogencarbonate aqueous solution and with a saturated sodium chloride aqueous solution and dried over anhydrous magnesium sulfate. The solvent was distilled off under reduced pressure, and the residue was purified by silica gel column chromatography (chloroform/methanol=60/1) to obtain 60.5 mg of the above identified compound as colorless powder.

Rf: 0.21 (chloroform/methanol=20/1).

Mass spectrum m/z 688(M+ +1).

EXAMPLE 45

(2S,3R,4S)-4-{L-O-acetyl-N-[(2S)-3-ethylsulfonyl-2-(1-naphthylmethyl)propionyl]homoseryl}amino-5-cyclohexyl-1-morpholino-2,3-pentandiol (1) L-O-acetyl-N-tert-butoxycarbonylhomoserine benzyl ester (a) 117 mg of L-homoserine was dissolved in 3 ml of ethanol/water (2/1), and 0.99 ml of a 1N sodium hydroxide aqueous solution was added thereto. Then, 1 ml of a THF solution of 240 mg of di-tert-butyl dicarbonate was added thereto. The mixture was stirred at room temperature overnight. The unreacted reagent was extracted from the reaction solution with diethyl ether, and the residual aqueous layer was adjusted to pH2 by an addition of 1N hydrochloric acid under cooling with ice. The aqueous layer was extracted with ethyl acetate, and the ethyl acetate layer was dried over anhydrous magnersium sulfate. Then, the solvent was distilled off under redcued pressure to obtain 210 mg of L-N-tert-butoxycarbonylhomoserine as colorless oily substance.

Rf: 0.22 (chloroform/methanol/acetic acid=10/1/0.2).

(b) 210 mg of L-N-tert-butoxycarbonylhomoserine was dissolved in 3 ml of ethanol, and 0.96 ml of a 1N sodium hydroxide aqueous solution was added thereto. The mixture was stirred at room temperature for one day. The solvent of the reaction solution was distilled off under reduced pressure, and the residue was dissolved in 3 ml of DMF. 132 μl of benzyl bromide was added to the solution, and the mixture was stirred at room temperature overnight. The reaction solution was diluted with 30 ml of ethyl acetate. The mixture was washed sequentially with a saturated sodium hydrogencarbonate aqueous solution, with water and with a saturated sodium chloride aqueous solution and dried over magnesium sulfate. The solvent was distilled off under reduced pressure, and the residue was purified by silica gel column chromatography (n-hexane/ethyl acetate=1/1) to obtain 266 mg of L-N-tert-butoxycarbonyl-homoserine benzyl ester as colorless oily substance.

Rf: 0.55 (n-hexane/ethyl acetate=½).

(c) 266 mg of L-N-tert-butoxycarbonylhomoserine benzyl ester was dissolved in 3 ml of pyridine, and 2 ml of acetic anhydride was added thereto. The mixture was stirred at room temperature for 18 hours. The reaction solution was poured into ice water and extracted with ethyl acetate. The mixture was washed sequentially with a 1N hydrochloric acid, with a saturated sodium hydrogencarbonate aqueous solution and with a saturated sodium chloride aqueous solution and dried over anhydrous magnesium sulfate. Then, the solvent was distilled off under reduced pressure, and the residue was purified by silica gel column chromatography (n-hexane/ethyl acetate=3/1) to obtain 273 mg of L-O-acetyl-N-tert-butoxycarbonylhomoserine benzyl ester as colorless oily substance.

Rf: 0.34 (n-hexane/ethyl acetate=2/1)

(2) L-O-acetylhomoserine benzyl ester hydrochloride 215 mg of L-O-acetyl-N-tert-butoxycarbonylhomoserine benzyl ester was dissolved in 2 ml of dioxane, and 3.4 ml of a 3.6M hydrogen chloride/dioxane solution was added thereto under cooling with ice. The mixture was stirred at room temperature for 2.5 hours. The reaction solution was subjected to distillation under reduced pressure for removal of the solvent to obtain 174 mg of L-O-acetylhomoserine benzyl ester hydrochloride as colorless oily substance.

Rf: 0.75 (chloroform/methanol/aqueous ammonia=10/1/0.5).

(3) L-O-acetyl-N-{(2S)-3-ethylsulfonyl-2-(1-naphthylmethyl)propionyl}homoserine (a) 128 mg of (2RS)-3-ethylsulfonyl-2-(1-naphthylmethyl)propionic acid was dissolved in 0.3 ml of DMF, and 78 mg of 1-hydroxybenzotriazole and 103 mg of DCC were sequentially added thereto under cooling with ice. A solution of 174 mg of L-O-acetylhomoserine benzyl ester hydrochloride dissolved in 0.5 ml of DMF and neutralized with 86 μl of triethylamine, was added thereto. The temperature was returned to room temperature, and the mixture was stirred overnight. The insolubles were removed from the reaction solution by filtration. The filtrate was diluted with ethyl acetate, washed with 1N hydrochloric acid, with a saturated sodium hydrogencarbonate aqueous solution and with a saturated sodium chloride aqueous solution and dried over anhydrous magnesium sulfate. Then, the solvent was distilled off under reduced pressure, and the residue was purified by silica gel column chromatography (n-hexane/ethyl acetate=1/1) to obtain 55.6 mg of L-O-acetyl-N-{(2S)-3-ethylsulfonyl-2-(1-naphthylmethyl)propionyl}homoserine benzyl ester as colorless crystals.

Rf: 0.50 (n-hexane/ethyl acetate=½).

(b) 55.6 mg of L-O-acetyl-N-{(2S)-3-ethylsulfonyl-2-(1-naphthylmethyl)propionyl}homoserine benzyl ester was dissolved in 3 ml of ethanol and hydrogenated at ordinary temperature under an atmospheric pressure by an addition of palladium black. The catalyst was removed by filtration, and then the solvent was distilled off under reduced pressure to obtain 46.3 mg of L-O-acetyl-N-{(2S)-3-ethylsulfonyl-2-(1-naphthylmethyl)-propionyl}homoserine as colorless oily substance.

Rf: 0.51 (chloroform/methanol/acetic acid=10/1/0.5).

(3) (2S,3R,4S)-4-{L-O-acetyl-N-[(2S)-3-ethylsulfonyl-2-(1-naphthylmethyl)propionyl]homoseryl}amino-5-cyclohexyl-1-morpholino-2,3-pentanediol 47.1 mg of L-O-acetyl-N-{(2S)-3-ethylsulfonyl-2-(1-naphthylmethyl)propionyl}homoserine was dissolved in 0.2 ml of dry DMF, and 19 μl of triethylamine, 29 μl of DPPA and 0.5 ml of a DMF solution of 51.5 mg of (2S,3R,4S)-4-amino-5-cyclohexyl-1-morpholino-2,3-pentanediol dihydrochloride neutralized with 40 μl of triethylamine, was added thereto. The mixture was stirred at room temperature overnight. To the reaction solution, 30 ml of ethyl acetate was added, and washed with water and with a saturated sodium chloride aqueous solution and dried over anhydrous magnesium sulfate. The solvent was distilled off under reduced pressure, and the residue was purified by silica gel column chromatography (chloroform/methanol=30/1) to obtain 43.0 mg of the above identified compound as colorless amorphous.

Rf: 0.50 (chloroform/methanol=10/1),

Mass spectrum m/z 718(M$^+$+1),

NMR (300 MHz, CDCl$_3$) δppm: 0.80–1.04(3H,m), 1.20(3H,t,J=7.6 Hz), 1.10–2.15(15H,m), 1.97(3H,s), 2.41–3.00(9H,m), 3.03(1H,dd,J=2,14 Hz), 3.25–3.78(10H,m), 3.96–4.48(4H,m), 4.52(1H,br s), 6.38(1H,d,J=9 Hz), 6.50(1H,d,J=6 Hz), 7.30–7.62(4H,m), 7.79(1H,d,J=8 Hz), 7.89(1H,d,J=8 Hz), 7.99(1H,d,J=8 Hz).

EXAMPLE 46

(2S,3R,4S)-4-{L-N-[(2S)-3-ethylsulfonyl-2-(1-naphthylmethyl)propionyl]homoseryl}amino-5-cyclohexyl-2,3-pentanediol 35.0 mg of the compound obtained in Example 45 was dissolved in 1 ml of methanol, and 180 μl of aqueous ammonia was added thereto. The mixture was stirred at room temperature overnight. The reaction solution was subjected to distillation under reduced pressure for removal of the solvent, and the residue was purified by silica gel column chromatography (chloroform/methanol=10/1) to obtain 19.8 mg of the above identified compound as colorless crystals.

Rf: 0.37 (chloroform/methanol=10/1).

Mass spectrum m/z 676 (M$^+$+1).

NMR (300 MHz, CDCl$_3$) δppm: 0.86–1.04(2H,m), 1.14–2.06(16H,m), 2.46–2.60(2H,m), 2.64–2.94(5H,m), 3.01(1H,dd,J=1.8,13.5 Hz), 3.29–3.51(5H,m), 3.59–3.78(7H,m), 4.22(1H,dt,J=6.0,9.3 Hz), 4.41–4.47(1H,m), 4.49(1H,br s), 6.22(1H,d,J=9.0 Hz), 6.81(1H,d,J=6.3 Hz), 7.32–7.62(4H,m), 7.79(1H,d,J=8.4 Hz), 7.89(1H,d,J=8.4 Hz), 7.98(1H,d,J=8.4 Hz).

EXAMPLE 47

(2S,3R,4S)-4-{L-N-[(2S)-3-furfurylsulfonyl-2-(1-naphthylmethyl)propinyl]norleucyl}amino-5-cyclohexyl-1-morpholino-2,3-pentanediol (1) (2R)-3-hydroxy-2-(1-naphthylmethyl)propionic acid (2R)-3-benzyloxy-2-(1-naphthylmethyl)propionic acid was dissolved in 6 ml of THF, and 3 ml of cyclohexene, 2.5 ml of 1N hydrochloric acid and 400 mg of 10% palladium carbon were added thereto. The mixture was refluxed under heating for 48 hours. After filtration, the solvent was distilled off under reduced pressure, and the residue was divided with ethyl acetate and a 4% sodium hydrogencarbonate aqueous solution.

The aqueous layer was adjusted to pH2 with 1N hydrochloric acid under cooling with ice and extracted with ethyl acetate. The ethyl acetate layer was washed sequentially with water and a saturated sodium chloride aqueous solution and dried over anhydride sodium sulfate to obtain 212 mg of (2R)-3-hydroxy-2-(1-naphthylmethyl)propionic acid as colorless oily substance.

Rf: 0.40 (n-hexane/ethyl acetate/acetic acid=6/6/0.2).

(2) L-N-[(2R)-3-hydroxy-2-(1-naphthylmethyl)propionyl]norleucine tert-butyl ester 79 mg of (2R)-3-hydroxy-2-(1-naphthylmethyl)propionic acid was dissolved in 0.5 ml of DMF, and 1.0 ml of a DMF solution of 84 mg of L-norleucine tert-butyl ester, 82 mg of 1-hydroxybenzotriazole monohydrate and 79 mg of DCC were added thereto under stirring at −15° C. The mixture was stirred at −15° C. for 1 hour and then at room temperature overnight. Then, the reaction solution was treated in the same manner as in Example 1 (3), and the product was purified by silica gel column chromatography (n-hexane/ethyl acetate=2/1) to obtain 79 mg of L-N-[(2R)-3-hydroxy-2-(1-naphthylmethyl)propionyl]norleucine tert-butyl ester as white solid.

Rf: 0.26 (n-hexane/ethyl acetate=2/1).

(3) L-N-[(2S)-3-furfurylthio-2-(1-naphthylmethyl)-propionyl]norleucine tert-butyl ester (a) 78 mg of L-N-[(2R)-3-hydroxy-2-(1-naphthylmethyl)propionyl]norleucine tert-butyl ester was dissolved in 0.8 ml of dry pyridine, 80 mg of p-toluenesulfonyl chloride was added thereto. The mixture was stirred at room temperature overnight. The reaction solution was poured into ice water and extracted with ethyl acetate. The extract was washed sequentially with 1N hydrochloric acid, water, a saturated sodium hydrogencarbonate aqueous solution and a saturated sodium chloride aqueous solution and dried over anhydrous sodium sulfate. Then, the solvent was distilled off under reduced pressure, and the residue was purified by silica gel column chromatography (n-hexane/ethyl acetate=3/1) to obtain 86 mg of L-N-[(2R)-2-(1-naphthylmethyl)-3-p-toluenesulfonyloxypropionyl]norleucine tert-butyl ester as colorless oily substance.

Rf: 0.54 (n-hexane/ethyl acetate=2/1).

(b) 11 mg of sodium hydride (60% in oil) was suspended in 0.3 ml of dry DMF, and 30 μl of furfurylmercaptan was added thereto at 0° C. under stirring. The mixture was stirred at room temperature for 30 minutes. Then, 0.7 ml of a dry DMF solution of 86 mg of L-N-[(2R)-2-(1-naphthylmethyl)-3-p-toluenesulfonyloxypropionyl]norleucine tert-butyl ester was added thereto at 0° C., and the mixture was stirred at room temperature for one hour. To the reaction solution, ethyl acetate was added, and the mixture was washed sequentially with water and a saturated sodium chloride aqueous solution. The organic layer was dried over anhydrous sodium sulfate, and the solvent was distilled off under reduced pressure. Then, the residue was purified by silica gel column chromatography (n-hexane/ethyl acetate=10/1) to obtain 64 mg of the above identified compound as colorless oily substance.

Rf: 0.28 (n-hexane/ethyl acetate=5/1).

(4) L-N-[(2S)-3-furfurylsulfonyl-2-(1-naphthylmethyl)propionyl]norleucine (a) 60 mg of L-N-[(2S)-3-furfurylthio-2-(1-naphthylmethyl)propionyl]norleucine tert-butyl ester was dissolved in 1.0 ml of methanol, and 0.21 ml of a 30% hydrogen peroxide aqueous solution and 6 mg of sodium tungstate dihydrate were added thereto. The mixture was stirred at room temperature for 4 hours. To the reaction solution, ethyl acetate was added, and the mixture was washed sequentially with water and a saturated sodium chloride aqueous solution. The organic layer was dried over anhydrous sodium sulfate. Then, the solvent was distilled off under reduced pressure to obtain 57 mg of L-N-[(2S)-3-furfurylsulfonyl-2-(1-naphthylmethyl)propionyl]norleucine tert-butyl ester as colorless oily substance.

Rf: 0.38 (n-hexane/ethyl acetate=2/1).

(b) 55 mg of L-N-[(2S)-3-furfurysulfonyl-2-(1-naphthylmethyl)propionyl]norleucine tert-butyl ester was dissolved in 0.3 ml of dichloromethane, and 0.3 ml of TFA was added thereto. The mixture was stirred at room temperature for one hour. To the reaction solution, ethyl acetate was added. The mixture was washed sequentially with water and a saturated sodium chloride aqueous solution and dried over anhydrous sodium sulfate. The solvent was distilled off under reduced pressure to obtain 52 mg of the above identified compound as colorless oily substance.

Rf: 0.27 (n-hexane/ethyl acetate/acetic acid=6/6/0.2).

(5) (2S,3R,4S)-4-{L-N-[(2S)-3-furfurylsulfonyl-2-(1-naphthylmethyl)propionyl]norleucyl}amino-5-cyclohexyl-1-morpholino-2,3-pentanediol 50 mg of L-N-[(2S)-3-furfurylsulfonyl-2-(1-naphthylmethyl)propionyl]norleucine was dissolved in 0.4 ml of dry DMF, and 18 μl of triethylamine, 28 μl of DPPA and 0.6 ml of a dry DMF solution of 53.5 mg of (2S,3R,4S)-4-amino-5-cyclohexyl-1-morpholino-2,3-pentanediol dihydrochloride was added thereto and 41 μl of triethylamine was further added thereto. The mixture was stirred at room temperature overnight. Then, the same procedure as in Example 16 (5)-(b) was conducted, and the purification by silica gel column chromatography (chloroform/methanol=100/1, and then 50/1) was conducted to obtain 64 mg of the above identified compound as white powder.

Rf: 0.29 (chloroform/methanol=20/1).

Mass spectrum (FAB) m/z 740(M+ +1).

NMR (300 MHz, CDCl$_3$) δppm: 0.79–0.82(3H,m), 1.05–1.38(6H,m), 1.38–1.80(9H,m), 2.40–2.55(2H,m), 2.55–2.82(4H,m), 3.05(1H,dd,J=14.2,3.2 Hz), 3.15–3.32(1H,m), 3.32–3.75(9H,m), 4.13–4.32(4H,m), 5.88(1H,d,J=7.9 Hz), 6.02(1H,d,J=8.7 Hz), 6.34(1H,d,J=0.8 Hz), 6.38(1H,d,J=0.8 Hz), 7.28–7.65(4H,m), 7.79(1H,d,J=7.9 Hz), 7.90(1H,d,J=7.9 Hz), 7.99(1H,d,J=7.9 Hz).

EXAMPLE 48

(2S,3R,4S)-4-{L-N-[(2S or R)-3-(2-hydroxyethyl)sulfinyl-2-(1-naphthylmethyl)propionyl]norleucyl}amino-5-cyclohexyl-1-morpholino-2,3-pentanediol (a) 114 mg of the isomer having a high Rf value of L-N-[(2S or R)-3-(2-hydroxyethyl)thio-2-(1-naphthylmethyl)propionyl]norleucine tert-butyl ester was dissolved in 1.06 ml of acetic acid, and 28.1 μl of a 30% hydrogen peroxide aqueous solution was added thereto. The mixture was stirred at room temperature for 30 minutes, and then the solvent was distilled off under reduced pressure. To the residue, benzene was added, and benzene was distilled off under reduced pressure. This operation was repeated. The syrup thereby obtained was purified by silica gel column chromatography (chloroform/methanol=30/1) to obtain 117 mg of L-N-[(2S or R)-3-(2-hydroxyethyl)sulfinyl-2-(1-naphthylmethyl)propionyl]norleucine tert-butyl ester as colorless oily substance.

Rf: 0.30 (chloroform/methanol=20/1).

NMR (300 MHz, CDCl₃) δppm: 0.84(3H,q,J=7.6 Hz), 1.10–1.47(13H), 1.47–1.85(2H), 2.63–3.08(3H), 3.20–3.62(4H), 4.00–4.38(3H), 5.98(0.3H,d,J=7.9 Hz), 6.34(0.7H,d,J=7.9 Hz), 7.28–7.42(2H), 7.50(2H,m), 7.73(1H,d,J=7.9 Hz), 7.85(1H,d,J=7.9 Hz), 8.00(0.7H,d,J=7.9 Hz), 8.06(0.3H,d,J=7.9 Hz).

(b) 109 mg of L-N-[(2S or R)-3-(2-hydroxyethyl)sulfinyl-2-(1-naphthylmethyl)propionyl]norleucine tert-butyl ester was dissolved in 0.4 ml of dry dichloromethane, and 0.4 ml of TFA was added thereto. The mixture was stirred at room temperature for 2.5 hours. Then, the solvent was distilled off. To the residue, benzene was added, and the mixture was concentrated under reduced pressure. This operation was repeated to obtain 94.8 mg of L-N-[(2S or R)-3-(2-hydroxyethyl)sulfinyl-2-(1-naphthylmethyl)propionyl]norleucine as colorless solid.

Rf: 0.30, 0.23 (chloroform/methanol/acetic acid=10/0.5/0.1).

NMR (300 MHz, CD₃OD) δppm: 0.90(3H), 1.20–1.42(4H), 1.55–1.85(2H), 2.72–3.02(3H), 3.02–3.62(4H), 3.80–3.96(2H), 4.24(0.3H,m), 4.35(0.7H,m), 7.37(2H,m), 7.52(2H,m), 7.75(1H,m), 7.85(1H,d,J=8.1 Hz), 8.18(1H,d,J=8.1 Hz).

(c) 54.6 mg of L-N-[(2S or R)-3-(2-hydroxyethyl)sulfinyl-2-(1-naphthylmethyl)propionyl]norleucine was dissolved in 0.2 ml of dry DMF, and 32.3 mg of 1-hydroxybenzotriazole and 41.2 mg of DCC were added thereto at 0° C. under stirring. Then, 60.4 mg of (2S,3R,4S)-4-amino-5-cyclohexyl-1-morpholino-2,3-pentanediol dihydrochloride was dissolved in 0.2 ml of dry DMF, and 34.0 mg of triethylamine was added thereto for neutralization. This solution was added to the previous solution, and the mixture was stirred at 0° C. for 2 hours and at 5° C. overnight. The precipitated dicyclohexyl urea was removed by filtration, and solvent of the filtrate was distilled off. To the residue, a small amount of chloroform was added, and the insolubles were removed by filtration. Then, the solvent of the filtrate was distilled off under reduced pressure. This operation was repeated twice. The residue thereby obtained was dissolved in 10 ml of ethyl acetate. The ethyl acetae layer was washed sequentially with a 4% sodium hydrogencarbonate aqueous solution, with water and with a saturated sodium aqueous solution and dried over anhydride sodium sulfate. The solvent was distilled off under reduced pressure, and the residue was purified by silica gel column chromatography (chlorofrom/methanol=15/1) to obtain 32.0 mg of the isomer having a high Rf value (Example 48-A) and 23.4 mg of the isomer having a low Rf value (Example 48-B) of (2S,3R,4S)-4-{L-N-[(2S or R)-3-(2-hydroxyethyl)sulfinyl-2-(1-naphthylmethyl)propionyl]norleucyl}amino-5-cyclohexyl-1-morpholino-2,3-pentanediol as colorless solids, respectively.

Isomer having a high Rf value (Example 48-A):
Rf: 0.33 (chloroform/methanol=10/1).
Mass spectrum m/z 688 (M⁺+1).
NMR (300 MHz, CDCl₃) δppm: 0.80–1.08 (4H), 1.10–1.85 (18H), 2.48(2H), 2.57–2.86(6H), 3.08(2H,m), 3.30–3.54(5H), 3.54–3.75(5H), 3.98(2H,m), 4.25(2H,m), 4.70(1H,br), 6.46(1H,d,J=8.4 Hz), 6.77(1H,br), 7.32–7.46(2H), 7.55(2H,m), 7.79(1H,d,J=7.8Hz), 7.89(1H,dd,J=2.1,7.5 Hz), 7.99(1H,d,J=8.1 Hz).

Isomer having a low Rf value (Example 48-B):
Rf: 0.29 (chloroform/methanol=10/1).
Mass spectrum m/z 688(M⁺+1).
NMR (300 MHz, CDCl₃) δppm: 0.70–1.05(4H), 1.05–1.38(8H), 1.38–1.90(10H), 2.48(2H,Br), 2.57–3.00(7H), 3.21–3.56(6H), 3.66(4H), 3.94–4.30(4H), 4.68(1H,br), 6.30(2H), 7.30–7.45(2H), 7.55(2H,m), 7.78(1H), 7.88(1H), 7.95–8.09(1H).

EXAMPLE 49

(2S,3R,4S)-4-{L-N-[(2S)-3-ethylsulfinyl-2-(1-naphthylmethyl)propionyl]norleucyl}amino-5-cyclohexyl-1-morpholiono-2,3-pentanediol (a) 133.3 mg of L-N-[(2S)-3-ethylthio-2-(1-naphthylmethyl)propionyl]norleucine tert-butyl ester was dissolved in 1 ml of acetic acid, and 31.9 μl of a 30% hydrogen peroxide aqueous solution was added thereto. The mixture was stirred at room temperature for 25 minutes. Then, the solvent was distilled off under reduced pressure. To the residue, benzene was added, and benzene was distilled off under reduced pressure. This operation was repeated to obtain 136.1 mg of L-N-[(2S)-3-ethylsulfinyl-2-(1-naphthylmethyl)propionyl]norleucine tert-butyl ester as colorless oily substance.

Rf: 0.33 (chloroform/ethyl acetate=1/1).
Mass spectrum m/z 460(M⁺+1).

(b) 129.2 mg of L-N-[(2S)-3-ethylsulfinyl-2-(1-naphthylmethyl)propionyl]norleucine tert-butyl ester was dissolved in 0.5 ml of dry dichloromethane, and 0.5 ml of TFA was added thereto. The mixture was stirred at room temperature for 2.5 hours. Then, the solvent was distilled off. The residue was dissolved in benzene, and the mixture was concentrated under reduced pressure. This operation was repeated to obtain oily substance. The oily substance was solidified with chloroform/diethyl ether. The solvent was distilled off under reduced pressure to obtain 117 mg of L-N-[(2S)-3-ethylsulfinyl-2-(1-naphthylmethyl)propionyl]norleucine as colorless solid.

Rf: 0.37, 0.41 (chloroform/methanol/acetic acid=10/0.5/0.1).

NMR (300 MHz, CDCl₃) δppm: 0.83(3H), 1.05–1.39(7H), 1.70(1H,m), 1.92(1H,m), 2.62–2.82(2H), 2.90(0.3H,dd,J=9.9,13.5 Hz), 3.08–3.58(3.7H), 3.70(1H,m), 4.22(0.3H,dt,J=5.4,5.4 Hz), 4.40(0.7H,dt,J=5.8,5.8 Hz), 7.28–7.67(6H), 7.92(0.7H), 8.08(0.3H,d,J=8.1 Hz).

(c) 60 mg of L-N-[(2S)-3-ethylsulfinyl-2-(1-naphthylmethyl)propionyl]norleucine was dissolved in 0.2 ml of dry DMF, and 36.4 mg of 1-hydroxybenzotriazole and 42.9 mg of DCC were added thereto at 0° C. under stirring. Then, 69.5 mg of (2S,3R,4S)-4-amino-5-cyclohexyl-1-morpholino-2,3-pentanediol dihydrochloride was dissolved in 0.2 ml of dry DMF, 39.1 mg of triethylamine was added thereto for neutralization. This solution was added to the previous reaction solution, and the mixture was stirred at 0° C. for two hours and at 5° C. overnight. The precipitated dicyclohexylurea was removed by filtration and washed with a small amount of chloroform. This washing solution and the filtrate were put together, and concentrated under reduced pressure. The concentrated solution was diluted with 20 ml of ethyl acetate. The organic layer was washed sequentially with a 4% sodium hydrogencarbonate aqueous solution, with water and with a saturated sodium chloride aqueous solution and dried over anhydrous sodium sulfate. The solvent was distilled off under reduced pressure, the residue was purified by silica gel column chromatography (chloroform/methanol=60/1) to obtain 38.3 mg of the isomer having a high Rf value (Example 49-A) and 16.1 mg of the isomer having a low Rf value (Example 49-B) of (2S,3R,4S)-4-{L-N-[(2S)-3-ethylsulfinyl-2-(1-naphthylmethyl)propionyl]-norleucyl}amino-5-cyclohexyl-1-morpholino-2,3-pentanediol as colorless solids, respectively.

Isomer having a high Rf value (Example 49-A):
Rf: 0.5 (chloroform/methanol=10/1)
Mass spectrum m/z 672(M++1)
NMR (300 MHz, CDCl$_3$) δppm: 0.75–1.86(25H), 2.27(1H,m), 2.40–2.69(4H), 2.78(4H), 3.04(1H,dd,J=9.2,13.1 Hz), 3.32(2H), 3.42–3.62(7H), 4.25(2H), 4.68(1H,br), 6.34(1H,d,J=9.3 Hz), 6.90(1H,d,J=5.4 Hz), 7.32–7.48(2H), 7.78(1H,d,J=7.8 Hz), 7.89(1H,dd,J=1.4,7.8 Hz) 7.98(1H,d,J=8.7 Hz)

Isomer having a low Rf value (Example 49-B):
Rf: 0.43 (chloroform/methanol=10/1).
Mass spectrum m/z 672(M++1).
NMR (300 MHz, CDCl$_3$) δppm: 0.77–2.00(25H), 2.49(2H), 2.55–2.85(7H), 3.04(1H,m), 3.32(1H,m), 3.46(4H), 3.64(4H), 4.15(1H,m), 4.25(1H,m), 6.19(1H), 6.46(1H), 7.32–7.47(2H), 7.47–7.63(2H), 7.78(1H,d,J=7.8 Hz), 7.89(1H,d,J=8.1 Hz), 8.08(1H,d,J=8.1 Hz).

EXAMPLE 50

N-[(2S,3R,4S)-4-[L-N-[(2R)-3-ethylsulfonyl-2-(1-naphthylmethyl)propionyl]norleucyl]amino-5-cyclohexyl-2,3-dihydroxypentyl]morpholine N-oxide 25 mg of (2S,3R,4S)-4-{L-N-[(2S)-3-ethylsulfonyl-2-(1-naphthylmethyl)propionyl]norleucyl}amino-5-cyclohexyl-1-morpholino-2,3-pentanediol was dissolved in 1.5 ml of methanol, and 150 μl of a 30% hydrogen peroxide aqueous solution was added thereto. 2mg of sodium tungstate dihydrate was added thereto as a catalyst, and the mixture was stirring. The mixture was stirred at room temperature for three hours, and the insolubles were removed by filtration. The filtrate was diluted with 15 ml of ethyl acetate and washed with a 4% sodium carbonate aqueous solution (10 ml×1 time) and then with a saturated sodium aqueous solution (10 ml×2 times). The ethyl acetate layer was dried over anhydrous sodium sulfate and then concentrated under reduced pressure to obtain 25 mg of the above identified compound as white solid.

Mass spectrum m/z 704(M++1).

EXAMPLE 51

(2S,3R,4S)-4-{L-N-[(2S or R)-3-cyclopentanesulfonyl-2-benzylpropionyl]norleucyl}amino-5-cyclohexyl-1-morpholino-2,3-pentanediol (a) 210 mg of (2S or R)-3-cyclopentanesulfonyl-2-benzylpropionic acid was dissolved in 3 ml of dry DMF, and 0.8 ml of a dry DMF solution of 0.15 ml of triethylamine, 0.18 ml of DPPA and 0.15 g of norleucine tert-butyl ester was added thereto at −15° C. by a usual DPPA method. The mixture was subjected to usual aftertreatment, and the product was purified by silica gel column chromatography to obtain 122 mg of L-N-((2S or R)-3-cyclopentanesulfonyl-2-benzylpropionyl)norleucine tert-butyl ester as white solid.

NMR (300 MHz, CDCl$_3$) δppm: 2.81–3.18(4H,m), 3.25(0.75H,m), 3.40(0.25H,m), 3.59(1H,m), 4.23(0.25H,m), 4.45(0.75H,m), 5.91(0.25H,d,J=8 Hz), 6.09(0.75H,d,J=8 Hz), 7.1–7.3(5H,m).

(b) L-N-((2S or R)-3-cyclopentanesulfonyl-2-benzylpropionyl)norleucine tert-butyl ester obtained in step (a) was subjected to deesterification with 4.2 ml of dichloromethane/TFA (1/1). 108 mg of L-N-(3-cyclopentanesulfonyl-2-benzylpropionyl)norleucine thereby obtained was condensed with (2S,3R,4S)-4-amino-5-cyclohexyl-1-morpholino-2,3-pentanediol in 3 ml of dry DMF by using a DPPA method. The product was subjected to usual work up and purified by silica gel column chromatography to obtain 62 mg of the above identified compound, 13 mg of (2S,3R,4S)-4-{L-N-[(2R or S)-3-cyclopentanesulfonyl-2-benzylpropionyl]norleucyl}amino-5-cyclohexyl-1-morpholino-2,3-pentanediol and 80 mg of a mixture of the both isomers as white solids, respectively.

S or R isomer:
NMR (300 MHz, CDCl$_3$) δppm: 2.49(2H,m), 2.62(1H,m), 2.70–3.05(6H,m), 3.15(1H,m), 3.26(1H,m), 3.6–3.7(3H,m), 3.68(4H,m), 4.18–4.31(2H,m), 4.60(1H,br s), 6.00(1H,d,J=9.5 Hz), 6.08(1H,d,J=7 Hz), 7.2–7.4(5H,m)

R or S isomer:
NMR (300 MHz, CDCl$_3$) δppm: 2.50(2H,m), 2.63(1H,m), 2.7–2.8(2H,m), 2.83–3.06(4H,m), 3.16(1H,m), 3.37–3.82(8H,m), 4.04(1H,m), 4.91(1H,br), 5.81(1H,d,J=8 Hz), 7.08(1H,d,J=9 Hz), 7.14–7.35(5H,m).

EXAMPLE 52

N-[(2S,3R,4S)-4-[L-N-[(2S)-3-cyclopentanesulfonyl-2-benzylpropionyl]norleucyl]amino-5-cyclohexyl-2,3-dihydroxypentyl]morpholine N-oxide 25 mg (2S,3R,4S)-4-{L-N-[(2S)-3-cyclopentanesulfonyl-2-benzylpropionyl]norleucyl}amino-5-cyclohexyl-1-morpholino-2,3-pentanediol obtained in Example 51 was dissolved in 1.5 ml of methanol, and 150 μl of a 30% hydrogen peroxide aqueous solution was added thereto. 2 mg of sodium tungstate dihydrate was added thereto as a catalyst, and the mixture was stirred. The mixture was stirred at room temperature for 3 hours, and then the insolubles were removed by filtration. The filtrate was diluted with 15 ml of ethyl acetate and washed with a 4% sodium carbonate aqueous solution (10 ml×1 time) and then with a saturated sodium chloride aqueous solution (10 ml×2 times). The ethyl acetate layer was dried over anhydride sodium sulfate, and then concentrated under reduced pressure to obtain 25 mg of the above identified compound as white solid.

Mass spectrum m/z 694(M++1).

EXAMPLE 53

(2R)-3-benzyloxy-2-(1-naphthylmethyl)propionic acid (1) (E)-4-benzyloxy-2-buten-1-ol (a) 14.6 g of sodium hydride (60% in oil) was washed with n-pentane under argon, and dried. 150 ml of dry DMF was added thereto for suspension, and 75 g of (Z)-2-buten-1,4-diol was dropwise added thereto over a period of 30 minutes under stirring at 0° C. The mixture was stirred at room temperature for 1.5 hours, and then 44 g of benzyl bromide was added thereto under stirring at 0° C. The mixture was stirred at the same time for 30 minutes and then the temperature was returned to room temperature and stirred at 50° C. overnight. The reaction solution was poured into ice water, extracted with ether, and the ether solution was washed sequentially with water and a saturated sodium chloride aqueous solution and dried over anhydrous magnesium sulfate. The solvent was distilled off under reduced pressure, and the residue was subjected to distillation under reduced pressure (2.5 mmHg, 134°–138° C.) to obtain 29 g of (Z)-4-benzyloxy-2-buten-1-ol as colorless oily substance.

Rf: 0.49 (n-hexane/ethyl acetate=1/1).

(b) 11.1 g of pyridinium chlorochromate and 12 g of celite were suspended in 100 ml of dry dichloromethane, and 6 g of (Z)-4-benzyloxy-2-buten-1-ol was added thereto under stirring at 0° C. The mixture was stirred at room temperature for three hours, and then diethyl ether was added thereto. The insolubles were removed by filtration. The filtrate was subjected to distillation under reduced pressure for removal of the solvent, and the residue was purified by silica gel column chromatography (diethyl ether) to obtain 3.9 g of (Z)-4-benzyloxy-butenal as slightly yellow oily substance.

Rf: 0.59 (n-hexane/ethyl acetate=1/1).

(c) 3.9 g of (Z)-4-benzyloxy-2-butenal was dissolved in 60 ml of ethanol, and 850 mg of sodium borohydride was added thereto under stirring at 0° C. The mixture was stirred at 0° C. for 1.5 hours. The reaction solution was poured into ice water and extracted with ethyl acetate. The ethyl acetate solution was washed sequentially with water and with a saturated sodium chloride aqueous solution and dried over anhydrous sodium sulfate. Then, the solvent was distilled off under reduced pressure, and the residue was subjected to distillation under reduced pressure (2.0 mmHg, 142° C.) to obtain 2.2 g of (E)-4-benzyloxy-2-buten-1-ol as colorless oily substance.

Rf: 0.49 (n-nexane/ethyl acetate=1/1).

(2) (2R,3R)-4-benzyloxy-1-tert-butyldimethylsilyloxy-3-(1-naphthylmethyl)-2-butanol (a) In 190 ml of dry dichloromethane, 3.3 g of a molecular sieves (powder, 3A) was suspended, and 4.2 ml of isopropyl orthotitanate and 2.9 ml of diethyl L(+)-tartarate were added thereto under stirring at −23° C. The mixture was stirred at the same temperature for 15 minutes. then, 3 ml of a dry dichloromethane solution of 4.7 g of (E)-benzyloxy-2-buten-1-ol was added thereto, and the mixture was stirred at the same temperature for 5 minutes. 11 ml of tert-butylhydroxyperoxide (5.17M dichloromethane solution) was added thereto, and the mixture was stirred for further seven hours. Then, the reaction solution was left to stand at −23° C. overnight. To the reaction solution, 190 ml of diethyl ether and 4.2 ml of a saturated sodium sulfate aqueous solution were added, and the mixture was stirred at room temperature for 4 hours. The insolubles were removed by filtration, and the solvent was distilled off under reduced pressure. The residue was dissolved in 240 ml of diethyl ether, and 42 ml of a 1N sodium chloride aqueous solution was added thereto under stirring at 0° C. The mixture was stirred at 0° C. for 30 minutes. The diethyl ether layer was washed sequentially with a saturated sodium hydrogencarbonate aqueous solution and a saturated sodium chloride aqueous solution and then dried over anhydrous sodium sulfate. The solvent was distilled off under reduced pressure, and then the residue was purified by silica gel column chromatography (n-hexane/ethyl acetate=1/1) to obtain 2.9 g of (2S,3S)-4-benzyloxy-2,3-epoxy-1-butanol as colorless oily substance.

Rf: 0.28 (n-hexane/ethyl acetate=1/1).
Angle of rotation: $[\alpha]_D^{20} -22.7°$ (C 0.988,CHCl$_3$).
Mass spectrum (FAB) m/z 195(M$^+$.+1).

(b) 2.15 g of (2S,3S)-4-benzyloxy-2,3-epoxy-1-butanol was dissolved in 13 ml of dry DMF, and 1.83 g of imidazole and 2 g of tert-butyldimethylchlorosilane were added thereto. The mixture was stirred at room temperature overnight. The reaction solution was diluted with ethyl acetate, washed sequentially with cold 1N hydrochloric acid, water and a saturated sodium chloride aqueous solution and dried over anhydrous sodium sulfate. Then, the solvent was distilled off under reduced pressure, and the residue was purified by silica gel column chromatography (n-hexane/ethyl acetate=10/1) to obtain 2.3 g of (2S,3S)-4-benzyloxy-2,3-epoxy-1-butanol tert-butyldimethylsilyl ether as colorless oily substance.

Rf: 0.59 (n-hexane/ethyl acetate=5/1).
Angle of rotation: $[\alpha]_D^{20} -9.0°$ (C 1.140,CHCl$_3$).
Mass spectrum (FAB) m/z 441(M$^+$+Cs).

(c) 123 mg of copper iodide was suspended in 2.3 ml of dry THF, and 8 ml of naphthylmethyl magnesium chloride (0.8M diethyl ether solution) was added thereto under stirring. The mixture was stirred at the same temperature for five minutes. Then, 1.0 ml of a dry THF solution of 1 g of (2S,3S)-4-benzyloxy-2,3-epoxy-1-butanol tert-butyldimethylsilyl ether was added thereto, and the mixture was stirred at room temperature for 1 hour. The reaction solution was poured into a saturated ammonium chloride aqueous solution and extracted with diethyl ether. The extract was washed sequentially with water and a saturated sodium chloride aqueous solution and dried over anhydrous sodium sulfate. Then, the solvent was distilled off under reduced pressure, and the residue was purified by silica gel column chromatography (n-hexane/ethyl acetate=20/1) to obtain 938 mg of the above identified compound as colorless oily substance.

Rf: 0.53 (n-hexane/ethyl acetate=5/1).
Angle of rotation: $[\alpha]_D^{20} -21.8°$ (C. 1.120CHCl$_3$).
Mass spectrum (FAB) m/z 451(M$^+$+1).

(3) (2R,3R)-4-benzyloxy-3-(1-naphthylmethyl)butan-1,2-diol 910 mg of (2R,3R)-4-benzyloxy-1-tert-butyldimethylsilyloxy-3-(1-naphthylmethyl)-2-butanol was treated with 7 ml of tetra-n-butylammonium fluoride (1M THF solution), and stirred at 0° C. for ten minutes and then at room temperature for 50 minutes. The reaction solution was diluted with diethyl ether, and then washed sequentially with a saturated sodium hydrogencarbonate aqueous solution and a saturated sodium chloride aqueous solution and dried over anhydrous sodium sulfate. The solvent was distilled off under reduced pressure, and the residue was purified by silica gel column chromatography (n-hexane/ethyl acetate=1/1) to obtain 642 mg of the above identified compound as colorless oily substance.

Rf: 0.29 (n-hexane/ethyl acetate=1/1).
Angle of rotation: $[\alpha]_D^{20} -42.6°$ (C 1.187, CHCl$_3$).
Mass spectrum m/z 337(M$^+$+1).

(4) (2R)-3-benzyloxy-2-(1-naphthylmethyl)propionic acid 740 mg of (2R,3R)-4-benzyloxy-3-(1-naphthylmethyl)butan-1,2-diol was dissolved in 50 ml of methanol, and 19 ml of an aqueous solution of 568 mg of sodium metaperiodate was added thereto under stirring at 0° C. The mixture was stirred at room temperature for 4 hours. The insolubles were removed by filtration, and then the solvent was concentrated under reduced pressure. The residue was diluted with a saturated sodium hydrogencarbonate aqueous solution, and extracted with diethyl ether. Then, the extract was washed with a saturated sodium chloride aqueous solution and dried over anhydrous sodium sulfate. The solvent was distilled off under reduced pressure. 620 mg of (2R)-3-benzyloxy-2-(1-naphthylmethyl)-1-propanal thereby obtained as oily substance, was dissolved in 50 ml of acetone, and Jones' reagent was added thereto under stirring at 0° C. The mixture was stirred at the same temperature for 1.5 hours. To the reaction solution, isopropanol was added for decomposition of the reagent. Then, the insolubles were removed by filtration, and the filtrate was concentrated under reduced pressure. The concentrated solution was diluted with ethyl acetate, washed sequentially with water and a saturated sodium chloride aqueous solution and dried over anhydrous sodium sulfate. Then, the solvent was distilled off under reduced pressure, and the residue was purified by silica gel column chromatography (n-hexane/ethyl acetate=2/1) to obtain 457 mg of the above identified compound as colorless oily substance.

Rf: 0.47 (n-hexane/ethyl acetate/acetic acid=1/1/0.5).

Angle of rotation: $[\alpha]_D^{20}$ −13.2° (C 1.04, CHCl$_3$).

Mass spectrum m/z 321(M$^+$ +1).

NMR (300 MHz, CDCl$_3$) δppm: 3.11–3.21(1H,m), 3.33(1H,dd,J=15.2,8.0 Hz), 3.57(1H,dd,J=15.2,7.6 Hz), 3.66(2H,d,J=7.2 Hz), 4.51(1H,d,J=16.0 Hz), 4.55(1H,d,J=16.0 Hz), 7.24–7.38(7H,m), 7.45–7.55(2H,m), 7.75(1H,d,J=8.0 Hz), 7.86(1H,d,J=8.0 Hz), 8.05(1H,d,J=8.0 Hz).

EXAMPLE 54

(2S,3R,4S)-4-amino-5-cyclohexyl-1-morpholino-2,3-pentanediol dihydrochloride (1) 3-O-benzyl-1,2-O-isopropylidene-α-D-allofuranose 3.0 g of sodium hydride was added to 50 ml of dry DMF, and 31 ml of a dry DMF solution of 30.7 g of 1,2:5,6-di-O-isopropylidene-α-D-allofuranose was added thereto under stirring and cooling with ice. The mixture was stirred at room temperature for one hour, and then 14.5 ml of benzyl bromide was dropwise added thereto under cooling with ice. The mixture was stirred at room temperature overnight. Then, 90 ml of water was added thereto under cooling for crystallization. The crystals were collected by filtration washed with 50 ml of cold water and then dried to obtain 3-O-benzyl derivative 39.1 g (yield: 95%) of slightly yellow crude crystals.

Then, the crystals was dissolved in 200 ml of 70% acetic acid, and the reaction was conducted at 37° C. for seven hours. The reaction solution was neutralized with aqueous sodium carbonate (200 g/300 ml) under cooling with ice and extracted with ethyl acetate (300 ml×1 time, 150 ml×1 time). The extract was washed with water (200 ml) and then with a saturated sodium chloride aqueous solution (200 ml) and then dried over anhydrous sodium sulfate. The filtrate was concentrated under reduced pressure to obtain the above identified compound 54.5 g of slightly yellow syrup (yield: 94%).

NMR (300 MHz, CHCl$_3$) δppm: 1.37(3H,s), 1.60(3H,s), 3.70(2H,s) 3.93(1H,dd,J=4.4,8.7 Hz), 4.01(1H,m), 4.12(1H,dd,J=3.2,8.9 Hz), 4.56(1H,d,J=11.2 Hz), 5.77(1H,d,J=3.6 Hz), 7.3–7.4(5H,m), Rf: 0.2 (chloroform/methanol=30/1).

(2) 3-O-benzyl-1,2-O-isopropylidene-α-D-ribo-pentodialdo-1,4-furanose 34.5 g of 3-O-benzyl-1,2-O-isopropylidene-α-D-allofuranose was dissolved in 280 ml of ethanol/water (7/1), and a sodium methaperiodate aqueous solution (25 g/210 ml) was dropwise added thereto. The mixture was stirred at room temperature for 1.5 hours, and then the precipitated inorganic salts were separated by filtration. The salt thereby separated was washed with a small amount of ethanol. The washing solution and the filtrate were put together and concentrated under reduced pressure. The syrup thereby obtained was dissolved in 300 ml of ethyl acetate and washed with 100 ml of water and then with 100 ml of a sodium chloride aqueous solution. The ethyl acetate layer was dried over anhydrous magnesium sulfate and then concentrated under reduced pressure. The syrup thereby obtained was dissolved in diethyl ether and the diethyl ether solution was concentrated again and dried under reduced pressure to obtain 32.6 g of the above identified compound as slightly yellow crude syrup. This syrup could be used as a starting material for Wittig reaction in the following step as it was.

Rf: 0.44 (chloroform/methanol=30/1).

(3) 3-O-benzyl-5-cyclohexylidene-5-deoxy-1,2-O-isopropylidene-α-D-ribofuranose 82.7 g of cyclohexyltriphenylphosphonium bromide was suspended under stirring in 600 ml of 1,2-dimethoxyethane purified by distillation. The reaction solution was sealed under an argon atmosphere, and 130 ml of n-butyl lithium (n-hexane solution, 1.5N) was dropwise added thereto at room temperature. The mixture was stirred for one hour to form a reddish brown ylide. The reactor was cooled with ice, and a 1,2-dimethoxyethane solution (36 g/70 ml) of 3-O-benzyl-1,2-O-isopropylidene-60-D-ribopentodialdo-1,4-furanose was added thereto over a period of 30 minutes. The temperature was returned to room temperature, and the reaction solution was stirred for 18 hours. Then, the precipitated salt was separated by filtration. The salt thereby separated was washed with a small amount of benzene. To the combined filtrate, 100 ml of water was added to decompose the excess ylide. The reaction solution was distillated off, and the residue thereby obtained was dissolved in 300 ml of benzene. The benzene solution was washed with 130 ml of water and then with 150 ml of a saturated sodium chloride aqueous solution. Then, the benzene layer was dried over anhydrous magnesium sulfate. The dried benzene layer was concentrated under reduced pressure, and the concentrate was purified by silica gel column chromatography (n-hexane/ethyl acetate=8/1). The eluted fractions containing the desired compound were put together, concentrated under reduced pressure and dried to obtain 28.9 g (yield: 64%) of white solid. The solid was recrystallized from 50 ml n-hexane to obtain 27.2 g (yield: 61%) of columnar crystals.

NMR (300 MHz, CDCl$_3$) δppm: 1.35 (3H,s), 1.58 (6H,m), 1.64(3H, s), 2.13(2H,br), 2.29(2H,br), 3.46(1H,dd,J=4.4,8.8 Hz), 4.53(1H,t,J=4.0 Hz), 4.63(1H,d,J=12.4 Hz), 4.73(1H,d,J=12.4 Hz), 4.82(1H,t,J=8.9 Hz), 5.02(1H,dd,J=1.5,8.7 Hz), 5.70(1H,d,J=3.6 Hz), 7.29–7.35(5H,m).

Melting point: 62°–64° C.

Angle of rotation: $[\alpha]_D^{20}$= −7.2° (C=0.97, CHCl$_3$).

IR νcm⁻¹: 2930, 2850, 1460, 1390, 1380, 1250, 1220, 1200, 1170, 1130, 1120, 1090, 1030, 1000, 890, 870, 730.

Elemental analysis: Calculated value C: 73.23, H: 8.19. Measured value C: 73.28, H: 8.12.

(4) Methyl 2,3-di-O-benzyl-5-cyclohexyl-5-deoxy-α-D-ribofuranoside and methyl 2,3-di-O-benzyl-3-cyclohexyl-5-deoxy-β-D-ribofuranoside 27.0 g of 3-O-benzyl-5-cyclohexylidene-5-deoxy-1,2-O-isopropylidene-α-D-ribofuranose was dissolved in 230 ml of ethanol, and Raney nickel (W1) in about 10 ml of ethanol was added thereto. The stirring was continued under a hydrogen atmospheric pressure. 4.5 hours later, the catalyst was separated by filtration on Celite, and the filtrate was concentrated under reduced pressure and dried under reduced pressure to obtain 28.4 g of 3-O-benzyl-5-cyclohexyl-5-deoxy-1,2-O-isopropylidene-α-D-ribofuranose as transparent syrup. Then, the syrup was dissolved in 66 ml of dry methanol. 66 ml of 10% dry methanol hydrochloride was added thereto and reacted therewith at room temperature under sealing for 66 hours. Then, 100 ml of methanol was added to the reaction solution and diluted it. 500 ml of an anion exchange resin Amberlite (IRA-400, OH⁻) was gradually added to the reaction solution for neutralization. The resin was removed by filtration, and then the reaction solution was concentrated under reduced pressure. The syrup thereby obtained was azeotropically concentrated to dryness from the diethyl ether solution and from the benzene solution under reduced pressure to obtain 24.7 g of methyl 3-O-benzyl-5-cyclohexyl-5-deoxy-α(or β)-D-ribofuranoside as yellow syrup. (Rf: 0.32, silica gel plate, n-hexane/ethyl acetate=3/1).

Then, the syrup was dissolved in 45 ml of dry DMF without purification, and the solution was added under cooling with ice to 30 ml of a dry DMF solution containing 1.9 g of sodium hydride prepared separately. The temperature was returned to room temperature, and the mixture was stirred for 30 minutes and cooled with ice. 9.3 ml of benzyl bromide was added thereto and the mixture was stirred at room temperature overnight. Then, the reaction solution was dissolved in 400 ml of ethyl acetate, and the solution was washed sequentially with 300 ml of water and with 300 ml of a saturated sodium chloride aqueous solution. The organic layer was dried over anhydrous sodium sulfate and then concentrated under reduced pressure. The concentrate was purificated by silica gel column chromatography (n-hexane/ethyl acetate=8/1-6/1) to obtain 3.55 g of methyl 2,3-di-O-benzyl-5-cyclohexyl-5-deoxy-α-D-ribofuranoside and 27.6 g of methyl 2,3-di-O-benzyl-5-cyclohexyl-5-deoxy-β-D-ribofuranoside as colorless transparent syrup.

α-anomer:

NMR (300 MHz, CDCl₃) δppm: 0.85(2H,m), 1.1–1.4(6H,m), 1.6–1.8(5H,m), 3.45(3H,s), 3.50(1H,dd,J=3.6,6.8 Hz), 3.76(1H,dd,J=4.0,6.8 Hz), 4.18(1H,m), 4.59(1H,d,J=12.7 Hz), 4.63(1H,d,J=12.2 Hz), 4.68 (1H,d,J=12.5 Hz), 4.74(1H,d,J=13.1 Hz), 4.83(1H,d,J=4.5 Hz), 7.28–7.40(10H,m).

Rf: 0.44 (n-hexane/ethyl acetate=3/1).

IR νcm⁻¹: 3050, 2930, 2850, 1510, 1460

β-anomer:

NMR (300 MNz, CDCl₃) ppm: 0.9(2H,m), 1.1–1.3(3H,m), 1.4–1.6(3H,m), 1.6–1.85(5H,m), 3.31(3H,s), 3.77(1H,dd,J=4.5,7 Hz), 3.82(1H,dd,J=1,4.5 Hz), 4.22(1H,m), 4.41(1H,d,J=12 Hz), 4.55(1H,d,J=12 Hz), 4.57(1H,d,J=12 Hz), 4.68(1H,d,J=12 Hz), 4.87(1H,s).

Rf: 0.60 (n-hexane/ethyl acetate=3/1).

IR νcm⁻¹: 3040, 2930, 2850, 1500, 1460.

(5) (2S,3R,4R)-2,3-dibenzyloxy-5-cyclohexyl-1-morpholinopentan-4-ol 30.8 g of the mixture of methyl 2,3-di-O-benzyl-5-cyclohexyl-5-deoxy-α-D-ribofuranoside and its β-anomer obtained step (4), was dissolved in 600 ml of acetic acid/hydrochloric acid/water (9/1/2), and reacted at 20° C. for 10 hours and then at 6° C. for 14 hours. The reaction solution was diluted with 1 liter of toluene and washed sequentially with water (400 ml×2 times), with a 4% sodium hydrogencarbonate aqueous solution (500 ml) and with saturated sodium chloride aqueous solution (500 ml). The organic layer was dried over anhydrous magnesium sulfate and then concentrated under reduced pressure to obtain 2,3-di-O-benzyl-5-cyclohexyl-5-deoxy-D-ribofuranose as yellow syrup. (Rf: 0.38, silica gel plate, solvent: hexane/ethyl acetate=3/1).

Then, the product was dissolved in 500 ml of methanol. 41.7 g of morpholine hydrochloride was added thereto and dissolved. A methanol solution of sodium cyanoborohydride (8.49 g/100 ml) was added thereto, and then the mixture was stirred. The mixture was stirred at room temperature for 39 hours, and then the reaction solution was concentrated under reduced pressure. The product was dissolved in 1 liter of benzene/ethyl acetate (4/6), and the mixture was washed with water (300 ml×2 times) with a saturated sodium chloride aqueous solution (300 ml). The organic layer was dried over anhydrous magnesium sulfate, and then concentrated under reduced pressure. The purification by silica gel column chromatography (chloroform/ethyl acetate=4/1) and the drying under reduced pressure were conducted to obtain 31.7 g of the above identified compound as white solid (yield: 90%).

NMR (300 MHz, 55° C., CDCl₃) δppm: 0.85(2H,m), 1.1–1.3(5H,m), 144(1H,m), 1.55–1.8(5H,m), 2.39(1H,dd,J=2.5,13.1 Hz), 2.51(4H,m), 3.02(1H,dd,J=8.9,13.1 Hz), 3.59(1H,dd,J=1.4,5.3 Hz), 3.66(4H,m), 3.77(2H,m), 4.56(1H,d,J=12.2 Hz), 4.59(1H,d,J=12.2 Hz), 4.63(1H,d,J=11.7 Hz), 4.76(1H,d,J=11.7 Hz), 7.2–7.4(10H,m).

IR νcm⁻¹: 3220(br), 2930, 2850, 1460, 1120, 1070, 1030.

Melting point: 54°–56° C.

Angle of rotation: $[\alpha]_D^{20}=+31.0°$ (C=1.09, CHCl₃).

Elemental analysis: Calculated value C: 74.48, H: 8.84, N: 3.00. Measured value C: 74.52, H: 8.87, N: 2.92.

(6) (2S,3R,4S)-4-azide-2,3-dibenzyloxy-5-cyclohexyl-1-morpholinopentane 27.7 g of (2S,3R,4R)-2,3-dibenzyloxy-5-cyclohexyl-1-morpholinopentan-4-ol was dissolved in 200 ml of dry THF, and 24.9 g of triphenylphosphine was added thereto and dissolved. Then, the reaction solution was stirred at −20° C. under cooling. To the reaction solution, 14.9 mg of diethyl azodicarboxylate and 20.5 ml of DPPA were dropwise added thereto, respectively. A few minutes later, the reaction solution was stirred at 20° C. 24 hours later, the reaction solution was concentrated under reduced pressure, the syrup thereby obtained was purified by silica gel column chromatography (n-hexane/ethyl acetate=5/1) to obtain 12.7 g (yield: 43%) of desired colorless transparent syrup.

NMR (300 MHz, CDCl₃) δppm: 0.89(2H,m), 1.1–1.5(5H,m), 1.7(6H,m), 2.37(2H,ddd,J=4.6,4.7,11.3 Hz), 2.59(2H,m), 2.65(2H,m), 3.56(1H,ddd,J=3.4,4.0,10.1 Hz), 3.64(1H,dd,J=3.1,6.6

Hz), 3.67(4H,m), 3.74(1H,m), 4.58(1H,d,J=11.1 Hz), 4.69(1H,d,J=11.1 Hz), 4.73(1H,d,J=11.5 Hz), 4.78(1H,d,J=11.5 Hz), 7.28–7.38(10H,m).

IR νcm⁻¹: 2930, 2850, 2110, 1750, 1740, 1500, 1460.

Mass spectrum (FAB) m/z 493(M⁺ +1).

(7) (2S,3R,4S)-4-amino-5-cyclohexyl-1-morpholino-2,3-pentanediol dihydrochloride 80 mg of (2S,3R,4S)-4-azide-2,3-dibenzyloxy-5-cyclohexyl-1-morpholinopentane was dissolved in 2 ml of ethanol, and 0.2 ml of 2N hydrochloric acid was added for acidification. Hydrogen gas was continuously blown thereinto in the presence of a palladium black catalyst. Two hours later, the catalyst was separated on celite by filtration, and the filtrate was concentrated under reduced pressure. The residue was concentrated under reduced pressure in the form of a mixed solution of ethanol/benzene and azeotropically dried. The dried solid was recrystallized from dichloromethane/diethyl ether to obtain 52 mg (yield: 90%) of white crystals.

¹H-NMR (300 MHz, CDCl₃, free salt) δppm: 0.95(2H,m), 1.23(3H,m), 1.43(2H,m), 1.57(1H,m), 1.72(5H,m), 2.55(2H,m), 3.40(1H,m), 3.50(1H,br dd,J=1.5,7.0 Hz), 3.70(4H,m), 3.88(1H,m), 4.26(4H,br).

¹³C-NMR (75 Hz, CDCl₃-D₂O, hydrochloride) δppm: 25.8(2C), 26.2, 32.6, 33.1, 33.2, 37.2, 48.9, 52.4, 53.5, 60.8, 63.5, 63.6, 65.1, 69.9.

EXAMPLE 55

(2S,3R,4R)-2,3-dibenzyloxy-5-cyclohexyl-1-morpholinopentan-4-ol (1) 1,4-pentadien-3-ol To 400 ml of a THF solution of 0.98M vinyl magnesium bromide, 11.0 ml of methyl formate was dropwise added over a period of 1 hour at a temperature of from 0° to 5° C. After completion of the dropwise addition, 100 ml of a saturated ammonium chloride aqueous solution was immediately added thereto, and the mixture was extracted with THF. The THF layer was dried over anhydrous magnesium sulfate, and then the solvent was distilled off under reduced pressure (100 mmHg). The residue was subjected to distillation under reduced pressure to obtain 9.6 g of the above identified compound as colorless liquid.

Rf: 0.52 (n-hexane/ethyl acetate=2/1).

Boiling point: 55°–57° C./78 mmHg).

(2) (2R,3S)-1,2-epoxypent-4-ene-3-ol 7 g of molecular sieves (3A, powder) were suspended in 500 ml of dichloromethane, and 10.2 g of tetraisopropyl orthotitanate and 8.8 g of diethyl L-(+)-tartarate were added thereto under an argon atmosphere at −30° C. Then, 40.5 ml of tert-butylhydroperoxide (5M dichloromethane solution, treated with molecular sieves 4A for 30 minutes before the dropwise addition) was dropwise added over a period of 10 minutes at the same temperature. The mixture was stirred at the same temperature for 10 minutes. A dichloromethane solution of 10 g of 1,4-pentadien-3-ol was dropwise added thereto over a period of 20 minutes. The mixture was left to stand at −20° C. for ten days, and then, 500 ml of acetone containing 10.5 ml of water was added to the reaction solution at −20° C. The mixture was stirred at room temperature for three hours. Then, the insoluble substances were removed by filtration, and the filtrate was concentrated under reduced pressure. The residual solution was subjected to distillation under reduced pressure, and the eluted fractions of a boiling point of 30°–60° C./18 mmHg (first fraction) and a boiling point of 60°–73° C./18 mmHg (second fraction) were collected. Each fraction was purified by silica gel column chromatography (n-pentane/diethyl ether=1/1) to obtain 2.3 g and 5.4 g of the above identified compound as colorless liquid, respectively.

Rf: 0.27 (n-hexane/ethyl acetate=2/1).

Angle of rotation: $[\alpha]_D^{20} = +57.3°$ (C=0.964, CHCl₃).

(3) (2R,3S)-3-benzyloxy-2-tert-butyldimethylsilyloxy-1-cyclohexyl-4-pentene (a) 428 mg of sodium hydride (60% in oil) was suspended in 8 ml of THF, and a THF solution (5 ml) of 970 mg of (2R,3S)-1,2-epoxypent-4-ene-3-ol was dropwise added thereto under an argon atmosphere at −10° C. The mixture was stirred at room temperature for 20 minutes. Then, 360 mg of tetra-n-butylammonium iodide and 1.27 ml of benzyl bromide were added thereto at −10° C. The mixture was stirred at room temperature for two hours, and then poured into a saturated ammonium chloride aqueous solution and extracted with ethyl acetate. The ethyl acetate layer was dried over anhydrous magnesium sulfate, and the solvent was distilled off. The residue was purified by silica gel column chromatography (n-hexane/ethyl acetate=10/1) to obtain 1.7 g of (2R,3S)-3-benzyloxy-1,2-epoxy-4-pentene as colorless oily substance.

Rf: 0.49 (n-hexane/ethyl acetate=4/1).

(b). 146 mg of copper (I) iodide was suspended in THF, and 3.85 ml of cyclohexyl magnesium chloride (2M diethyl ether solution) was added thereto under an argon atmosphere at −78° C. The mixture was stirred at the same temperature for ten minutes. Then, a THF solution (5 ml) of 969 mg of (2R, 3S)-3-benzyloxy-1,2-epoxy-4-pentene was dropwise added thereto over a period of 10 minutes at −78° C. The mixture was stirred at −10° C. for two hours, and then poured into a saturated ammonium chloride aqueous solution and extracted with ethyl acetate. The extract layer was washed with a saturated sodium chloride aqueous solution and dried over anhydrous magnesium sulfate. The solvent was distilled off under reduced pressure to obtain 1.2 g of (2R,3S)-3-benzyloxy-1-cyclohexyl-4-penten-2-ol as slightly brown oily substance. This alcohol was dissolved in DMF, and 923 mg of tert-butyldimethylsilyl chloride, 312 mg of 4-dimethylaminopyridine and 923 μl of triethylamine were added thereto at 0° C. The mixture was stirred at room temperature overnight. Then, water and ethyl acetate were added to the reaction solution, and the organic layer was separated. The organic layer was washed sequentially with 1N hydrochloric acid, with 4% sodium hydrogencarbonate, with water and with a saturated sodium chloride aqueous solution and dried over anhydrous magnesium sulfate. The solvent was distilled off under reduced pressure, and the residue was purified by silica gel column chromatography (n-hexane/benzene=10/1) to obtain 1.3 g of the above identified compound as colorless oily substance.

Rf: 0.53 (n-hexane/benzene=5/1).

Angle of rotation: $[\alpha]_D^{20} = +28.9°$ (C=0.944, CHCl₃).

(4) (2S,3R,4R)-3-benzyloxy-4-tert-butyldimethylsilyloxy-5-cyclohexyl-1,2-epoxypentane (a) 1.27 g of 4-penten-2,3-diol having a protected hydroxyl group obtained in step (3), was dissolved in a solvent mixture of acetone (12 ml)/water (1.2 ml), and 42 mg of osmium tetraoxide and 790 mg of N-methylmorpholine N-oxide were added thereto. The mixture was stirred at room temperature overnight. Then, 35 ml of a saturated sodium hydrogen sulfate aqueous solution was added thereto and the mixture was extracted with ethyl acetate. The organic layer was washed with a saturated sodium chloride aqueous solution and the solvent was distilled off under reduced pressure. The residue was purified by silica gel column chromatography (n-hexane/ethyl acetate=2/1) to obtain 1.12 g of (2S,3R,4R)-3-benzyloxy-4-tert-butyldimethylsilyloxy-5-cyclohexylpentan-1,2-diol as colorless oily substance.

Rf: 0.43 (n-hexane/ethyl acetate=2/1).

(b) The diol obtained in step (a) was dissolved in 3 ml of dichloromethane, and 46 µl of methanesulphonyl chloride and 94 µl of triethylamine were dropwise added thereto at 0° C. The mixture was stirred at room temperature for 20 minutes. Then, ethyl acetate was added thereto. The mixture was washed sequentially with water, with 1N hydrochloric acid, with a 4% sodium hydrogencarbonate aqueous solution, with water and with a saturated sodium chloride aqueous solution and dried over anhydrous magnesium sulfate. Then, the solvent was distilled off under reduced pressure. The residue was dissolved in 4 ml of methanol, and 124 mg of potassium carbonate was added thereto at 0° C. The mixture was stirred at room temperature overnight. Then, 78 µl of acetic acid, water and ethyl acetate were added to the reaction solution. The organic layer was separated, washed with a saturated sodium chloride aqueous solution and then dried over anhydrous magnesium sulfate. The solvent was distilled off under reduced pressure, and the residue was purified by silica gel column chromatography (n-hexane/ethyl acetate=4/1) to obtain 125 mg of the above identified compound as colorless oily substance.

Rf: 0.76 (n-hexane/ethyl acetate=4/1).

NMR (300 MHz, CDCl$_3$) δppm: 0.06(3H,s), 0.08(3H,s), 0.90(9H,s), 0.75–1.05(1H,m), 1.10–1.70(12H,m), 2.69(1H,dd,J=2.7,5.4 Hz), 2.75(1H,dd,J=3.9,5.4 Hz), 3.12(1H,ddd,J=2.7,3.9,5.4 Hz), 3.23(1H,dd,J=2.4,5.1 Hz), 3.98(1H,ddd,J=2.4,4.5,8.3 Hz), 4.60(2H,s), 7.23–7.38(5H,m).

(5) (2S,3R,4R)-2,3-dibenzyloxy-5-cyclohexyl-1-morpholinopentan-4-ol (a) 122 mg of the epoxy compound obtained in step (4) was dissolved in 1.5 ml of methanol, and 32 µl of morpholine was added thereto. The mixture was heated at a temperature of from 75° to 80° C. for two hours and further at 60° C. overnight. The reaction solution was concentrated under reduced pressure to dryness, and the residue was purified by silica gel column chromatography (n-hexane/ethyl acetate=4/1) to obtain 139 mg of (2S,3R,4R)-3-benzyloxy-4-tert-butyldimethylsilyloxy-5-cyclohexyl-1-morpholinopentan-2-ol as colorless oily substance.

Rf: 0.11 (n-hexane/ethyl acetate=4/1).

NMR (300 MHz, CDCl$_3$) δ ppm: 0.10(3H,s), 0.12(3H,s), 0.75–1.05(2H,m), 0.91(9H,s), 1.07–1.85(11H,m), 2.30–2.47(3H,m), 2.55–2.72(3H,m), 3.41(1H,dd,J=1.8,7.1 Hz), 3.62–3.75(5H,m), 4.16(1H,ddd,J=1.8,3.3,8.7 Hz), 4.55(1H,d,J=11.7 Hz), 4.87(1H,d,J=11.7 Hz), 7.25–7.40(5H,m).

(b) 12 mg of sodium hydride (60% in oil) was suspended in 0.5 ml of THF, and a THF solution (0.5 ml) of 135 mg of the amino alcohol obtained in step (a) was dropwise added thereto under an argon atmosphere at −20° C. The mixture was stirred at room temperature for one hour. Then, 11 mg of tetra-n-butylammonium iodide and 36 µl of benzyl bromide were added thereto. The mixture was stirred at room temperature overnight. Then, the reaction solution was poured into a saturated ammonium chloride aqueous solution and the mixture was extracted with ethyl acetate. The extract was dried over anhydrous magnesium sulfate. Then, the solvent was distilled off under reduced pressure, and the residue was purified by silica gel column chromatography (n-hexane/ethyl acetate =8/1) to obtain 30 mg of (2S,3R,4R)-2,3-dibenxyloxy-4-tert-butyldimethyl-silyloxy-5-cyclohexyl-1-morpholinopentane as colorless oily substance. Further, 103 mg of the starting material was recovered.

Rf: 0.70 (n-hexane/ethyl acetate =2/1).

NMR (300 MHz, CDCl$_3$) δppm: 0.07(3H,s), 0.10(3H,s), 0.70–1.00(2H,m), 0.92(9H,s), 1.10–1.78(11H,m), 2.34–2.44(2H,m), 2.50–2.76(4H,m), 3.59(1H,dt,J=2.4,6.5 Hz), 3.64–3.76(5H,m), 4.14(1H,m), 4.52(1H,d,J=11.4 Hz), 4.61(1H,d,J=11.4 Hz), 4.70(1H,d,J=11.4 Hz), 4.87(1H,d,J=11.4 Hz), 7.20–7.40(10H,m).

(c) The protected triol obtained in step (b) was dissolved in 0.2 ml of THF, and 80 µl of a RHF solution of 1M tetra-n-butylammonium chloride was added thereto. The mixture was stirred at room temperature. Further, two hours later, 160 µl of a THF solution of 1M tetra-n-butylammonium chloride was added thereto and four hours later, 200 µl of the THF solution was added thereto. The mixture was stirred at room temperature overnight. Diethyl ether was added to the reaction solution. The mixture was washed with water and with a saturated sodium chloride aqueous solution and dried over anhydrous magnesium sulfate. Then, the solvent was distilled off under reduced pressure, and the residue was purified by silica gel column chromatography (n-hexane/ethyl acetate=1/1) to obtain 15.5 mg of the above identified compound as colorless solid.

Rf: 0.64 (n-hexane/ethyl acetate=2/1).

This compound completely agreed with a product derived from 1,2:5,6-diisopropylidene-2-D-allofuranose in a 300 MHz NMR analysis.

EXAMPLE 56

(2S,3R,4S)-4-{L-N-[(2S)-2-benzyl-3-furfurylsulfonyl-propionyl[norleucyl}amino-5-cyclohexyl-1-morpholino-2,3-pentanediol (a) 1.2 g of (2S,3S)-4-benzyloxy-2,3-epoxy-1-butanal tert-butyldimethylsilyl ether obtained in Example 53 was subjected to Grignard reaction by using benzyl magnesium bromide (0.8M diethyl ether solution) in the same manner as in Example 53 to obtain 975 mg of (2R,3R)-3-benzyl-4-benzyloxy-1-tert-butyldimethyl-silyloxy-2-butanal as colorless oily substance.

Then, the removal of the silyl group by 5 ml of tetra-n-butylammonium fluoride (1M THF solution) was conducted in the same manner as in Example 53. Then the product was converted to an aldehyde by using 625 mg of sodium metaperiodate and subjected to chromic acid oxidation (Jones' reagent) to obtain 427 mg of (2R)-2-benzyl-3-benzyloxypropionic acid.

Rf: 0.57 (n-hexane/ethyl acetate/acetic acid=6/6/0.2).

Angle of rotation: $[\alpha]_D^{26}$ = −4.8° (C=0.765, CHCl$_3$).

Mass spectrum (FAB) m/z 293(M$^+$+Na), 271(M$^+$+1).

(b) 420 mg of (2R)-2-benzyl-3-benzyloxypropionic acid was dissolved in 5.5 ml of ethanol, and hydrogenated at an ordinary temperature under an atmospheric pressure for two hours in the presence of palladium black. The insolubles were removed by filtration, and then the solvent was distilled off under reduced pressure to obtain 290 mg of (2R)-2-benzyl-3-hydroxypropionic acid as colorless oily substance.

Rf: 0.24 (n-hexane/ethyl acetate/acetic acid=6/6/0.2).

Angle of rotation: $[\alpha]_D^{26} = +4.9°$ (C=0.853, CHCl$_3$).

Mass spectrum (FAB) m/z 203(M$^+$+Na), 181(M$^+$+1).

(c) 274 mg of (2R)-2-benzyl-3-hydroxypropionic acid was dissolved in 2 ml of dry DMF, and subjected to coupling raction with 322 mg of L-norleucine tert-butyl ester by a DCC-HOBT method in the same manner as in Example 47 to obtain 306 mg of L-N-[(2S)-2-benzyl-3-hydroxypropionyl]norleucine tert-butyl ester as white solid.

Rf: 0.25 (n-hexane/ethyl acetate=2/1).

(d) 68 mg of L-N-[(2S)-2-benzyl-3-hydroxypropionyl]norleucine tert-butyl ester was subjected to tosylation (p-toluenesulfonyl chloride). Then, the product was substituted with furfurylmercaptan to convert to the furfurylthio ether. Then, the furfurylthio ether was oxidized by hydrogen peroxide/sodium tungstate to the sulfone compound, and the sulfone compound was treated with TFA to obtain 60 mg of L-N-[(2S)-2-benzyl-3-furfurylsulfonylpropionyl]norleucine as colorless oily substance.

Rf: 0.22 (n-hexane/ethyl acetate/acetic acid=6/6/0.2)

(e) 60 mg of L-N-[(2S)-2-benzyl-3-furfurylsulfonylpropionyl]norleucine was dissolved in 0.4 ml of dry DMF, and subjected to coupling reaction conducted in the same manner as in Example 47 with 62 mg of (2S,3R,4S)-4-amino-5-cyclohexyl-1-morpholino-2,3-pentanediol dihydrochloride by a DPPA method to obtain 72 mg of the above identified compound as white powder.

Rf: 0.40 (chloroform/methanol=20/1)

Mass spectrum (FAB) m/z 690(M$^+$+1)

NMR (300 MHz, CDCl$_3$) δppm: 0.79–1.06(3H,m), 1.06–1.94(19H,m), 2.40–3.15(10H,m), 3.39–3.85(7H,m), 4.17–4.31(4H,m), 5.90(1H,d,J=7.9 Hz), 5.98(1H,d,J=8.7 Hz), 6.41(1H,d,J=0.8 Hz), 6.46(1H,d,J=0.8 Hz), 7.18–7.52(5H,m)

EXAMPLE 57

(2S,3R,4S)-4-{L-N-[(2S)-3-ethylsulfonyl-2-[(5,6,7,8-tetrahydro-1-naphthyl)methyl]propionyl]norleucyl}amino-5-cyclohexyl-1-morpholino-2,3-pentanediol (a) 107 mg of L-N-[(2R)-3-benzyloxy-2-(1-naphthylmethyl)propionyl]norleucine tert-butyl ester was dissolved in 2 ml of ethanol and hydrogenated at a ordinally temperature under an atmospheric pressure by an addition of palladium black. The catalyst was removed by filtration, and then the solvent was distilled off to obtain 89 mg of L-N-{(2R)-3-hydroxy-2-[(5,6,7,8-tetrahydro-1-naphthyl)methyl]propionyl}norleucine tert-butyl ester as colorless oily substance.

Rf: 0.33 (n-hexane/ethyl acetate=2/1).

(b) 87 mg of L-N-{(2R)-3-hydroxy-2-[(5,6,7,8-tetrahydro-1-naphthyl)methyl]propionyl}norleucine tert-butyl ester was subjected to tosylation in the same manner as in Example 1, and then converted to the thio compound by using ethylmercaptan. Then, the thio compound was oxidized to the sulfone compound and treated with TFA to obtain 61 mg of L-N-{(2S)-3-ethylsulfonyl-2-[(5,6,7,8-tetrahydro-1-naphthyl)methyl]propionyl}norleucine as colorless oily substance. This compound was subjected to coupling reaction in the same manner as in Example 3 with 39 mg of (2S,3R,4S)-4-amino-5-cyclohexyl-1-morpholino-2,3-pentanediol dihydrochloride by a DPPA method to obtain 27 mg of the above identified compound as white powder.

Rf: 0.42 (chloroform/methanol=20/1).

Mass spectrum m/z 692(M$^+$+1).

EXAMPLE 58

N-[(2S,3R,4S)-4-[L-N-[(2S)-3-ethylsulfonyl-2-(1-naphthylmethyl)propionyl]norleucyl]amino-5-cyclohexyl-2,3-dihydroxypentyl]piperidine N-oxide 10.6 mg of (2R,3R,4S)-4-{L-N-[(2S)-3-ethylsulfonyl-2-(1-naphthylmethyl)propionyl]norleucyl}amino-5-cyclohexyl-1-piperidino-2,3-pentanediol obtained in Example 17, was dissolved in 0.5 ml of methanol. 50 μl of a 30% hydrogen peroxide aqueous solution and 2 mg of sodium tungstate dihydrate were added thereto for oxidation in the same manner as in Example 50 to obtain 11.4 mg of the above identified compound as white solid.

Rf: 0.39 (chloroform/methanol=10/1).

Mass spectrum m/z 702(M$^+$+1).

EXAMPLE 59

N-[(2S,3R,4S)-4-[L-N-[(2S)-3-ethylsulfonyl-2-(1-naphthylmethyl)propionyl]norleucyl]amino-5-cyclohexyl-2,3-dihydroxypentyl]-N-methyl morpholinonium iodide 8.8 mg of (2S,3R,4S)-4-{L-N-[(2S)-3-ethylsulfonyl-2-(1-naphthylmethyl)propionyl]norleucyl}amino-5-cyclohexyl-1-morpholino-2,3-pentanediol was dissolved in 0.3 ml of dry methanol, and 0.3 ml of methyl iodide was added thereto. The mixture was refluxed under heating at 50° C. for three hours. The solvent was distilled off under reduced pressure, and the residue was treated with acetone/n-hexane to obtain 8.4 mg of the above identified compound as slightly yellow solid.

Rf: 0.10 (chloroform/methanol=20/1).

Mass spectrum (FAB) m/z 702(M$^+$−I).

EXAMPLE 60

(2S,3R,4S)-4-{L-N-[(2S)-3-ethylsulfonyl-2-(3-tolylmethyl)propionyl]norleucyl}amino-5-cyclohexyl-1-morpholino-2,3-pentanediol (1) (2R)-3-hydroxy-2-(3-tolylmethyl)propionic acid (a) 325 mg of (2S,3S)-4-benzyloxy-2,3-epoxy-1-butanol tert-butyldimethylsilyl ether obtained in Example 53, was subjected to Grignard reaction in the same manner as in Example 53 by using 3-tolylmethyl magnesium bromide (0.8M diethyl ether solution). The product was purificated by silica gel column chromatography to obtain 210 mg of (2R,3R)-4-benzyloxy-1-tert-butyldimethylsilyloxy-3-(3-tolylmethyl)-2-butanol as colorless oily substance.

(b) Then, 328 mg of (2R,3R)-4-benzyloxy-1-tert-butyldimethylsilyloxy-3-(3-tolylmethyl)-2-butanol was subjected to removal of the silyl group with 1.4 ml of tetra-n-butylammonium fluoride (1M THF solution). The product was converted to the aldehyde by using 168 mg of sodium metaperiodate, and the aldehyde was subjected to chromic acid oxidation (Jones' reagent) to obtain 177 mg of (2R)-3-benzyloxy-2-(3-trimethyl)propionic acid as colorless oily substance.

(c) 157 mg of the compound obtained in step (b) was dissolved in ethanol, and hydrogenated at a ordinary temperature under an atmospheric pressure in the presence of palladium black to obtain 108 mg of the above identified compound as colorless oily substance.

(2) L-N-[(2S)-3-ethylsulfonyl-2-(3-tolylmethyl)propionyl]norleucine (a) 89 mg of the compound obtained in step (1) was dissolved in dry DMF, and subjected to coupling reaction with 102 mg of L-norleucine tert-butyl ester by a DCC-HOBT method to obtain 144 mg of L-N-[(2R)-3-hydroxy-2-(3-tolylmethyl)propionyl]norleucine tert-butyl ester as colorless oily substance.

(b) 71 mg of the compound obtained in step (a) was subjected to tosylation in pyridine by using p-toluenesulfonyl chloride. Then, the product was subjected to substitution reaction with ethylmercaptan/sodium hydride to obtain 46 mg of L-N-[(2S)-3-ethylthio-2-(3-tolylmethyl)propionyl]norleucine tert-butyl ester as colorless oily substance.

(c) The compound obtained in step (b) was sulfonated in methanol with aqueous hydrogen peroxide/sodium tungstate to convert from the sulfide to the sulfone, and the sulfone compound was treated with TFA in dichloromethane to obtain 38 mg of the above identified compound as colorless oily substance.

(3) (2S,3R,4S)-4-{L-N-[(2S)-3-ethylsulfonyl-2-(3-tolylmethyl)propionyl[norleucyl}amino-5-cyclohexyl-1-morpholino-2,3-pentanediol 38 mg of the compound of step (2) was dissolved in 0.3 ml of dry DMF and subjected to coupling reaction with 48 mg of (2S,3R,4S)-4-amino-5-cyclohexyl-1-morpholino-2,3-pentanediol dihydrochloride by a DPPA method. The product was purified by silica gel column chromatography (chloroform/methanol=100/1) to obtain 32 mg of the above identified compound as colorless solid.

Rf: 0.50 (chloroform/methanol=10/1).

Mass spectrum m/z 652(M+ +1).

NMR (300 MHz, CDCl3) δppm: 0.79–1.35(5H,m), 1.40–1.86(20H,m), 2.33(3H,s), 2.42–3.28(12H,m), 3.37–3.53(3H,m), 3.58–3.75(4H,m), 4.19–4.31(2H,m), 4.58(1H,br s), 6.03(1H,d,J=9 Hz), 6.14(1H,d,J=6 Hz), 6.97–7.10(3H,m), 7.17–7.23(1H,m).

EXAMPLE 61

(2S,3R,4S)-4-{L-N-[(2S)-3-ethylsulfonyl-2-(2-tolymethyl)propionyl]norleucyl}amino-5-cyclohexyl-1-morpholino-2,3-pentanediol (1) (2R)-3-hydroxy-2-(2-tolylmethyl)propionic acid (a) 351 mg of (2S,3S)-4-benzyloxy-2,3-epoxy-1-butanol tert-butyldimethylsilyl ether obtained in Example 53, was subjected to Grignard reaction in the same manner as in Example 53 by using 2-tolylmethyl magnesium bromide (0.8M diethyl ether solution). The product was purificated by silica gel column chromatography to obtain 210 mg of (2R,3R)-4-benzyloxy-1-tert-butyldimethylsilyloxy-3-(2-tolylmethyl)-2-butanol as colorless oily substance.

(b) Then, 266 mg of (2R,3R)-4-benzyloxy-1-tertbutyldimethylsilyloxy-3-(2-tolylmethyl)-2-butanol was subjected to removal of the silyl group in the same manner as in Example 60 with tetra-n-butylammonium fluoride (1N THF solution). The product was converted to the aldehyde by using sodium methaperiodate, and the aldehyde was subjected to chromic acid oxidation by Jones' reagent. Then, the carboxylic acid thereby obtained was hydrogenated by palladium balck catalyst at a ordinally temperature under an atmospheric pressure to obtain 88 mg of the above identified compound as colorless oily substance.

(2) (2S,3R,4S)-4-{L-N-[(2S)-3-ethylsulfonyl-2-(2-tolylmethyl)propionyl]norleucyl}amino-5-cyclohexyl-1-morpholino-2,3-pentanediol (a) The compound of step (1) was subjected to coupling reaction in the same manner as in Example 60 with L-norleucine tert-butyl ester by a DCC-HOBT method. The product was subjected to tosylation with p-toluenesulfonyl chloride to obtain the tosyl compound. The tosyl compound was converted to the ethylsulfide by ethylmercaptan/sodium hydride. The ethylsulfide was oxidized to the sulfone compound by using aqueous hydrogen peroxide/sodium tungstate. The sulfone compound was treated with THF in dichloromethane to convert to L-N-[(2S)-3-ethylsulfonyl-2-(2-tolylmethyl)-propionyl]norleucine.

(b) 14.1 mg of the carboxylic acid obtained in step (a) was subjected to coupling reaction with 19.3 mg of (2S,3R,4S)-4-amino-5-cyclohexyl-1-morpholino-2,3-pentanediol dihydrochloride by a DPPA method to obtain 6.8 mg of the above identified compound as colorless solid.

NMR (300 MHz, CDCl3) δppm: 0.75–1.00(6H,m) 1.07–1.95(19H,m), 2.32(3H,s) 2.38–3.12(11H,m), 3.32–3.72(8H,m), 4.16–4.27(2H,m), 5.96(1H,d,J=9 Hz), 6.08–6.15(1H,m), 7.05–7.18(4H,m).

The compounds of the present invention have strong renin-inhibiting activities against a renin-angiotensin hypertensive system and thus expected to be useful as curing agents of hypertention due to the progress of the renin-angiotensin system.

We claim:

1. An N-acylamino acid derivative of the following formula or its innocuous salt:

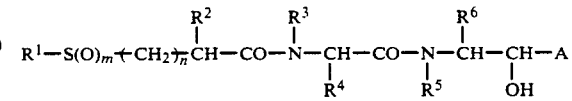

wherein m is an integer of 0 to 2;

n in an integer of 0 to 3;

$R^1$ represents thiazolyl group, thiazolylmethyl group, dihydrothiazolyl group, dihydrothiazolylmethyl group, thiadiazolyl group, thiadiazolylmethyl group, pyrimidyl group, pyrimidylmethyl group, furyl group, furfuryl group, pyridyl group, pyridylmethyl group, tetrazolymethyl group, imidazolyl group, imidazolylmethyl group, pyrazolyl group, pyrazolylmethyl group, pyrazinyl group, pyrazinylmethyl group, pyridazinyl group, pyridazinylmethyl group, indolyl group, indolylmethyl group, quinolyl group, quinolylmethyl group, phthalazinyl group, phthalazinylmethyl group, naphthidinyl group, naphthidinylmethyl group, quinoxalinyl group, quinoxalinylmethyl group, quinazolinyl group, quinazolinylmethyl group, triazolyl group, triazolylmethyl group, tetrahydropyranyl group, tetrahydropyranylmethyl group, tetrahydrofuryl group, tetrahydrofurylmethyl group, tetrahydrothienyl group, tetrahydrothienylmethyl group, pyrrolidinyl group, pyrrolidinylmethyl group, morpholino group, piperidinyl group, piperidinylmethyl group, tetrazolyl group which may be substituted with a $C_{1-4}$ alkyl group, or a pyrrolidinylmethyl group which may have a carbobenzoxy group on a nitrogen atom;

$R^2$ represents a $C_{1-5}$ alkyl group, tetrahydronaphthylmethyl group, naphthylmethyl group, quinolylmethyl group, or a benzyl group which may be substituted with a $C_{1-5}$ alkyl group;

$R^3$ and $R^5$ represent hydrogen;

$R^4$ represents a $C_{1-5}$ alkyl group which may be substituted with a hydroxy group, carboxy group, amino group, $C_{2-5}$ alkylcarbonyloxy group, $C_{1-5}$ alkylthio group or imidazolyl group;

$R^6$ represents a $C_{1-5}$ alkyl group, $C_{4-8}$ cycloalkylalkyl group, $C_{6-10}$ aryl group or $C_{7-15}$ aralkyl group;

A is a group represented by the formula —CH(OH)—$(CH_2)_q$—$R^7$ wherein q is 1; $R^7$ represents a hydrogen atom; $C_{1-5}$ alkyl group; $C_{3-6}$ cycloalkyl group; $C_{6-10}$ aryl group; $C_{7-15}$ aralkyl group; $C_{1-6}$ mono- or di-alkylamino group wherein the alkyl group of said mono- or di-alkylamino group may have the same or different 1 to 3 substituents selected from the group consisting of a hydroxy group and $C_{1-5}$ alkoxy group; pyrrolidinyl group, piperidino group, thiazolidinyl group, morpholino group, thiomorpholino group or perhydroazepinyl group wherein these heterocyclic groups may have a $C_{1-5}$ alkyl substituent; piperidino N-oxide group which may have a $C_{1-5}$ alkyl substituent; N-($C_{1-4}$ alkyl)piperidino group; or $C_{1-5}$ alkylthio group.

2. The N-acylamino acid derivative or its innocuous salt according to claim 1, wherein m is an integer of 0 to 2;

n in an integer of 0 to 3;

$R^1$ represents a thiadiazolylmethyl group, pyrimidyl group, pyrimidylmethyl group, furyl group, furfuryl group, pyridyl group, pyridylmethyl group, imidazolyl group, imidazolylmethyl group, pyrazolyl group, pyrazolylmethyl group, thiazolyl group, thiazolylmethyl group, dihydrothiazolyl group, dihydrothiazolylmethyl group, pyrazinyl group, pyrazinylmethyl group, pyridazinyl group, pyridazinylmethyl group, indolyl group, indolylmethyl group, quinolyl group, quinolylmethyl group, phthalazinyl group, phthalazinylmethyl group, naphthidinyl group, naphthidinylmethyl group, quinoxalinyl group, quinoxalinylmethyl group, quinazolinyl group, quinazolinylmethyl group, triazolyl group, triazolylmethyl group, tetrahydropyranyl group, tetrahydropyranylmethyl group, tetrahydrofuryl group, tetrahydrofurylmethyl group, tetrahydrothienyl group, tetrahydrothienylmethyl group, pyrrolidinyl group, pyrrolidinylmethyl group, morpholino group, piperidinyl group, piperidinylmethyl group, tetrazolylmethyl group which may be substituted with a $C_{1-4}$ alkyl group, or a pyrrolidinylmethyl group which may have a carbobenzoxy group on a nitrogen atom;

$R^2$ represents a $C_{1-5}$ alkyl group, tetrahydronaphthylmethyl group, naphthylmethyl group, quinolylmethyl group, or a benzyl group which may be substituted with a $C_{1-5}$ alkyl group;

$R^3$ and $R^5$ represent hydrogen;

$R^4$ represents a $C_{1-5}$ alkyl group which may be substituted with a hydroxy group, carboxy group, amino group, $C_{2-5}$ alkylcarbonyloxy group, $C_{1-5}$ alkylthio group or imidazolyl group;

$R^6$ represents a $C_{1-5}$ alkyl group or $C_{4-8}$ cycloalkylalkyl group;

A is a group represented by the formula —CH(OH)—$(CH_2)_q$—$R^7$ wherein q is 1; $R^7$ represents a $C_{1-6}$ mono- or di-alkylamino group wherein the alkyl group of said mono- or di-alkylamino group may have the same or different 1 to 3 substituents selected from the group consisting of hydroxy group and $C_{1-5}$ alkoxy group; pyrrolidinyl group, piperidino group, thiazolidinyl group, morpholino group, thiomorpholino group or perhydroazepinyl group wherein these heterocyclic groups may have a $C_{1-5}$ alkyl substituent; piperidino N-oxide group which may have a $C_{1-5}$ alkyl substituent; N-($C_{1-4}$ alkyl)piperidino group or $C_{1-5}$ alkylthio group.

3. The N-acylamino acid derivative; or its innocuous salt according to claim 1, wherein m is an integer of 0 to 2;

n is an integer of 0 to 3;

$R^1$ represents a thiadiazolyl group, dihydrothiazolyl group, pyrimidyl group, furfuryl group, tetrazolyl group which may be substituted with a $C_{1-4}$ alkyl group, or a pyrrolidinylmethyl group which may have a carbobenzoxy group on a nitrogen atom;

$R^2$ represents a $C_{1-5}$ alkyl group, tetrahydronaphthylmethyl group, naphthylmethyl group, quinolylmethyl group, or a benzyl group which may be substituted with a $C_{1-5}$ alkyl group;

$R^3$ and $R^5$ represent hydrogen;

$R^4$ represents a $C_{1-5}$ alkyl group which may be substituted with a hydroxy group, $C_{2-5}$ alkylcarbonyloxy group, $C_{1-5}$ alkylthio group or imidazolyl group;

$R^6$ represents a $C_{1-5}$ alkyl group or a $C_{4-8}$ cycloalkylalkyl group;

A is a group represented by the formula —CH(OH)—$(CH_2)_q$—$R^7$ wherein q is 1; $R^7$ represents a $C_{1-6}$ mono- or di-alkylamino group wherein the alkyl group of said mono- or di-alkylamino group may have the same or different 1 to 3 substituents selected from the group consisting of hydroxy group and $C_{1-5}$ alkoxy group; piperidino group, morpholino group or thiomorpholino group wherein these heterocyclic groups may have a $C_{1-5}$ alkyl substituent; piperidino N-oxide group; N-($C_{1-4}$ alkyl)piperidino group; or $C_{1-5}$ alkylthio group.

4. An N-acylamino acid derivative or its salt, which is (2S,3R,4S)-4-[L-N-(2S)-3-[[(2S)-N-benzyloxycarbonyl-2-pyrrolidinyl]methyl]sulfonyl-2-(1-naphthylmethyl)propionyl]norleucyl]amino-5-cyclohexyl-1-morpholino-2,3-pentanediol, (2S,3R,4S)-4-{L-N-[(2S)-2-benzyl-3-furfurylsulfonylpropionyl]norleucyl}amino-5-cyclohexyl-1-morpholino-2,3-pentanediol, (2S,3R,4S)-4-{L-N-[(2S)-2-(1-naphthylmethyl)-3-pyrimidin-2-yl)thiopropionyl]norleucyl}amino-5-cyclohexyl-1-morpholino-2,3-pentanediol, (2S,3R,4S)-4-{L-N-[(2S)-2-(1-naphthylmethyl)-3-(pyrimidin-2-yl)sulfonylpropionyl]norleucyl}amino-5-cyclohexyl-1-morpholino-2,3-pentanediol, (2S,3R,4S)-4-{L-N-[(2S)-2-(1-naphthylmethyl)-3-(pyrimidin-2-yl)sulfinylpropionyl]norleucyl}amino-5-cyclohexyl-1-morpholino-2,3-pentanediol, (2S,3R,4S)-4-{L-N-[(2S)-2-(1-naphthylmethyl)-3-[(2S)-2-pyrrolidinylmethyl]sulfonylpropionyl]norleucyl}-amino-5-cyclohexyl-1-morpholino-2,3-pentanediol dihydrochloride, (2S,3R,4S)-4-{L-N-[(2S)-2-benzyl-3-(pyrimidin-2-yl)sulfonylpropionyl]norleucyl}amino-5-cyclohexyl-1-morpholino-2,3-pentanediol, (2S,3R,4S)-4-{L-N-[(2S)-3-furfurylsulfonyl-2-(1-naphthylmethyl)propionyl]norleucyl}amino-5-cyclohexyl-1-morpholino-2,3-pentanediol.

5. A hypotensive pharmaceutical composition comprising an effective amount of an N-acylamino acid derivative of the formula I as defined in claim 1 or its pharmaceutically acceptable salt and a pharmaceutically acceptable carrier.

6. A hypotensive pharmaceutical composition comprising an effective amount of an N-acylamino acid derivative as defined in claim 4 or its pharmaceutically acceptable salt and a pharmaceutically acceptable carrier.

* * * * *